(12) United States Patent
Demers et al.

(10) Patent No.: US 8,105,265 B2
(45) Date of Patent: Jan. 31, 2012

(54) SYSTEMS, DEVICES AND METHODS FOR CARDIOPULMONARY TREATMENT AND PROCEDURES

(75) Inventors: Jason A. Demers, Manchester, NH (US); Larry B. Gray, Merrimack, NH (US); James D. Dale, Nashua, NH (US); N. Christopher Perry, Manchester, NH (US); David E. Altobelli, Hollis, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 494 days.

(21) Appl. No.: 12/249,668

(22) Filed: Oct. 10, 2008

(65) Prior Publication Data

US 2009/0099498 A1    Apr. 16, 2009

Related U.S. Application Data

(60) Provisional application No. 60/998,881, filed on Oct. 12, 2007.

(51) Int. Cl.
*A61M 37/00*    (2006.01)
(52) U.S. Cl. ............ 604/6.15; 604/4.01; 604/6.09; 604/6.11; 210/739; 210/741
(58) Field of Classification Search .......... 604/4.01, 604/6.09, 6.11, 6.15; 210/739, 741
See application file for complete search history.

(56) References Cited

U.S. PATENT DOCUMENTS

| | | | |
|---|---|---|---|
| 3,656,873 A | 4/1972 | Schiff | |
| 4,293,961 A | 10/1981 | Runge | |
| 4,479,761 A | 10/1984 | Bilstad et al. | |
| 4,927,411 A | 5/1990 | Pastrone et al. | |
| 4,976,162 A | 12/1990 | Kamen | |
| 5,245,693 A | 9/1993 | Ford et al. | |
| 5,290,239 A | 3/1994 | Classey et al. | |
| 5,378,126 A | 1/1995 | Abrahamson et al. | |
| 5,413,566 A | 5/1995 | Sevrain et al. | |
| 5,458,468 A | 10/1995 | Ye | |
| 5,482,440 A | 1/1996 | Dennehey et al. | |
| 5,593,290 A | 1/1997 | Greisch et al. | |

(Continued)

FOREIGN PATENT DOCUMENTS

EP    1180375    2/2002

(Continued)

OTHER PUBLICATIONS

SJ Mitchell, T. Wilcox, C. McDougal, DF Gorman, *Emboli Generation by the Medtronic Maxima Hard-Shell Adult Venous Reservoir in Cardiopulmonary Bypass Circuits: a preliminary report*, Perfusion, 1996 11: pp. 145-155.

(Continued)

*Primary Examiner* — Leslie Deak
(74) *Attorney, Agent, or Firm* — Marc J. Gorayeb

(57) ABSTRACT

A cardiopulmonary bypass system utilizing membrane-based reciprocating positive displacement blood pumps ("pod pumps"). In one aspect, the pod pumps are constructed to provide reduced shear forces on the blood being pumped. In another aspect blood flow through the pod pumps can be controlled by a controller using information from pressure sensors in the control chamber of the pod pumps. In another aspect, the pod pumps are included on a disposable unit that can be received and held by a receptacle means on a base unit, the base unit also providing pressurized control fluid to the pod pumps on the disposable unit through the receptacle means.

22 Claims, 54 Drawing Sheets

U.S. PATENT DOCUMENTS

| | | | |
|---|---|---|---|
| 5,645,531 A | 7/1997 | Thompson et al. | |
| 5,899,873 A | 5/1999 | Jones et al. | |
| 5,935,093 A | 8/1999 | Elgas et al. | |
| 6,044,691 A * | 4/2000 | Kenley et al. | 73/40.5 R |
| 6,101,406 A | 8/2000 | Hacker et al. | |
| 6,302,653 B1 | 10/2001 | Bryant et al. | |
| 6,331,778 B1 | 12/2001 | Daily et al. | |
| 6,336,911 B1 | 1/2002 | Westerbeck | |
| 6,382,923 B1 | 5/2002 | Gray | |
| 6,413,233 B1 | 7/2002 | Sites et al. | |
| 6,415,797 B1 | 7/2002 | Groth et al. | |
| 6,464,666 B1 | 10/2002 | Augustine et al. | |
| 6,478,962 B1 | 11/2002 | Brockhoff et al. | |
| 6,480,257 B2 | 11/2002 | Cassidy et al. | |
| 6,485,263 B1 | 11/2002 | Bryant et al. | |
| 6,491,656 B1 | 12/2002 | Morris | |
| 6,497,676 B1 | 12/2002 | Childers et al. | |
| 6,503,062 B1 | 1/2003 | Gray et al. | |
| 6,620,121 B1 | 9/2003 | McCotter | |
| 6,709,417 B1 | 3/2004 | Houle et al. | |
| 6,722,865 B2 | 4/2004 | Domroese | |
| 6,726,656 B2 | 4/2004 | Kamen et al. | |
| 6,743,201 B1 | 6/2004 | Doing et al. | |
| 6,749,403 B2 | 6/2004 | Bryant et al. | |
| 6,749,591 B1 | 6/2004 | McNally et al. | |
| 6,752,172 B2 | 6/2004 | Lauer | |
| 6,783,328 B2 | 8/2004 | Lucke et al. | |
| 6,808,369 B2 | 10/2004 | Gray et al. | |
| 6,814,547 B2 | 11/2004 | Childers et al. | |
| 6,852,280 B2 | 2/2005 | Vijay et al. | |
| 6,877,713 B1 | 4/2005 | Gray et al. | |
| 6,878,283 B2 | 4/2005 | Thompson | |
| 6,899,693 B2 | 5/2005 | Ghelli et al. | |
| 6,929,751 B2 | 8/2005 | Bowman et al. | |
| 6,939,471 B2 | 9/2005 | Gross et al. | |
| 6,949,079 B1 | 9/2005 | Westberg et al. | |
| 6,974,434 B2 | 12/2005 | Roberts et al. | |
| 7,083,719 B2 | 8/2006 | Bowman et al. | |
| 7,175,397 B2 | 2/2007 | Claude et al. | |
| 7,175,606 B2 | 2/2007 | Bowman et al. | |
| 7,238,164 B2 | 7/2007 | Childers et al. | |
| 7,273,465 B2 | 9/2007 | Ash | |
| 7,364,563 B2 | 4/2008 | Lucke et al. | |
| 7,410,294 B2 | 8/2008 | Shiraki et al. | |
| 7,488,448 B2 | 2/2009 | Wieting et al. | |
| 7,544,179 B2 | 6/2009 | Distler et al. | |
| 7,736,328 B2 | 6/2010 | Childers et al. | |
| 2002/0110485 A1* | 8/2002 | Stringer et al. | 422/45 |
| 2003/0229302 A1 | 12/2003 | Robinson et al. | |
| 2004/0091374 A1 | 5/2004 | Gray | |
| 2004/0138607 A1 | 7/2004 | Burbank et al. | |
| 2005/0051466 A1 | 3/2005 | Carter et al. | |
| 2005/0069425 A1 | 3/2005 | Gray et al. | |
| 2005/0095154 A1 | 5/2005 | Tracey et al. | |
| 2005/0130332 A1 | 6/2005 | Ishii et al. | |
| 2005/0131332 A1 | 6/2005 | Kelly et al. | |
| 2005/0230292 A1 | 10/2005 | Beden et al. | |
| 2006/0041215 A1 | 2/2006 | Lindsay et al. | |
| 2006/0079827 A1 | 4/2006 | Jensen et al. | |
| 2006/0155237 A1 | 7/2006 | Vijay | |
| 2006/0195064 A1 | 8/2006 | Plahey et al. | |
| 2006/0241550 A1 | 10/2006 | Kamen et al. | |
| 2007/0077156 A1 | 4/2007 | Orr | |
| 2007/0112297 A1 | 5/2007 | Plahey et al. | |
| 2007/0135758 A1 | 6/2007 | Childers et al. | |
| 2007/0197857 A1 | 8/2007 | Palmer | |
| 2007/0253463 A1 | 11/2007 | Perry et al. | |
| 2008/0015493 A1 | 1/2008 | Childers et al. | |
| 2008/0033346 A1 | 2/2008 | Childers et al. | |
| 2008/0058697 A1 | 3/2008 | Kamen et al. | |
| 2008/0058712 A1 | 3/2008 | Plahey | |
| 2008/0077068 A1 | 3/2008 | Orr | |
| 2008/0097283 A1 | 4/2008 | Plahey | |
| 2008/0125693 A1 | 5/2008 | Gavin et al. | |
| 2008/0161751 A1 | 7/2008 | Plahey et al. | |
| 2008/0203023 A1 | 8/2008 | Burbank et al. | |
| 2008/0208111 A1 | 8/2008 | Kamen et al. | |
| 2008/0240929 A1 | 10/2008 | Kamen et al. | |
| 2008/0253427 A1 | 10/2008 | Kamen et al. | |
| 2009/0007642 A1 | 1/2009 | Busby et al. | |
| 2009/0008331 A1 | 1/2009 | Wilt et al. | |
| 2009/0009290 A1 | 1/2009 | Knelp et al. | |
| 2009/0012447 A1 | 1/2009 | Huitt et al. | |
| 2009/0012448 A1 | 1/2009 | Childers et al. | |
| 2009/0012449 A1 | 1/2009 | Lee et al. | |
| 2009/0012450 A1 | 1/2009 | Shah et al. | |
| 2009/0012452 A1 | 1/2009 | Slepicka et al. | |
| 2009/0012453 A1 | 1/2009 | Childers et al. | |
| 2009/0012454 A1 | 1/2009 | Childers | |
| 2009/0012455 A1 | 1/2009 | Childers et al. | |
| 2009/0012456 A1 | 1/2009 | Childers et al. | |
| 2009/0012457 A1 | 1/2009 | Childers et al. | |
| 2009/0012458 A1 | 1/2009 | Childers et al. | |
| 2009/0012460 A1 | 1/2009 | Steck et al. | |
| 2009/0012461 A1 | 1/2009 | Childers et al. | |
| 2009/0043239 A1 | 2/2009 | Gagel et al. | |
| 2009/0076434 A1 | 3/2009 | Mischelevich et al. | |
| 2009/0084721 A1* | 4/2009 | Yardimci et al. | 210/188 |
| 2009/0112151 A1 | 4/2009 | Chapman et al. | |
| 2009/0113335 A1 | 4/2009 | Sandoe et al. | |
| 2009/0137940 A1 | 5/2009 | Orr | |
| 2009/0222119 A1 | 9/2009 | Plahey et al. | |
| 2009/0275875 A1 | 11/2009 | Liebing et al. | |
| 2009/0294359 A1 | 12/2009 | Hopping et al. | |
| 2010/0137782 A1 | 6/2010 | Jansson et al. | |
| 2010/0185132 A1 | 7/2010 | Han et al. | |
| 2010/0187176 A1 | 7/2010 | Lopez | |
| 2010/0191180 A1 | 7/2010 | Childers et al. | |
| 2010/0191181 A1 | 7/2010 | Childers et al. | |
| 2010/0204633 A1 | 8/2010 | Kopperschmidt | |
| 2010/0234786 A1 | 9/2010 | Fulkerson et al. | |
| 2010/0241024 A1 | 9/2010 | Konig et al. | |
| 2010/0312162 A1 | 12/2010 | Masaoka et al. | |

FOREIGN PATENT DOCUMENTS

| | | |
|---|---|---|
| EP | 1716335 | 5/2008 |
| WO | WO0230267 | 4/2002 |
| WO | WO 2006/120415 | 11/2006 |
| WO | WO 2009/044221 | 4/2009 |

OTHER PUBLICATIONS

M. Schoenburg, MD, B. Kraus, MD, A. Mudding, MD, U. Taborski, MD, H. Hofmann, PhD, G. Erhardt, CCP, S. Hein, MD, M. Roth, MD, P. R. Vogt, MD, Fetcs, G. F. Karliczck, MD, W. P. Kloevckorn, MD, *The Dynamic Air Bubble Trap Reduces Cerebral Microembolism During Cardiopulmonary Bypass*, J Thorac Cardiovasc Surg 2003;126:1455-60.

Timothy W. Wilcox, CCP, *Vacuum-Assisted Venous Drainage: To Air or Not to Air, That is the Question. Has the Bubble Burst?*, Journal of the American Society for Extra-Corporeal Technology, 2002, 34: pp. 24-28.

T. Gourlay, J. Fleming, KM Taylor, *The Eftects of Pulsatile Flow on the Leukocyte Depleting Qualities of theh Pall LG6 Leukocyte Depleting Arterial Line Filter: a Laboratory Investigation*, Perfusion, 1992:7:227-232.

Aditya K. Kaza, MD, Jeffrey T. Cope, MD, Steven M. Fiser, MD, Stewart M. Long, MD, John A. Kern, MD, Irving L. Kron, MD, Curtis G. Tribble, MD, *Elimination of Fat Microemboli During Cardiopulmonary Bypass*, Ann Thorac Surg 2003:75:555-9.

Pramote Hochareon, Keefe B. Manning, Arnold A. Fontaine, Steven Deutsch, John M. Tarbell, *Diaphragm Motion Affects Flow Patterns in an Artificial Heart*, Artificial Organs 2003 27(12):1102-1109.

Cardiopulmonary Bypass—Principles and Practice, Second Edition, © 2000 Lippincott Williams & Wilkins: Chapter 5, Circuitry and Cannulation Techniques, and Chapter 6, Cardiotomy Suction and Venting.

Partial International Search Report, dated Mar. 3, 2009, received in International Patent Application No. PCT/US2008/079616, 6 pgs.

Kelvin Lau, Hetul Shah, Andrea Kelleher, Neil Moat, *Coronary Artery Surgery: Cardiotomy Suction or Cell Salvage?*, Journal of Cardiothoracic Surgery 2007, 2:46, Published Oct. 25, 2007.

*Heart-Lung Bypass Units; Oxygenators, Extracorporeal Bubble/ Membrane; Pumps, Extracorporeal Perfusion*,Healthcare Product Comparison System, Published Mar. 2003.

Tijen Alkali, Atif Akeevin, Akif Undar, Halil Turkoglu, Tufan Paker, Aydin Aytac, *Benefits of Pulsatile Perfusion on Vital Organ Recovery During and After Pediatric Open Heart Surgery*, ASAIO Journal, Nov./Dec. 2007. 53:651-654.

Francesco Onorati, MD, Pierangela Presta, MD, Giorgio Fuiano, MD, Pasquale Mastroroberto, MD, Nicolino Comi, MD, Francesco Pezzo, MD, Cannela Tozzo, MD, Attilio Renzulli, MD, PhD, FETCS, *A Randomized Trial of Pulsatile Perfusion Using an Intra-Aortic Balloon Pump Versus Nonpulsatile Perfusion on Short-Term Changes in Kidney Function During Cardiopulmonary Bypass During Myocardial Reperfusion*, Am J Kidney Dis, vol. 50, No. 2, Aug. 2007 pp. 229-238.

Francesco Onorati, Lucia Cristodoro, Massimo Bilotta, Barbara Impiombato, Francesco Pezzo, Pasquale Mastroroberto, Antonio di Virgilio, Attilio Renzulli, *Intraaortic Balloon Pumping During Cardioplegic Arrest Preserves Lung Function in Patients with Chronic Obstructive Pulmonary Disease*, Ann Thorac Surg, 2606;82:35-43.

Guy M. McKhann, Maura A. Grega, Louis M. Borowicz, Jr., William A. Baumgartner, Ola A. Seines, *Stroke and Encephalopathy After Cardiac Surgery and Update*, Stroke, 2006;37;562-57, originally published Dec. 22, 2005.

Bahaaldin Alsoufi, MD, Christopher A. Caldarone, MD, Chadi T. Abouassaly, MD, *Hypothermia, Circulatory Arrest and Cardiopulmonary Bypass*, eMedicine from WebMD, Aug. 1, 2006, accessed at http://www.emedicine.com/ped/TOPIC2813.HTM.

Hollow Fiber Oxygenator CAPIOX SX 10 Instructions for Use, Apr. 1997.

PALL Medical AutoVentSV, Pall Blood Filter for Extracorporeal Service, Filtration, Separation, Solution. SM, Product Catalogue EC44B PALL Corp. © 1993, 2000.

PALL Medical LeukoGuard BC, Pall Leukocyte Reduction Blood Cardioplegia Filter, Filtration, Separation, Solution.SM, Product Catalogue EC56D © 1999 Pall Europe Ltd.

Pall Corporation, Cardiovascular, accessed at web page http://www.pall.com/medical_6662.asp?level10=1, Apr. 13, 2004.

Xavier M. Mueller, Hendrik T. Tevaearai, David Jegger, Ludwig K. Von Segesser, *Air Filtering Capacity of an Integrated Cardiopulmonary Bypass Unit*, ASAIO Journal 2003; 49;365-369.

Sean P. Rider, BS, CCP; Lorri V. Simon, BS, CCP; Billy J. Rice, CCP; Chad C. Poulton, BS, CCP, *Assisted Venous Drainage, Venous Air, and Gaseous Microemboli Transmission into the Arterial Line: An In-Vitro Study*, Journal of Extra-Corporeal Technology, vol. 30, No. 4, Dec. 1998 pp. 160-165.

Ruth L. Taylor, MSc, Michael A. Borger, MD, Richard D. Weisel, MD, Ludwig Fedorko, MD, PhD, Christopher M. Feindel, MD, *Cerebral Microemboli During Cardiopulmonary Bypass: Increased Emboli During Perfusionist Interventions*, Ann Thorac Surg 1999;68:89-93.

Masanori Morita, Ryohei Yozu, Toni Matayoshi, Atsuhiro Mitsumarau, Hankei Shin, Shiaki Kawada, *Closed Circuit Cardiopulmonary Bypass with Centrifugal Pump for Open-Heart Surgery: New Trial for Air Removal*, Artificial Organs 2000;24(6):442-445.

\* cited by examiner

SYSTEMS, DEVICES AND METHODS FOR CARDIOPULMONARY TREATMENT AND PROCEDURES

CROSS REFERENCE TO RELATED APPLICATIONS

The present application is a Non-provisional Application which claims priority from U.S. Provisional Patent Application Ser. No. 60/998,881, filed Oct. 12, 2007.

TECHNICAL FIELD

The present inventions relate to systems, devices and methods of cardiopulmonary treatment and procedures. Additionally, the present invention relates to pumps and other flow-control systems and methods, and in particular to pumps that impart low shear forces and turbulence on the fluid being pumped for systems, devices and methods of cardiopulmonary treatment and procedures. Flow control systems in the present invention can include devices for sensing pressures within pumps, determining pumping volumes and flow rates, and for altering fluid flow paths among several pumps using actively controlled valves interposed in fluid flow paths. Additionally, the present invention relates to heat exchanger systems for systems, devices and methods of cardiopulmonary treatment and procedures. Further, the present invention relates to sensors and more particularly, to a temperature and/or conductivity sensor apparatus and a method of using thereof for systems, devices and methods of cardiopulmonary treatment and procedures.

BACKGROUND OF THE INVENTION

Cardiopulmonary bypass ("CPB") is most frequently used to divert blood away from the heart and lungs during open-heart surgery or major repair of the ascending aorta. In its basic form, the bypass circuit typically includes a cannula inserted into the right atrium or one of the major veins leading to the heart, connected to tubing to transport the patient's deoxygenated venous blood to a reservoir, the blood then being passed through a centrifugal pump to an oxygenator and heat exchanger; and tubing to carry oxygenated blood to an arterial filter and air bubble trap, the blood then being returned to the patient through a cannula in the wall of the ascending aorta or other major artery. During surgery, the heart can be paralyzed by infusing into the heart a cardioplegia solution containing a high concentration of potassium, both to allow the surgeon to control the operative field and to reduce energy and oxygen consumption by the heart muscle. Infusion of the cardioplegia solution is commonly achieved through a separate pump-driven branch circuit ("cardioplegia circuit") of the CPB circuit, carrying chilled, oxygenated blood coming from the oxygenator/heat exchanger through tubing to a cannula inserted into the heart. An infusion pump allows for the introduction of a high concentration/low volume cardioplegia solution at a precise rate into the blood of the cardioplegia circuit. Optionally, there may also be a cardiotomy circuit comprising a suction cannula attached to a pump for aspirating shed blood in the chest cavity, the blood then being passed through a filter and into the venous reservoir, and ultimately recirculated to the patient.

The CPB circuit must be purged of air and primed with a saline solution prior to commencing bypass, which causes a substantial volume of extra fluid to be delivered to the patient. It is generally believed that the amount of volume occupying the various tubings, pumps, reservoirs and filters in a CPB circuit should be minimized in order to reduce some of the complications associated with CPB. Some of these complications include anemia and edema, as well as inflammatory responses caused by the exposure of blood to plastic components, all of which can lead to pulmonary, renal and cerebral dysfunction. These complications can be exacerbated by the damage caused to the cellular elements of the blood (such as red blood cells) by the pumps used in a typical CPB circuit. The typical CPB circuit usually includes a centrifugal pump or roller pump for the high flow-rate main circuit, and peristaltic or roller pumps for branch circuits and medication infusion lines. Any of these types of pumps can create high shear forces on the cellular elements of the blood, leading to hemolysis and platelet activation, which can have several detrimental effects on the patient. Furthermore, microemboli of air, fat, platelet aggregates, thrombi, atheromatous plaque fragments and other debris can enter the patient's circulatory system, also leading to ischemic and inflammatory events in various organs.

Efforts have been directed to reducing the size of the priming volume of CPB circuits, an example of which is described in U.S. Pat. No. 6,852,280. Shortening interconnections between devices, reducing the diameter of tubing, and minimizing the volume of the venous reservoir can lead to significant reductions in the priming volume, for example, from approximately 1700 cc's to less than 600 cc's. If the priming volume can be made sufficiently small, it may be possible to prime the CPB circuit with the patient's own blood, reducing the amount of excess fluid ultimately delivered to the patient, and thus also reducing the amount of blood transfusions needed to maintain an acceptable hematocrit. In some cases, it is possible to reduce the priming volume further by eliminating arterial-line filters and in-line blood cardioplegia. Also, using vacuum-assisted venous drainage allows for the use of smaller diameter cannulas and tubing while maintaining adequate flow rates. In other cases, it may be possible to reduce priming volume by consolidating components (such as filters, reservoirs, pumps) into single elements that require less interconnecting tubing.

However, reducing the priming volume alone does not necessarily ameliorate other major problems associated with CPB, including, for example, hemolysis and the propagation of microemboli. The incidence of stroke after cardiac surgical procedures can range from 3-9%, the highest incidence being associated with hypothermic circulatory arrest and CPB. The incidence of post-operative encephalopathy can range from 8-32%. Since the advent of newer cerebral imaging techniques that can detect brain lesions due to microemboli, many clinicians have concluded that microembolization is probably a significant contributing factor to post-CPB encephalopathy. As many as 45% of post-operative patients may exhibit brain lesions due to microemboli, despite having no signs of impaired cerebral function. (See G. McKhann et al., Stroke and Encephalopathy After Cardiac Surgery—An Update, Stroke 2006; 37:562-71). As many as 25 percent of infants undergoing CPB and deep hypothermic circulatory arrest show post-operative evidence of at least transient neurologic injury. Although the mechanisms that lead to post-operative neurological impairment are thought to be multifactorial, microembolization is considered to be significant factor.

The risk of microembolization may be increased if arterial-line filters are eliminated; and there may be increased risk of air embolization with the use of vacuum-assisted venous drainage, or if venous reservoirs are bypassed. Thus, there is a trade-off between the desire to minimize the priming volume and the need to minimize microembolization (See B. Alsoufi et al., Hypothermia, Circulatory Arrest and Cardiopulmonary Bypass, available at www.emedicine.com/ped/TOPIC2813.HTM (article last updated Aug. 1, 2006)).

Concerns have also been raised about the potential detrimental effects of continuous flow vs. pulsatile flow in both CPB and in other forms of assisted circulation. Absence of pulsatile blood flow could lead to a loss of baroreceptor-mediated control of blood circulation in the patient, and result in a decrease in regional blood flow and oxygen delivery. Non-pulsatile perfusion during CPB may have an adverse effect on renal function (See F. Onorati et al., Am. J. Kidney Dis. 2007 August; 50(2):229-38). Adding pulsatile flow from an intra-aortic balloon pump during CPB may help to preserve lung function in patients with chronic obstructive pulmonary disease (See F. Onorati, et al., Ann. Thorac. Surg. 2006 July; 82(1):35-43). Use of pulsatile flow during CPB in children undergoing heart surgery for repair of congenital heart defects may improve cardiac, renal and pulmonary functions in the early post-CPB period (See T. Alkan et al., ASAIO J. 2007 November-December; 53(6):651-4). There have been various attempts to introduce pulsatile blood flow during CPB. For example, U.S. Pat. No. 6,620,121 describes the use of a pulse wave generator for CPB, consisting of a compression assembly acting on an in-line collapsible chamber placed downstream from a roller pump and membrane oxygenator. However, most of these attempts require the addition of devices to the CPB circuit, increasing their complexity, the priming volume and the opportunity for additional shear stress to be applied to the cellular elements of the blood.

There remains a need for an improved CPB apparatus and method, having a reduced priming volume, simplified extracorporeal circuit, and having pump and valve control systems that simplify and increase the reliability and precision of the operation of CPB apparatus. Moreover, there continues to be a need to incorporate pumps that have the ability to meet the flow requirements of CPB and yet minimize trauma to the blood. Furthermore, it would be advantageous to have CPB apparatus with the flexibility to introduce pulsatile flow if desired, and that can employ modular elements to reduce costs and increase the flexibility of using the equipment in a variety of settings.

SUMMARY OF THE INVENTION

The present invention generally relates to cardiopulmonary bypass ("CPB") systems and similar systems for extracorporeal blood flow and treatment. The subject matter of the invention involves, in some cases, interrelated devices, alternative solutions to a particular problem, and/or a plurality of different uses of one or more systems and/or devices. Although the various systems and methods are described herein in relation to standard CPB, it should be understood that the various systems and methods described herein are applicable to a variety of perfusion systems able to circulate and treat blood extracorporeally, such as, for example, femoral vessel access CPB, emergency/resuscitative CPB systems, extracorporeal membrane oxygenation systems and ventricular assist systems.

In some embodiments of the invention the pumps used to pump blood during or in connection with systems, devices and methods of cardiopulmonary treatment and procedures are pod pumps having a geometry that reduces shear forces on the blood.

In one aspect, a method and system of conducting cardiopulmonary bypass includes an extracorporeal blood flow path beginning at a venous cannula accessing a subject's venous blood and ending at an arterial cannula accessing a subject's arterial blood comprising: an oxygenator and one or more reciprocating positive-displacement arterial blood pumps, each pump having a curved rigid chamber wall, a flexible membrane attached to the rigid chamber wall, the flexible membrane and rigid chamber wall defining a pumping chamber, an inlet for directing flow through the rigid chamber wall into the pumping chamber in a direction substantially tangential to the rigid chamber wall, and an outlet for directing flow through the rigid chamber wall out of the pumping chamber in a direction substantially tangential to the rigid chamber wall. The method and system can additionally include a venous reservoir and a filter. The filter can include a bubble trap and at least two filter elements. The method and system can further include a heat exchanger.

Additionally, the inlet of the pumps can further direct flow through the rigid chamber wall into the pumping chamber in a direction that provides low-shear flow into the pumping chamber; and the outlet of the pumps can further direct flow through the rigid chamber wall out of the pumping chamber in a direction that provides low-shear flow out of the pumping chamber.

In a particular embodiment, the reciprocating positive-displacement pump uses a flexible membrane made from a material that reduces hard snapping of the membrane as the membrane reciprocates from one position in the pump chamber to the other. The central portion of the membrane may include protuberances that space the central portion away from the rigid chamber wall when the membrane is in a minimum-pumping-chamber-volume position. Such protuberances prevent blood from being trapped between a portion of the membrane and the wall, and reduce the shear forces exerted on the blood being pumped. In another embodiment, the rigid inner wall of the pumping chamber can have a channel or recess fluidly connecting the inlet fluid path with the outlet fluid path of the pump, the channel or recess at least partially inaccessible to contact with the flexible membrane when it is pressed against the rigid chamber wall of the pumping chamber.

In an additional embodiment, the one or more reciprocating positive-displacement arterial blood pumps can further comprise a rigid limit structure for limiting movement of the membrane and limiting the maximum volume of the pumping chamber, the flexible membrane and the rigid limit structure defining a control chamber, an opening in the rigid limit structure through which pressurized fluid can cause movement of the membrane, a valve fluidly connected to the opening for directing pressurized fluid to the control chamber; a pressure sensor in fluid communication with the control chamber, and a controller connected to the pressure sensor; wherein the controller can calculate the volume of liquid in the pumping chamber and control the valve to regulate the pressure in the control chamber. In a further embodiment, the pumping chamber defines a spheroid volume when the flexible membrane is urged against the rigid limit structure and the pumping chamber is at maximum volume.

In another aspect of the invention a system is provided as stated above, wherein a pneumatic actuation system intermittently provides either a positive or a negative pressure to the control chamber of the reciprocating positive-displacement pump.

In accordance with another aspect of the invention there is provided a system for pumping a biological fluid during or in connection with systems, devices and methods of cardiopulmonary treatment and procedures. The system includes a disposable unit, first and second pod pumps, and a base unit. The disposable unit includes an inlet line for the biological fluid and an outlet line for the biological fluid. Each pump is capable of delivering a stroke volume during each stroke and includes a rigid pod wall enclosing a pump chamber, a reciprocating member adjacent the pump chamber, an inlet valve for permitting flow from the inlet line into the pumping chamber but preventing flow out of the pumping chamber into the inlet line, an outlet valve for permitting flow from the pumping chamber into the outlet line but preventing flow from the outlet line into the pumping chamber, and a control port defined by the rigid pod wall. The base unit includes receptacle means for receiving and holding the disposable unit and an actuation system for providing a control fluid under positive or negative pressure to each of the control ports, wherein the base unit is capable of receiving and holding disposable units having pod pumps with different stroke volumes.

The method and system can additionally include a cardiotomy blood system for collecting and returning blood that has been shed during a medical procedure comprising: blood tubing leading from a subject, a filter, and a reciprocating positive-displacement cardiotomy blood pump fluidly connected to the venous reservoir. The cardiotomy blood pump can further comprise a curved rigid chamber wall, a flexible membrane attached to the rigid chamber wall, the flexible membrane and rigid chamber wall defining a pumping chamber, an inlet for directing flow through the rigid chamber wall into the pumping chamber in a direction substantially tangential to the rigid chamber wall, and an outlet for directing flow through the rigid chamber wall out of the pumping chamber in a direction substantially tangential to the rigid chamber wall.

The method and system can additionally include a cardioplegia system for infusing a medical solution into blood that has passed through the oxygenator and that is directed to a subject's heart comprising: a valve to direct oxygenated blood to a reciprocating positive-displacement cardioplegia blood pump defining a cardioplegia blood flow path, a cardioplegia solution reservoir fluidly connected to a reciprocating positive displacement cardioplegia solution pump, and a valve fluidly connecting the cardioplegia solution pump to the cardioplegia blood flow path. The reciprocating positive displacement cardioplegia blood pump and the reciprocating positive displacement solution pump can additionally each further comprise: a curved rigid chamber wall, a flexible membrane attached to the rigid chamber wall, the flexible membrane and rigid chamber wall defining a pumping chamber, an inlet for directing flow through the rigid chamber wall into the pumping chamber, an outlet for directing flow through the rigid chamber wall out of the pumping chamber, a rigid limit structure for limiting movement of the membrane and limiting the maximum volume of the pumping chamber, the flexible membrane and the rigid limit structure defining a control chamber, a port in the rigid limit structure through which pressurized fluid can cause movement of the membrane, a valve fluidly connected to the port for directing pressurized fluid to the control chamber; a pressure sensor in fluid communication with the control chamber, and a controller connected to the pressure sensor; wherein the controller can calculate the volume of liquid in the pumping chamber and regulate the valve.

In another aspect the method and system can additionally include A cardiopulmonary bypass system comprising
a blood flow inlet channel fluidly connected to the outlet of the oxygenator,
the inlet blood flow channel fluidly connected to the inlet of a reciprocating positive displacement first pump having a pumping chamber separated from a control chamber by a flexible membrane, the control chamber fluidly connected to a first pressure transducer;
a blood flow outlet channel fluidly connected to the outlet of the reciprocating positive displacement first pump;
a medical solution inlet channel fluidly connected to the outlet of a container containing a medical solution;
the medical solution inlet channel fluidly connected to the inlet of a reciprocating positive displacement second pump having a pumping chamber separated from a control chamber by a flexible membrane, the control chamber fluidly connected to a second pressure transducer;
a medical solution outlet channel fluidly connected at a first end to the outlet of the reciprocating positive displacement second pump, and fluidly connected at a second end to the blood flow outlet channel; and
a controller for receiving information from the first and second pressure transducers and for controlling the fluid output of the first pump and the second pump; wherein
the controller can calculate the flow rate through the first pump and the flow rate through die second pump, and can adjust the flow rate of the second pump according to the flow rate of the first pump, thereby maintaining a desired ratio of a medical solution flow rate with a blood flow rate.

In another aspect, the method and system can additionally include a combination blood filter having an upper inlet and first and second lower outlets comprising: a housing defining a first cylindroid volume for directing blood in a circular downward path; a first filter for removing matter larger than a first size from blood, the first filter defining a second volume and being located within the first volume, the second volume fluidly connected to the first outlet; a second filter for removing matter larger than a second size from blood, the second size being smaller than the first size, the second filter defining a third volume and being located within the second volume, the third volume fluidly connected to the second outlet; and a selector valve for selectably directing blood flow through the first outlet with the selector valve in a first mode, and for selectably directing blood flow through the second outlet with the selector valve in a second mode.

In another embodiment, the venous reservoir of the system further comprises a soft shell receptacle having a fluid inlet and a fluid outlet, the receptacle capable of expanding as fluid enters the receptacle, and collapsing as fluid leaves the receptacle; the venous reservoir being fluidly connected to the one or more arterial blood pumps, wherein the fluid outlet of the venous reservoir is fluidly connected to a branch circuit of the inlet of the one or more arterial blood pumps, and the fluid inlet of the venous reservoir is fluidly connected to a branch circuit of the outlet of the one or more arterial blood pumps, and wherein a first valve controls the rate of fluid flow from the venous reservoir to the inlet of the one or more arterial blood pumps, and a second valve controls the rate of fluid flow from the one or more arterial blood pumps to the venous reservoir.

In another embodiment, the one or more reciprocating positive-displacement arterial pumps additionally are enclosed in an arterial blood pump cassette, the arterial blood pump cassette further comprising a housing enclosing (a) an inlet port fluidly connected to a primary inlet line; (b) an outlet port fluidly connected to a primary outlet line; (c) one or more secondary inlet lines, each secondary inlet line fluidly connecting one of the one or more arterial pumps with the primary inlet line; (d) one or more secondary outlet lines, each secondary outlet line fluidly connecting one of the one or more arterial pumps with the primary outlet line; and (e) a primary inlet valve interposed in the primary inlet line. In a further embodiment, a secondary inlet valve is additionally interposed in one or more secondary inlet lines. In a further embodiment, a primary outlet valve is interposed in the primary outlet line. In yet a further embodiment, a secondary outlet valve is additionally interposed in one or more secondary outlet lines.

In further embodiments, the arterial blood pump cassette may include a purge port in fluid communication with the pumping chambers of the one or more arterial pumps, the purge port permitting expulsion of air from the pumping chambers.

In another embodiment, the reciprocating positive displacement cardioplegia blood pump and cardioplegia solution pump additionally are enclosed in a cardioplegia cassette, the cardioplegia cassette further comprising a housing enclosing (a) a primary inlet line fluidly connecting an inlet port to the inlet of the cardioplegia blood pump; (b) a secondary inlet line fluidly connecting a secondary inlet port to the inlet of the cardioplegia solution pump; (c) a primary outlet line fluidly connecting the outlet of the cardioplegia blood pump to an outlet port; (d) a secondary outlet line fluidly connecting the outlet of the cardioplegia solution pump to the outlet port; and (e) a primary inlet valve interposed in the primary inlet line. In a further embodiment, a secondary inlet valve is interposed in the secondary inlet line. In yet a further embodiment, a secondary outlet valve is interposed in the secondary outlet line. In yet a further embodiment, a primary outlet valve is interposed in the primary outlet line.

In an additional embodiment, the pumps and valves of the cassette are pneumatically actuated membrane-based pumps and valves. The pumps comprise a pump chamber hermetically separated from a control chamber by a flexible membrane. The valves comprise a flow chamber hermetically separated from a control chamber also by a flexible membrane. The control chambers of the pumps and valves each have ports fluidly connectable to at least one pressurized fluid source. Each control chamber of each pump is fluidly connected to a pressure sensor that can communicate the control chamber pressures of each pump to a controller. The controller can calculate the liquid volume of each pump using information from the pressure sensors, and can control the movement of the membrane of each pump by controlling valves interposed in the fluid flow paths between the pump control chambers and the at least one pressure source.

In further embodiments, the cardioplegia cassette may include a purge port in fluid communication with the pumping chambers of the one or more cardioplegia blood pumps, the purge port permitting expulsion of air from the pumping chambers of the pumps. The cardioplegia cassette may include a secondary inlet in fluid communication with one or more pumping chambers of the one or more cardioplegia blood pumps, the secondary inlet permitting introduction of a secondary fluid into the blood flow path of the cardioplegia cassette. The secondary inlet may be a luer port, a syringe port, or a hollow spike. The secondary fluid may include a medical solution, a chemical solution, a diluent, a blood thinner, an anticoagulant, or a cardioplegia solution.

In another aspect of the invention methods are provided as stated above, wherein a pneumatic actuation system intermittently provides either a positive or a negative pressure to the control chamber of the reciprocating positive-displacement pump.

In one aspect of the invention an extracorporeal blood flow system comprises:
an air removal container having an upper blood inlet, a lower blood outlet and an air vent near the top of the air removal container, the air vent sealingly connected to a negative pressure source;
a blood pump having a pump inlet and a pump outlet;
a fluid path from the outlet of the air removal container to the inlet of the blood pump;
a reservoir containing a liquid with a blood inlet and a blood outlet;
a secondary reservoir inlet fluid path branching from the pump outlet and fluidly connected to the inlet of the reservoir;
a secondary reservoir outlet fluid path branching from the pump inlet and fluidly connected to the outlet of the reservoir;
a first valve means to control flow of blood from the reservoir to the pump inlet and a second valve means to control flow of blood from the pump outlet to the reservoir;
a pressure sensor in fluid communication with the air vent, and capable of measuring air pressure within the air removal container; and
a controller for receiving the pressure information from the pressure sensor, and for controlling the valve means, wherein the controller can monitor the air pressure within the air removal container, and control the first and second valve means to cause the liquid from the reservoir to flow into the blood pump upon detection of a change in the air pressure within the air removal container.

In another aspect of the invention a cardiac bypass system comprises: an air eliminator having a blood inlet and a blood outlet; a blood pump having a pump inlet and a pump outlet; a fluid path from the blood outlet of the air eliminator through the blood pump; a variable-volume reservoir with a blood inlet and a blood outlet; a secondary fluid circuit branching from the pump outlet through the variable-volume reservoir to the pump inlet; valve means to control flow of blood from the air eliminator or the variable-volume reservoir to the pump inlet and valve means to control the flow of blood from the pump outlet to the variable-volume reservoir. In another aspect of the invention a cardiac bypass system is provided as stated above, wherein the air eliminator includes a filter. In another aspect of the invention a cardiac bypass system is provided as stated above, further including a pair of electrically conductive plates, wherein the variable-volume reservoir is mounted between the plates; and means for measuring the volume of blood in the variable-volume reservoir based on the capacitance of the plates and the variable-volume reservoir. In another aspect of the invention a cardiac bypass system is provided as stated above, wherein the variable-volume reservoir is a collapsible bag. In another aspect of the invention a cardiac bypass system is provided as stated above, wherein the maximum volume of the variable-volume reservoir is greater than the volume of the air eliminator.

In one aspect of the invention a cardioplegia system comprises: first and second reciprocating positive-displacement pumps, each of which has a curved rigid chamber wall; a flexible membrane attached to the rigid chamber wall, the flexible membrane and rigid chamber defining a pumping chamber; an inlet for directing flow through the rigid chamber wall into the pumping chamber in a direction that is substantially tangential to the rigid chamber wall; and an outlet for directing flow through the rigid chamber wall out of the pumping chamber in a direction that is substantially tangential to the rigid chamber wall; an inlet blood line for providing oxygenated blood to the first pump's inlet; a cardioplegia fluid source for providing a cardioplegia fluid to the second pump's inlet; a controller, in communication with the first and second pumps, for measuring a flow rate of the blood and a flow rate of the cardioplegia fluid and for controlling the first and second pumps; and an outlet blood line for providing blood to a patient's heart.

In one aspect of the invention a method is provided for heating or cooling a fluid such as blood in connection with systems, devices and methods of cardiopulmonary treatment and procedures, the method comprising: providing at least one reciprocating positive-displacement pump, each pump having: a curved rigid chamber wall; a flexible membrane attached to the rigid chamber wall, so that the flexible membrane and rigid chamber wall define a pumping chamber; an inlet for directing fluid through the rigid chamber wall into the pumping chamber in at least one of (a) a direction that is substantially tangential to the rigid chamber wall and (b) a direction that provides low-shear flow into the pumping chamber; and an outlet for directing fluid through the rigid chamber wall out of the pumping chamber in at least one of (a) a direction that is substantially tangential to the rigid chamber wall and (b) a direction that provides low-shear flow out of the pumping chamber; providing a heat exchanger; and pumping the fluid from a source using the at least one reciprocating positive-displacement pump so as to cause the fluid to pass through the heat exchanger.

In another aspect of the invention a disposable unit for use in a heat exchanger system is provided for systems, devices and methods of cardiopulmonary treatment and procedures, the disposable unit comprising: at least one reciprocating positive-displacement pump, said pump having a curved rigid chamber wall; a flexible membrane attached to the rigid chamber wall, so that the flexible membrane and rigid chamber wall define a pumping chamber; an inlet for directing fluid through the rigid chamber wall into the pumping chamber in at least one of (a) a direction that is substantially tangential to the rigid chamber wall and (b) a direction that provides low-shear flow into the pumping chamber; and an outlet for directing fluid through the rigid chamber wall out of the pumping chamber in at least one of (a) a direction that is substantially tangential to the rigid chamber wall and (b) a direction that provides low-shear flow out of the pumping chamber; and a heat-exchanger conduit, in fluid communication with the at least one pump and adapted to be incorporated into a heat exchanger.

In another aspect of the invention a heat-exchanger system is provided for use with systems, devices and methods of cardiopulmonary treatment and procedures comprising: a heat exchanger for receiving a heat-exchanger conduit residing within a disposable unit; a pneumatic actuation system for operating at least one pump in the disposable unit for pumping fluid through the heat-exchanger conduit; and a controller for controlling the pneumatic actuation system. The heat-exchanger conduit may comprise a flexible bag that defines a flow path therewithin. The flexible bag may be substantially planar.

In another aspect of the invention a method of moving blood between a patient-circulatory access device and a heat exchanger is provided for altering the temperature of the blood in systems, devices and methods of cardiopulmonary treatment and procedures, the method comprising: providing a reciprocating positive-displacement pump; providing a flow line having a first portion between the circulatory access device and the pump and having a second portion between the pump and the heat exchanger; providing for each of the first and second portions of the flow line a valve for permitting flow in only one direction of the flow line; and actuating the pump to cause the flow of blood between the circulatory-access device and the heat exchanger.

In another aspect of the invention a heat exchanger for altering the temperature of extracorporeal blood and for maintaining or altering the internal temperature of a patient is provided in connection with systems, devices and methods of cardiopulmonary treatment and procedures, the heat exchanger comprising a pump according to one of above claims, and further including a heat-exchange flow path having an inlet for thermally unaltered blood an outlet for thermally altered blood; a thermal converter that converts electrical power into heat or cold for absorption by the blood; a first temperature sensor located at the inlet for measuring the temperature of the blood entering the heat exchanger; a second temperature sensor located at the outlet for measuring the temperature of the blood exiting the heat exchanger; a metering system that measures the flow rate of blood passing through the heat exchanger; and a controller in communication with the converter, the first and second temperature sensors, and the metering system, the controller receiving information regarding the amount of power being used by the converter, receiving temperature information from the first and second temperature sensors, receiving flow-rate information from the metering system, analyzing the received information in order to determine whether a fault condition exists, and generating a signal if a fault condition is detected.

In accordance with another aspect of the invention a heat exchanger for altering the temperature of extracorporeal blood is provided for maintaining or altering the internal temperature of a patient during or in connection with systems, devices and methods of cardiopulmonary treatment and procedures, the heat exchanger comprising: an inlet for thermally unaltered blood; an outlet for thermally altered blood; a flow path from the inlet to the outlet; a set of heating or cooling elements overlapping the flow path, including at least first and second heating or cooling elements, the second element being located adjacent the flow path near the outlet, and the first element being located adjacent the flow path at a point upstream of the second element; a first temperature sensor located adjacent the flow path upstream of the first element; a second temperature sensor located adjacent the flow path between the first and second elements; and a controller for receiving temperature information from the first and second temperature sensors and for generating a signal if a temperature difference being measured by the first and second sensors exceeds a limit.

In accordance with another aspect of the invention there is provided a heat exchanger for heating or cooling extracorporeal blood for maintaining or altering the internal temperature of a patient during or in connection with systems, devices and methods of cardiopulmonary treatment and procedures, the heat exchanger comprising: a disposable unit having an inlet for thermally unaltered blood, an outlet for thermally altered blood, and a flow path of the blood from the inlet to the outlet; and a base unit having a heater and cooler for heating or cooling blood in the flow path, the heater and cooler including a first thermally conductive plate for conducting heat to or from a first side of the disposable unit, and a second thermally conductive plate for conducting heat to or from a second side of the disposable unit opposite the first plate, the first and second plates being adapted to squeeze together, upon actuation by a controller, in order to urge blood out of the disposable unit.

In certain embodiments, the reciprocating positive-displacement pump is provided with a pneumatic actuation system that intermittently provides either a positive or a negative pressure to the control chamber. The pneumatic actuation system in some embodiments includes a reservoir containing a gas at either a positive or a negative pressure, and a valving mechanism for controlling the flow of gas between the control chamber and the gas reservoir. The reciprocating positive-displacement pump may include a control-chamber pressure transducer for measuring the pressure of the control chamber, and a controller that receives pressure information from the control-chamber pressure transducer and controls the valving mechanism. In certain embodiments, a reservoir pressure transducer for measuring the pressure of gas in the reservoir is provided, and the controller receives pressure information from the reservoir pressure transducer. The controller in some embodiments compares the pressure information from the control-chamber and reservoir pressure transducers to determine whether either of the pressure transducers is malfunctioning.

In certain embodiments, the pneumatic actuation system alternately provides positive and negative pressure to the control chamber. In one arrangement, the pneumatic actuation system includes a positive-pressure gas reservoir, a negative-pressure gas reservoir, and a valving mechanism for controlling the flow of gas between the control chamber and each of the gas reservoirs. In such embodiments, a control-chamber pressure transducer measures the pressure of the control chamber, and a controller receives pressure information from the control-chamber pressure transducer and controls the valving mechanism. In addition, such embodiments may include a positive-pressure reservoir pressure transducer for measuring the pressure of the positive-pressure gas reservoir, and a negative-pressure reservoir pressure transducer for measuring the pressure of the negative-pressure gas reservoir. The controller receives pressure information from these transducers and analyzes the pressure information to determine whether any of the pressure transducers are malfunctioning. The controller also controls the pressure of the reservoir or reservoirs to ensure it does not exceed a pre-set limit.

In certain embodiments, the controller causes dithering of the valving mechanism and determines when a stroke ends from pressure information from the control-chamber pressure transducer. In further embodiments, the controller controls the valving mechanism to cause the flexible membrane to reach either the rigid chamber wall or the rigid limit structure at each of a stroke's beginning and end. In this embodiment, the controller can determine the amount of flow through the pump based on a number of strokes. In addition, the controller may integrate pressure information from the control-chamber pressure transducer over time during a stroke (or otherwise determines the work done during a stroke) as a way of detecting an aberrant flow condition.

In accordance with another aspect of the invention there is provided a pump having means for drawing fluid into or urging fluid out of a pumping chamber; means for determining a flow rate through the pumping chamber; and a controller for determining an amount of work required to achieve the flow rate and for generating an alarm if the amount of work indicates an aberrant flow condition.

In accordance with another aspect of the invention there is provided a reciprocating positive-displacement pump comprising a reciprocating member having a first face towards a pumping chamber and a second face towards a control chamber; an inlet for directing flow into the pumping chamber; an outlet for directing flow out of the pumping chamber; a control-chamber pressure transducer for measuring the pressure of the control chamber; an actuation system that intermittently provides positive or negative pressure to the control chamber, and a controller. The actuation system includes a reservoir containing control fluid under positive or negative pressure, a valving mechanism for controlling the flow of control fluid between the control chamber and the reservoir, and a reservoir pressure transducer for measuring the pressure of the control fluid in the reservoir. The controller that controls the actuation system to move the reciprocating member, receives pressure information from the control-chamber and reservoir pressure transducers, and compares the pressure information to determine whether either of the pressure transducers is malfunctioning.

In certain embodiments, the pumps are paired or ganged together so that an inlet line is in fluid communication with each pump's inlet and wherein an outlet line is in fluid communication with each pump's outlet. In the case of two pumps, the pumps may be operated out of phase such that when one pump's pumping chamber is substantially full the other pump's pumping chamber is substantially empty. Alternatively, the pumps may be operated at any selectable phase relationship, from 0 degrees (pumping and filling simultaneously) to 180 degrees (one pump filling as the other empties). In the case of multiple pumps, the pumps may also be operated at any selectable phase relationship with respect to each other.

In various alternative embodiments, the first and second pod pumps may be rigidly attached to each other, and the receptacle means may include means for receiving both the first and second pod pumps in a single step. The base unit may further include first and second pressure transducers for measuring respectively pressures of the control fluid provided to first pod pump's control port and of the control fluid provided to the second pod pump's control port and a controller for receiving pressure information from the first and second pressure transducers and for controlling the actuation system. The controller may be adapted to cause the actuation system to actuate the pod pumps out of phase with each other, such that when one pod pump's pumping chamber is substantially full the other pod pump's pumping chamber is substantially empty. The controller can also be adapted to cause the actuation system to actuate the pod pumps in any phase relationship ranging between 0 degrees (completely in-phase) to 180 degrees (completely out-of-phase).

In various alternative embodiments, a pumping system may include a pump cassette containing a plurality of pumps, each pump including a pumping chamber and a control chamber, each pump being actuatable by a control fluid in the control chamber; a control cassette having a plurality of fluid-interface ports for providing fluid communication with a control fluid from a base unit; and a plurality of tubes extending between the pump cassette and the control cassette, each tube providing fluid communication between a fluid-interface port and at least one control chamber, such that the base unit can actuate a pump by pressurizing control fluid in a fluid interface port. The pump cassette may include a valve actuatable by a control fluid, wherein the plurality of tubes includes a tube providing fluid communication between a fluid-interface port and the valve, such that the base unit can actuate the valve by pressurizing control fluid in a fluid interface port.

In accordance with another aspect of the invention there is provided a pumping system comprising an actuation system for operating a pod pump, the actuation system including a standardized control interface for interconnection with pod pumps having different stroke lengths; a control-chamber pressure transducer for measuring pressure in a control chamber of the pod pump; and a controller that controls the actuation system to operate the pod pump based on pressure information received from the control-chamber pressure transducer, whereby operation of pod pumps is independent of stroke length.

In accordance with one aspect of the invention there is provided a sensing probe comprising a probe housing; a thermal sensor in said probe housing having a sensing end and a connector end; a probe tip thermally coupled to said sensing end of the thermal sensor and attached to said probe housing, the probe tip adapted for thermal coupling with an inner surface of a thermal well; and at least two leads connected to said connector end of said thermal sensor, whereby thermal energy is transferred from said thermal well to said thermal sensor and whereby temperature information is conveyed through said leads. In various alternative embodiments, the sensing probe may further include a third lead attached to one of the probe housing, the thermal sensor, and the probe tip for permitting conductivity sensing. Alternatively, the sensing probe may further include a conductivity sensor attached to one of the probe housing, the thermal sensor, and the probe tip for permitting conductivity sensing; and a third lead attached to the conductivity sensor for transmitting conductivity information.

These aspects of the invention are not meant to be exclusive or comprehensive and other features, aspects, and advantages of the present invention are possible and will be readily apparent to those of ordinary skill in the art when read in conjunction with the following description, the appended claims, and the accompanying drawings.

BRIEF DESCRIPTION OF THE DRAWINGS

The foregoing features of the invention will be more readily understood by reference to the following detailed description, taken with reference to the accompanying drawings, wherein.

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Figure 1:
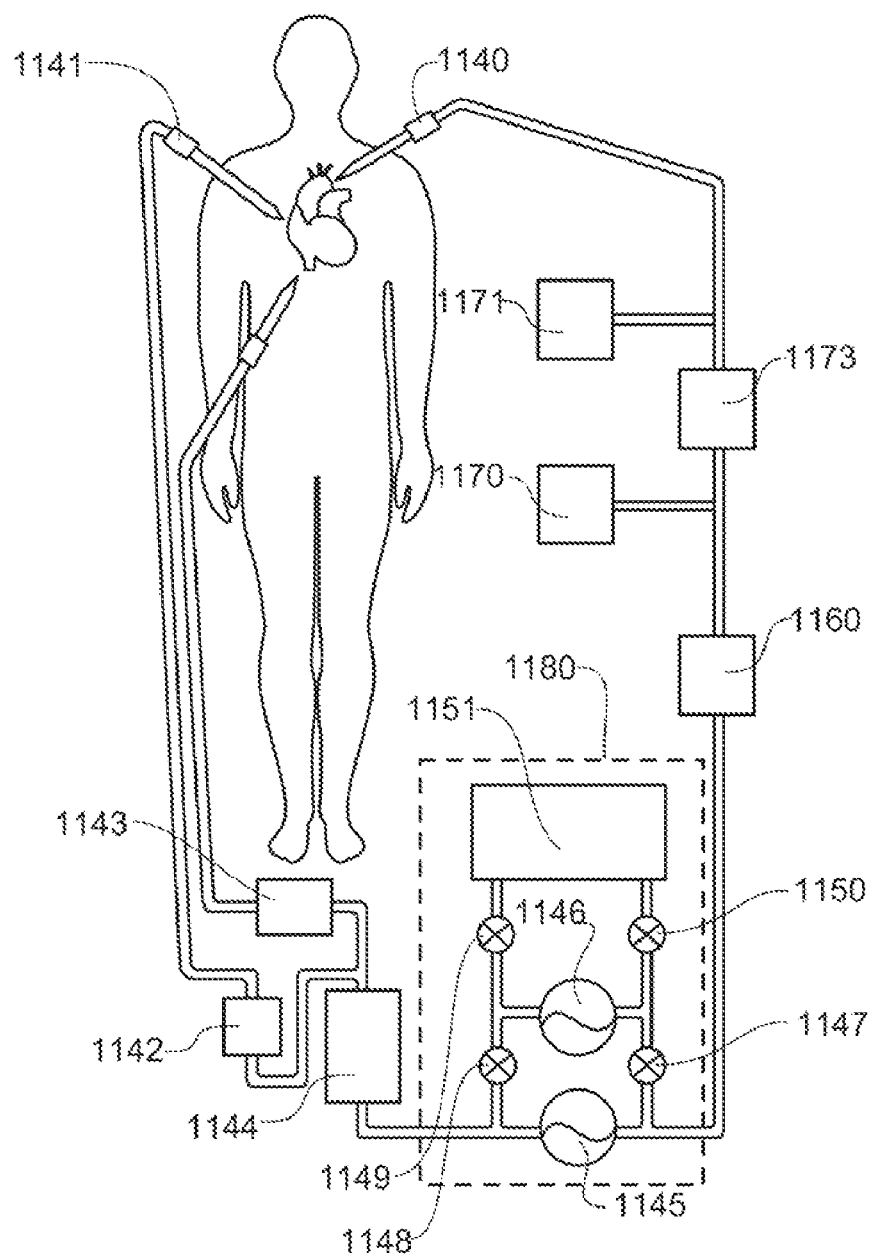
FIG. 1 is a schematic representation of a cardiopulmonary treatment system according to one embodiment of the invention.

Definitions. As used in this description and the accompanying claims, the following terms shall have the meanings indicated, unless the context otherwise requires:

"Spheroid" means any three-dimensional shape that generally corresponds to an oval rotated about one of its principal axes, major or minor, and includes three-dimensional egg shapes, oblate and prolate spheroids, spheres, and substantially equivalent shapes.

"Hemispheroid" means any three-dimensional shape that generally corresponds to approximately half a spheroid.

"Spherical" means generally spherical.

"Hemispherical" means generally hemispherical.

"Dithering" a valve means rapidly opening and closing the valve.

"Pneumatic" means using air or other gas to move a flexible membrane or other member.

"Substantially tangential" means at an angle less than 75° to a tangent, or in the case of a flat wall, at an angle of less than 75° to the wall.

"Fluid" shall mean a substance, a liquid or gas for example, that is capable of being pumped through a flow line. Blood is a specific example of a fluid.

"Impedance" shall mean the opposition to the flow of fluid.

A "patient" includes a person or animal from whom, or to whom, fluid is pumped, whether as part of a medical treatment or otherwise.

"Subject media" is any material, including any fluid, solid, liquid or gas that is in contact with either a sensing probe or a thermal well.

The term "pump" or "pumping" as used herein refers to the forcing, controlling or metering of the flow of a fluid through a line either by metering a flow of a fluid that is moving under the influence of a pre-existing pressure drop within the line, or by forcing a fluid through a line by increasing the pressure of the fluid within the line. Many embodiments described herein involve systems where the pressure of the fluid being pumped is increased (e.g., increased cyclically) by using a pump chamber and a source of mechanical force acting on an external surface of the pump chamber.

A "chamber" as used herein, for example in the context of a pump chamber, refers to a volumetric container having a constant or variable internal volume, which is able to contain a fluid. A "fluid" as used herein can refer to a material that is either a liquid or gas.

The methods and systems provided in some embodiments of the present invention, in preferred embodiments, include pumping systems with pump chambers having at least one moveable surface. A "moveable surface" as used herein in this context refers to a surface of a chamber that can be displaced by a force applied thereto, so as to change an internal volume of the chamber. A non-limiting list of pumping systems that employ pump chambers including at least one moveable surface include: diaphragm pumps, piston pumps, peristaltic pumps, flexible bulb pumps, collapsible bag pumps, and a wide variety of other pump configurations, as apparent to those of ordinary skill in the art.

Embodiments of the present invention relate generally to certain types of reciprocating positive-displacement pumps (which may be referred to hereinafter as "pods," "pod pumps," or "membrane-based pumps") used to pump liquids, such as a biological liquid (e.g., blood or peritoneal fluid), a therapeutic liquid (e.g., a medication solution), or a surfactant fluid. In general, the pod pumps operate through the application of positive or negative fluid pressure (hydraulic or pneumatic) on a membrane that forms a wall of a pumping chamber. The liquid being pumped enters through an inlet of the pumping chamber, and exits through an outlet of the pumping chamber. A chamber on the other side of the membrane (the control chamber) receives positively or negatively pressurized fluid (preferably a gas) via a hydraulic or pneumatic control port. Certain embodiments have pressure sensors to measure the pressure in the control chamber of the pump, allowing a control system to monitor and control liquid flow rates through the pump. Certain embodiments are configured specifically to impart low shear forces and low turbulence on the liquid as the liquid is pumped from an inlet to an outlet. Such embodiments may be particularly useful in pumping liquids that may be damaged by such shear forces (e.g., blood, and particularly heated blood, which is prone to hemolysis) or turbulence (e.g., surfactants or other fluids that may foam or otherwise be damaged or become unstable in the presence of turbulence).

Preferred embodiments of the invention involve pumping systems including a pump chamber which comprises an isolatable chamber. An "isolatable chamber" as used herein refers to a volumetric chamber or container for holding a fluid, which can isolate the fluid from fluid communication with fluids outside of the isolatable chamber (e.g., by sealing or closing inlets and outlets to the chamber). The term "fluid communication" as used herein refers to two chambers, or other components or regions containing a fluid, where the chambers, components, or regions are connected together (e.g., by a line, pipe, or tubing) so that a fluid can flow between the two chambers, components, or regions. Therefore, two chambers which are in "fluid communication" can, for example, be connected together by a line between the two chambers, such that a fluid can flow freely between the two chambers. For embodiments involving an isolatable chamber, for example an isolatable pump chamber, lines connecting the isolatable chamber to other chambers or regions of the pumping system may include at least one valve (or other device) therein which may be closed, or occluded, in order to block fluid communication between the chambers.

The term "valve" as used herein refers to a component of a pumping system disposed in, or adjacent to, a fluid line or fluid flow path within the system, which component is able to block the flow of a fluid therethrough. Valves, which may be utilized in various aspects of the invention, include, but are not limited to, duckbill valves, reed valves, ball valves, gate valves, needle valves, globe valves, and actively controlled valves such as solenoid-activated valves or pneumatically activate membrane-type valves. Valves may also include mechanisms or components for applying an external force to a fluid flow path so as to block or occlude the flow path (for example, by pinching or collapsing a length of flexible tubing). "Able to be placed in fluid communication" as used herein refers to components, regions, or chambers within a pumping system, which components, regions, or chambers are either connected in unrestricted fluid communication or have at least one valve therebetween that can be selectively opened to place the components, regions, or chambers in fluid communication. As used herein, components, regions, or chambers connected together by a fluid flow path that includes no valves or obstructions therein are said to be in "unrestricted fluid communication." Components that are in "fluid communication" generally can be either in unrestricted fluid communication or able to be placed in fluid communication.

Reciprocating positive-displacement pumps and related control systems of the types described herein may be used in a wide variety of fluid pumping applications, and are particularly well-suited for (although not limited to) use in applications that involve cardiopulmonary treatments and procedures, particularly cardiac bypass procedures and other assisted blood circulation treatments (e.g., ventricular assist), cardioplegia (as part of cardiac bypass or otherwise), lung bypass or artificial lung, and other applications involving extracorporeal blood oxygenation. The need to pump liquids to and from the body of a patient arises in a wide variety of other medical treatments and procedures, including, for example, hemodialysis for the treatment of kidney failure, plasmapheresis for separating blood cells from plasma, general infusion of intravenous fluids and/or medications, and other applications apparent to those of ordinary skill in the art. The methods and systems of the current invention can be adapted and used for any of the above-mentioned liquid pumping applications, or any other fluid pumping application, including various industrial applications.

The systems, apparatus, and methods for cardiopulmonary treatments and procedures as described herein may be of a variety of embodiments. In various embodiments, the systems, apparatus, and methods may allow for reduced blood prime volume and reduced blood contact surface area, may minimize blood/air interface, reduce the possibilities for generation of micro-emboli, reduce disposable costs (and thus overall treatment costs), simplify (and, in some embodiments, standardize) systems set-up, operation and cost (again reducing overall treatment time and cost), and potentially increase patient safety and outcomes.

In the following sections, exemplary embodiments of the various subsystems and features of the invention are described. While certain of these embodiments are described in the context of an extracorporeal blood heat exchanger affecting or controlling a patient's core body temperature, for example, these embodiments can also be used in various aspects of the CPB systems, devices and methods. Various other aspects of the present invention are described below with reference to other exemplary embodiments. It should be noted that headings are included for convenience and do not limit the present invention in any way.

Cardiopulmonary Bypass ("CPB") System

FIG. 1 is a schematic representation of the flow path for one embodiment of the invention. Connector 1141 can be one of several standard connectors used for CPB circuits. Venous blood is drawn from the patient via connector 1141 into the CPB circuit. In this embodiment, blood passes through air eliminator 1142. In some embodiments, a venous reservoir 1144 may be used. A cardiotomy circuit for collecting, processing and recirculating shed blood may optionally be used, which may comprise a filter, cardiotomy pump and reservoir 1143. Blood then flows through one or more paths of blood storage system 1180. Blood can flow through one or more pumps 1145 and 1146, and then through the remainder of the bypass circuit. Alternatively, for example, when valves 1148 and 1150 are open, blood can be pumped by pump 1146 to fluid reservoir 1151. Fluid reservoir 1151 may be a heating/cooling system bag further described herein or simply a venous blood container.

Preferably, reservoir 1151 is a flexible, soft, collapsible bag that remains air-free as fluid enters and leaves it. By closing valves 1148 and 1150, and opening valves 1149 and 1147 pump 1146 can pump blood from reservoir 1151 to the main blood path flowing through pump 1145. If reservoir 1151 is being used in conjunction with a heat exchanger, cooled or heated blood from reservoir 1151 may be added to the blood flowing through pump 1145 in order to control the temperature of the blood in the bypass circuit. If reservoir 1151 is being used as a blood reservoir, blood from reservoir 1151 can be added to the amount of blood flowing through pump 1145 if it there is a need to increase the blood flow rate through the bypass circuit, if the patient's blood pressure drops, or if there is a need to increase the patient's hematocrit, for example. Pump 1146 can operate independently of pump 1145, allowing either both pumps to contribute to blood flow in the main circuit, or allowing pump 1146 to circulate blood in reservoir 1151 to keep the blood in reservoir from stagnating. Pump 1146 can also add and remove blood or fluid to and from reservoir 1151 without disturbing blood flow in the main circuit. In addition, pump 1146 can be controlled by actively managing valves 1147-1150 to perform double duty; alternating stroke volume deliveries between reservoir 1151 and the main blood flow path.

There is an increased risk of turbulent flow and air entrainment into the extracorporeal blood flow path if pumps 1145 or 1146 attempt to maintain a flow rate greater than the patient's venous return can provide (or, for example, if a partial obstruction occurs in the tubing of the circuit or elsewhere). A control system (not shown) can monitor flow in the main blood circuit (e.g., using a fluid level indicator or an air sensor in venous reservoir 1144), and automatically control valves 1147-1150 to increase the flow of blood (or other physiological solution, for example) from reservoir 1151 into the main blood flow circuit (which in this illustration is flowing through pump 1145). In a preferred embodiment, the control system can also detect when the low flow condition is resolved, and control valves 1147-1150 to re-establish a predetermined liquid reserve volume in reservoir 1151. The control system can monitor the amount of blood or other fluid present in reservoir 1151, using, for example, a capacitance-based measurement system, in which the electrical capacitance between two plates situated on opposite sides of a collapsible reservoir 1151 can be monitored. Of course, other measurement systems can be used, including, for example, systems based on optical sensors, gravimetric sensors or ultrasonic sensors.

Blood may then optionally flow through element 1160, which in an embodiment may be an oxygenator. In various other embodiments, blood may be diverted and/or returned to the blood circuit at elements 1170 and/or 1171. Element 1173 may be an arterial filter or a leukocyte reduction filter. In an embodiment, element 1173 may be a combined arterial and leukocyte reduction filter, in which a valve system may be utilized to select whether the blood flows through the arterial filter (for example, during the later stages of CPB) or through the leukocyte reduction filter (which may be beneficial during certain phases of the CPB procedure). Once the blood has passed through the various processing elements of the CPB circuit, it is then returned to the patient's arterial circulation via connector 1140.

Figure 40:
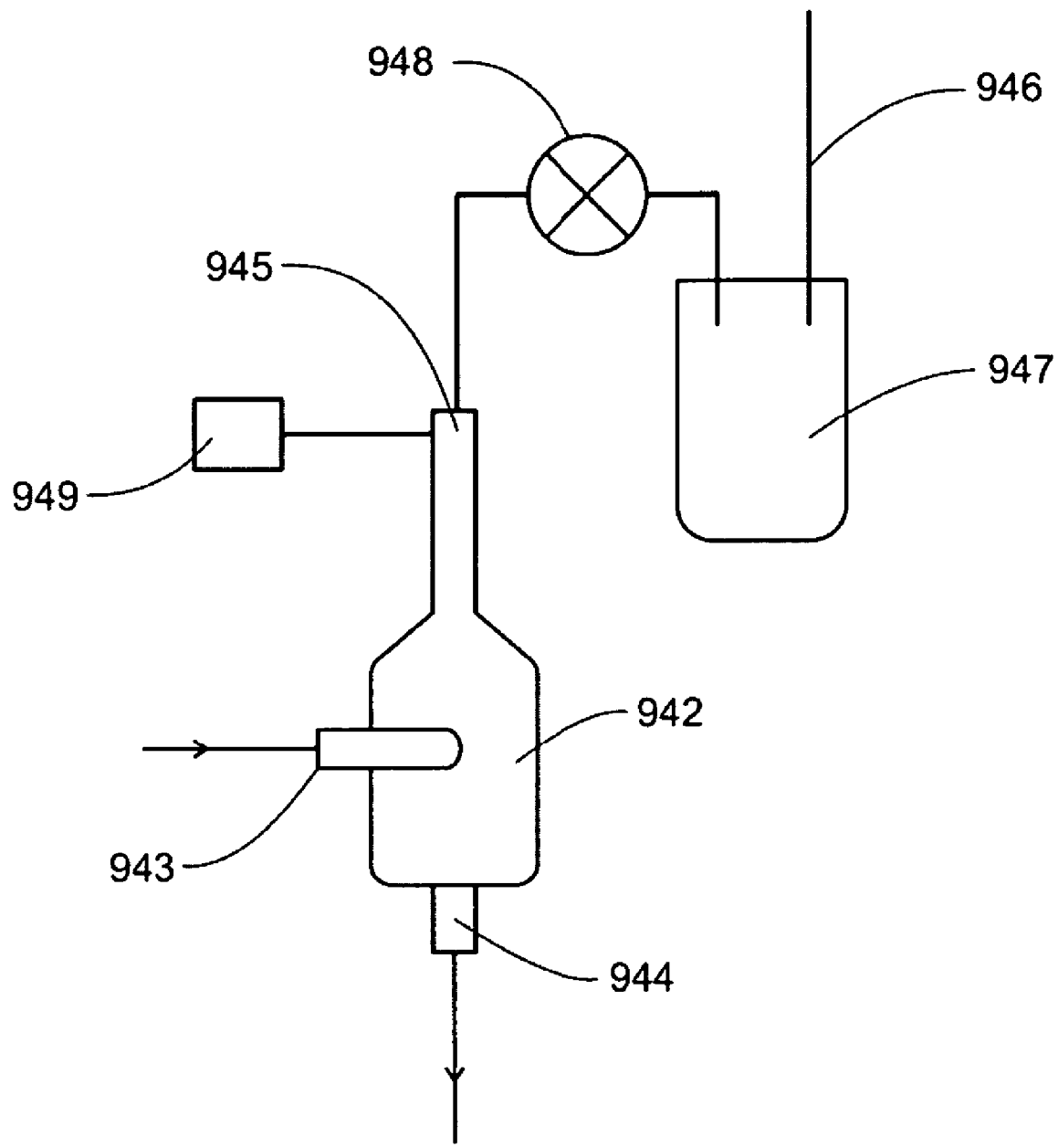
FIG. 40 is a schematic view of an air eliminator with pressure sensor in accordance with an exemplary embodiment of the invention.

In another embodiment, venous reservoir 1144 can be eliminated from the CPB circuit by using reservoir 1151 and a control system to continuously monitor the flow conditions in the flow path, and adjusting flow into or out of reservoir 1151 accordingly. Minimizing the amount of venous blood stored in the CPB circuit is important in any attempt to reduce the priming volume. For example, air eliminator 942, shown in FIG. 40, could be placed in the flow path upstream of pump 1145. In a preferred embodiment, the blood inlet 943 is located above the blood outlet 944. A small amount of suction can be applied to air vent 945 to expel any air that migrates out of the blood as it circulates and pools in air eliminator 942. In this illustration, a vacuum 946 is applied to air trap 947, which in turn can be applied to air vent 945 upon actuating valve 948. The amount of suction is kept well below any amount that could pull liquid up the container and out of the air vent. A pressure sensor 949 can be placed at or near air vent 945, providing a controller (not shown) with information about the air pressure in air eliminator 942. A rapid reduction in venous blood entering inlet 943 will cause the fluid level in the air eliminator to decrease because of the pull provided by pump 1145 (FIG. 1). This will result in a change in the monitored air pressure in air eliminator 942, which can be detected by pressure sensor 949. The controller can respond by immediately triggering an infusion of blood or fluid from reservoir 1151 (FIG. 1) into the main blood flow path by controlling valves 1147-1150. Fluctuations in the forces being applied by pump 1145 to the blood in the circuit can therefore be dampened, and the risk of air entrainment into the blood flow circuit minimized, all while maintaining a relatively small reservoir of venous blood in the system.

In an alternate embodiment, valves 1149 and 1150 in FIG. 1 can be tubing occluders, able to mechanically constrict flexible tubing leading into and out of reservoir 1151. The occluders can be actuated by a number of means readily apparent to one of ordinary skill (including, for example, electrical, magnetic, hydraulic or pneumatic actuators).

Figure 2A:
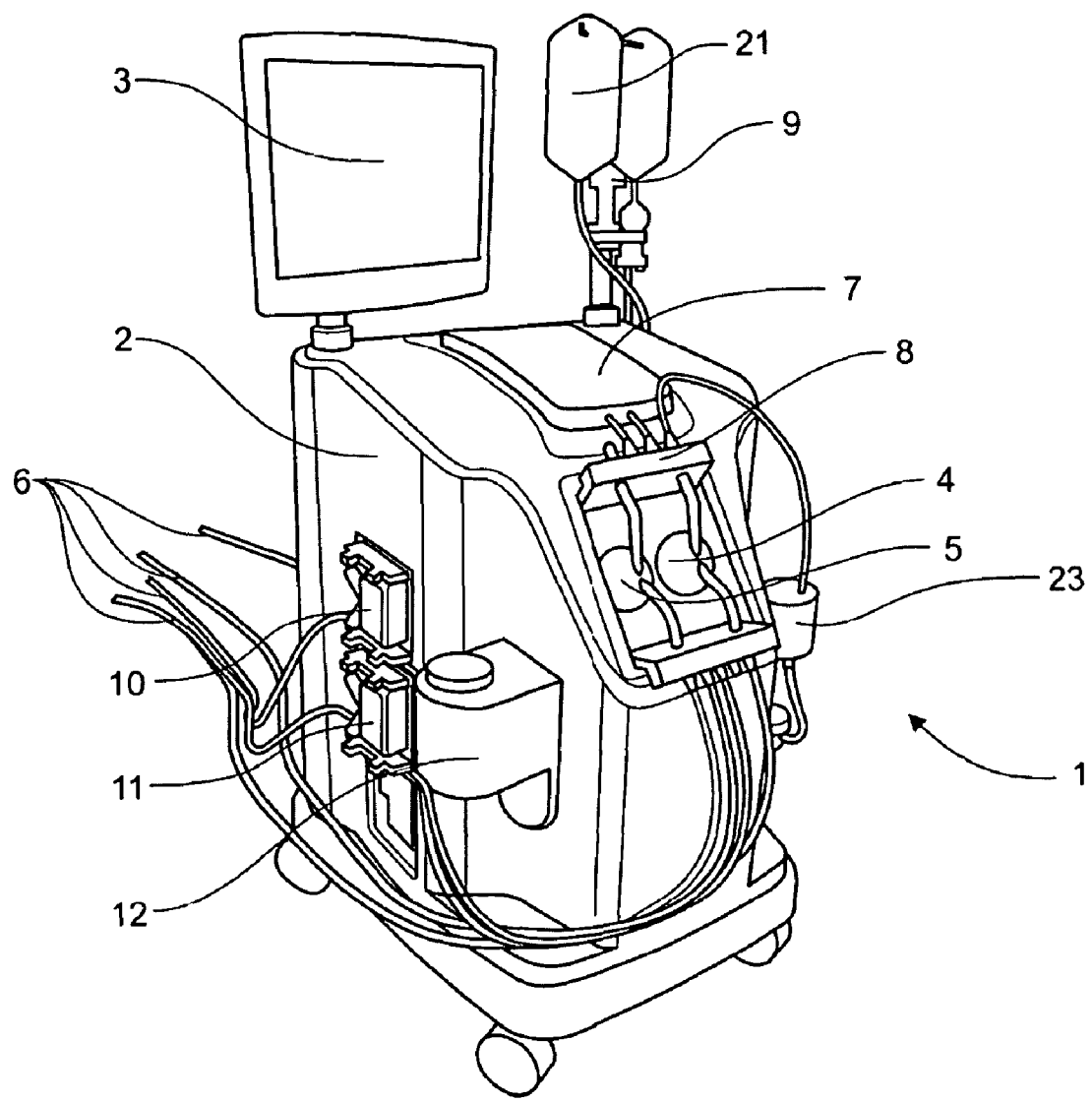
FIG. 2A is a view of a cardiac treatment device having a base unit with a disposable unit according to one embodiment of the invention.
Figure 2B:
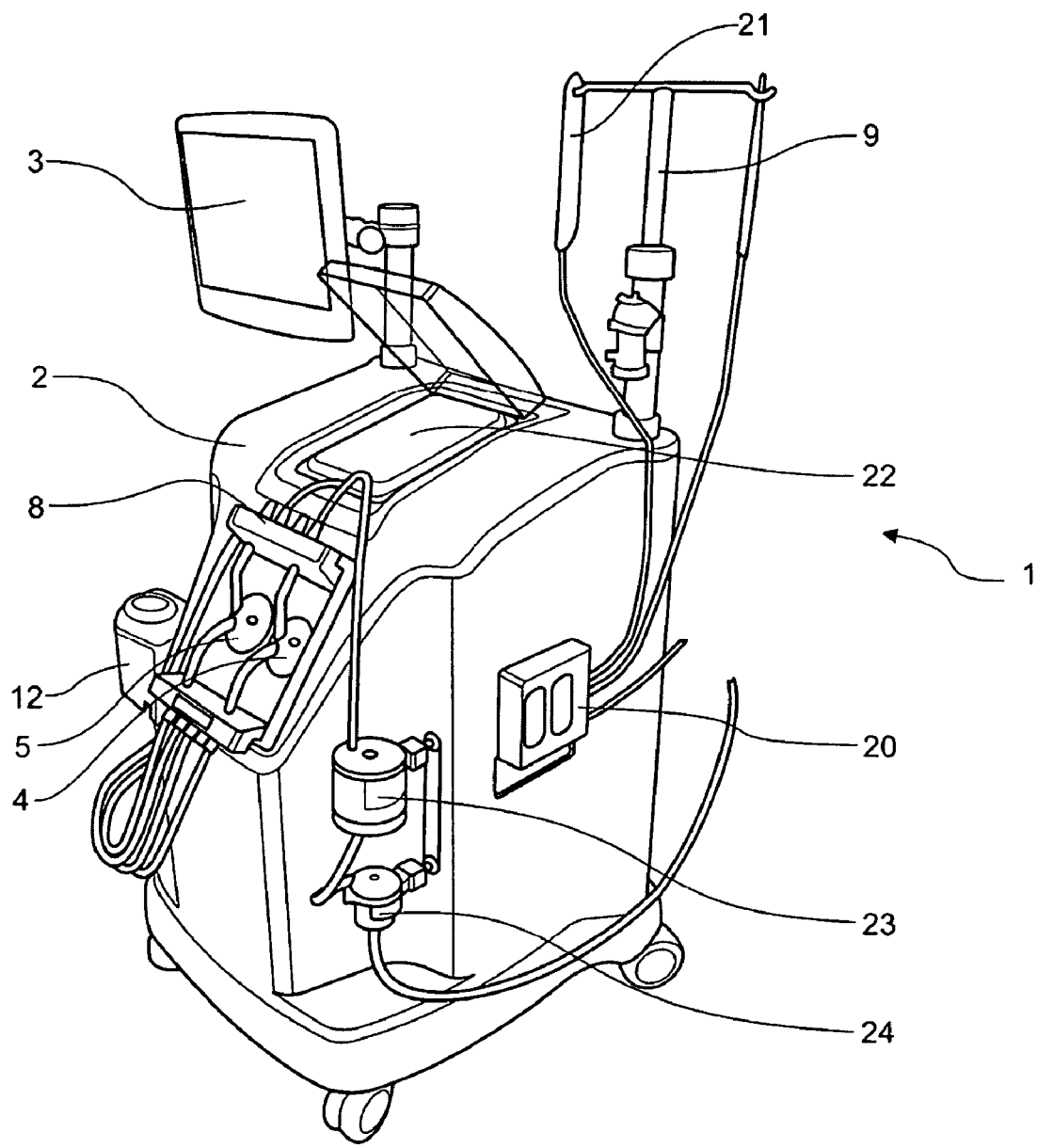
FIG. 2B is another view of a cardiac treatment device having a base unit with a disposable unit according to one embodiment of the invention.

FIGS. 2A and 2B show one embodiment of a cardiac bypass system that can accommodate the components and flow paths depicted in FIG. 1. In this embodiment, separate modules are installed in various locations on a single base unit. Preferably, the CPB system 1 includes a base unit 2 and one or more disposable components (such as, for example, elements 4 and 5, 10-12 and 20-24). As described further below, the disposable components are installed onto the base unit 2. As blood from a patient circulates through the various components of the CPB system, the blood remains within the disposable components and generally does not come into contact with components of the base unit 2. The disposable components are considered to be "disposable" in that they are generally discarded after a patient treatment, whereas the base unit 2 can be re-used repeatedly by simply installing new disposable components. The base unit 2 may include mechanisms to prevent re-use of a disposable component (e.g., using a bar code, RFID tag, or other unique identifier associated with the disposable component).

The disposable components can include, among other things: pumps 4 and 5 (which can form part of a pump module) for circulating the blood from and to the patient; disposable tubings 6 for connection to the patient; and a heat-exchanger bag 22 (as shown in greater detail in FIG. 14) for providing temperature control of the patient's blood (and, by extension, the patient). In other embodiments, component 22 can be a blood collector bag (used, for example, as a venous reservoir to provide a supplemental blood source on demand for the main blood flow circuit when needed). Other disposable components can include an oxygenator 23, filters and/or air eliminators 24; and venous reservoir 12, which optionally may be used in some embodiments. The base unit 2 includes, among other things: a heat exchanger system 7; a pneumatic actuation system for interfacing with pumps 4 and 5; a manifold 8 for connecting the pumps 4 and 5 to the base unit; various temperature and/or conductivity sensors (described below); one or more hangers 9 for hanging bags of various biological and therapeutic fluids that may be used in connection with the cardiac bypass procedure, such as cardioplegia; modules 10 and 11 that may be used to connect a cardiotomy pump/filter/reservoir, and venous filters and/or air eliminators for use in connection with the cardiac bypass procedure.

Pumps 4 and 5 may include any number or any type of pump. Preferably, pumps 4 and 5 are pod pumps of the types described below.

The heat exchanger system 7 may be of the type described below to heat or cool the blood to raise, lower, or maintain the temperature of the patient during the cardiac bypass procedure. The heat exchanger system may include one or more flexible or collapsible blood bags 22 of the types described below in connection with the heat exchange systems. In various embodiments, one or more flexible blood bags may be used to store blood as a venous reservoir. The volume of blood in blood bag 22 can be determined by various methods, one of which, for example is via capacitance measurement. The graphical user interface can display the amount of blood in the bag. In an embodiment, the user may select the amount of blood to be maintained in the bag, may program or manually instruct the CPB unit to continuously recirculate blood through the bag, and/or may program or manually trigger the CPB unit to infuse additional blood from the bag into the blood flow circuit if certain conditions are met. During the cardiac bypass procedure, the patient's hematocrit may be measured by standard manual methods, or by use of in-line sensor systems utilizing, for example, ultrasound waves or light waves. The hematocrit values can be used by the CPB control system to maintain closed-loop control of the patient's hematocrit by regulating the amount of blood infused into the blood circuit from a venous reservoir such as blood bag 22.

Manifold 8 may be of the type generally described below that operates in conjunction with two or more pod pumps, and one or more temperature and/or conductivity sensing probes. Temperature sensors contained in manifold 8, in other locations in the blood flow path, or in conjunction with temperature probes on the patient can be used to maintain closed-loop patient temperature control.

Modules 10 or 11 may include a cassette containing a pod pump of the type generally described below and a filter and air eliminator. Such module may be used to create suction for a cardiotomy circuit that may be used during CPB. In certain embodiments a vent may also be included in the module.

Venous reservoir 12 optionally may be used with various embodiments of the present invention. Venous reservoir 12 can be used as a blood buffer drawn from the patient for use during CPB in cases of hypotension or anemia. Venous reservoir 12 may optionally contain a filter, and may be equipped with ultrasonic sensors to indicate the level or volume of blood in the reservoir. In typical operation, the blood level can be maintained between the low blood level mark and the high blood level mark. Alternatively, blood from the patient may be stored in one or more blood storage devices, including collapsible blood bags. In one embodiment the collapsible blood bags can be similar to the flexible bag 22 described herein for use with the heat exchanger system. Blood for the blood storage bags and/or venous reservoir can be obtained by gravity from the patient's venous system by placing the bag in a position lower than the patient. Negative pressure can also be applied through the blood pumps 4 and/or 5 to draw blood from the patient's venous system, and cardiotomy blood can also be used to fill the venous reservoir after appropriate filtering. Filtering of cardiotomy blood is generally necessary because of the presence of air, debris of traumatized red cells, and other debris such as fat, bone chips, and the like.

FIG. 2B shows another view of the cardiac bypass system 1 shown in FIG. 2A. Modules 23 or 24 can have various functions according to various embodiments of the invention, including an oxygenator or a combined oxygenator/heat exchanger (in which case bag 22 can be used as a collapsible venous reservoir). Modules 23 or 24 may also be used as an arterial filter, air trap/eliminator and/or leukocyte reduction filter. In an embodiment, a combined arterial and leukocyte reduction filter may be used. In the combined arterial and leukocyte reduction filter a valve system or switch can be used to select whether the blood flows through the arterial filter or the leukocyte reduction filter. In some cases, it may be preferable to direct the blood through the arterial filter as the duration of the CPB procedure increases. In other cases, it may be desirable to have the blood pass through a leukocyte reduction filter for certain stages of the procedure in order to reduce leukocyte-mediated inflammatory injury to pulmonary and cardiac vascular beds.

Referring again to an exemplary embodiment shown in FIGS. 2A and 2B, base unit 2 of CPB system 1 includes a graphical user interface 3 to display information to the health care professionals involved in delivering the treatment. Graphical user interface 3 may be a touch-screen user interface to allow health care professionals to obtain real-time data regarding the patient's condition, and may allow for on-demand functions, such as, for example, real-time concentration and rate adjustment during cardioplegia, blood pump flow rate adjustments, adjustments to flow into and out of a venous reservoir, adjustments to blood temperature and oxygenation, as well as selection of various blood filtering operations.

Base unit 2 also includes a variety of individual computer control systems for controlling and operating the various components and pump modules of CPB system 1. Base unit 2 can include an overall system controller and user interface 3 that sends commands to and receives inputs from a master pump system control module, which provides pneumatic or hydraulic control to the various pump modules and other pneumatic modules attached to base unit 2. The controller/interface can be implemented using a microprocessor and associated software. The master control module can also include a microprocessor and appropriate software, and can send both electronic and pneumatic commands to and receive input from individual pump drive system modules, door or lid control modules, and modules to control tubing occluder devices situated near the individual pump modules. Base unit 2 also includes a power supply for providing electrical power to the various modules, and a pump for providing pressurized control and measurement fluid to the pneumatic or hydraulic supply tanks of the system. In an embodiment an air pump is pneumatically connected to a master pump control module which, in turn, is pneumatically connected to the individual pump modules and other pneumatically operated devices on base unit 2.

Each pump module preferably includes valves, pressure transducers, and a reference chamber dedicated to its respective pump chamber. Each pump module also preferably contains additional pneumatic valves to selectively provide pressurized measurement gas to actuate the various valving chambers associated with its respective pump chamber. In addition, there can be a dedicated microprocessor associated with each pump module for controlling the operation of the individual pump chambers and performing the various calculations associated with the operation of the pump chambers.

A master pump control module is preferably configured to handle all of the input/output communications with a user interface/system control module. Commands relayed from a user interface/system control module to a master pump control module can be processed by the microprocessor of the master pump control module, and in turn can be translated by the microprocessor into appropriate commands for individual microprocessors dedicated to individual pump modules that attach to base unit 2, and to other pneumatically controlled devices on base unit 2.

In an embodiment, an overall system control module includes the majority of application-specific programming and provides for communication between the reusable system and a user of the system. Upon receipt by a master pump control module of a command from the system control module, the master pump control module is preferably configured to: (1) determine which valves of the system are to be opened or closed; (2) determine which pump module or other pneumatic device contains the valves; and (3) issue an appropriate command to open or close such valves. All valve mapping (i.e., physical location of the various valves in the system) unique to the operation of the particular pumping module being utilized, is preferably resident in the microprocessor of master pump control module.

In other embodiments, a system control module or subsidiary can also include other types of closed loop control systems using various sensors. For example, the system could control anticoagulant delivery to the patient using a user-defined protocol entered via the user interface, or using a standardized protocol programmed into the computer control system. The system control module could also control the delivery of additional fluid to the patient using a fluid reservoir connected to a inlet port of the arterial pump module or the cardioplegia pump module, or via a separate fluid infusion pump module. The control system can include a hematocrit sensor and/or blood pressure monitor to detect whether the patient would benefit from fluid infusion. The system control module could also include a hemolysis sensor to monitor for excessive amounts of hemolysis, and to alert the individual overseeing the operation of the CPB system. Some of this sensing may involve conductivity sensing using the thermal wells/sensors, or other mechanisms. In other embodiments, each of these closed-loop control functions can be controlled by separate subsidiary control modules communicating with the system control module.

Cassette-Based Pump Modules for CPB

Referring again to FIG. 2B, in an embodiment, cardioplegia can be provided through pump module 20. In cardioplegia, certain solutions are added to a branch of the CPB blood flow path directed to the heart to keep the heart from beating during delicate surgical procedures. The cardioplegia solution can contain, for example, high concentrations of potassium ("$K^+$"). Pump module 20 may be a flexible membrane pump cassette of the type generally described below. In some embodiments, pump module 20 includes one or more blood pump chambers, one or more valves, and one or more potassium pump chambers. In some embodiments pump module 20 includes one or more pre-dilution chambers. The blood pump chambers, valves, and/or potassium pump chambers may be actuated by hydraulic or pneumatic pressure. Hanging bag 21 may contain potassium for use with cardioplegia pump module 20. Conductivity sensors contained in pump module 20, or in other locations in the cardioplegia blood flow path can be used to maintain closed-loop control of the electrolyte (such as $K^+$) concentration of the cardioplegia blood being delivered to the patient's heart.

Figure 3:
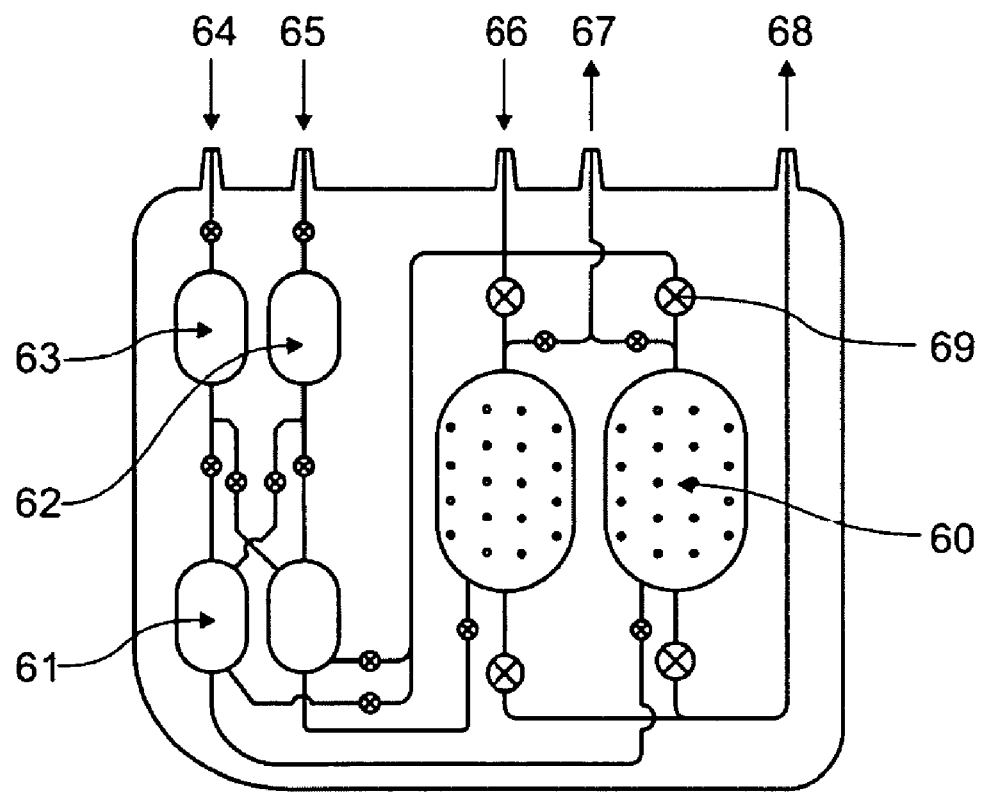
FIG. 3 is a schematic representation of a diaphragm pump module according to one embodiment of the invention.

FIG. 3 is a schematic representation of one exemplary embodiment of pump module 20 shown in FIG. 2B. In this embodiment, the cassette contains two pumping chambers 60 for pumping the blood, and valves 69 to regulate the amount of oxygenated blood 66 drawn for the main CPB blood flow path and returned to the patient's heart. Any air that collects within the pumping chambers 60 can be vented via additional valves to air purge line 67. In this embodiment, potassium pump chamber 63 pumps potassium at a metered rate from potassium inlet 64. Pump 62 optionally may be used in various embodiments to pump other compounds via inlet 65. Pre-dilution chamber 61 can be used to dilute the potassium prior to mixing with the blood in one or more of blood pumps 60. Blood pumped by pumping chambers 60, and solutions pumped by pumps 62 and 63 can be measured with some degree of precision using various volumetric measurement methods, including, for example some of the Fluid Management System ("FMS") methods described below. In an embodiment, the concentration of potassium in the cardioplegia solution can be maintained within a specified range using a closed loop control system during CPB by using electrolyte or conductivity sensors in the fluid path associated with blood cardioplegia outlet 68. The cardioplegia blood flow and the cardioplegia solution flow in pump module 20 can be automatically adjusted using FMS methods, for example, in response to variations in the sensor inputs. In an embodiment, the desired cardioplegia concentration level can be adjusted by the health care professional using the graphical user interface 3 shown in FIGS. 2A and 2B.

In some embodiments, the priming volume of the CPB circuit can be reduced (and the operation of the CPB system simplified) by placing the pumps and valves close to one another in one or more disposable cassettes. For example, pneumatically controlled reciprocating membrane pumps, valves and flow paths can be grouped closely together in a cassette module. The control (or actuation) ports for the various pumps and valves can be arrayed on one side of the module, which can then be plugged into or otherwise connected to a base unit similar to base unit 2. For example, the module can be connected to a mating control bracket mounted on a CPB base unit, with pressurizing control ports arrayed on the control bracket to correspond to the control ports of the module. The pneumatic pressure and vacuum sources, the pneumatic manifolds and feed valves, and associated computer and user control systems can all reside within the CPB unit, such as base unit 2 in FIGS. 2A and 2B.

Figure 4:
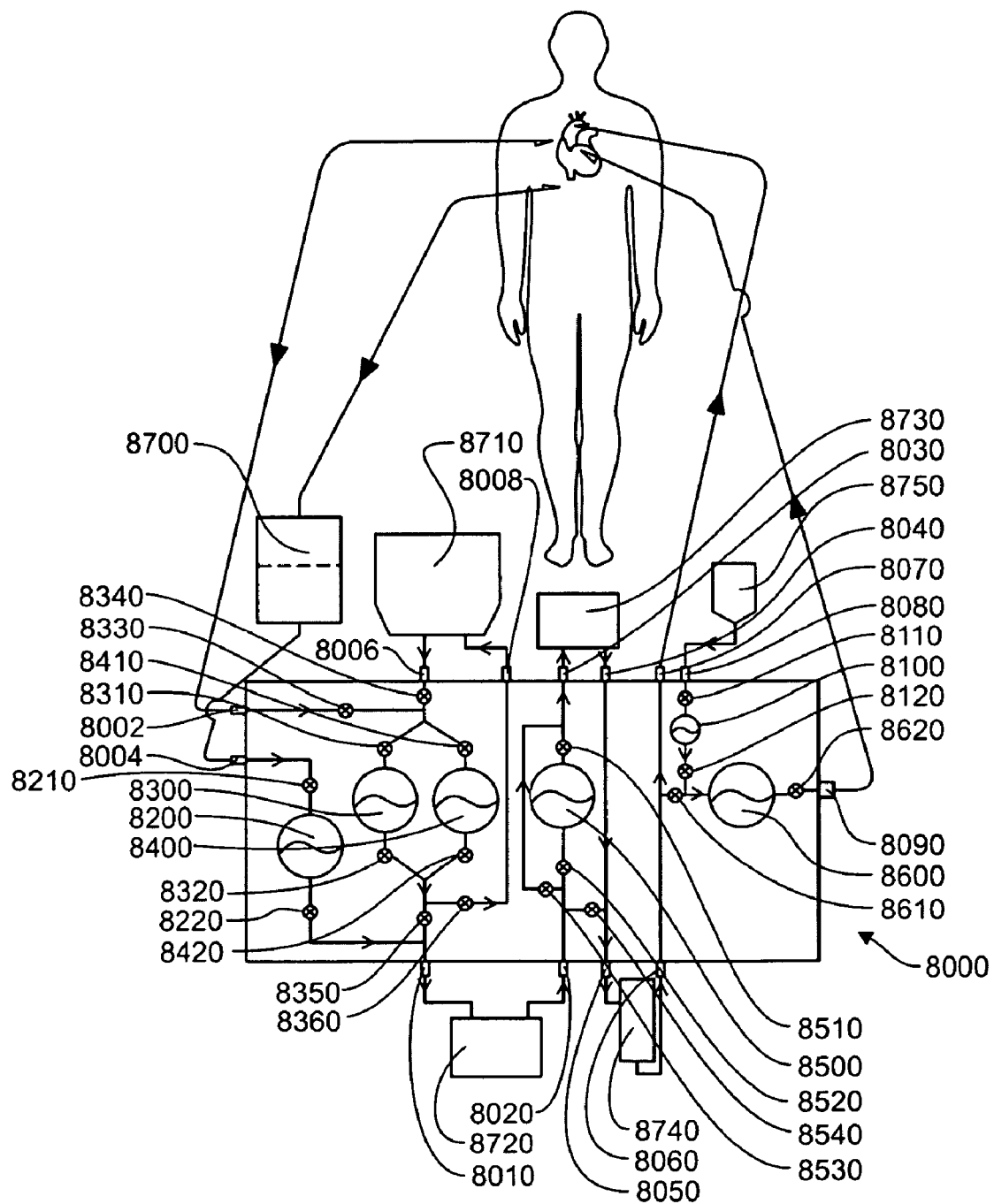
FIG. 4 is a schematic representation of a cardiopulmonary treatment system according to one embodiment of the invention.

FIG. 4 is a schematic representation of an exemplary embodiment of a pneumatically actuated membrane-based pump and valve module for CPB. In this embodiment, the module includes pumps and valves needed to provide: blood flow through the main CPB circuit with appropriate oxygenation and filtering, the infusion of a cardioplegia solution, the recirculation of recaptured and reprocessed shed blood from the operative field, and the control of extracorporeal blood temperature via a heat exchanger. Some of the pumps may be configured to deliver high flow rates with reduced hemolysis In the exemplary embodiment shown in FIG. 4, module 8000 includes main blood pumps 8300 and 8400 for high flow-rate extracorporeal circulation of blood. Although two pumps are shown, it should be understood that more than two pumps could be ganged together in order to achieve a higher flow rate using smaller volume pumps, or with fewer pump strokes per minute, or both. In addition, the two (or more) main blood pumps can be operated independently of each other to allow one of the pumps to be used to fill or empty the venous reservoir 8710 as needed during CPB. In a preferred embodiment, main blood pumps 8300 and 8400 can be specifically configured to minimize hemolysis while still achieving high flow rates (up to approximately 6 L/min., 7 L/min., or even 8 L/min.).

The cardiotomy blood pump 8200 provides a suction force through cardiotomy filter/reservoir 8700 sufficient to remove blood from the chest cavity that has been shed during surgery. Heat exchanger pump 8500 allows for independently metered flow of blood to the heat exchanger unit 8730. Cardioplegia blood pump 8600 provides for independently metered flow of blood from the main CPB circuit to the patient's heart. Cardioplegia solution pump 8100 provides for independent metering of cardioplegia solution 8750 into the blood being diverted to cardioplegia blood pump 8600.

In the embodiment illustrated by FIG. 4, venous blood from the patient is directed via tubing connected to blood port 8002 to main blood pumps 8300 and 8400. In some embodiments, there may be a filter and/or air trap/eliminator (not shown) interposed in the venous blood flow path prior to tubing connection at blood port 8002. Valves 8320, 8330, 8350 and 8420 may be unidirectional flow valves to prevent reverse blood flow in the main blood flow path (or, in the case of valve 8350, to prevent inadvertent blood flow from pump 8200 through valve 8360). Unidirectional flow valves can be actively controlled membrane-based valves that operate via the pneumatic control system in the CPB unit, or alternatively may be passive check valves, examples of which include duckbill or reed valves, ball valves, or diaphragm valves. Valves 8310 and 8410 may also be unidirectional flow valves, or may be active valves additionally used to switch on or off individual flow paths to certain blood pumps (for example, pumps 8300 and 8400), depending on the blood flow requirements of the particular procedure or patient.

In an embodiment, valves 8340 and 8360 can be independently controllable variable flow valves, which can be used to regulate the amount of venous blood to be passed through and/or retained in venous reservoir 8710. In some embodiments, particularly when the flow rates generated by pumps 8300 and 8400 do not exceed the capacity of the venous return to the patient's heart, valve 8360 can be kept closed in order to avoid filling venous reservoir 8710 at all, consequently helping to minimize the volume of blood in the extracorporeal circuit. In an embodiment, venous reservoir 8710 is a collapsible bag that eliminates or minimizes any air-blood interface that would otherwise exist in a rigid container.

In another embodiment, valves 8340 and 8360 can simply be actively controlled on/off valves, with one of the blood pumps 8300 and 8400 being used to divert the desired amount of blood to venous reservoir 8710. This can be accomplished, for example, by having pumps 8300 and 8400 operate out of phase. Pump 8300 can provide a stroke volume to the main blood flow circuit via port 8010 by having valve 8350 open and valve 8360 closed. During this time, pump 8400 can be filling with blood from port 8002. Once pump 8400 is ready to deliver its stroke volume, valve 8350 can be closed and valve 8360 opened, directing blood flow to port 8008. The rate of blood delivery to venous reservoir 8710 can be controlled by controlling the number of strokes per minute pump 8400 is allowed to divert blood to port 8008. Similarly, blood can be withdrawn from venous reservoir 8710 at any desired rate by controlling valves 8330 and 8340, and by selecting one of blood pumps 8300 or 8400 to draw blood from port 8006.

The cardiotomy blood flow path enters module 8000 at port 8004, after the blood has been appropriately filtered and stored in cardiotomy filter/reservoir 8700. The flow rate of filtered cardiotomy blood is controlled by cardiotomy blood pump 8200, which directs the blood to the main blood circuit prior to its exit to the oxygenator 8720 via port 8010.

Oxygenated blood reenters module 8000 at port 8020, where it may be directed partially or fully to heat exchanger 8730. If the entire blood flow is to be directed to the heat exchanger 8730, it is possible to bypass heat exchanger pump 8500 by opening valve 8530 and closing valves 8620 and 8540. If valves 8530 and 8540 are variable flow valves, it is possible to regulate the amount of CPB blood flow diverted to heat exchanger 8730.

In other embodiments, two or more modules can be used to locate pumps and valves dedicated to discrete CPB operations. For example, there can be a separate cardiotomy pump module, cardioplegia pump module, and heat exchanging pump module, each with its own corresponding pneumatic control bracket on the base CPB unit. Although using separate pump modules could increase the total priming volume of the circuit, a net reduction of priming volume may be realized if only a subset of the available modules are needed for a particular surgical procedure. For example, extracorporeal membrane oxygenation for infants and children may require few or no modules other than an oxygenator pump module.

In yet other embodiments, the oxygenator 8720 and heat exchanger 8730 shown in FIG. 4 can be replaced by a device that combines both operations. In certain cases, all of the blood that flows through an oxygenator will also flow through a heat exchanger. To accommodate such cases, a modified module (not shown) can have the features of module 8000 depicted in FIG. 4 without the heat exchanger pump 8500 and its associated flow paths.

In further embodiments, the unidirectional flow valves depicted in FIG. 4 can be passive check valves such as, for example, duckbill valves. However, one advantage of having actively controlled check valves such as pneumatically actuated check valves is that liquid flow can be deliberately reversed through any of the pumps and associated flow paths by reversing the opening and closing sequence of the valves on either side of the pump. Flow reversal may be useful, for example, for priming a flow path with either fluid or blood.

In other embodiments, liquid flow through a path can be interrupted by mechanical occluders acting on plastic tubing of a flow path, rather than using pneumatically actuated membrane-type on/off valves. Liquid flow in a section of tubing can be interrupted by positioning the tubing between two mechanically actuated pincers or between a pincer and a stationary member. The pincers can be actuated by any means known in the art, including, for example, pneumatic, hydraulic or electromagnetic means. In some embodiments, a pump module can incorporate mechanical occluders adjacent to short sections of plastic tubing instead of pneumatically actuated membrane-type valves.

Reciprocating Positive Displacement Membrane-Based Pod Pump Systems

Generally speaking, the pod pump is a modular pump apparatus. The pod pump can be connected to any subject fluid (i.e., liquid, gas or variations thereof) source, which includes but is not limited to a path, line or fluid container, in order to provide movement of said subject fluid. A single pod pump or multiple pod pumps can be used. The pod pump can additionally be connected to at least one actuation source, which can be, for example, an air chamber. The pod pump can be modularly connected to any device or machine. However, in other embodiments, the pod pump can be part of a device, machine or container that is attachable to another device, machine or container. Although the pod pump is modular, the pod pump may also be part of another modular structure that interacts with any machine, device, or container.

In one embodiment, the pod pump includes a housing having a diaphragm or movable impermeable membrane attached to the interior of the housing. The diaphragm defines two chambers. One chamber does not come into contact with the pumped fluid; this chamber is referred to as the control (or actuation) chamber. The second chamber comes into contact with the pumped fluid. This chamber is referred to as the pump or pumping chamber.

The pod pump can include an inlet fluid path and an outlet fluid path. In this embodiment, a subject fluid is pumped into the pump chamber via the inlet fluid path, then out of the pump chamber via the outlet fluid path. Valving mechanisms can be used to ensure that the fluid moves in the intended direction. In other embodiments, the inlet fluid path and the outlet fluid path are one and the same.

The actuation of the diaphragm is provided for by a change in pressure in the control chamber. Either positive or negative pressure, or both, can be used to effectuate this change in pressure. In one embodiment, a pneumatic mechanism can be used to fill the control chamber with air (creating a positive pressure) and then to evacuate the air out of the control chamber (creating a negative pressure). In some embodiments, the air flows through a port which can be, but is not limited to, an opening or aperture in the control chamber. In other embodiments, other types of fluid (i.e., liquid, gas or combinations thereof) can be used as a control fluid.

For purposes of this description, exemplary embodiments are shown and described. However, other embodiments are contemplated, thus, the description provided are meant to bring an understanding of the pod pump embodiments, other variations will be apparent.

Pod pump Configurations

Figure 5:
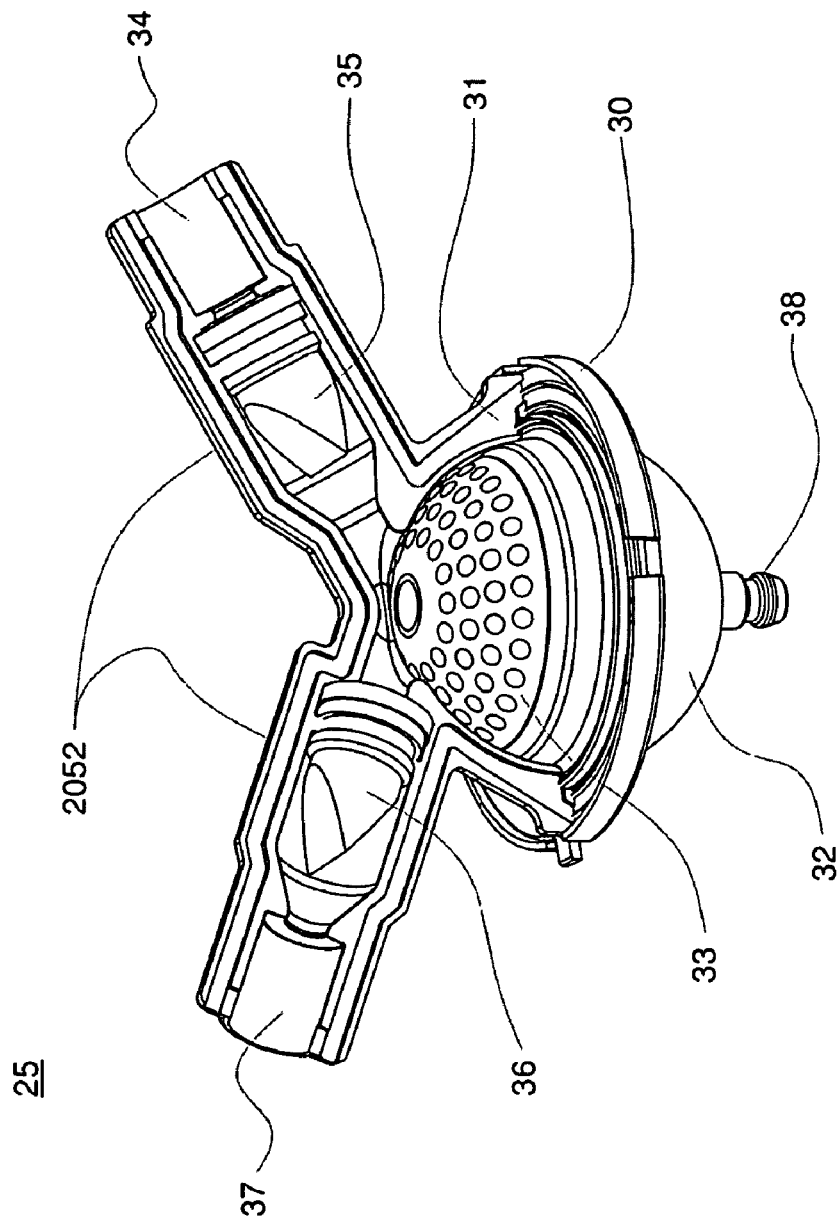
FIG. 5 is a perspective view of a pod pump of the disposable unit shown in FIG. 102.

FIG. 5 shows one example of a reciprocating positive-displacement pump 25 that can be used in the present invention. In this embodiment, the reciprocating positive-displacement pump 25 is essentially a self-contained unit (which may be referred to hereinafter as a "pod") that may be used as a component of a larger pumping system. The reciprocating positive-displacement pump 25 includes a "top" portion (also referred to as the "pumping chamber wall") 31 and a "bottom" portion (also referred to as the "control chamber wall") 32 that are coupled together at pod wall 30, for example, by ultrasonic welding or other technique. It should be noted that the terms "top" and "bottom" are relative and are used here for convenience with reference to the orientation shown in FIG. 5. Each of the portions 31 and 32 has a rigid interior surface that is preferably (although not necessarily) hemispherical, such that the pod has an interior cavity that is preferably (although not necessarily) spherical.

In the embodiment shown in FIG. 5, the control chamber wall 32 is a unitary structure while the pumping chamber wall 31 is formed from two halves that are coupled together along perimeter 2052, for example, by ultrasonic welding or other technique (which facilitates assembly of the integral valves, discussed below). Where the two portions of the pump chamber are molded, this design may allow for minimum flash or burrs, which is more likely to present a gentler pumping environment. This embodiment may be advantageous for use with fluids vulnerable to shear forces, and where flash or burrs therefore should be avoided.

During typical fluid pumping operations, the application of negative pneumatic pressure to the pneumatic interface 38 tends to withdraw the membrane 33 toward the control chamber wall 32 so as to expand the pumping chamber and draw fluid into the pumping chamber through the inlet 34, while the application of positive pneumatic pressure tends to push the membrane 33 toward the pumping chamber wall 31 so as to collapse the pumping chamber and expel fluid in the pumping chamber through the outlet 37. During such pumping operations, the interior surfaces of the pumping chamber wall 31 and the control chamber wall 32 limit movement of the membrane 33 as it reciprocates back and forth. In the embodiment shown in FIG. 5, the interior surfaces of the pumping chamber wall 31 and the control chamber wall 32 are rigid, smooth, and approximately hemispherical. In lieu of a rigid control-chamber wall 32, an alternative rigid limit structure—for example, a portion of a bezel used for providing pneumatic pressure and/or a set of ribs—may be used to limit the movement of the membrane as the pumping chamber approaches maximum value. Bezels and rib structures are described generally in U.S. patent application Ser. No. 10/697,450 entitled BEZEL ASSEMBLY FOR PNEUMATIC CONTROL filed on Oct. 30, 2003 and published as Publication No. US 2005/0095154 and related PCT Application No. PCT/US2004/035952 entitled BEZEL ASSEMBLY FOR PNEUMATIC CONTROL filed on Oct. 29, 2004 and published as Publication No. WO 2005/044435, both of which are hereby incorporated herein by reference in their entireties. Thus, the rigid limit structure—such as the rigid control chamber wall 32, a bezel, or a set of ribs—defines the shape of the membrane 33 when the pumping chamber is at its maximum value. In a preferred embodiment, the membrane 33 (when urged against the rigid limit structure) and the rigid interior surface of the pumping chamber wall 31 define a spheroid pumping-chamber volume when the pumping chamber volume is at a maximum.

Thus, in the embodiment shown in FIG. 5, movement of the membrane 33 is limited by the pumping-chamber wall 31 and the control-chamber wall 32. As long as the positive and negative pressurizations provided through the pneumatic port 38 are strong enough, the membrane 33 will move from a position limited by the control-chamber wall 32 to a position limited by the pumping-chamber wall 31. When the membrane is forced against the control-chamber wall 32, the membrane and the pumping-chamber wall 31 define the maximum volume of the pumping chamber. When the membrane is forced against the pumping-chamber wall 31, the pumping chamber is at its minimum volume.

In a preferred embodiment, the pumping-chamber wall 31 and the control-chamber wall 32 both have a hemispheroid shape so that the pumping chamber will have a spheroid shape when it is at its maximum volume. More preferably, the pumping-chamber wall 31 and the control-chamber wall 32 both have a hemispherical shape so that the pumping chamber will have a spherical shape when it is at its maximum volume. By using a pumping chamber that attains a spheroid shape—and particularly a spherical shape—at maximum volume, circulating flow may be attained throughout the pumping chamber. Such shapes accordingly tend to avoid stagnant pockets of fluid in the pumping chamber. As discussed further below, the orientations of the inlet 34 and outlet 37—with each being substantially tangential to the interior surface of the pumping chamber wall 31—also tend to improve circulation of fluid through the pumping chamber and reduce the likelihood of stagnant pockets of fluid forming. Additionally, compared to other volumetric shapes, the spherical shape (and spheroid shapes in general) tends to create less shear and turbulence as the fluid circulates into, through, and out of the pumping chamber.

The pod pump components can be manufactured using any one of a number of methods of manufacturing, including but not limited to injection molding, compression molding, casting, thermoforming or machining. In some embodiments, where the pod pump chambers are machined, they can be fused together using mechanical fasteners or heat fused. In one embodiment of a disposable pump, the pump housing made from a thin film made of a material which includes, but is not limited to PETE, PETG, and PET. In these embodiments, the housing may be thermoformed, for example, vacuum or pressure formed, and the pump membrane is formed from a thin plastic film that can be heat sealed to the housing. In some embodiments, the pump housing is a multi-layer film. This embodiment is conducive to bonding the pump housing to another component.

Pump Membranes

Figure 6:
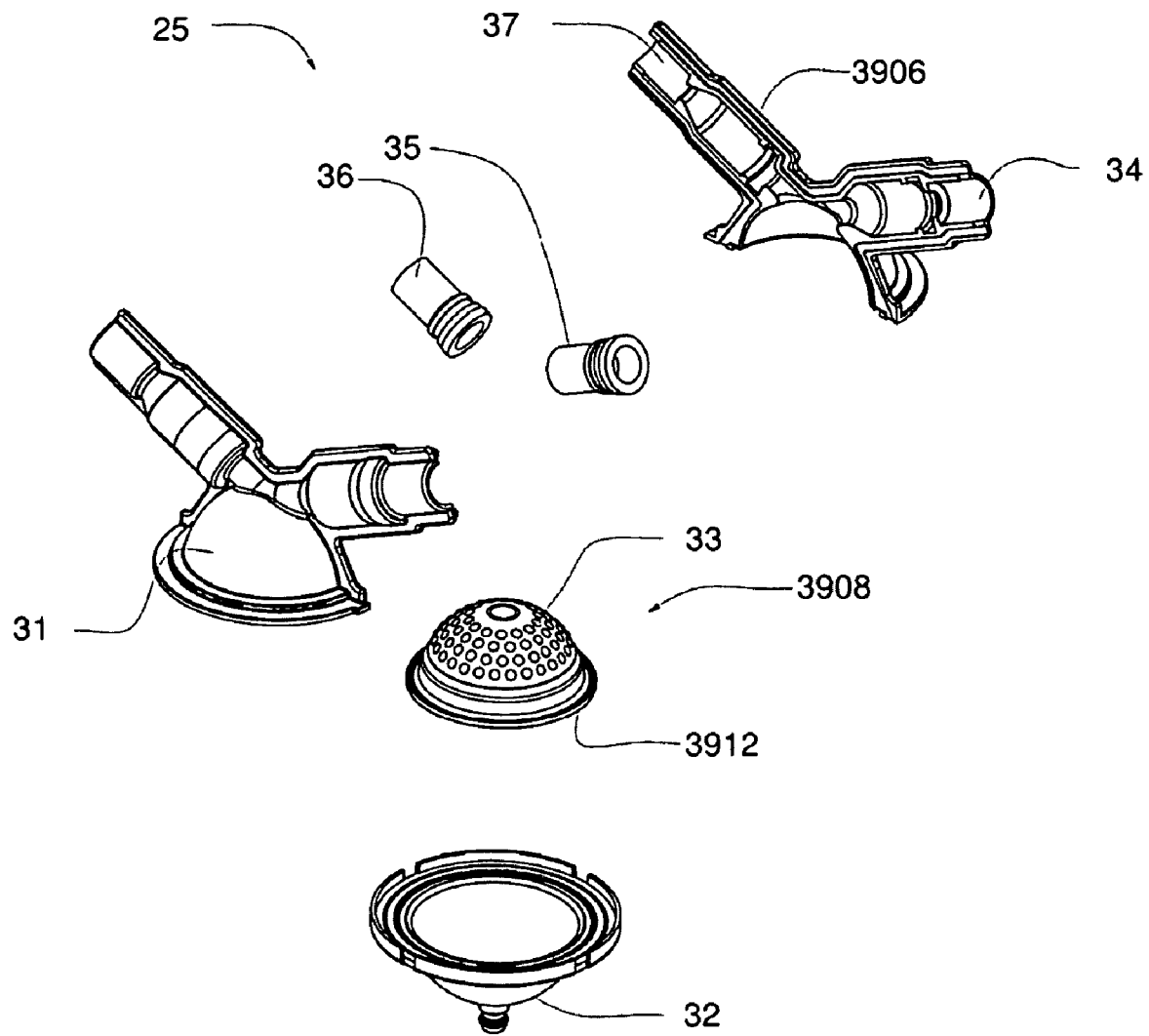
FIG. 6 is an exploded pictorial view of a pod pump assembly.

FIG. 6 shows an exploded view of the three pod pump wall sections in accordance with an exemplary embodiment of the present invention. Within the reciprocating positive-displacement pump 25, a flexible membrane 33 (also referred to as the "pump diaphragm") is mounted where the pumping-chamber wall 31 and the control-chamber wall 32 meet (i.e., at the pod wall 30). The pump diaphragm 33 effectively divides that interior cavity into a variable-volume pumping chamber (defined by the rigid interior surface of the pumping chamber wall 31 and a top surface of the membrane 33) and a complementary variable-volume control chamber (defined by the rigid interior surface of the control chamber wall 32 and a bottom side of the membrane 33). The top portion 31 includes a fluid inlet 34 and a fluid outlet 37, both of which are in fluid communication with the pumping chamber. The bottom portion 32 includes a pneumatic interface 38 in fluid communication with the control chamber. As discussed in greater detail below, the membrane 33 can be urged to move back and forth within the cavity by alternately applying negative and positive pneumatic pressure at the pneumatic interface 38. As the membrane 33 reciprocates back and forth in the embodiment shown in FIG. 5, the sum of the volumes of the pumping and control chambers remains constant.

The membrane 33 may be made of any flexible material having a desired durability and compatibility with the subject fluid. The membrane 33 can be made from any material that may flex in response to liquid or gas pressure or vacuum applied to the control chamber. The membrane material may also be chosen for particular bio-compatibility, temperature compatibility or compatibility with various subject fluids that may be pumped by the membrane 33 or introduced to the chambers to facilitate movement of the membrane 33. In the exemplary embodiment, the membrane 33 is made from high elongation silicone. However, in other embodiments, the membrane 33 is made from any elastomer or rubber, including, but not limited to, silicone, urethane, nitrile, EPDM or any other rubber or elastomer. The membrane may be made from any of a wide variety of flexible materials, but is preferably made of a high-elongation silicone or similar material in order to maintain smooth pumping of the membrane and to reduce the tendency of membrane to "snap hard" into its minimum-pumping-chamber-volume position. By reducing hard snapping, sharp localized spikes of force on the fluid are reduced. Such hard snapping could cause disruptions in the fluid rotation in the chamber and could result in excessive shear forces and turbulence, which, the case of blood pumping, could cause hemolysis, and in the case of surfactant pumping, could result in foaming. Alternatively, the membrane may be made of a variety of thermoplastic elastomers or rubbers. Also, the membrane may be provided with dimples or grooves to make the membrane more flexible.

The shape of the membrane 33 is dependent on multiple variables. These variables include, but are not limited to: the shape of the chamber; the size of the chamber; the subject fluid characteristics; the volume of subject fluid pumped per stroke; and the means or mode of attachment of the membrane 33 to the housing. The size of the membrane 33 is dependent on multiple variables. These variables include, but are not limited to: the shape of the chamber; the size of the chamber; the subject fluid characteristics; the volume of subject fluid pumped per stroke; and the means or mode of attachment of the membrane 33 to the housing. Thus, depending on these or other variables, the shape and size of the membrane 33 may vary in various embodiments. The membrane 33 can have any thickness. However, in some embodiments, the range of thickness is between 0.002 inches to 0.125 inches. Depending on the material used for the membrane, the desired thickness may vary. In one embodiment, high elongation silicone is used in a thickness ranging from 0.015 inches to 0.050 inches.

In the exemplary embodiment, the membrane 33 is preformed to include a substantially dome-shape in at least part of the area of the membrane 33. One embodiment of the dome-shaped membrane 33 is shown in FIG. 6 as element 33. In the exemplary embodiment, the membrane 33 dome is formed using compression molding. However, in other embodiments, the dome may be formed by using injection molding. In other embodiments, the membrane 33 may not include a pre-formed dome shape. In alternate embodiments, the membrane 33 is substantially flat until actuated.

Either or both surfaces of membrane 33 may be smooth or include one or more features including but not limited to protuberances, projections, bumps, dimples, dots, rings, ribs, grooves or bars that stand above or below surrounding surfaces. In this embodiment, an arrangement of raised dots or protuberances is shown on the exterior surface of the diaphragm. Such protuberances or other raised structures prevent pockets of fluid from being caught away from the inlet and outlet, specifically by keeping the membrane spaced away from the rigid pumping chamber wall even when the pumping chamber volume is at a minimum. This spacing keeps flow passages open for blood to flow from the periphery of the pumping chamber to the outlets. In the exemplary embodiment shown in FIG. 6, the raised dots are located on a portion of the membrane spaced away from the edge of the membrane such that the membrane lacks protuberances in the area near the edge of the membrane. Generally speaking, such a configuration allows the portion of the membrane around the edge to contact the pumping chamber wall, which tends to force fluid from the edge toward the outlet.

The surface features, or lack thereof, may serve a number of various functions. One of these may be to provide space for fluid to pass through the pump chamber. Shear forces on the liquid being pumped may be reduced at the end of a pump stroke. Another may be to aid in the diaphragm sealing against the pump chamber housing for applications where it is desirable to prevent the flow of fluid through the pump chamber when the diaphragm is pressed against the pump chamber housing by liquid or gas pressure in the control chamber. Some diaphragm surfaces may provide one or more of these features, or provide another function or feature.

Geometry on the exterior or interior surface of the diaphragm may also serve to cushion the movement of the diaphragm at either end of the diaphragm stroke. When geometry on the diaphragm contacts the pump or control chamber walls those features will stop moving but the diaphragm material between the features may continue to move to allow the fluid that is being pumped to be gently accelerated or decelerated as it enters or leaves the pump chamber.

Inlet/Outlet Valves

Generally speaking, reciprocating positive-displacement pumps of the types just described may include, or may be used in conjunction with, various valves to control fluid flow through the pump. Thus, for example, the reciprocating positive-displacement pump may include, or be used in conjunction with, an inlet valve and/or an outlet valve. The valves may be passive or active. In the exemplary embodiment shown in FIG. 5, the reciprocating positive-displacement pump 25 includes a passive one-way inlet check valve 35 and a passive one-way outlet check valve 36. The inlet check valve 35 allows fluid to be drawn into the pumping chamber through the inlet 34 but substantially prevents backflow through the inlet 34. The outlet check valve 36 allows fluid to be pumped out of the pumping chamber through the outlet 37 but substantially prevents backflow through the outlet 37. The valves 35 and 36 may any passive or active valve, including but not limited to, duck bill valves, ball check valves, flapper valves, volcano valves, umbrella valves, a poppet, a controlled valve or other types of valves used in the art to control the flow of fluid.

Thus, in an exemplary embodiment using the reciprocating positive-displacement pump 25, the membrane 33 is urged back and forth by positive and negative pressurizations of a gas provided through the pneumatic port 38, which connects the control chamber to a pressure-actuation system. The resulting reciprocating action of the membrane 33 pulls liquid into the pumping chamber from the inlet 34 (the outlet check valve 36 prevents liquid from being sucked back into the pumping chamber from the outlet 37) and then pushes the liquid out of pumping chamber through the outlet 37 (the inlet check valve 35 prevents liquid being forced back into the inlet 34).

In alternative embodiments, active on-off valves may be used in lieu of the passive check valves 35 and 36. The active valves may be actuated by a controller in conjunction with actuation of the pod pump 25 in such a manner as to direct flow in a desired direction. Such an arrangement would generally permit the controller to cause flow in either direction through the pod pump 25. In a typical system, the flow would normally be in a first direction, e.g., from the inlet to the outlet. At certain other times, the flow may be directed in the opposite direction, e.g., from the outlet to the inlet. Such reversal of flow may be employed, for example, during priming of the pump, to check for an aberrant line condition (e.g., a line occlusion, blockage, disconnect, or leak), or to clear an aberrant line condition (e.g., to try to dislodge a blockage).

Pump Inlet/Outlet Orientations

In the embodiment shown in FIG. 103, the inlet 34 and the outlet 37 are oriented so as to direct fluid into and out of the pumping chamber at angles that are substantially tangential to the interior surface of the pumping chamber wall 31. Thus, the fluid flow through the inlet 34 into the pumping chamber avoids being perpendicular to the membrane 33, even as the membrane approaches a position where the pumping chamber is at its minimum volume. This orientation of the inlet 34 and the outlet 37 tends to reduce the shear forces on the liquid being pumped, particularly when compared to centrifugal pumps, which generally apply a great deal of stress on the fluid being pumped.

The orientation of the inlet 34 and outlet 37 with respect to each other also tends to reduce shear flow and turbulence. When the pumping chamber reaches its maximum volume, the fluid continues circulating through the pumping chamber even as fluid stops flowing through the inlet 34. The direction of this circulating flow is a result of the direction of the inlet 34 and the internal flow geometry. Generally speaking, after a very short pause, the membrane 33 will be actuated to start moving to reduce the volume of the pumping chamber and fluid will start flowing through the outlet 37. When the fluid enters the pumping chamber, it moves in a rotating current and stays rotating until exiting the pumping chamber. The exiting fluid peels off from the outer layer of the rotating current in the same direction in which it was rotating. The spherical shape of the pod pumps is particularly advantageous to achieve the desired flow circulation. The orientation of the outlet 37 with respect to circulating flow within the pumping chamber at the moment of maximum pumping chamber volume is such that flow does not have to change direction sharply when it begins to be urged through the outlet 37. By avoiding sharp changes in flow direction, shear and turbulence is reduced. Thus, the orientation of the inlet 34 and outlet 37 with respect to each other and the internal flow geometry reduces shear and turbulence on the liquid being pumped. For example, in FIG. 5, there is only a small change in direction in a path extending from the inlet 34 directly to the outlet 37, but other arrangements will also reduce sharp changes in direction as the pod pump transitions from a fill stroke to an expel stroke.

Thus, when the fluid being pumped is whole blood, centrifugal pumps (which apply a great deal of stress on the red blood cells) can cause a large amount of hemolysis and therefore can reduce a patient's hematocrit to the detriment of the patient, whereas pod pumps of the types described above (which apply low shear forces and turbulence) tend to produce substantially lower hemolysis. Similarly, when the fluid being pumped is a surfactant or other fluid prone to foaming, the reduced shear forces and reduced turbulence of the pod pumps tends to reduce foaming.

Figure 7:
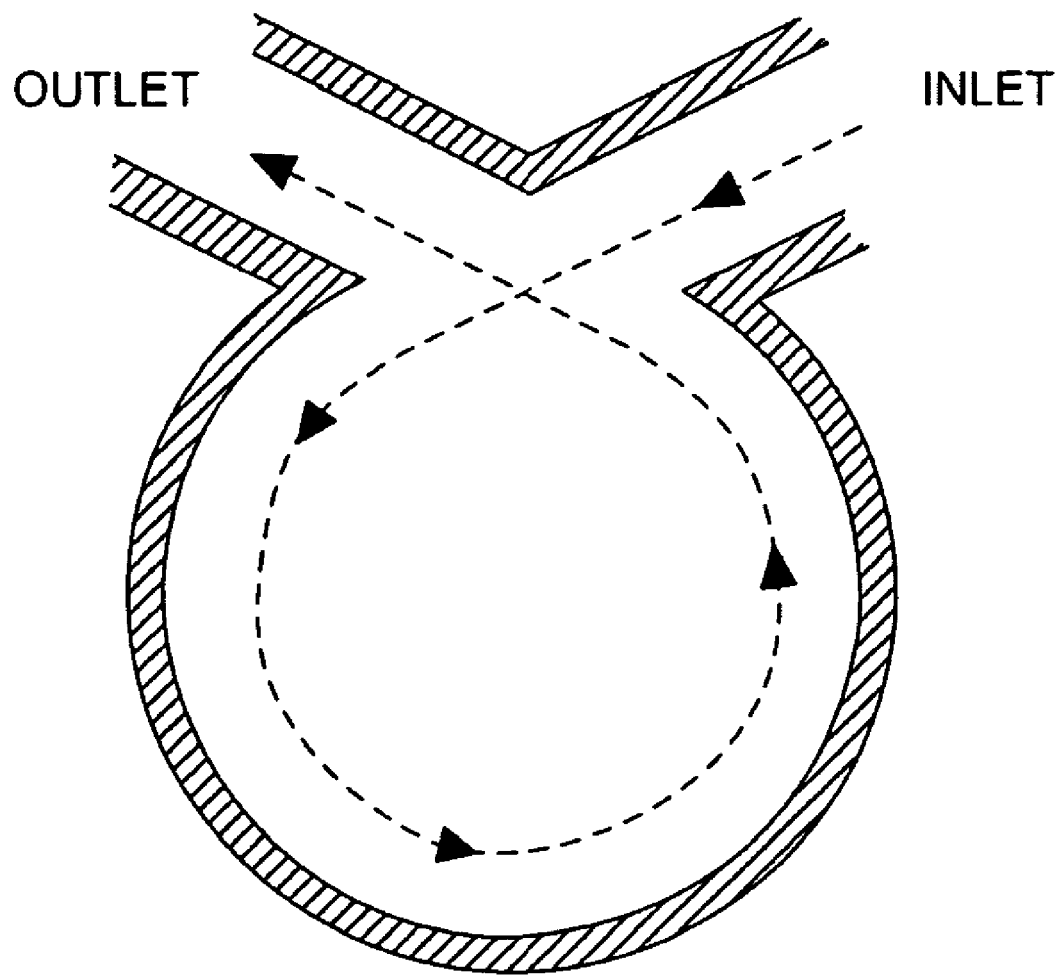
FIG. 7 is a schematic representation of circulatory fluid flow in the pod pump; shown in FIG. 5, in accordance with an exemplary embodiment of the present invention.

FIG. 7 is a schematic representation of circulatory fluid flow in the pod pump 25 shown in FIG. 5, in accordance with an exemplary embodiment of the present invention. As fluid enters the pumping chamber through the inlet, the orientation of the inlet directs fluid tangentially to the inside surface of the pumping chamber wall so as to create a circulatory flow. As fluid approaches the outlet, the fluid is already flowing substantially in the direction of the outlet so that the fluid is not required to make any drastic changes in direction when being pumped from the outlet. The fluid therefore tends to peel off of the circulatory flow in a laminar fashion to provide reduced shear forces on the fluid.

Generally speaking, for low shear and/or low turbulence applications, it is desirable for the inlet and outlet to be configured so as to avoid sharp or abrupt changes of fluid direction. It is also generally desirable for the inlet and outlet (and the pump chamber itself) to be free of flash or burrs. The inlet and/or outlet may include rounded edges to help smooth out fluid flow.

Alternate Pump Configurations

Figure 8:
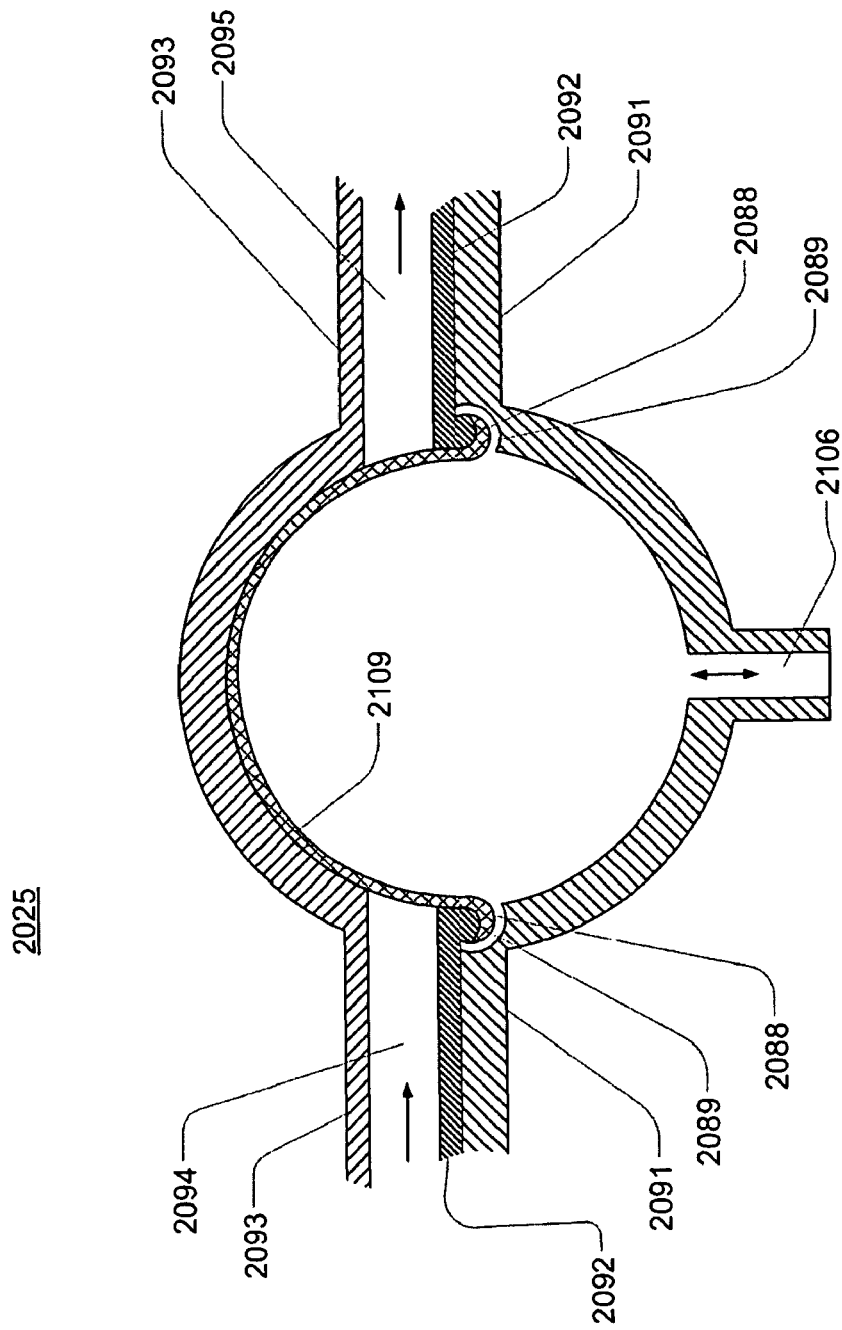
FIG. 8 is a sectional view of a pod-pump that may be incorporated into embodiments of fluid-control cassettes.

FIG. 8 is a sectional view of an alternative pod pump 2025 such as may be incorporated into a larger fluid-control cassette, in accordance with an alternative embodiment of the present invention. In this embodiment, the pod pump is formed from three rigid pieces, namely a "top" plate 2091, a middle plate 2092, and a "bottom" plate 2093 (it should be noted that the terms "top" and "bottom" are relative and are used here for convenience with reference to the orientation shown in FIG. 8). The top and bottom plates 2091 and 2093 may be flat on both sides, while the middle plate 2092 is provided with channels, indentations and holes to define the various fluid paths, chambers, and ports. To form the pod pump 2025, the top and bottom plates 2091 and 2093 may include generally hemispheroid portions that together define a hemispheroid chamber.

A membrane 2109 separates the central cavity of the pod pump into a chamber (the pumping chamber) that receives the fluid to be pumped and another chamber (the control chamber) for receiving the control gas that pneumatically actuates the pump. An inlet 2094 allows fluid to enter the pumping chamber, and an outlet 2095 allows fluid to exit the pumping chamber. The inlet 2094 and the outlet 2095 may be formed between middle plate 2092 and the bottom plate 2093. Pneumatic pressure is provided through a pneumatic port 2106 to either force, with positive gas pressure, the membrane 2109 against one wall of pod pump's cavity to minimize the pumping chamber's volume (as shown in FIG. 8), or to draw, with negative gas pressure, the membrane towards the other wall of the pod pump's cavity to maximize the pumping chamber's volume.

The membrane 2109 is provided with a thickened rim 2088, which is held tightly in a groove 2089 in the middle plate 2092. Thus, the membrane 2109 can be placed in and held by the groove 2089 before the top plate 2091 is ultrasonically welded to the middle plate 2092, so the membrane will not interfere with the ultrasonic welding of the two plates together, and so that securing the membrane does not depend on the two plates being ultrasonically welded together with exacting precision. Thus, it should be possible to manufacture this pod pump without requiring very tight tolerances during ultrasonic welding.

Figure 9:
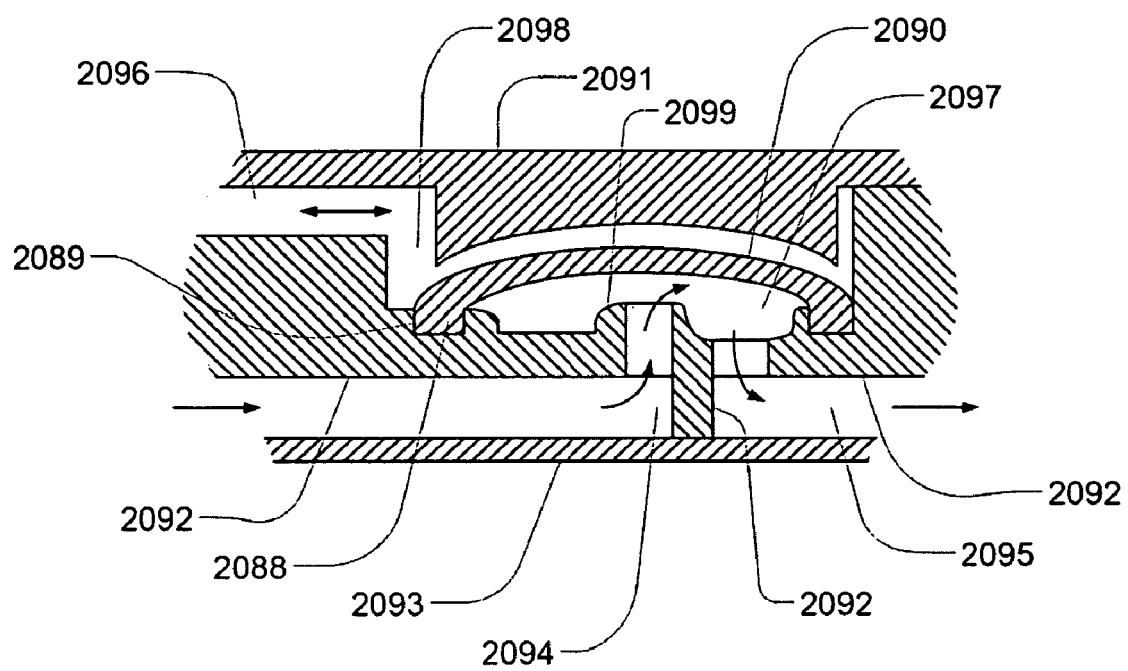
FIG. 9 is a sectional view of a valve that may be incorporated into embodiments of fluid-control cassettes.

One or more pod pumps 2025 may be incorporated into a single cassette, which may also include one or more valves 2000. FIG. 9 is a sectional view of a pneumatically controlled valve 2000 that may be used in embodiments of the above-mentioned cassette. A membrane 2090, along with the middle plate 2092, defines a valving chamber 2097. Pneumatic pressure is provided through a pneumatic port 2096 to either force, with positive gas pressure, the membrane 2090 against a valve seat 2099 to close the valve, or to draw, with negative gas pressure, the membrane away from the valve seat to open the valve. A control gas chamber 2098 is defined by the membrane 2090, the top plate 2091, and the middle plate 2092. The middle plate 2092 has an indentation formed on it, into which the membrane 2090 is placed so as to form the control gas chamber 2098 on one side of the membrane and the valving chamber 2097 on the other side.

The pneumatic port 2096 is defined by a channel formed on the "top" surface of the middle plate 2092, along with the top plate 2091. By providing fluid communication between several valving chambers in a cassette, valves can be ganged together so that all the valves ganged together can be opened on closed at the same lime by a single source of pneumatic pressure. Channels formed on the "bottom" surface of the middle plate 2092, along with the bottom plate, define the valve inlet 2094 and the valve outlet 2095. Holes formed through the middle plate 2092 provide communication between the inlet 2094 and the valving chamber 2097 (through the valve seat 2099) and between the valving chamber and the outlet 2095.

The membrane 2090 is provided with a thickened rim 2088, which fits tightly in a groove 2089 in the middle plate 2092. Thus, the membrane 2090 can be placed in and held by the groove 2088 before the top plate 2091 is ultrasonically welded to the middle plate 2092, so the membrane will not interfere with the ultrasonic welding of the two plates together, and so that securing the membrane does not depend on the two plates being ultrasonically welded together with exacting precision. Thus, it should be possible to manufacture this valve without requiring very tight tolerances during ultrasonic welding. As shown in FIG. 9, the top plate 2091 may include additional material extending into control gas chamber 2098 so as to prevent the membrane 2090 from being urged too much in a direction away from the groove 2089, so as to prevent the membrane's thickened rim 2088 from popping out of the groove 2089.

Although in this embodiment, the pod pump is spheroid shaped, in still other embodiments, the pod pump can be any shape desired, such as an ovoid shape. Many of the embodiments of the pod pumps will include a pump chamber, a control chamber, a diaphragm (or movable member), at least one control port and at least one inlet/outlet port. In some embodiments, the pod pump includes an inlet and an outlet port. Various embodiments are described herein and features described with respect to one embodiment should be understood to be available for any embodiment, thus the embodiment features can be mixed and matched, and any embodiment can include one or more of the features described herein.

Figure 10A:
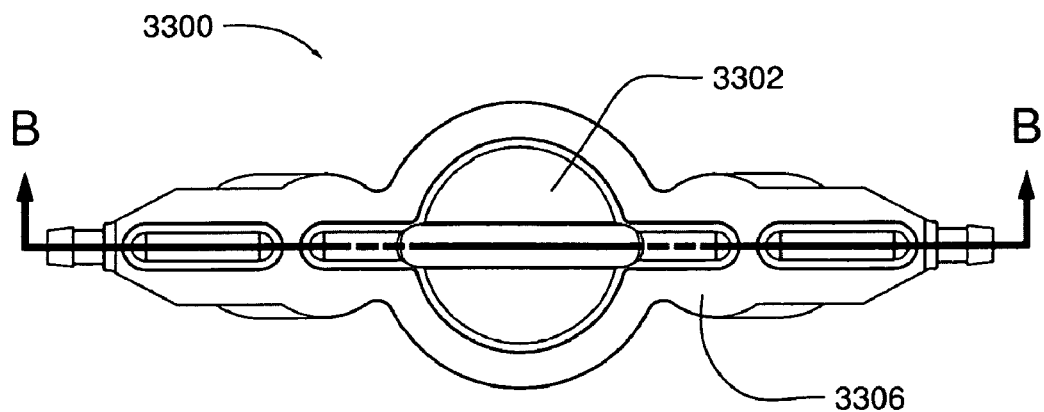
FIGS. 10A-10B are top and section views of a pod pump with a laminated construction.
Figure 10B:
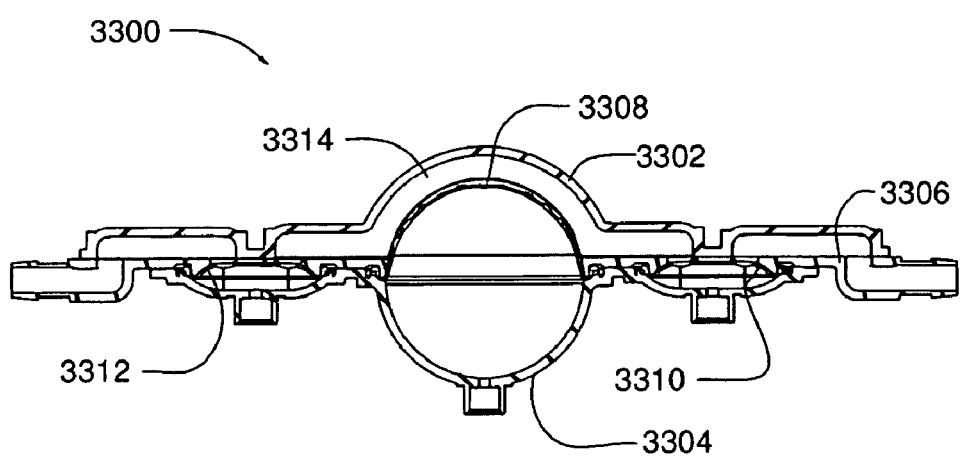

Referring to FIGS. 10A and 10B, an alternate embodiment of a pod pump 3300 is shown with a pump chamber cover 3302, a control chamber cover 3304 and a mid plate portion 3306. In this embodiment the mid plate 3306 and the control chamber cover 3304 retain the diaphragm 3308 and one or more secondary diaphragms 3310 or 3312. The secondary diaphragms may act passively or may be actuated by gas, liquid or mechanical forces to serve as active valves to control the flow of fluid through the pump chamber cover fluid path 3314. In this embodiment of the pod pump 3300, a fluid path 3314 is formed in the pump chamber cover 3302 such that fluid may flow through the flow path 3314 regardless of the position of the diaphragm 3308. In this embodiment as in other embodiments the pump chamber cover 3302, control chamber cover 3304 and mid plate 3306, in one embodiment, are made of plastic but in other embodiments, may be made from other materials including but not limited to metal or glass. In one exemplary embodiment, covers 3302 and 3304, and mid plate 3306 are made from polysulfone. In another exemplary embodiment, they are made from medical grade polycarbonate. In this embodiment the pump chamber cover 3302, control chamber cover 3304 and mid plate 3306 may be joined by laser welding or may be joined by various other methods as deemed appropriate for the chosen component materials and the desired pod pump use. Other joining possibilities include but are not limited to snap together tabs, press fit, snap fit, solvent bonding, heat welding, electromagnetic welding, resistance welding, RF welding, screws, bolts, ultrasonic welding, adhesive, clamping by components that neighbor the pump when in use or other joining methods commonly used in the art.

Figure 11A:
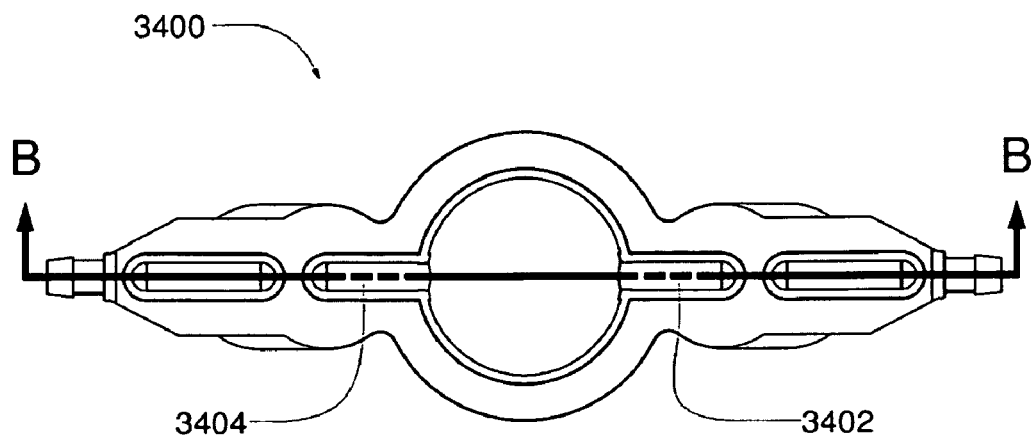
FIGS. 11A-11B are top and section views of a pod pump with a laminated construction.
Figure 11B:
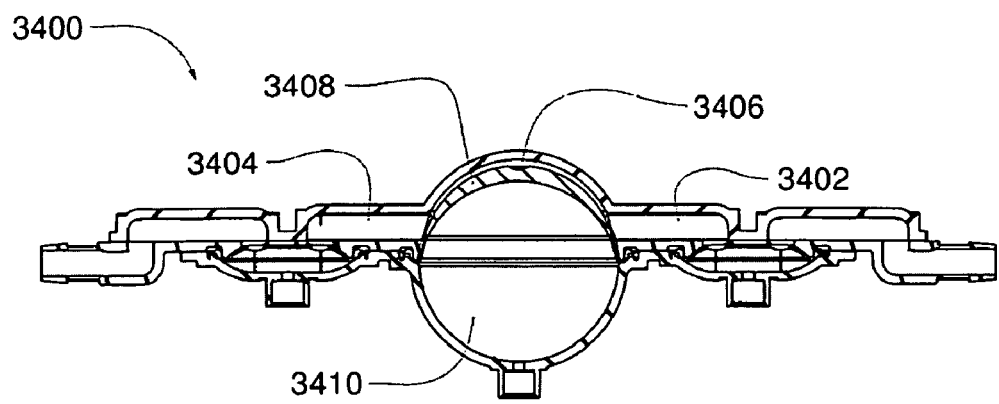

Referring now to FIGS. 11A and 11B one embodiment of a pod pump 3400 is shown. In this embodiment inlet and outlet ports are located at opposite ends of the pump chamber 3406 and are interchangeable depending on the configuration of the pump or its intended use. The diaphragm 3408 is shown nearly fully extended into the pump chamber 3406. In this embodiment the inlet and outlet ports 3402 and 3404 may be partially or fully obscured by the diaphragm 3408 when fully actuated by fluid pressure in the control chamber 3410. Blocking of the inlet or outlet ports may serve to limit or switch the flow of subject fluid through the pump chamber 3406 as may be desired in certain applications. In this embodiment the pumping side of the diaphragm 3408, i.e., the side of the diaphragm 3408 that contacts the subject fluid, is smooth, which may provide different flow characteristics with some subject fluids or provide different contact between the diaphragm 3408 and pump chamber 3406 when reduction of flow through the inlet or outlet ports 3402 and 3404 is desired when the diaphragm is fully extended into the pump chamber 3406.

In some embodiments, the diaphragm has a variable cross-sectional thickness, as shown in FIG. 11B. Thinner, thicker or variable thickness diaphragms may be used to accommodate the strength, flexural and other properties of the chosen diaphragm materials. Thinner, thicker or variable diaphragm wall thickness may also be used to manage the diaphragm thereby encouraging it to flex more easily in some areas than in other areas, thereby aiding in the management of pumping action and flow of subject fluid in the pump chamber 3406. This embodiment the diaphragm 3408 is shown having its thickest cross-sectional area closest to its center. However in other embodiments having a diaphragm 3408 with a varying cross-sectional, the thickest and thinnest areas may be in any location on the diaphragm 3408. Thus, for example, the thinner cross-section may be located near the center and the thicker cross-sections located closer to the perimeter of the diaphragm 3408. Still other configurations are possible.

In some embodiments, a soft, flexible, elastomeric or porous spacer can be placed along the rigid inner wall of the control chamber to limit motion of the diaphragm, dampen the diaphragm's travel, filter fluid entering or leaving the control chamber, dampen sound or vibration in the pod pump, and perform fluid management system measurements on fluid in the pumping chamber. Non-limiting examples of pumps that can be used as membrane-based pumps or pod pumps are described in U.S. patent application Ser. No. 11/787,212, filed Apr. 13, 2007, incorporated herein by reference in its entirety.

Pump Cassette Systems

In some embodiments, the pod pump can be incorporated into a device also housing valves and fluid paths which is then integrated or attached to a machine, device, or container. One example of this embodiment is a cassette having integrated pod pumps, valves, fluid paths, fluid ports, control ports and control fluid paths. Two embodiments of a cassette are described with respect to FIGS. 12A-12C and 13A-13B. It is understood that these are merely exemplary embodiments, and that many additional embodiments having different numbers and arrangements of pumps, valves and flow paths can be constructed using similar principles.

Figure 12A:
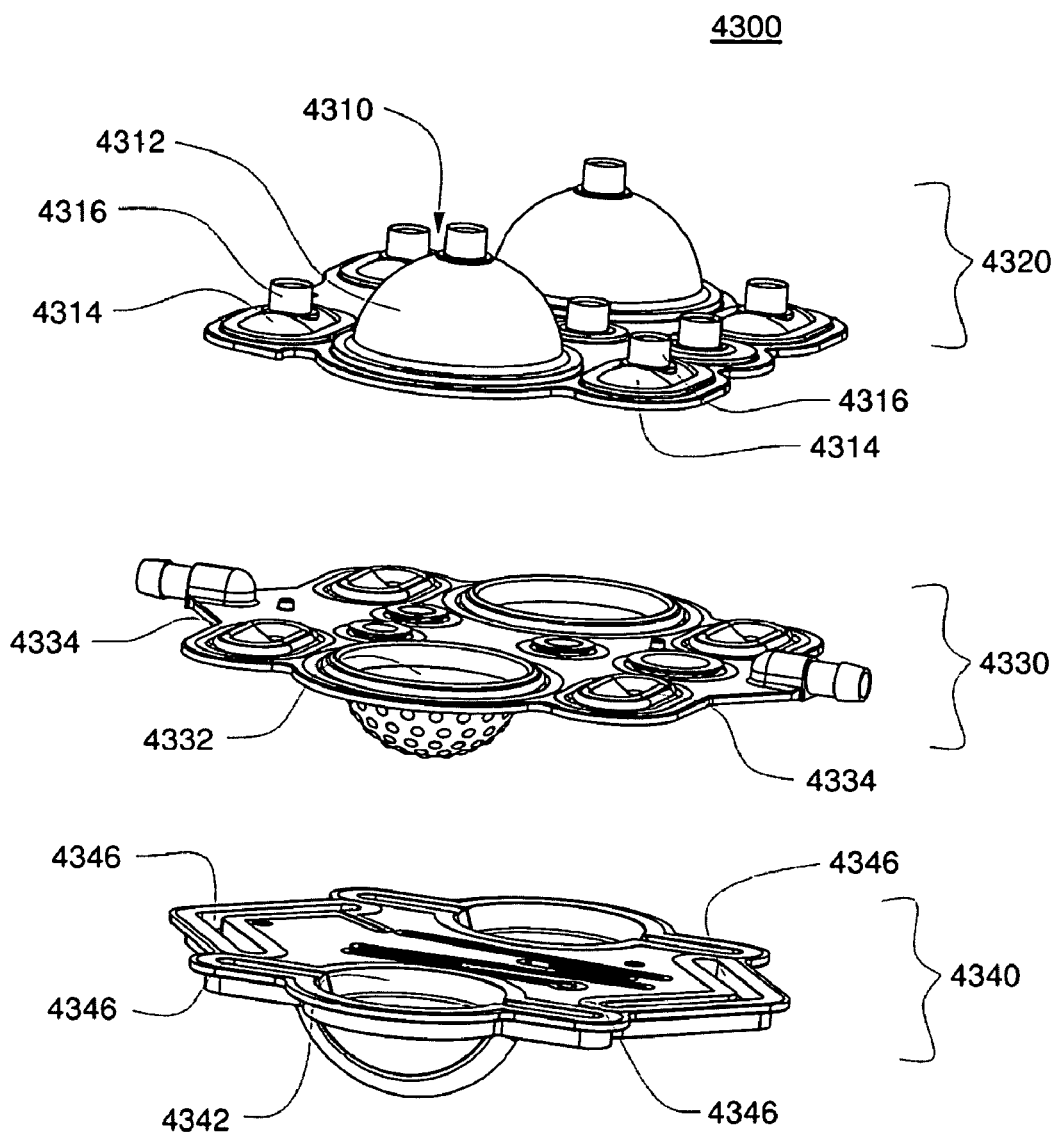
FIGS. 12A-12C are exploded and section views of one embodiment of a pod pump cassette.
Figure 12B:
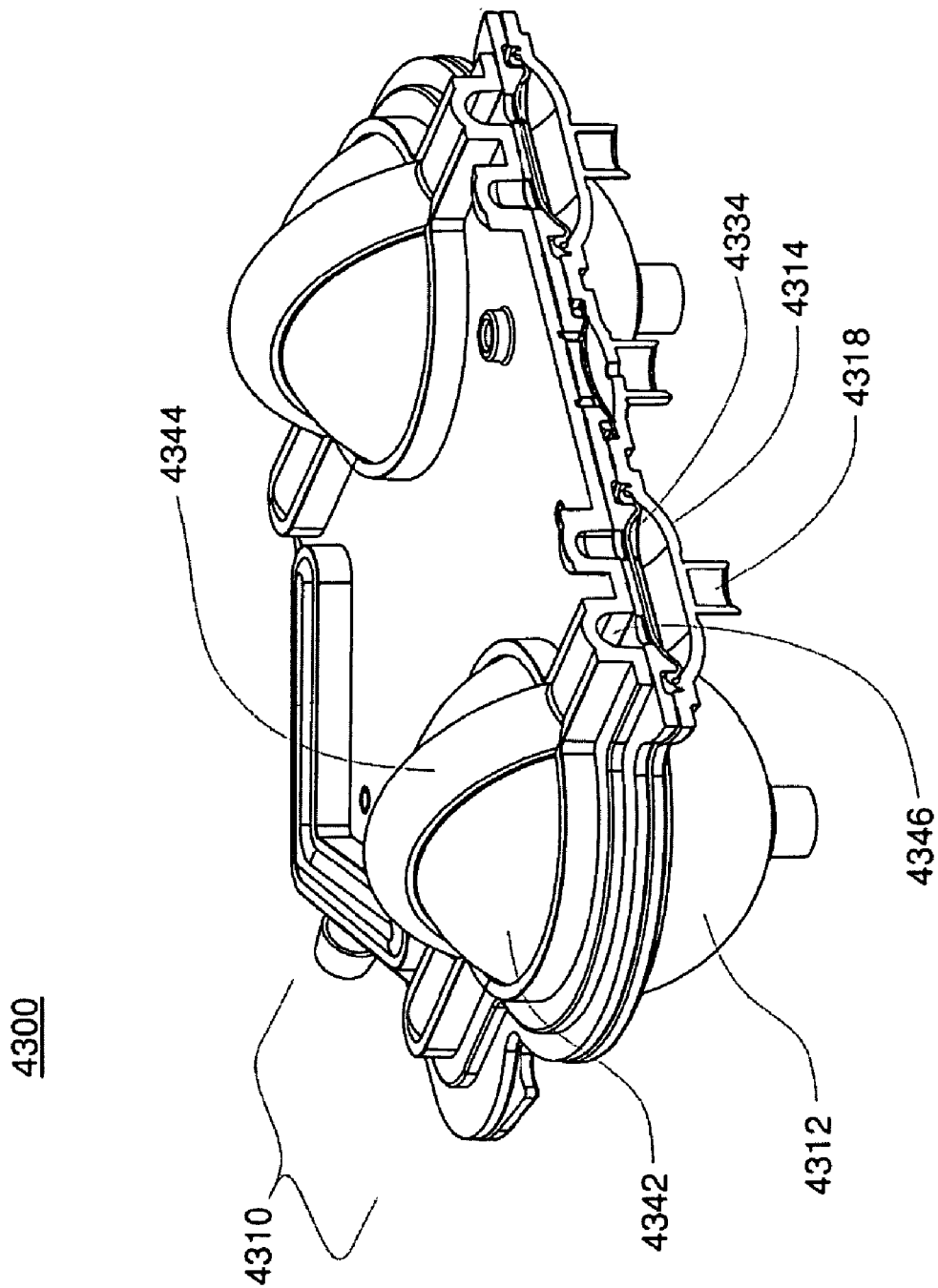
Figure 12C:
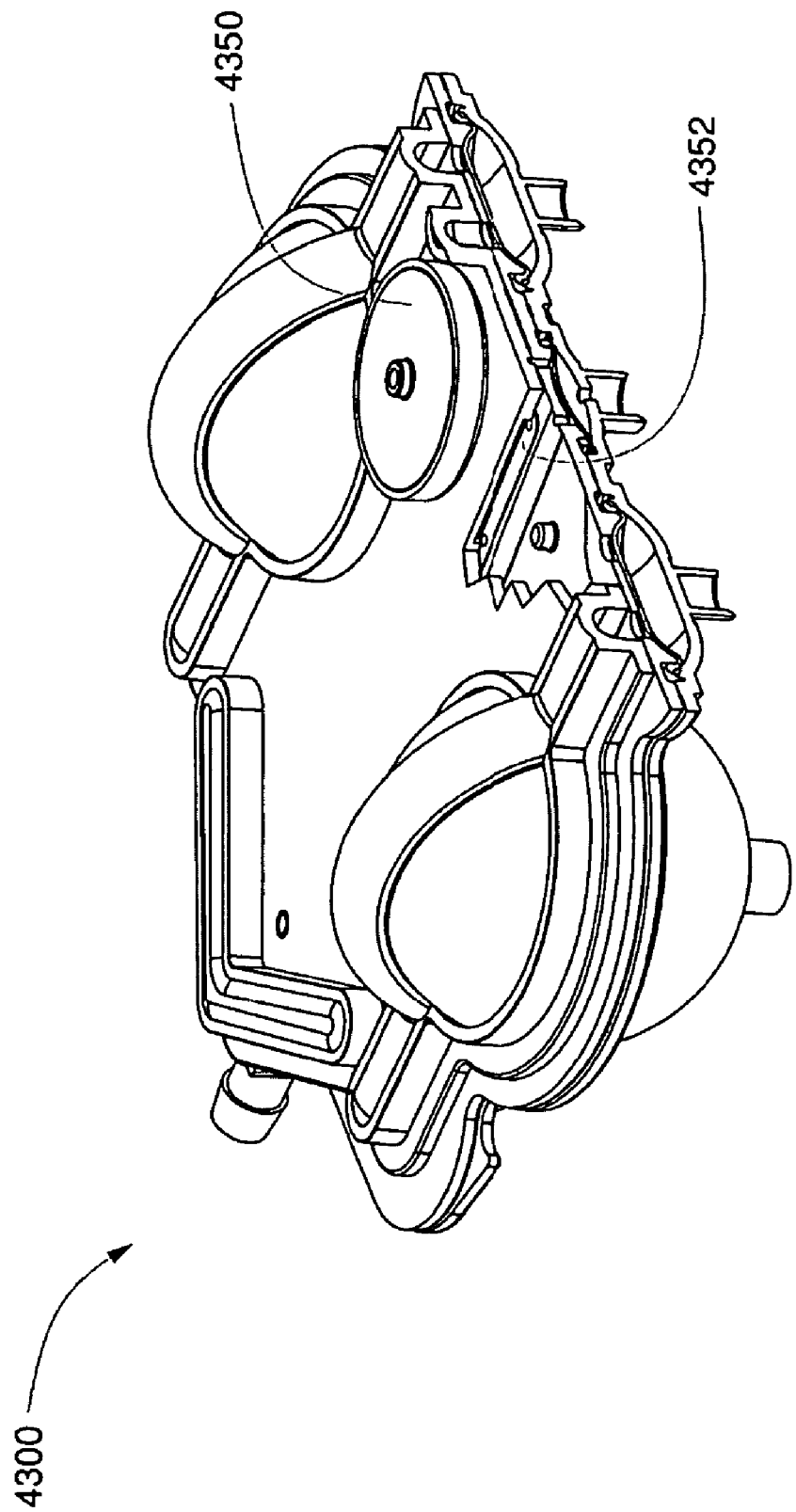

Referring now to FIGS. 12A-12C, one embodiment of a pod pump cassette 4300 is shown. Referring now to FIG. 12A, this embodiment of the pod pump cassette includes two pod pumps 4310. The pod pumps 4310 can be any pod pump embodiment, but in this exemplary embodiment, the pod pumps 4310 are similar to the pod pump shown in FIGS. 10 and 11. The cassette 4300 includes three plates, an actuation plate 4320, a mid plate 4330 and a pump chamber plate 4340.

The actuation plate 4320 includes, for each pod pump 4310, a pod pump control chamber housing 4312 portion and two valves control housing 4314 portions. The valve control housing 4314 includes a valve control port 4316. In addition to pod pumps, the cassette 4300, in some embodiments, may contain additional ports and/or containers for various fluids to be pumped to and from.

The mid plate 4330 includes, for each pod pump, a pump diaphragm 4332 and two valve diaphragms 4334. In the embodiment shown, the valves are volcano or active valves actuated by a diaphragm 4334 which is actuated by a fluid, which in this embodiment is pneumatic air. Also shown on this embodiment of the cassette 4300 are additional diaphragms in the mid plate 4330. These are for embodiments that may contain additional container for various fluids to be pumped to and from.

Referring now to the pump plate 4340, each pod pump 4310 includes a pump chamber housing 4342 which includes an integral fluid path 4344. The integral fluid path 4344 ensures that a pocket of fluid in the pump chamber does not become trapped by the membrane if it happens to encroach on the outlet of the pump chamber before it reaches the chamber wall in its entirety. The pump chamber housing 4342 is in fluid connection with an exterior fluid path 4346.

In this exemplary embodiment, the three plates 4320, 4330, 4340 are laser welded together. However, in other embodiments, various modes of attachment, some of which are described above, may be used.

Referring now to FIG. 12B, a cross sectional view of the cassette 4300 is shown. The volcano valves are shown including the valve diaphragms 4334, the valves control housing 4314 portions and the exterior fluid line 4346. The valves are actuated by pneumatic air through control ports 4318.

Figure 13A:
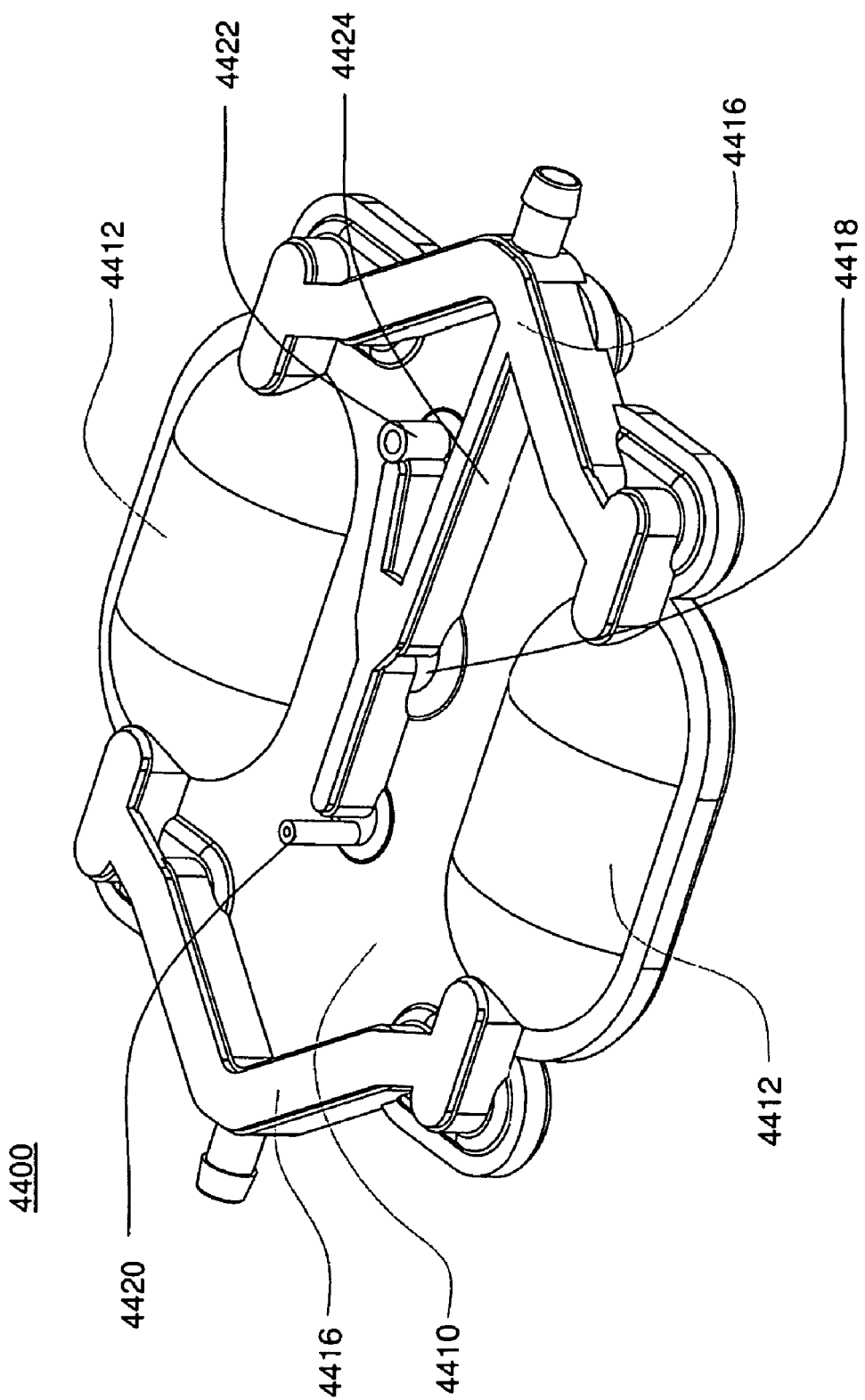
FIGS. 13A-13B are pictorial views of one embodiment of a pod pump cassette.
Figure 13B:
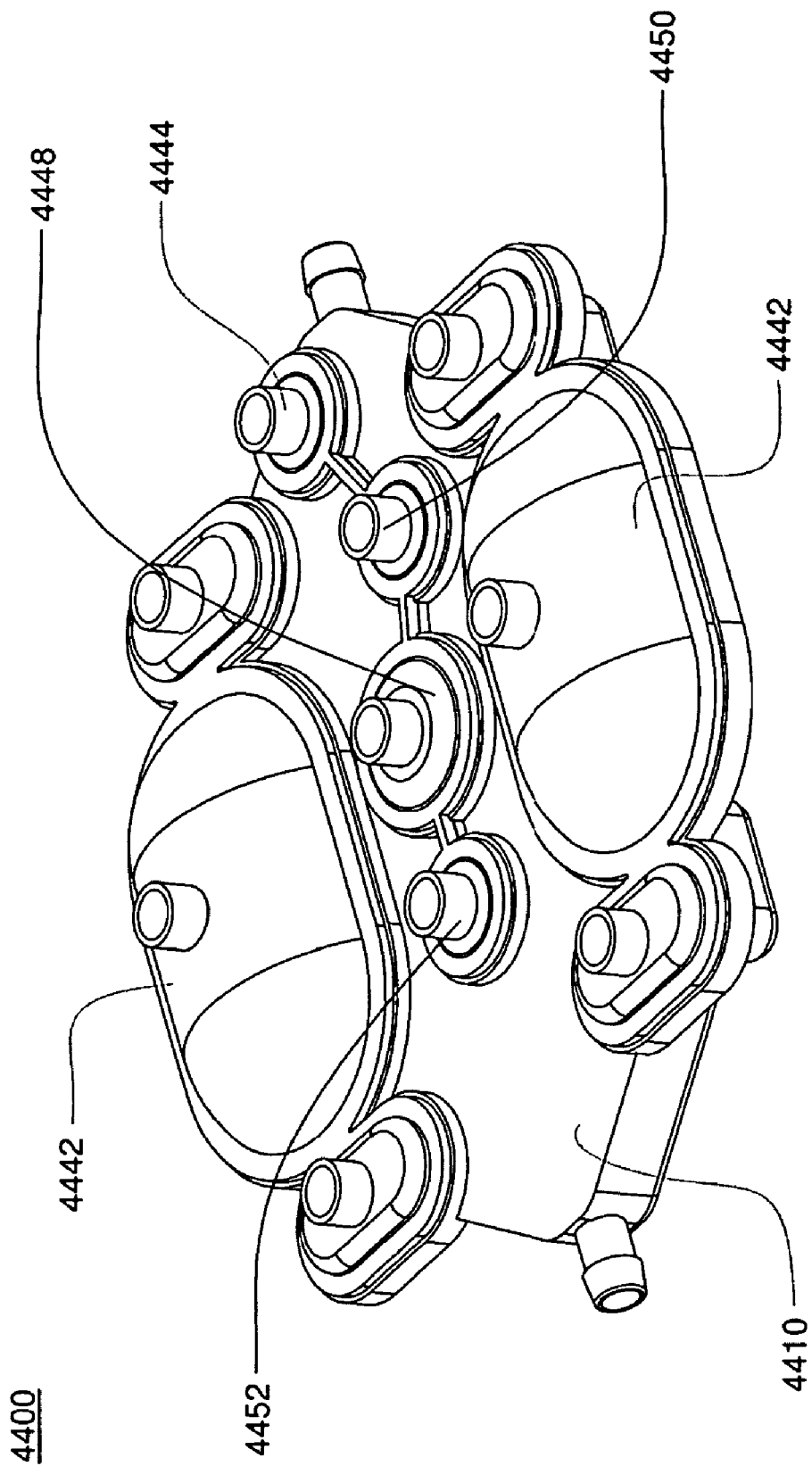

An alternate embodiment of the cassette is shown in FIGS. 13A and 13B. Referring now to FIG. 13A, the cassette 4400 includes greater than three portions. The portions include a mid plate 4410 with multiple covers 4412-4416 laser welded onto the mid plate. These multiple covers 4412-4416 are used rather than the pump plate shown in FIG. 12A as 4340. Referring now to FIG. 13B, the mid plate 4410 again is shown. However, in this embodiment, multiple covers 4442-4444 are used rather than a single actuation plate as shown in FIG. 12A as 4320. FIGS. 13A-13C show one embodiment; in other embodiments, the number of multiple covers may vary.

Both cassette 4300 and 4400 are capable of having one or more additional pumps for infusing liquid into a flow path of either or both pod pumps of the cassette. Referring now to FIG. 12C, in some embodiments, an air filter 4350 and an additional fluid line 4352 may be included in the cassette to accommodate this additional fluid path. In FIG. 13A, metering pump 4418 is capable of pulling in liquid from an external source fluidly connected to port 4420. If the external fluid source is in a rigid container (e.g., bottle or glass vial), metering pump 4418 can be programmed to prevent accumulation of a vacuum in the container by periodically drawing air vent 4422 to deliver the air to the external fluid source via the same port 4420. Liquid drawn from port 4420 can be directed by metering pump 4418 to one or more pod pump outlet paths via flow path 4424. The direction of flow to and from the port 4420, vent 4422, and flow path 4424 can be controlled by valves having pneumatic control ports 4444, 4450 and 4452 shown in FIG. 13B. This arrangement can be useful, for example, if medication such as heparin is to be infused into a CPB blood flow path, of for infusion of cardioplegia solution into a cardioplegia blood flow path.

It should also be noted that pumping systems may employ multiple pod pumps for pumping fluid. Pod pumps may be employed independently, in which case the pod pumps may be individually controlled. The pod pumps also may be interconnected in various ways, such as, for example, interconnecting the inlets of multiple pod pumps in order to draw fluid from a common source, interconnecting the outlets of multiple pod pumps in order to pump fluid to a common destination, and/or interconnecting the pneumatic ports of multiple pod pumps in order to control the pod pumps through a common pneumatic interface. In various embodiments, multiple pod pumps may be operated out-of-phase (i.e., one pumping chamber is emptying while the other is filling) in order to provide a substantially continuous flow, in-phase in order to provide a pulsatile flow, or in other ways. For example, one pod pump may be operated independently of another, particularly if the pumps are operated out of phase with one another. The valves associated with each pump can be controlled to direct the flow from one pump to a path different from the other pump, while the other pump is in a filling phase. For in-phase operation, a single pneumatic interface may be provided for multiple pod pumps so that the base station can operate the pod pumps simultaneously. Similarly, a single pneumatic interface may be provided for multiple valves so that the base station can operate the valves simultaneously.

Figure 14:
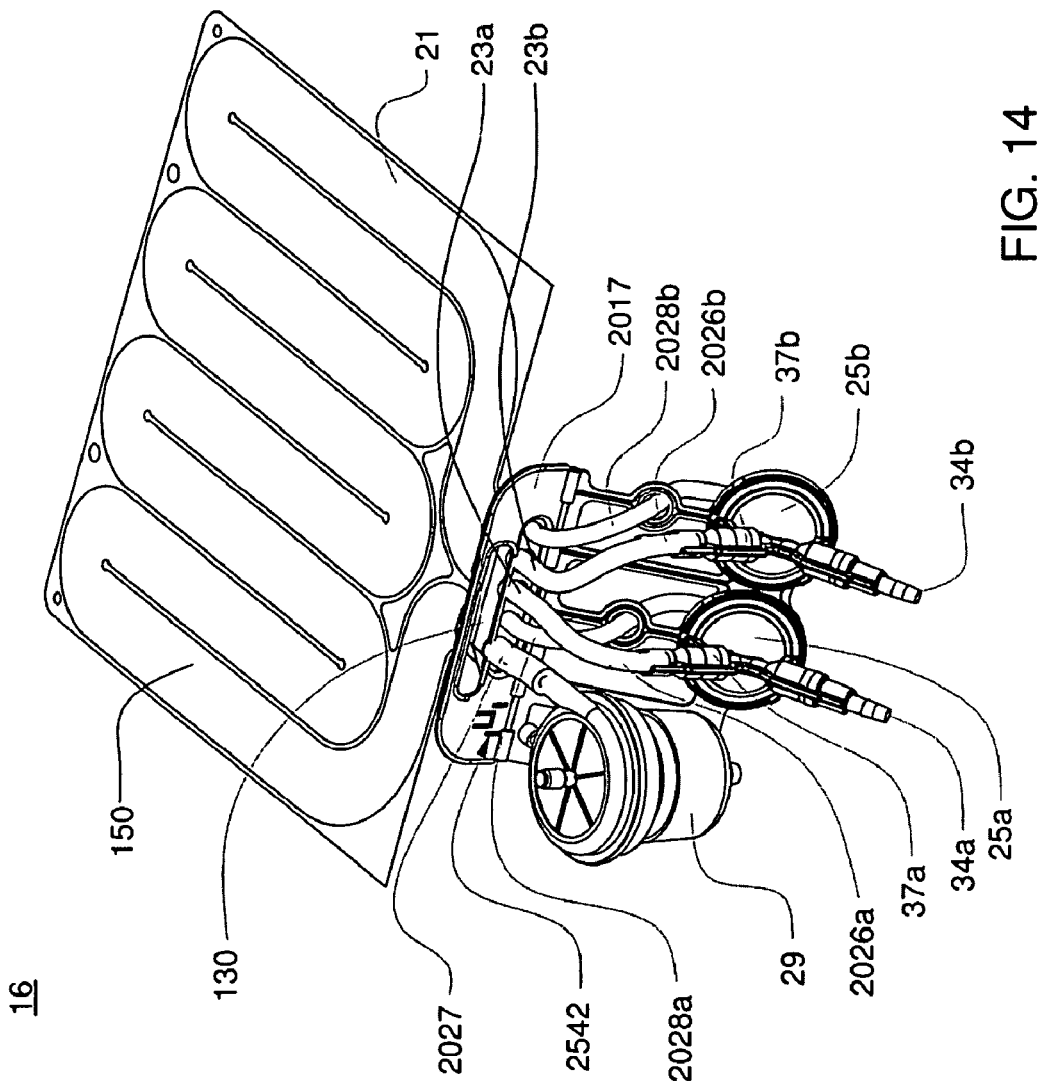
FIG. 14 shows an exemplary disposable unit in accordance with an exemplary embodiment of the present invention.

In the embodiment shown in FIG. 14 two individual self-contained pod pumps 25a and 25b of the type shown in FIG. 5 are included in a disposable system, including a filter 29 and a blood conduit bag 21 for a heat exchanger. In this embodiment, each of the pod pumps 25a and 25b has its own pneumatic port 38, so the pod pumps 25a and 25b can be controlled separately.

Figure 15A:
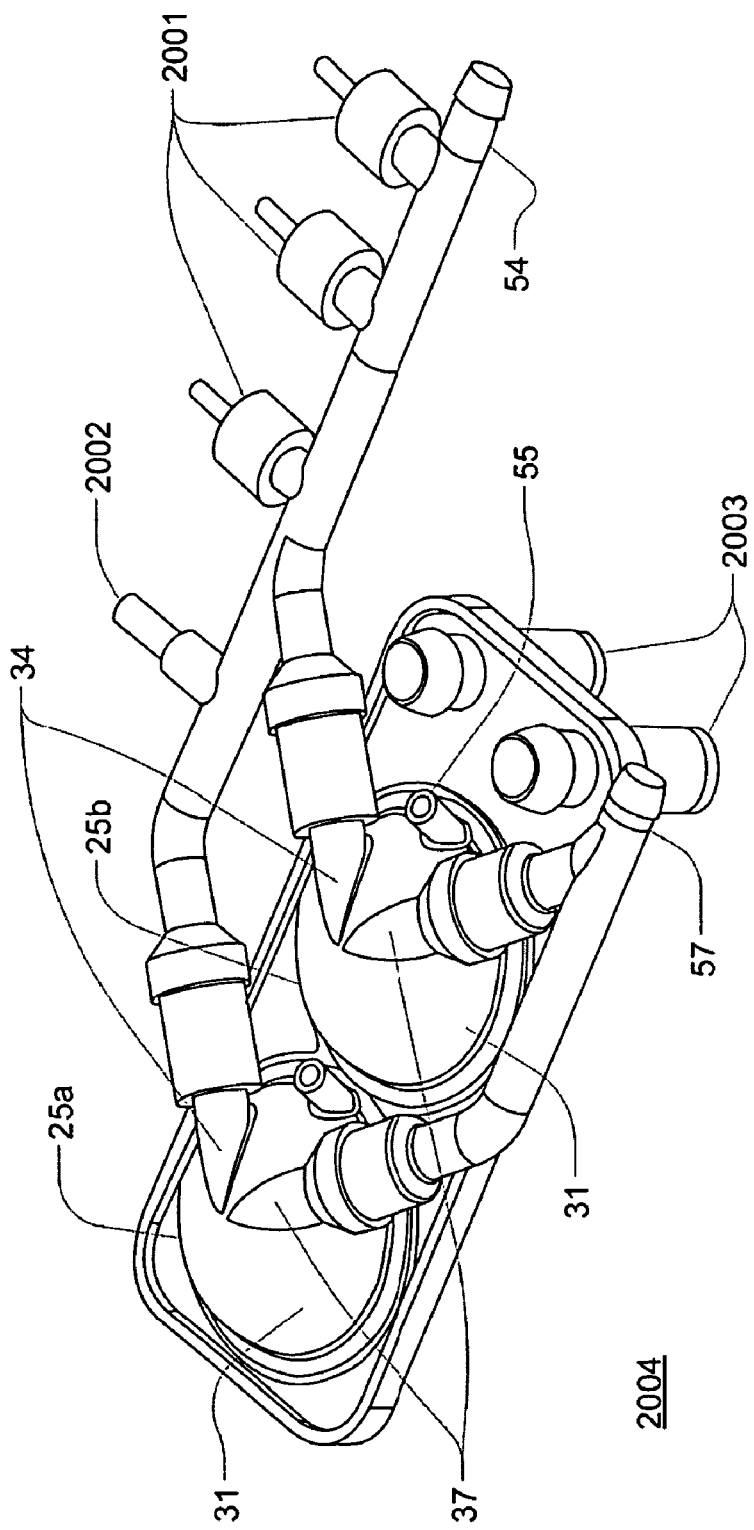
FIGS. 15A-15B are respectively upper and lower perspective views of an alternative embodiment of a pod pump arrangement.
Figure 15B:
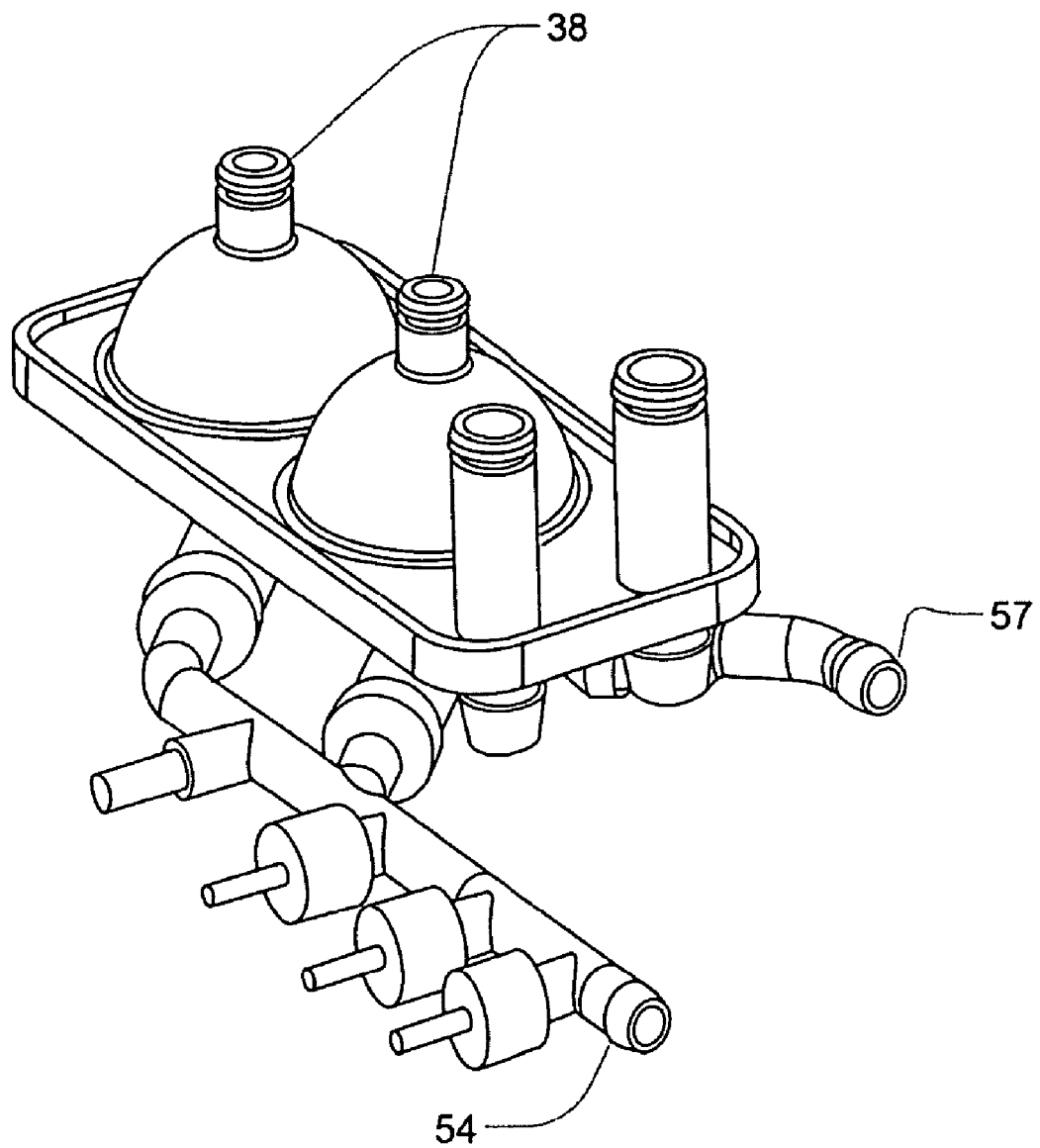

In the embodiment shown in FIGS. 15A and 15B, two pod pumps 25a and 25b are incorporated into larger assembly 2004 such that the inlets of two pod pumps 25a and 25b are connected to a common inlet line 54 and the outlets of both pod pumps 25a and 25b are connected to a common outlet line 57. FIG. 15B shows the pneumatic ports 38 of the pod pumps 25a and 25b. The inlets 34 and outlets 37 of the pod pumps 25a and 25b are arranged to direct the flows into and out of the pumping chambers at angles that are substantially tangential with the rigid pumping-chamber walls 31 of each pod pump, in order to reduce shear force and turbulence on the fluid and to improve circulation through the pumping chambers. In this embodiment, the pod pumps 25a and 25b have purge ports 55, which allow air to be purged from the system, for example, during priming. Also in this embodiment, the common inlet line 54 is fitted with a number of luer ports 2001 (e.g., to permit attachment of additional fluid sources, such as medical solutions, chemical solutions, diluants, etc.) and is also fitted with a thermocouple 2002 (e.g., to allow for monitoring the temperature of the fluid entering the pod pumps 25a and 25b). Also in this embodiment, the assembly 2004 includes two flow-through ports 2003 having tube connections on the top side (shown in FIG. 15A) and o-ring connections on the bottom side (shown in FIG. 105B). The flow-through ports 2003 can be used to facilitate installation or use of the assembly 2004 with a base station, for example, by allowing all pneumatic and fluidic connections to be made from the bottom of the assembly 2004, in which case the inlet line 54 may be pre-connected via tubing to one of the flow-through ports 2003 and the outlet line 57 may be pre-connected via tubing to the other flow-through port 2003.

Figure 16A:
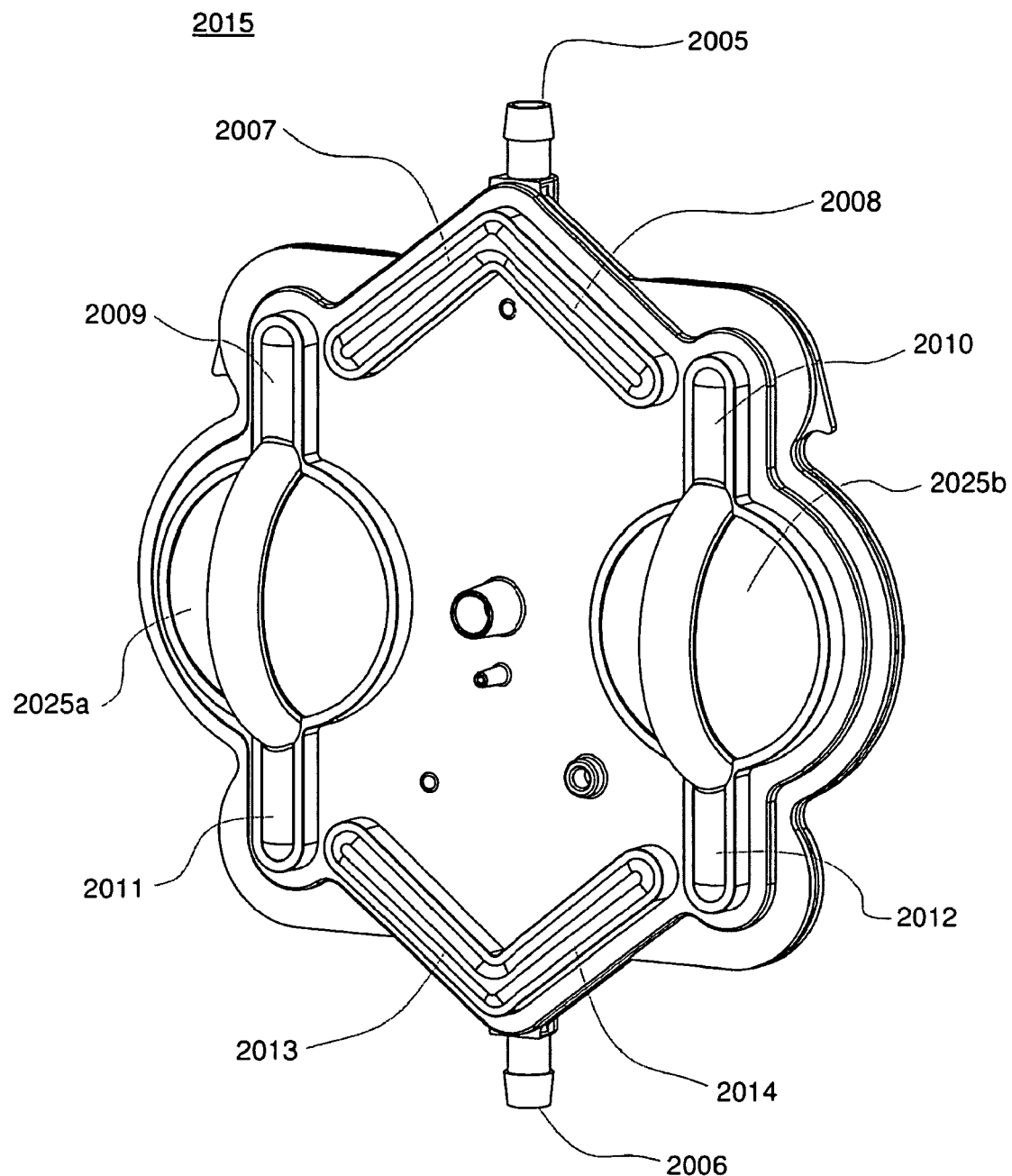
FIGS. 16A-16B show a pump cassette incorporating two pod pumps of the type shown in FIG. 8 and a number of valves of the type shown in FIG. 9 along with various fluid paths and other components, in accordance with an exemplary embodiment of the present invention.
Figure 16B:
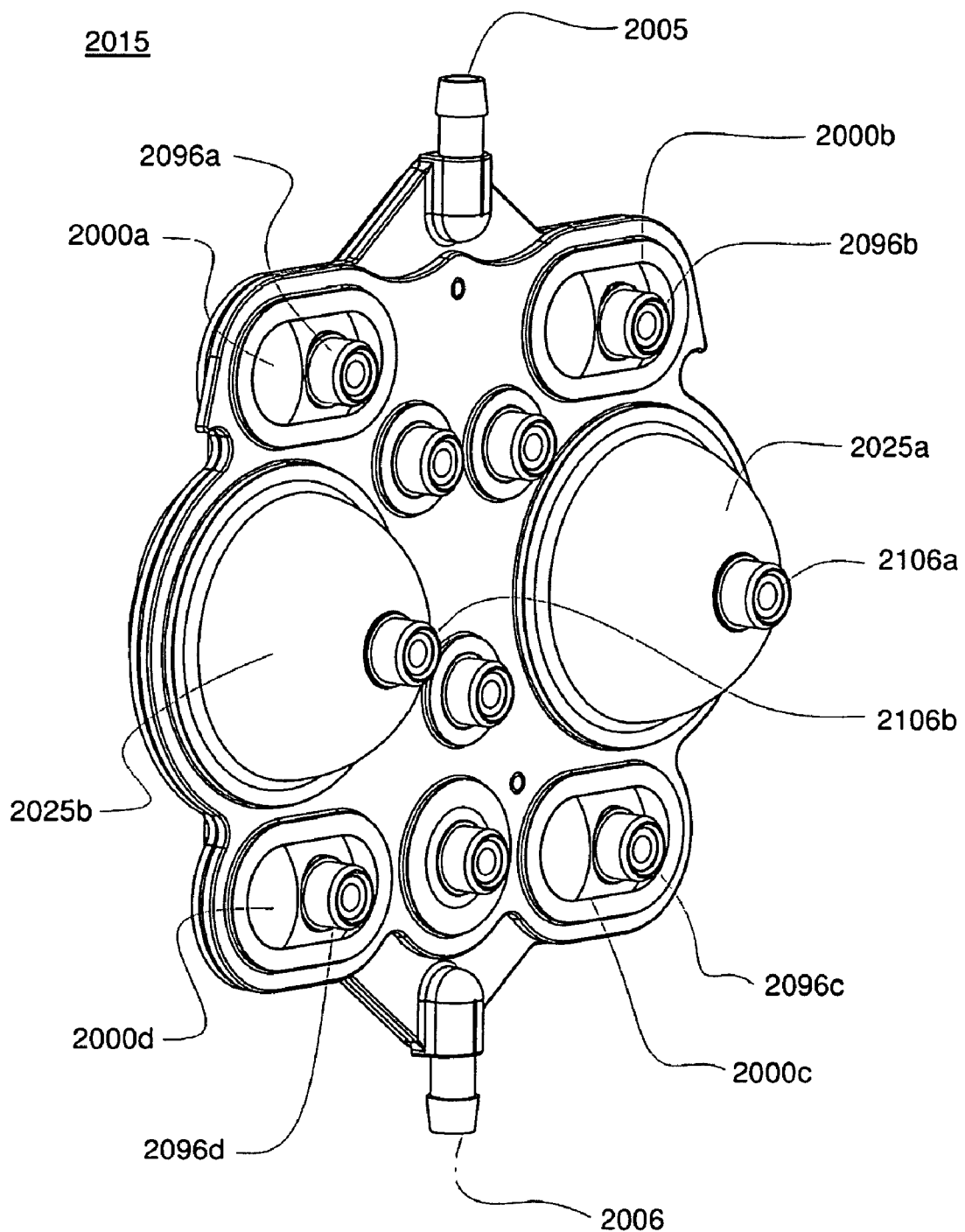

In the embodiment shown in FIGS. 16A and 16B, two pod pumps 2025a and 2025b of the type shown in FIG. 12A-12C and a number of valves 2000a-2000d of the type shown in FIG. 9 are incorporated in a pump cassette 2015 along with various fluid paths and other components. The pump cassette 2015 includes a common inlet 2005 in fluid communication with pod pump 2025a via fluid paths 2007 and 2009 and with pod pump 2025b via fluid paths 2008 and 2010. The pump cassette 2015 also includes a common outlet 2006 in fluid communication with pod pump 2025a via fluid paths 2011 and 2013 and with pod pump 2025b via fluid paths 2012 and 2014. Thus, pod pumps 2025a and 2025b draw fluid from the common inlet 2005 and pump fluid to the common outlet 2006. That being said, valve 2000a is used to control fluid flow at the intersection of fluid paths 2008 and 2010 (i.e., at the inlet to pod pump 2025b); valve 2000b is used to control fluid flow at the intersection of fluid paths 2007 and 2009 (i.e., at the inlet to pod pump 2025a); valve 2000c is used to control fluid flow at the intersection of fluid paths 2011 and 2013 (i.e., at the outlet of pod pump 2025a); and valve 2000d is used to control fluid flow at the intersection of fluid paths 2012 and 2014 (i.e., at the outlet of pod pump 2025b). Each of the pod pumps 2025a and 2025b has its own pneumatic interface 2106a and 2106b, respectively. Also, each of the valves 2000a-2000d has its own pneumatic interface 2096a-2096d, respectively. Thus, each of pod pumps and each of the valves can be independently controlled by a base station.

In an embodiment, there are recesses or channels within the rigid inner wall of the pumping chambers of pod pumps 2025a and 2025b. In the case of pump 2025a, the channel fluidly connects inlet fluid path 2009 with outlet fluid path 2011. In the case of pump 2025b, the channel fluidly connects inlet fluid path 2010 with outlet fluid path 2012. These channels permit the blood to continue to flow from the inlet path to the outlet path of each pump even when the pump membrane has reached the end of its delivery stroke. This feature helps to reduce any damage to red cells caused by the shear forces generated by the membrane as it reaches the end of its stroke. In addition, it provides an outlet for fluid pockets that may form within the pump chamber due to uneven membrane movement (or membrane buckling) and premature closure over the pump chamber outlet.

Figure 17:
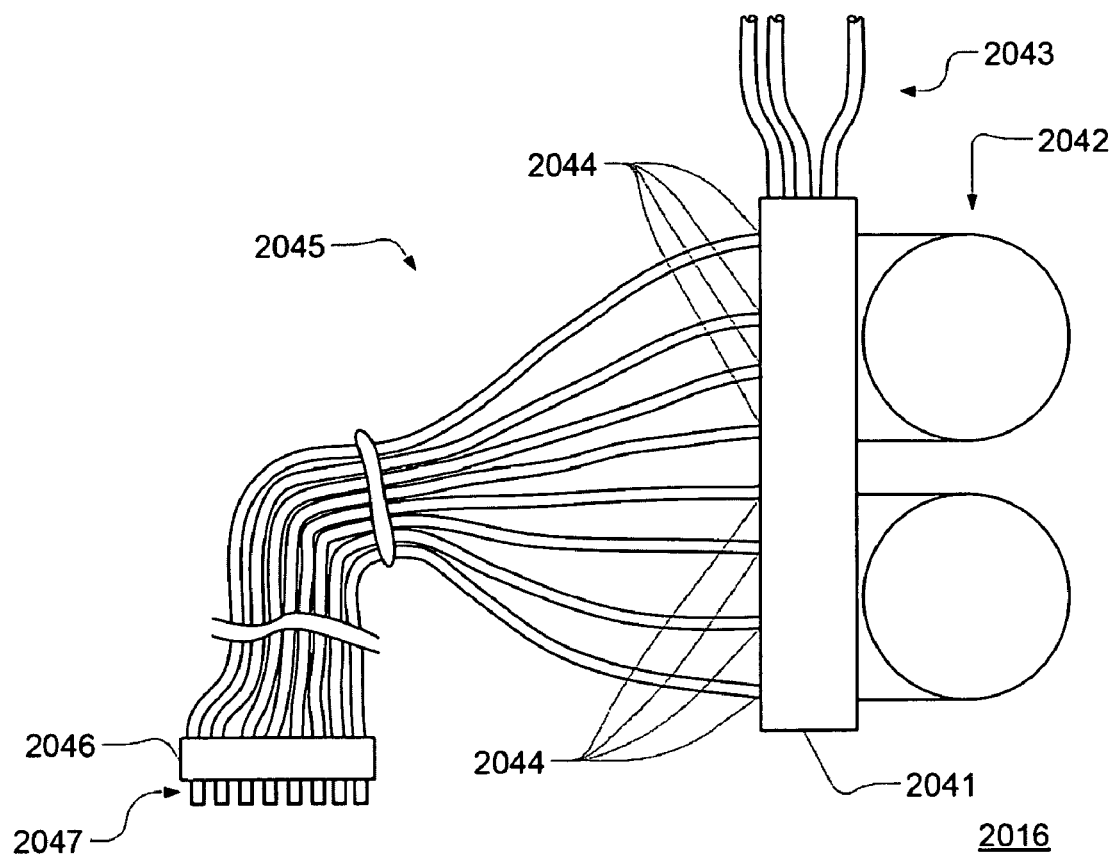
FIG. 17 is a schematic representation of dual-housing cassette arrangement according to one embodiment.

FIG. 17 is a schematic representation of dual-housing arrangement 2016 according to another embodiment of the invention. This arrangement may be advantageously used with disposable cassettes that include many pneumatically actuated pumps and/or valves. If the number of pneumatically actuated pumps and/or valves in a cassette is large enough, the cassette containing these pumps and valves can become so large—and the pump pressures so great—that it may become difficult to properly seal and position all of the pumps and valves. This difficulty may be alleviated by using two different housings. The valves and pumps (such as pod pumps 2042) are placed in a main housing 2041, from which connecting tubes 2045 lead from pneumatic ports 2044. The main housing 2041 also has inlet and outlet tubes 2043, which allow liquid to flow into and out of the main housing. The connecting tubes 2045 provide pneumatic communication between valves and pumps in the main housing 2041 and a smaller, secondary tube-support housing 2046, which is provided with a pneumatic interface 2047 for each of the tubes. The proper positioning and sealing of all the pneumatic interfaces 2047 against receptacles in the base unit can be accomplished more easily with the smaller tube-support housing 2046 than it would be if the pneumatic actuation was applied to the larger main housing directly.

Alternative Chamber Configurations and Stroke Sizes

It should be noted that pod pumps of the types described above can be configured with different chamber configurations and/or different stroke sizes. Thus, for example, pod pumps having different pump volumes may be provided. Furthermore, pod pumps having different pump volumes may be provided with a standardized pneumatic port configuration (and perhaps standardized control chamber wall configuration) so that pod pumps having different volumes may be easily swapped into and out of a common pumping system or apparatus (e.g., a base unit) having a corresponding standardized pneumatic port interface. For example, the base unit may be able to receive lower-volume pod pumps for pediatric use and receive higher-volume pod pumps for adult use. The pneumatic ports are preferably adapted to be quickly and easily connected to—and disconnected from—the pneumatic actuation system of the base unit. In certain embodiments, the pod pumps may be considered to be disposable and may be provided individually or as part of a larger disposable system.

Thus, for example, in the embodiment shown in FIG. 14, disposable systems include two self-contained pod pumps 25a and 25b, a filter 29, and a bag 21 adapted for use with a heat exchanger. Different versions of such disposable systems having pod pumps of different pump volumes could be provided for different applications (e.g., one version with smaller pump volumes for children, another version with larger pump volumes for adults). Similarly, in the embodiment shown in FIGS. 15A and 15B, different versions of the assembly 2004 having pod pumps of different pump volumes could be provided, and in the embodiment shown in FIGS. 16A and 16B, different versions of the cassette 2015 having pod pumps of different pump volumes could be provided. Similarly, in the embodiment shown in FIG. 17, different versions of the main housing 2041 having pod pumps of different pump volumes could be provided for use with a common secondary tube-support housing 2046.

The pumping chamber wall may be molded, formed, produced, or otherwise configured with various features facilitate intake, circulation, and/or delivery of the fluid. For example, the inside wall of the pumping chamber may include certain features or materials to help induce circular flow, induce smooth/laminar flow, reduce boundary layer effects, or even produce turbulence (e.g., to facilitate mixing of materials or prevent coagulation within the pumping chamber).

Pressure Actuation Systems for Membrane-Based Pod Pumps

Figure 18:
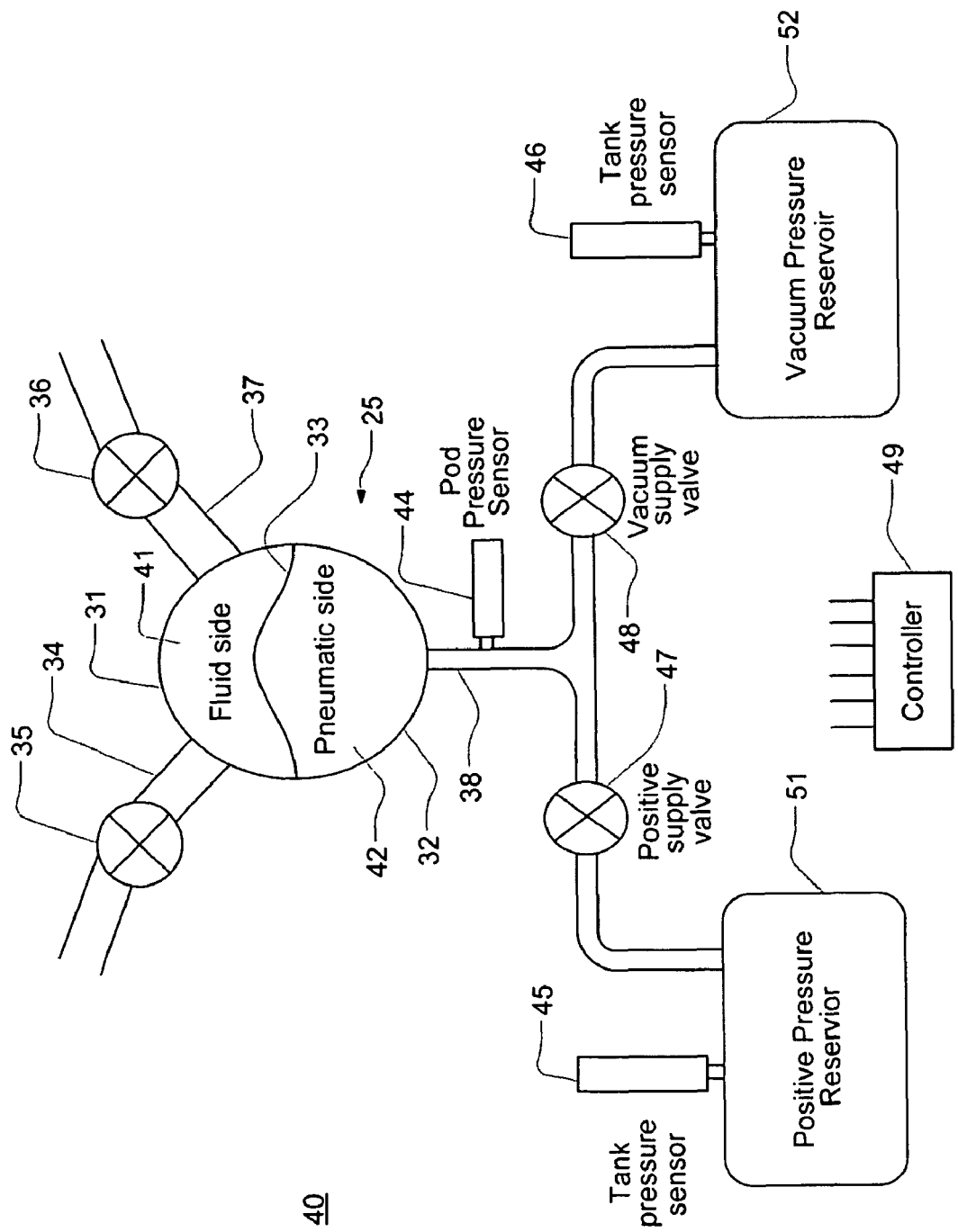
FIG. 18 is a schematic showing a pressure actuation system that may be used to actuate the pod pump shown in FIG. 5.

FIG. 18 is a schematic showing an embodiment of a pressure actuation system 40 that may be used to actuate a pod pump, such as the pod pump 25 shown in FIG. 5. The pressure actuation system 40 is capable of intermittently or alternately providing positive and negative pressurizations to the gas in the control chamber 42 of the pod pump 25. The pod pump 25—including the flexible membrane 33, the inlet 34, the outlet 37, the pneumatic port 38, the pumping chamber 41, the control chamber 42, and possibly including an inlet check valve 35 and an outlet check valve 36 or other valves—may be part of a larger disposable system. The pneumatic actuation system 40—including a control-chamber pressure transducer 44, a positive-supply valve 47, a negative-supply valve 48, a positive-pressure gas reservoir 51, a negative-pressure gas reservoir 52, a positive-pressure-reservoir pressure transducer 45, a negative-pressure-reservoir pressure transducer 46, as well as an electronic controller 49 including a user interface console (such as a touch-panel screen)—may be part of a base unit.

The positive-pressure reservoir 51 provides to the control chamber 42 the positive pressurization of a control gas to urge the membrane 33 towards a position where the pumping chamber 41 is at its minimum volume (i.e., the position where the membrane is against the rigid pumping-chamber wall 31). The negative-pressure reservoir 52 provides to the control chamber 42 the negative pressurization of the control gas to urge the membrane 33 in the opposite direction, towards a position where the pumping chamber 41 is at its maximum volume (i.e., the position where the membrane is against the rigid control-chamber wall 32).

A valving mechanism is used to control fluid communication between each of these reservoirs 51, 52 and the control chamber 42. In FIG. 18, a separate valve is used for each of the reservoirs; a positive-supply valve 47 controls fluid communication between the positive-pressure reservoir 51 and the control chamber 42, and a negative-supply valve 48 controls fluid communication between the negative-pressure reservoir 52 and the control chamber 42. These two valves 47, 48 are controlled by the controller 49. Alternatively, a single three-way valve may be used in lieu of the two separate valves 47, 48. The valves 47, 48 may be binary on-off valves or variable-restriction valves.

The controller 49 also receives pressure information from the three pressure transducers shown in FIG. 18: a control-chamber pressure transducer 44, a positive-pressure-reservoir pressure transducer 45, and a negative-pressure-reservoir pressure transducer 46. As their names suggest, these transducers respectively measure the pressure in the control chamber 42, the positive-pressure reservoir 51, and the negative-pressure reservoir 52. The control-chamber-pressure transducer is located in the base unit but is in fluid communication with the control chamber 42 through the pneumatic port 38 of the pod pump. The controller 49 monitors the pressure in the two reservoirs 51, 52 to ensure they are properly pressurized (either positively or negatively). In one exemplary embodiment, the positive-pressure reservoir 51 may be maintained at around 750 mmHG, while the negative-pressure reservoir 52 may be maintained at around (−) 450 mmHG.

A compressor-type pump or pumps (not shown) may be used to maintain the desired pressures in these reservoirs 51, 52. For example, two independent compressors may be used to respectively service the reservoirs 51, 52. Pressure in the reservoirs 51, 52 may be managed using a simple bang-bang control technique in which the compressor servicing the positive-pressure reservoir 51 is turned on if the pressure in the reservoir 51 falls below a predetermined threshold and the compressor servicing the negative-pressure reservoir 52 is turned on if the pressure in the reservoir 52 is above a predetermined threshold. The amount of hysteresis may be the same for both reservoirs or may be different. Tighter control of the pressure in the reservoirs can be achieved by reducing the size of the hysteresis band, although this will generally result in higher cycling frequencies of the compressors. If very tight control of the reservoir pressures is required or otherwise desirable for a particular application, the bang-bang technique could be replaced with a proportional-integral-derivative (PID) control technique and could use pulse width modulation (PWM) signals on the compressors.

The pressure provided by the positive-pressure reservoir 51 is preferably strong enough—under normal conditions—to urge the membrane 33 all the way against the rigid pumping-chamber wall 31. Similarly, the negative pressure (i.e., the vacuum) provided by the negative-pressure reservoir 52 is preferably strong enough—under normal conditions—to urge the membrane all the way against the control-chamber wall 32. In a further preferred embodiment, however, these positive and negative pressures provided by the reservoirs 51, 52 are within safe enough limits that even with either the positive-supply valve 47 or the negative-supply valve 48 open all the way, the positive or negative pressure applied against the membrane 70 is not so strong as to damage the pod pump or create unsafe fluid pressures (e.g., that may harm a patient receiving pumped blood or other fluid).

Although a two-reservoir pneumatic actuation system as shown in FIG. 18 is generally preferred, other types of actuation systems may be used to move the membrane back and forth. For example, alternative pneumatic actuation systems may include either a single positive-pressure reservoir or a single negative-pressure reservoir along with a single supply valve and a single tank pressure sensor, particularly in combination with a resilient diaphragm. Such pneumatic actuation systems may intermittently provide either a positive gas pressure or a negative gas pressure to the control chamber of the pod pump. In embodiments having a single positive-pressure reservoir, the pump may be operated by intermittently providing positive gas pressure to the control chamber, causing the diaphragm to move toward the pumping chamber wall and expel the contents of the pumping chamber, and releasing the gas pressure, causing the diaphragm to return to its relaxed position and draw fluid into the pumping chamber. In embodiments having a single negative-pressure reservoir, the pump may be operated by intermittently providing negative gas pressure to the control chamber causing the diaphragm to move toward the control chamber wall and draw fluid into the pumping chamber, and releasing the gas pressure, causing the diaphragm to return to its relaxed position and expel fluid from the pumping chamber.

Active Inlet/Outlet Valves

As discussed above, active valves may be used instead of passive check valves at the pod pump inlet and output. Active valves would allow for greater control and flexibility (generally at the expense of added complexity and cost). Among other things, active valves would allow for reversal of fluid flow, which could be used, for example, to facilitate priming, air purging, and/or detection and mitigation of certain conditions (e.g., occlusion, blockage, leakage, line disconnect). With regard to detection of a line disconnect, a reversal of flow may cause air to be drawn into the pumping chamber through the outlet if the outlet line is disconnected. Such air flow could be detected using any of a variety of techniques, including the amount of work needed to move the pump diaphragm. If the line is safely connected, some amount of work would normally be necessary to reverse flow and draw fluid in through the outlet, whereas if the return line has been disconnected, much less work would generally be necessary to reverse flow, since the pump would be drawing air into the return line. If upon reversing flow, the controller detects an aberrant flow condition, the controller would preferably cause the system to stop pumping blood from the patient.

During normal pump operations, the active valves generally would be operated as follows. During a fill stroke, when fluid is drawn into the pumping chamber, the controller 49 would typically open the inlet valve and close the outlet valve so as to allow fluid to enter the pumping chamber through the inlet but prevent fluid from being drawn back in from the outlet. During a delivery stroke when fluid is pumped out of the pumping chamber (e.g., after the pumping chamber is full or at other appropriate times), the controller 49 would generally close the inlet valve and open the outlet valve so as to allow fluid to be pumped out of the outlet but prevent fluid from being pumped back through the inlet. Between strokes, the controller 49 may cause both the inlet valve and the outlet valve to be closed for some time interval.

For those embodiments in which pneumatically actuated inlet and outlet valves (e.g.; binary on-off valves either integral to the pod pump or external to the pod pump) are used in place of passive inlet and outlet check valves, such valves may be coupled to the positive and/or negative pressure reservoirs 51, 52 through appropriate supply valves actuated by the controller 49.

The use of active inlet and outlet valves can facilitate detection of air in the pumping chamber. For example, following a full draw stroke to bring the pumping chamber to its maximum volume, positive pressure can be applied to the control chamber and the rate at which the pressure in the control chamber (or the pumping chamber) increases can be monitored. If the pumping chamber is full of air, then the pressure should increase more gradually, as the air in the pumping chamber will allow the diaphragm to move more readily. If, however, the pumping chamber is full of liquid, then the pressure should increase more rapidly because the pump diaphragm will be held more firmly by the uncompressible liquid.

Control of Membrane-Based Pod Pumps

During normal pumping operations, the controller 49 typically monitors the pressure information from the control-chamber-pressure transducer 44 and, based on this information, controls the valving mechanism (valves 47, 48) to urge the membrane 33 all the way to its minimum-pumping-chamber-volume position and then after this position is reached to pull the membrane 33 all the way back to its maximum-pumping-chamber-volume position. In this embodiment, volume may be measured by counting full strokes of fluid delivery (e.g., volume=number of fill strokes×pumping chamber volume).

In typical embodiments of the invention, the controller may be able to detect the end of a stroke, i.e., when the membrane reaches one of the rigid pumping-chamber or control-chamber walls. Referring to FIG. 18, an expel stroke is started by opening positive-supply valve 47, thereby resulting in positive pressure being exerted against the membrane 33. Preferably, the positive-supply valve 47 is cycled on and off (dithered) to create a ripple in the control chamber's pressure as long as the membrane 33 is moving. When the membrane 33 reaches the pumping-chamber wall 31 the pressure ripple stops. The controller 49, receiving pressure information from control-chamber-pressure transducer 44, monitors this pressure ripple and detects the end of stroke when this pressure ripple stops.

When the controller 49 detects the end of the expel stroke, the controller closes positive-supply valve 47 and dithers the negative-supply valve 48, thereby causing a vacuum to be applied to the membrane 33. The same process followed in the expel stroke is repeated for the fill stroke. The controller determines the time to complete each stroke and uses that information to calculate flow rate. The flow rate information is then used to set the commands for pressure and valving for the next stroke.

The controller 49 sets the flow rate using a timed sequence of alternately applying positive pressure and vacuum to the membrane 33. A positive pressure will be applied for a determined time interval to achieve a desired delivery (i.e., expelling) flow rate. When this time interval has expired, a vacuum is applied to achieve a fill flow rate. This control of time intervals can be an open-loop system without feedback on flow rate; thus, there can be delays between the end of one stroke and the start of another. Such an open-loop time-based system may be used when closed-loop systems based on flow-rate will not operate properly, such as during priming when there is a mixture of liquid and air in the pod pumps.

As mentioned above, a stroke is preferably effected by delivering a sequence of pressure pulses (forming a pressure ripple) to the membrane 33. The speed of a stroke can be adjusted by changing how frequently a supply valve is opened and/or by changing how long it is opened each time it is opened. A pressure pulse involves opening the valve between the control chamber and the reservoir for a fixed time and then closing it for the rest of the pulse period. The total length of a pressure pulse is 1/(pulse pumping frequency). In one embodiment, the pulse pumping frequency increases from 2 Hz to 16 Hz as the controller's pumping command increases from 0 to 100%. The minimum frequency of 2 Hz is intended to ensure a minimum flow rate is met when there is water in the system. A maximum frequency of 16 Hz is intended to correspond to the minimum time required for the valve to be at a 50% duty cycle. The pumping algorithm preferably divides a stroke into two periods, the initial pumping period and the end-of-stroke period. During the initial pumping period, the valve open time of the pressure pulse is preferably 166 ms (100% duty cycle at 16 Hz). Thus, with a maximum command from the controller, the valve to the reservoir is always open. The number of pressure pulses in the initial period is increased from one to ten as the pumping command increase from zero to 100%.

End-of-Stroke Detection

Figure 19:
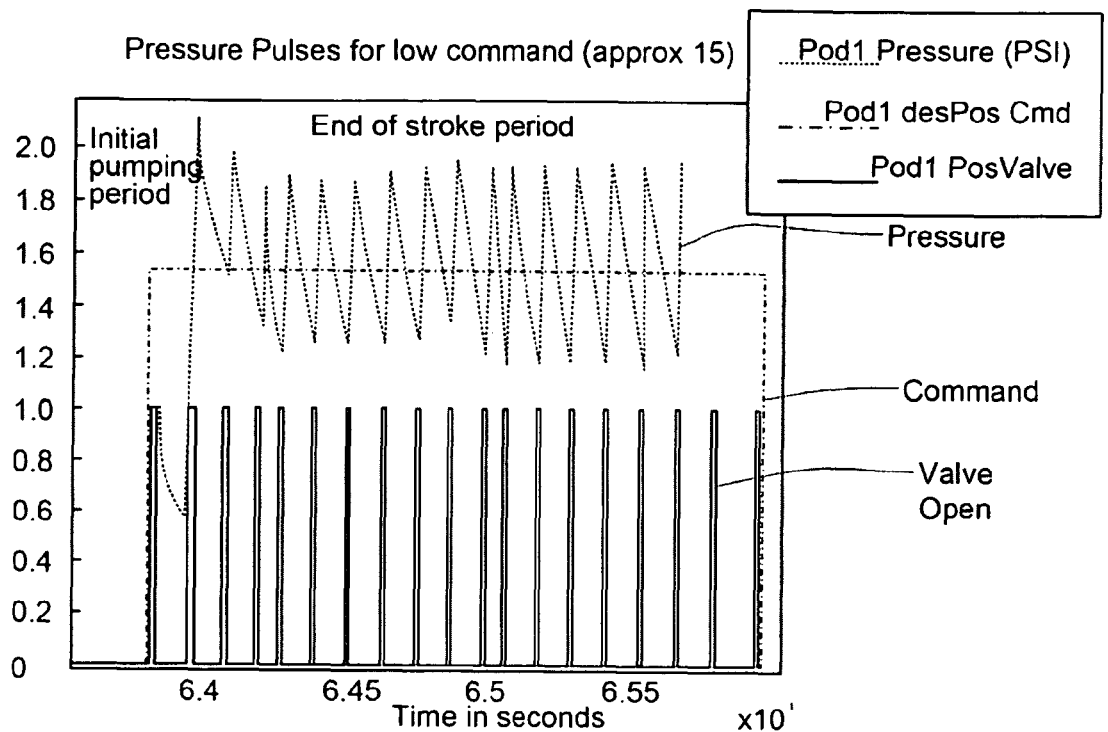
FIGS. 19-20 are graphs showing how pressure measurements can be used detect the end of a stroke, in one embodiment.
Figure 20:
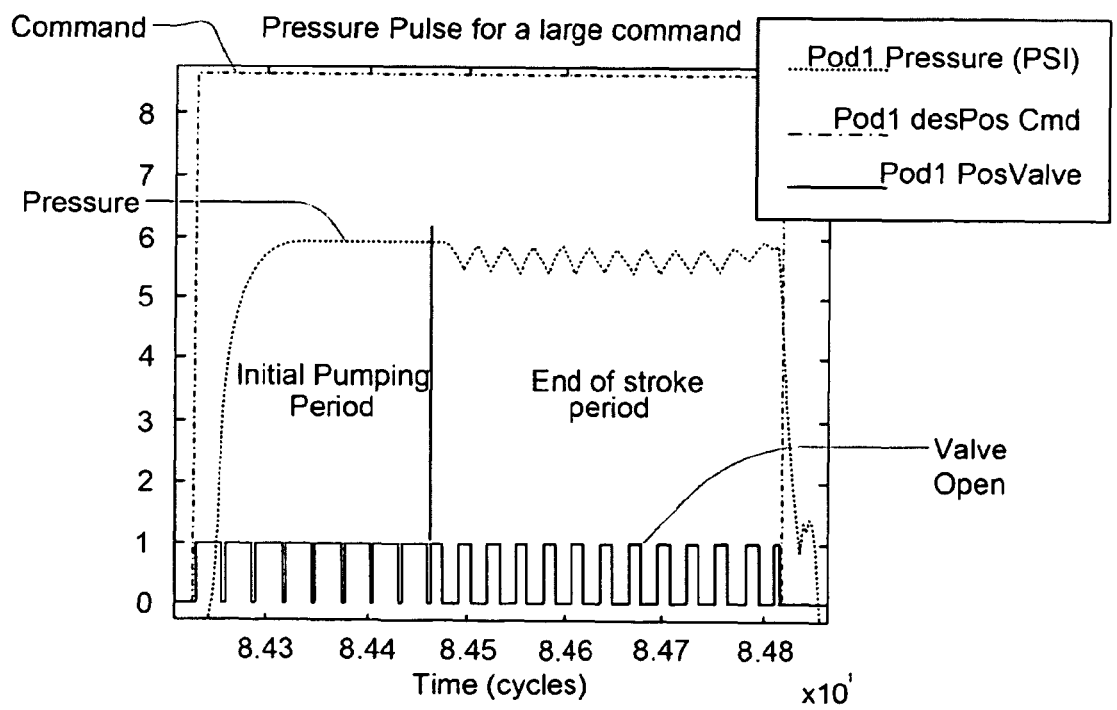

After the initial pumping period, there is a transition to the end-of-stroke pumping period. In this respect, software filters are preferably used to determine when a stroke ends, with at least five pressure pulses used in the end-of-stroke period for the end-of-stroke filters to initialize. The end-of-stroke period ends when the end of stroke is detected. During the end-of-stroke period, the valve open time of the pressure pulse is preferably 83.3 ms (50% duty cycle at 16 Hz). FIGS. 19 and 20 show the pressure pulses during the initial and end-of-stroke periods. FIG. 19 shows pressure pulses for a low-flow command by the controller, and FIG. 20 shows a pressure pulse for a large-flow command by the controller. Note that the on time for a pulse is much longer for higher commands.

The pressure pulses generate a ripple in the measured pressure in the control chamber while the membrane is moving. By filtering and isolating this pressure ripple, the end-of-stroke algorithm can detect when the diaphragm has reached the chamber wall and stopped moving. This end-of-stroke information may be used for flow calculations and for sequencing the pod pumps for fill and expel strokes. If the end of a stroke does not actually occur within a predetermined number of pressure pulses, the controller preferably generates an error signal. Excessive time to complete a stroke may indicate a pneumatic leak, a condition that can be monitored during priming as well as during the CPB procedure.

The controller can also detect aberrant flow conditions by integrating the pressure readings over time to obtain a measure of the work done in moving the liquid. If the amount of work done goes up or down, the controller preferably generates an alarm signal indicating that something has gone wrong in the line, such as an occlusion, a leak, or a disconnect. The ability to rapidly detect a disconnect or a leak may be important, particularly when pumping blood or other critical fluids, because of the relatively large flow rates of fluids being pumped. In one embodiment, by integrating the pressure readings and determining the work function, the controller can detect a line disconnect within approximately three seconds.

As discussed above, preferred systems will also include an end of stroke detection procedure to determine when liquid has stopped flowing into the pump chamber and when liquid has stopped flowing out of the pump chamber during filling and delivery strokes respectively. This end of stroke detection methodology is described in detail in commonly owned co-pending application Ser. No. 09/108,528, which is hereby incorporated by reference in its entirety. Briefly, in preferred embodiments, pump drive system 502 of FIG. 23 continuously monitors and controls the pressure of measurement gas in control chamber 110 during filling and dispensing of liquid from pump chamber 108. The system can detect the end of stroke as follows.

During the filling or delivery step, processor 506 controls variable size orifice valve 536 so that the pressure of measurement gas in control chamber 110 has an average value essentially equal to the desired delivery or fill pressure, superimposed on which is a cyclically varying, low-amplitude variation in the pressure. For example, for a fill or delivery pressure in the range of a few psig, the superimposed variable component can have an amplitude that differs from the average target pressure by, for example, +/−about 0.05 psig, varying at a frequency of, for example, about 1 Hz. While the pump chamber 108 is filling or emptying, flexible membrane 112 will be in motion, and the system will detect the cyclical variations in pressure discussed above. However, at the end of a stroke, when the membrane is essentially no longer free to move in at least one direction and when liquid flow into or out of the pump chamber has essentially stopped, the pressure in control chamber 110 will no longer be able to be cyclically varied as described above. The system can detect this condition by continuously monitoring the pressure signal, for example, from transducer 122 on control chamber 110. The pressure signal can then be differentiated with respect to time, and an absolute value of the differentiated signal can be taken. The absolute value of the differentiated pressure signal can then be compared to a minimum threshold value. At the end of the stroke, when the pressure in control chamber 110 is no longer cyclically varying, a derivative of the pressure with respect to time will approach zero; therefore, by comparing the time derivative to a minimum threshold value, the system can determine when flexible membrane 112 has reached the end of its stroke. The system can then discontinue filling or dispensing. In preferred embodiments, in order to smooth the signal and derive a more stable value, the absolute value of the derivative of the pressure signal with respect to time is first subjected to a low pass filter before comparing to the threshold value.

Preferred pumping systems according to the invention are also able to detect a line blockage or occlusion in the inlet or outlet line of pump chamber 108 during operation, and are able to create an alarm condition and, in some embodiments, shut down the pumping cycle, when such blockage or occlusion is detected. Such a no-flow condition is detected by the system by comparing the volume of liquid delivered during the pump delivery stroke and the volume of liquid filling the pump chamber during the pump chamber filling stroke and comparing the volume, determined as described above, to the known minimum and maximum volumes for the pump chamber respectively. The system can then determine if the volume of liquid delivered by the pump chamber or the volume of liquid entering the pump chamber differs significantly from the volumes expected for a full stroke. If so, the system can create an alarm condition indicating a no/low flow condition or occlusion in the line exists. The no/low flow condition threshold value can be set based on the needs of the various applications of the inventive pumping systems and can be, in some embodiments, about one half of the maximum stroke volume of the pump chamber. In applications in which extracorporeal blood flow should not be interrupted, such as cardiopulmonary bypass applications, a no/low flow condition in one pump can trigger both an alarm condition and a preprogrammed recruitment of a secondary pump to maintain the required blood flow rate, pending relief of the obstructing condition or replacement of the affected pump.

Pulsed Output

In certain embodiments, it is possible to provide an alternative way of operating a pump chamber for delivering a liquid with improved accuracy and precision, which is particularly useful when delivering very small quantities of liquid, liquid at very low average flow rates, and in other circumstances in which precise measurement is needed. An exemplary method includes: filling the pump chamber with a liquid, isolating the pump chamber, applying a force to the flexible membrane or moveable surface of the pump chamber, and regulating the flow of liquid from the pump chamber while maintaining the force on the membrane or surface. For example, in the context of pumping system 500 shown in FIG. 23, the method may involve first filling pump chamber 108 with a liquid as described previously with respect to FIG. 28, closing inlet valve 116 and taking an initial volume measurement of the pump chamber, placing control chamber 110 in fluid communication with the positive pressure tank 508 and controlling the pressure in control chamber 110 at a desired value utilizing variable size orifice valve 536, and then selectively actuating outlet valve 120 on the outlet line 118 of the pump chamber 108 to open and close the valve for predetermined time periods at predetermined intervals while maintaining the desired delivery pressure in control chamber 110. Volume measurements of pump chamber 108 can be performed either after each pulse (opening and subsequent closing) of outlet valve 120, or, alternatively, can be performed after a series of pulses of the outlet valve over a measured cumulative time interval. In this fashion, the volume delivered per pulse or the average liquid flow rate over a series of pulses can be determined, and the system can be configured to adjust the length of the time periods during which outlet valve 120 is opened and to adjust the time intervals between the pulsed openings of outlet valve 120 in order to achieve a desired predetermined average liquid flow rate. While the pulsed delivery mode of delivering a liquid from a pump chamber has been described in the context of FIG. 23, any of the other systems previously described (and other systems, as well) can also be used to perform a pulsed delivery of liquid from a pump chamber.

Extracorporeal Blood Flow Management

Generally speaking, a single pod pump operates in a pulsatile fashion, first drawing in fluid and then pumping out fluid. Pulsatile operation may be necessary, desirable, or inherent in certain applications. Foe example, in certain types of extracorporeal blood treatment, blood is drawn from a patient and returned to the patient through a single needle. The flow in this case is inherently pulsatile, since blood generally cannot be drawn from the patient and pumped back into the patient at the same time through the single needle.

Figure 21A:
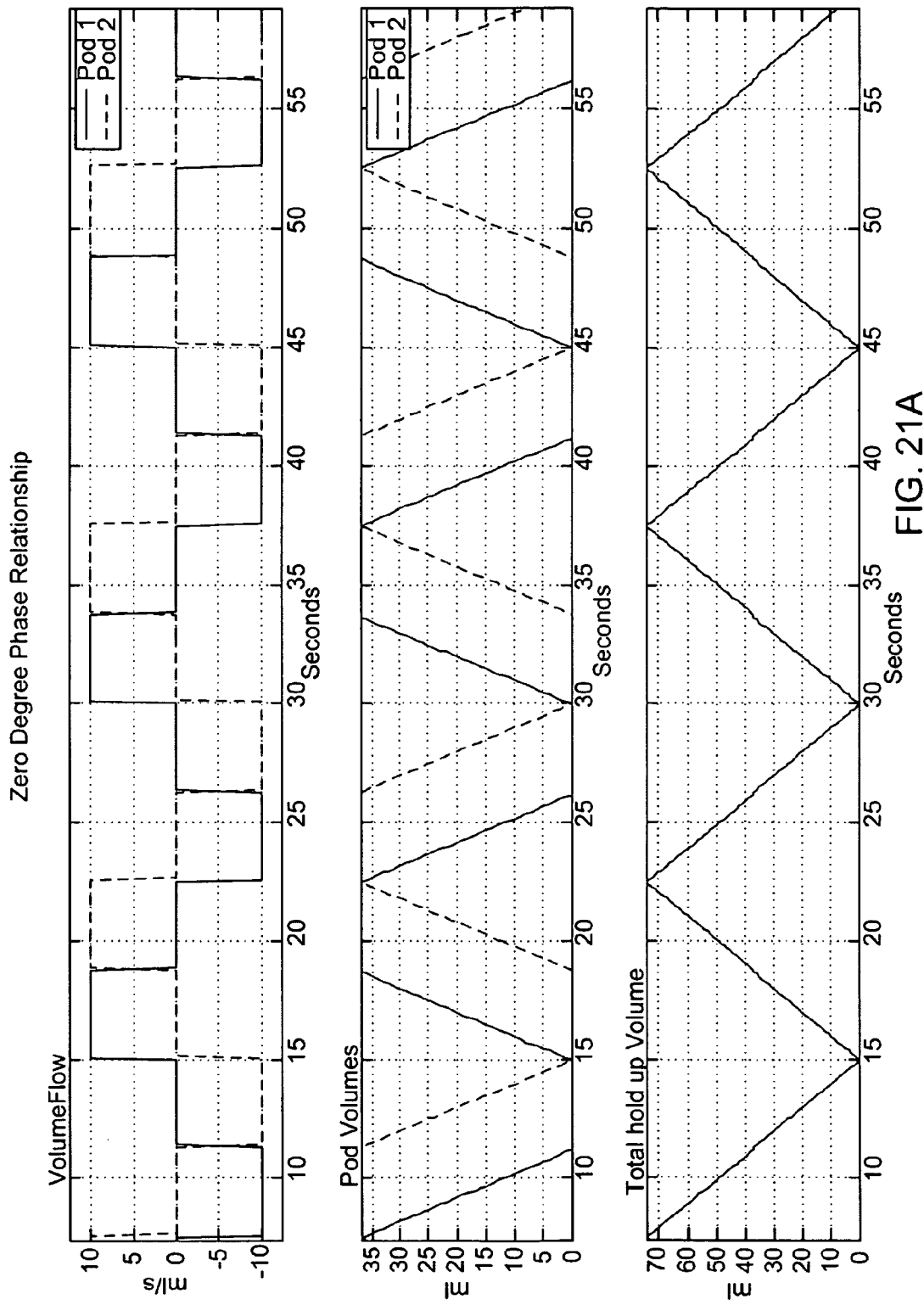
FIGS. 21A-21C show plots for volume flow, pod volumes, and total hold up flow for two pod pumps operating in a zero degree phase relationship, a 180 degree phase relationship, and a 90 degree phase relationship, respectively, in accordance with exemplary embodiments of the present invention.
Figure 21B:
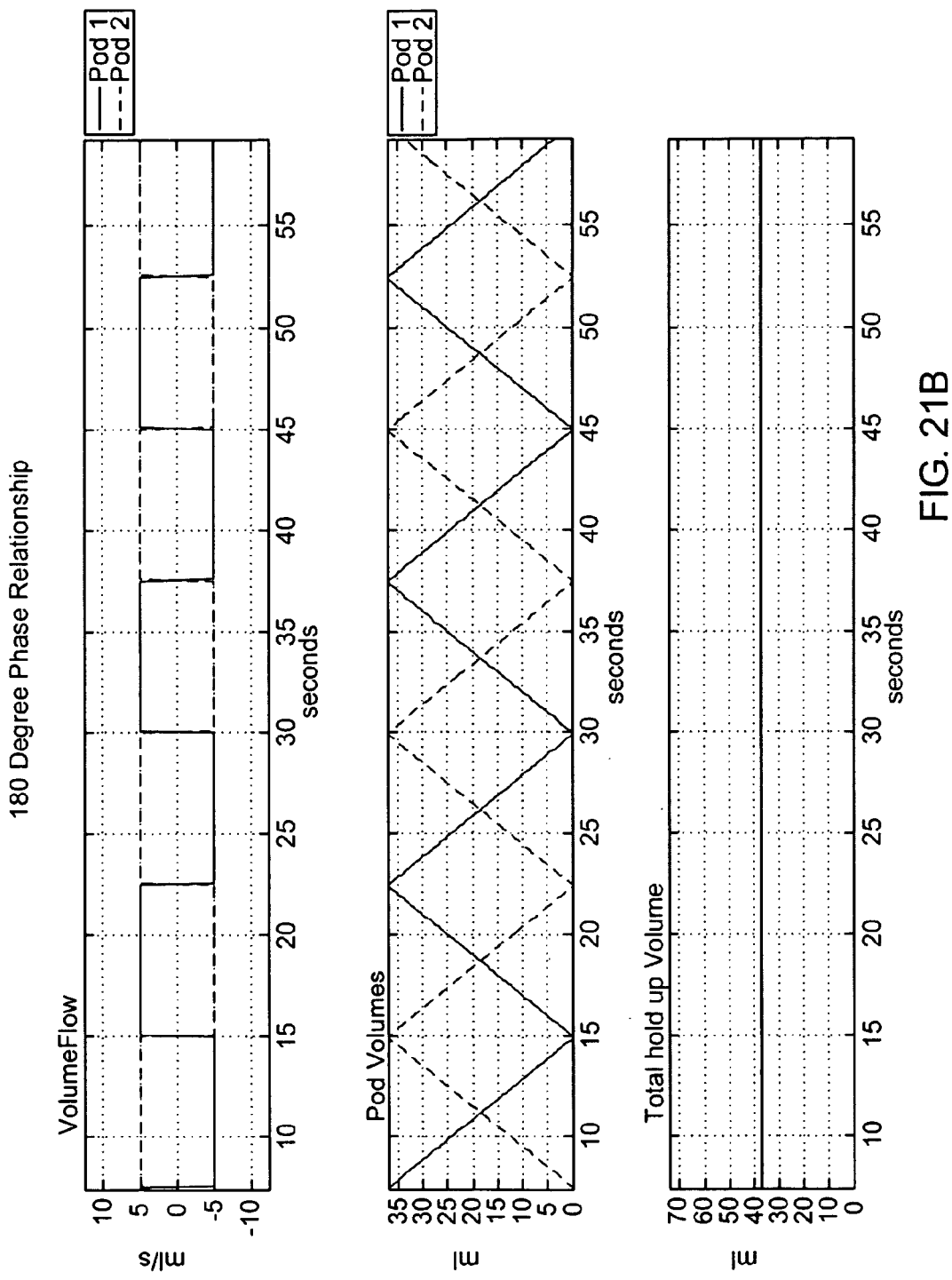
Figure 21C:
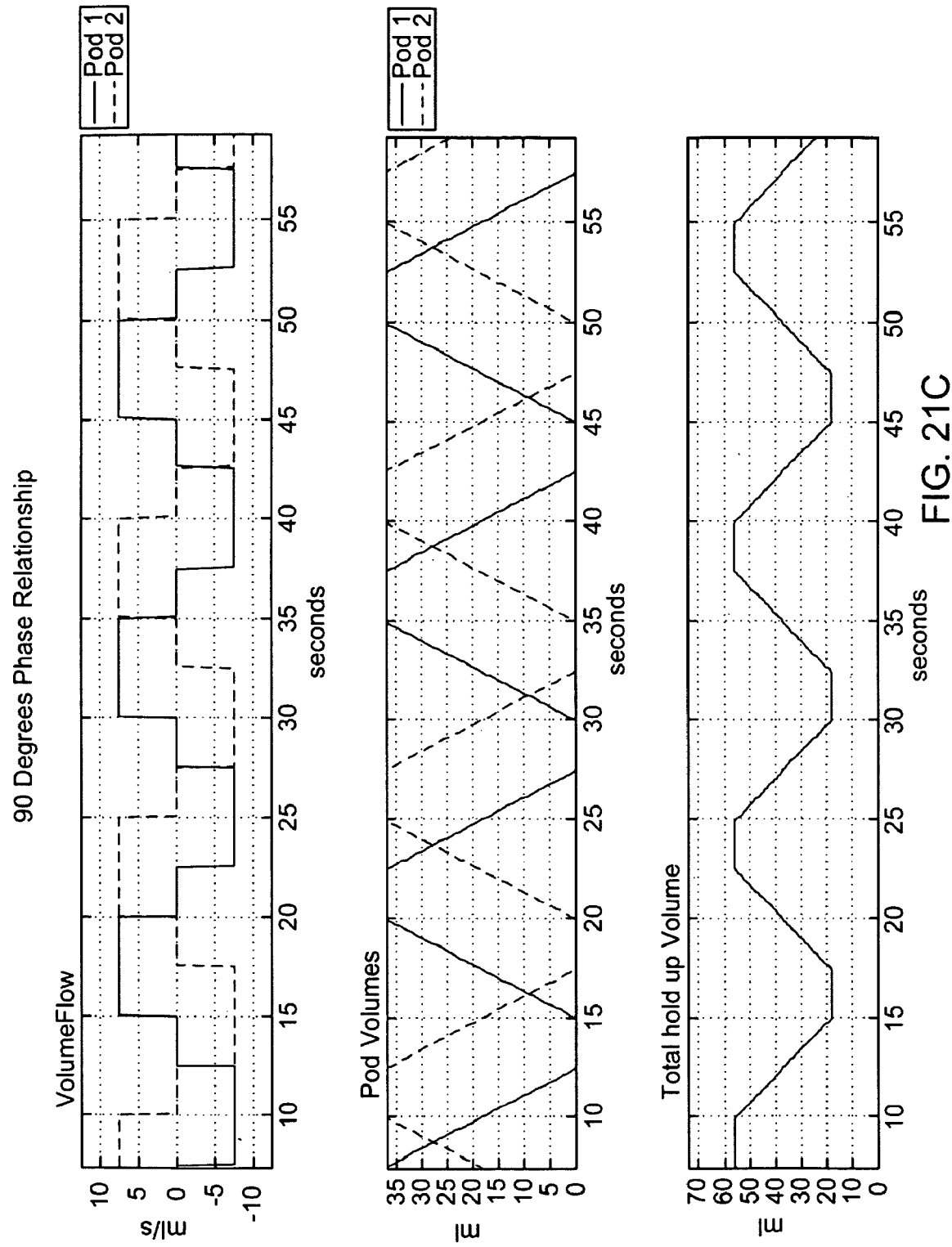

When two or more pumps are used to pump fluid in a flow path, delivery of fluid from each pump can be phased in any manner desired. In a dual pump configuration, the two pod pumps may be operated from a zero degree phase relationship (i.e., both pumping chambers act in the same direction) to a 180 degree phase relationship (i.e., the pumping chambers act in opposite directions). A zero degree phase relationship can be used to produce a substantially pulsatile fluid flow, similar to a single pod pump. A 180 degree phase relationship can be used to produce a substantially continuous fluid flow both toward the pumps and from the pumps. A 90 degree phase relationship can be used to produce a substantially sinusoidal fluid flow. FIGS. 21A-21C show plots for volume flow, pod volumes, and total hold up flow for a zero degree phase relationship, a 180 degree phase relationship, and a 90 degree phase relationship, respectively.

In some applications, it may be necessary or desirable to provide substantially continuous fluid flow to the pod pump(s) and/or from the pod pump(s). As discussed above, substantially continuous fluid flow may be provided using two pod pumps operating with a 180 degree phase relationship. For one or more pod pumps operating in a pulsatile mode (e.g., a single pod pump or two pod pumps operating in a zero degree phase relationship), one way to produce a more continuous fluid flow output is to fill the pod pump(s) as quickly as possible and then pump out the fluid over an extended period of time (e.g., the desired deliver time could be set to be a total desired stroke time minus the time that the fill stroke took).

Even when operating two pod pumps in a 180 degree phase relationship, it is possible for there to be discontinuous fluid flow under some conditions, particularly when the input impedance is significantly different than the output impedance. For example, in extracorporeal blood treatment applications, input impedance may be higher than output impedance due to such things as needle size (e.g., the needle used to draw blood from the patient may be smaller than the needle used to return blood to the patient), blood viscosity (e.g., the patient may have very viscous blood that is thinned as part of the treatment), or poor patient access (e.g., poor patient circulation may limit the rate at which blood can be drawn). Such impedance differences can result in different pod pump fill and delivery times, particularly if the system cannot be balanced by applying more pressure to one pod pump than the other pod pump (in theory, it should be possible to ensure a precise 180 degree phase relationship if there were no limit on the amount of pneumatic pressure that could be applied to the pod pumps, but there are typically both physical limits—the maximum pressures in the two reservoirs—and practical limits to the amount of pressure that can be applied). Therefore, in some situations, the stroke of one pod pump might finish before the corresponding stroke of the other pod pump, in which case it may be necessary to delay the former pod pump while the latter pod pump completes its stroke, resulting in a pause in the fluid flow produced by the former pod pump. Assuming that the blood flow through the CPB circuit can safely be adjusted, one possible solution is to limit the flow rate to the slowest of the fill and deliver strokes. Although this would result in slower blood delivery flow rates, the flow rate would still be known and would be continuous. It should be noted that in other embodiments in which more than two pumps are used, there is significantly broader flexibility in creating customized flow profiles.

Variable-Restriction Pneumatic Supply Valves

The positive-supply valve 47 and the negative-supply valve 48 in the pneumatic actuation system 40 of FIG. 18 may be variable-restriction valves, as opposed to binary on-off valves. By using variable valves, the pressure applied to the control chamber 42 and the membrane 33 can be adjusted to be just a fraction of the pressure in reservoirs 51, 52, instead of applying the full reservoir pressure to the membrane. This facilitates use of the same reservoir or set of reservoirs for pod pumps having different operating parameters, such as pump volume, pump stroke size, or pump actuation pressure. Although the reservoir pressure generally needs to be greater than the pressures required to actuate the membranes of the various pod pumps, one pod pump can be operated at one fraction of the reservoir pressure, and another pod pump operating off the same reservoir can be actuated at a different fraction of the reservoir pressure. The pressures used in a pod pump may be changed to address conditions that may arise or change during pumping. For example, if flow through the system's tubing becomes constricted because the tubes get twisted, one or both of the positive or negative pressures used in the pod pump can be increased in order to compensate for the increased restriction.

Under normal circumstances when the flow controller is running, the control loop preferably adjusts the pressure for any changes in flow rate. If the impedance in the circuit increases dramatically and the pressure limits are saturated before the flow has a chance to reach the target rate, the flow controller generally will not be capable of adjusting the pressures higher to reach the desired flow rate. These situations may arise if a line is partially occluded (e.g., a blockage, such as a blood clot in a blood pumping embodiment) has formed in the circuit. Pressure saturation when the flow has not reached the target flow rate can be detected and used in error handling.

If there are problems with the valves or the pneumatics, such as a leaking fluid valve or a noisy pressure signal, ripple may continue on the stroke indefinitely and the end of stroke algorithm may not see enough of a change in the pressure ripple to detect end of stroke. For this reason a safety check is preferably added to detect if the time to complete a stroke is excessive. This information can be used for error handling.

Alternative Pump Cassette Systems that do not Include Control Chambers

Figure 22:
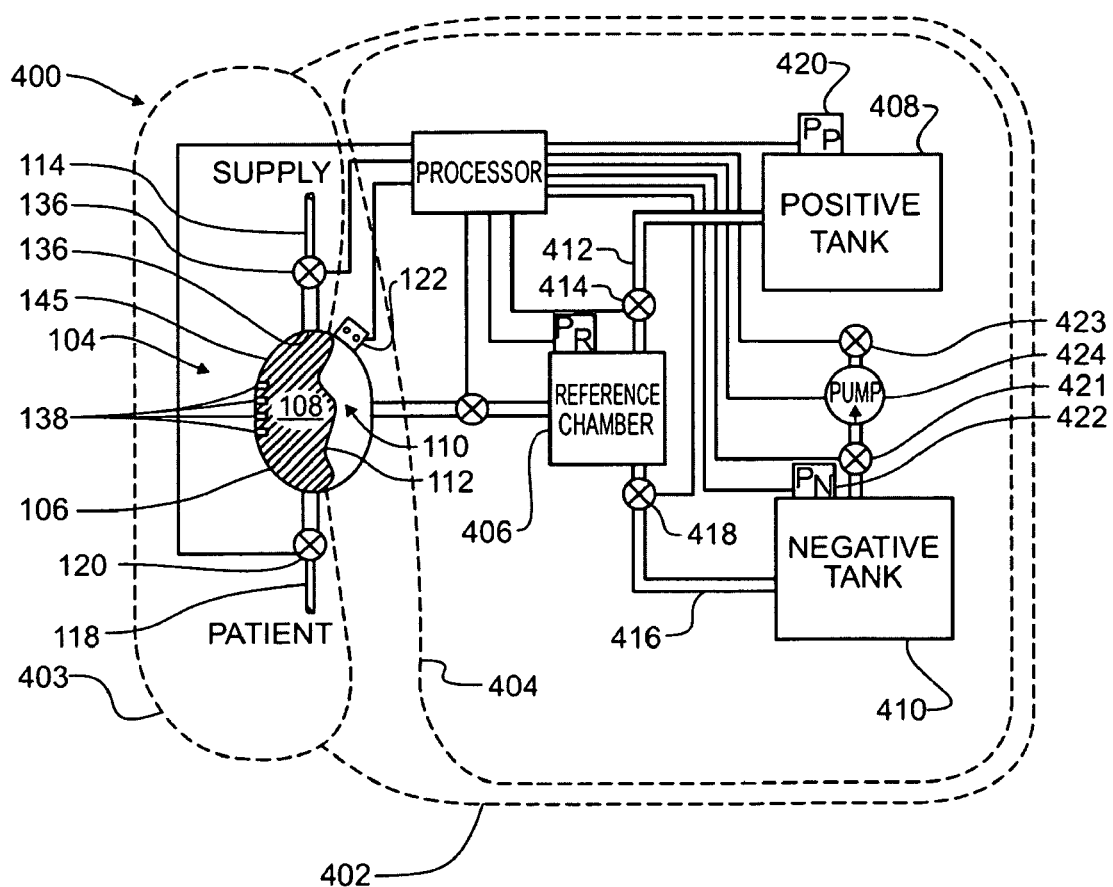
FIG. 22 is a schematic illustration of a pumping system according to one embodiment of the invention.

In some applications, it may be preferable for the pump and valve drive mechanisms to be part of (or attached to) the reusable base unit (such as unit 2 in FIGS. 2A and 2B). The removable/disposable portion of the system may include the pump chamber and the pump chamber inlet and outlet lines, including the valves therein, and the other components which are in contact with the liquid being pumped with the pumping system. The removable/disposable component of such a system is referred to herein as the "pumping cassette," which can be configured and designed with a plurality of pump chambers, flow paths, valves, etc., specifically designed for a particular application. For example, in pumping system 400 of FIG. 22 would comprise a reusable component 402 coupled to pumping cassette 403, and pumping system 500 shown in FIG. 23 would include reusable component 502 coupled to a pumping cassette 503.

For embodiments involving removable/disposable pumping cassettes and reusable pump drive systems, the pumping cassette and the reusable component are constructed and arranged to be couplable to each other. "Constructed and arranged to be couplable" as used herein indicates that the separable components are shaped and sized to be attachable to and/or mateable with each other so that the two components can be joined together in an operative association. Those of ordinary skill in the art would understand and envision a variety of ways to construct and arrange pumping cassettes and components of reusable systems to be couplable in operative association. A variety of such systems which may be employed in the present invention have been described previously in commonly owned U.S. Pat. Nos. 4,808,161; 4,976,162; 5,088,515; and 5,178,182.

Typically, the pumping cassette and reusable component will be coupled together with an interface therebetween, where the reusable component adjacent to the interface will have a series of depressions formed in a surface of the interface, which depressions are sized and positioned to mate with similar depressions in the pumping cassette, when the pumping cassette and the reusable component are coupled together, so that upon coupling, the depressions in the pumping cassette and the reusable components together form the various chambers utilized by the pumping system. Also, when coupled together, the pumping cassette and the reusable component preferably interact at an interface therebetween such that the interface creates a fluid impermeable/fluid-tight seal between the components, so that the measurement fluid contained by the reusable component and the liquid present in the pumping cassette are not in fluid communication with each other during operation of the system. The components may be held together in operative association, for example, by clips, bolts, screws, clamps, other fasteners, etc., or the reusable component may include slots, channels, doors, or other components as part of a housing for holding the pumping cassette in operative association with the reusable component. Such techniques for coupling together disposable/reusable pumping cassettes and reusable pump drive systems are well known in the art, and may be useful in the context of the present invention.

Figure 23:
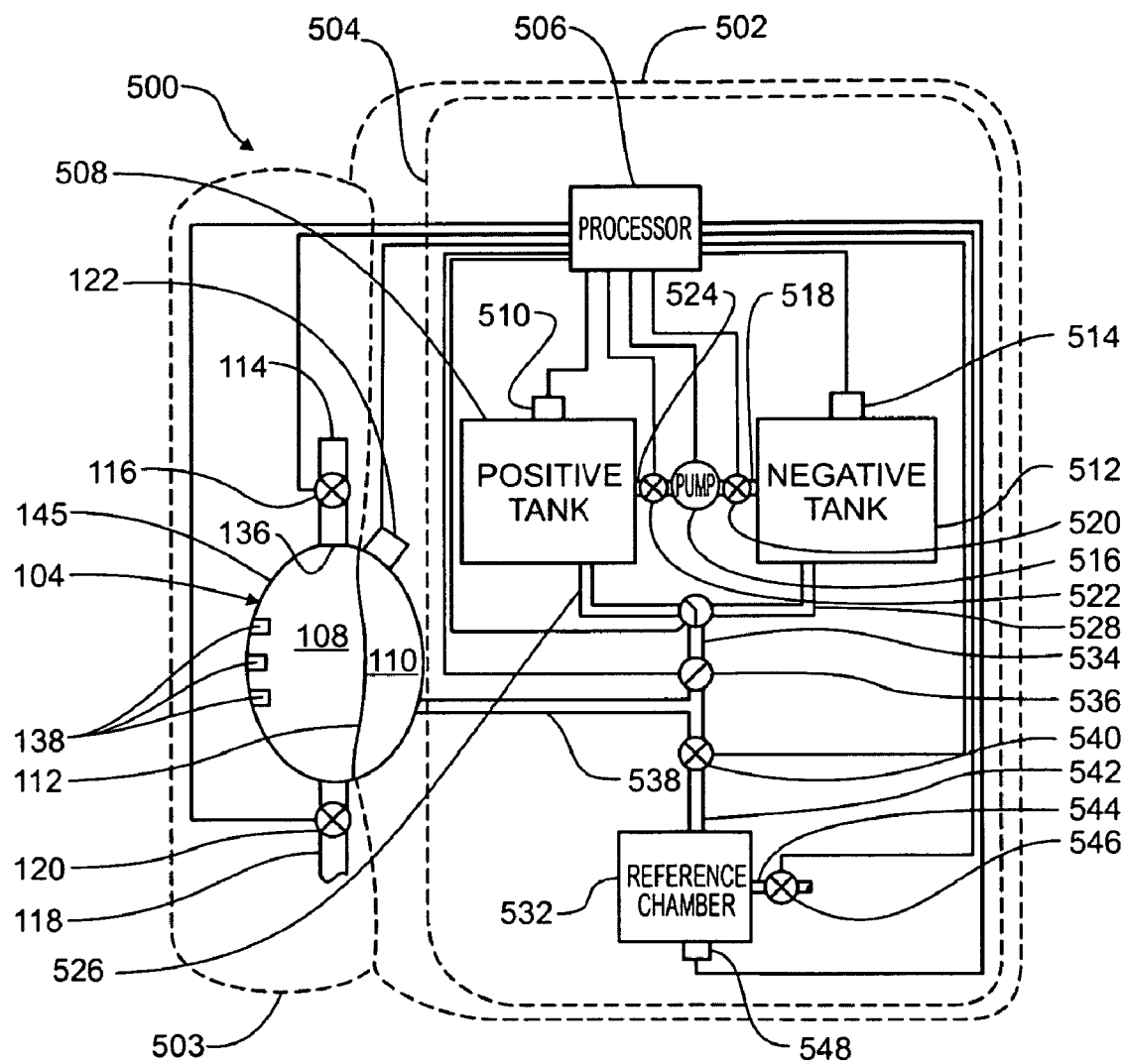
FIG. 23 is a schematic illustration of a pumping system according to one embodiment of the invention.
Figure 24:
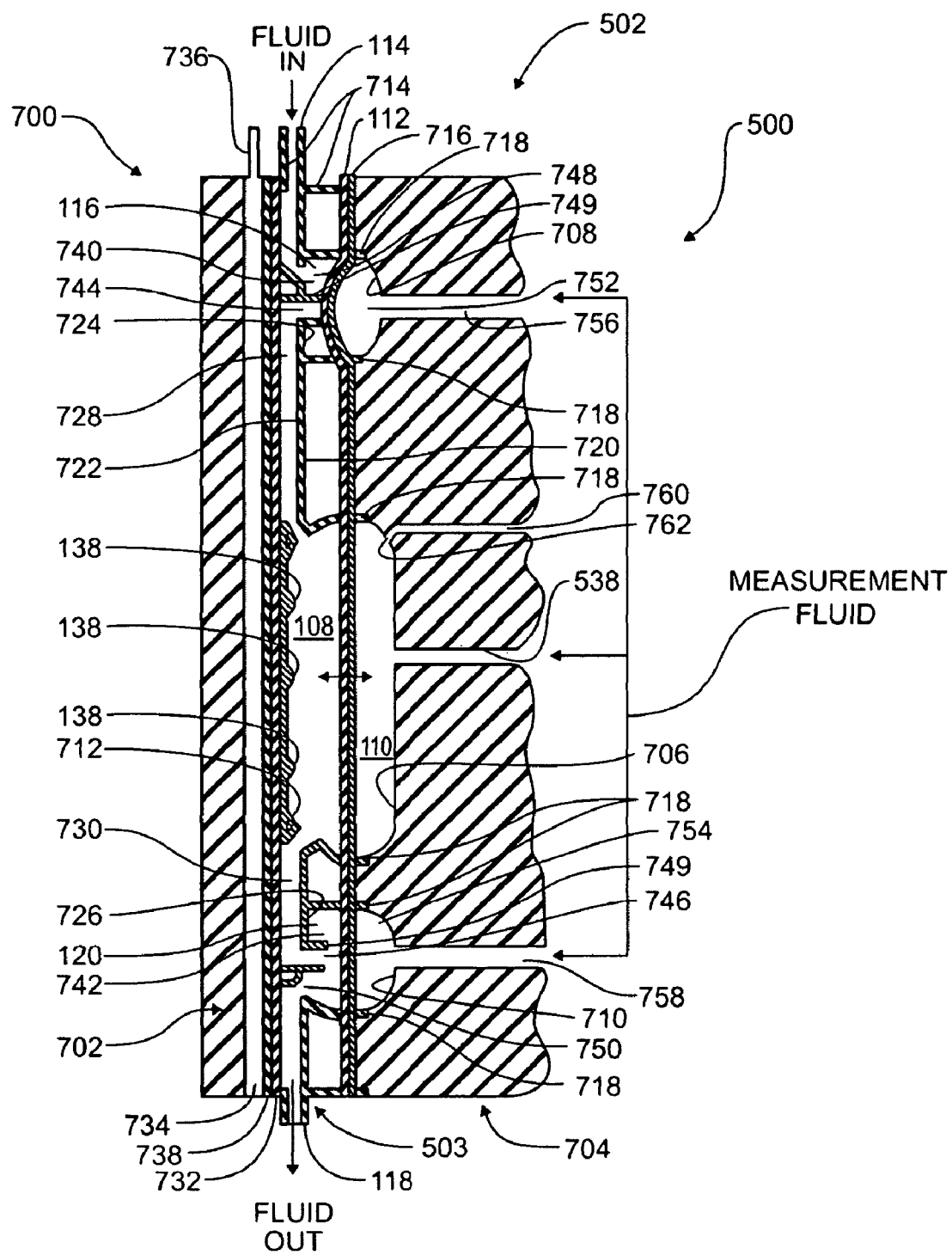
FIG. 24 is a partially-cutaway cross-sectional illustration of a removable pumping cassette and pump housing component according to one embodiment of the invention.

FIG. 24 shows in cross section a preferred embodiment of the interface between pumping cassette 503 and reusable pump drive system 502 of pumping system 500 shown schematically in FIG. 23. FIG. 24 is a cut-a-way view showing only the portion of reusable component 502 which mates with and is in contact with pumping cassette 503 when the components are coupled together in operative association. Such portion of the reusable component will hereinafter be referred to as the "pump housing component." Also shown in FIG. 24 is a preferred arrangement for providing valves in fluid communication with the liquid flow paths of the pumping cassette.

Pump housing component 700 includes a door 702 and a mating block 704 the surface of which forms an interface when pumping cassette 503 is coupled to pump housing component 700. Mating block 704 has a generally planar surface in contact with the pumping cassette having a variety of depressions 706, 708, 710 therein which mate with complementary depressions contained within pumping cassette 503 for forming various chambers of the pumping system when the components are coupled together. For example, depression 706 in mating block 704 is coupled to depression 712 in pumping cassette 503 thus forming a pump chamber 108 in pumping cassette 503 and an adjacent control chamber 110 in mating block 704, when the components are coupled together.

Pumping cassette 503 comprises a substantially rigid component 714 covered, on at least one side thereof, by a flexible membrane, which in preferred embodiments is an elastic membrane. In a preferred embodiment shown, mating block 704 is also covered by a flexible membrane 716 which is in contact with flexible membrane 112 covering pumping cassette 503, when the components are coupled together. Flexible membrane 716 is an optional component which provides an additional layer of safeguarding against potential leakage of fluids between pumping cassette 503 and the reusable component thus preventing contamination of the reusable component by the liquids in the pumping cassette.

Upon coupling, a fluid-tight seal should be made between the flexible membranes and the surfaces of mating block 704 and pumping cassette rigid component 714 forming the various chambers. In order to obtain such a seal, there should be some degree of compression between pumping cassette 503 and mating block 704 when the components are coupled together. In addition, seals 718 may be provided around the periphery of the depression within mating block 704, which seals are positioned adjacent to the periphery of complementary depressions in pumping cassette 503 in order to create additional compression of the flexible membranes for forming a leak-tight seal. Alternatively, such seals could be provided around the perimeter of the depressions in pumping cassette 503 in addition to, or instead of, mating block 704. Such seals may be provided by a variety of materials, as apparent to those of ordinary skill in the art, for example, properly sized rubber or elastomer O-rings can be used which fit into complementary grooves within mating block 704 or, alternatively, are affixed to the mating block by adhesives, etc.

In the embodiment shown, pumping cassette 503 includes a substantially rigid component 714 that is preferably constructed of a substantially rigid medical grade material, such as rigid plastic or metal. In preferred embodiments, substantially rigid component 714 is constructed from a biocompatible medical grade polyacrylate plastic. In one exemplary embodiment, the rigid component 714 is made from polysulfone. In another exemplary embodiment, the rigid component 714 is made from medical grade polycarbonate. Substantially rigid component 714 can be molded into a generally planar shape having a variety of depressions and grooves or channels therein forming, when coupled to the reusable component, the various chambers and flow paths provided by the pumping cassette.

In some embodiments, the substantially rigid component of the pumping cassette can include a first side, which mates with the mating block, which first side contains various depressions and channels therein for forming flow paths and chambers within the pumping cassette upon coupling to the reusable component. This first side of such pumping cassettes is covered with a flexible, preferably elastic membrane, which can be bonded to the first side of the substantially rigid component at the periphery thereof and/or at other locations on the first side. Alternatively, instead of being a single continuous sheet, the flexible membrane may comprise a plurality of individual membranes which are bonded to the substantially rigid component only in regions comprising chambers, or other components, in operative association with the reusable component.

FIG. 24 shows such an embodiment of a pumping cassette 503 which has a first side 720, facing mating block 704, and a second side 722, facing door 702 of pump housing component 700, each of which sides is covered by a flexible membrane. First side 720 of pumping cassette 503, as shown, includes depressions 712, 724, and 726 and is covered by flexible membrane 112. The second side 722 of pump cassette 503 includes a variety of channels 728, 730 formed therein, which channels are covered by flexible membrane 732, which is disposed on the second side 722 of pump cassette 503, the combination of which channels and flexible membrane provide fluid-tight liquid flow paths within pumping cassette 503, upon coupling to the reusable component.

The flexible membranes for use in pumping cassette 503 and, in some embodiments, mating block 704, can be comprised of a variety of flexible materials known in the art, such as flexible plastics, rubber, etc. Preferably, the material comprising the flexible membranes used for the pumping cassette is an elastic material that is biocompatible and designed for medical use, when used for applications where the pumping cassette is used for pumping liquid to and from the body of a patient. The material comprising the flexible membranes should also be selected based on its ability to form a fluid-tight seal with the substantially rigid component 714 of pumping cassette 503 and with mating block 704 of the reusable component. In a preferred embodiment, where rigid component 714 of pumping cassette 503 is formed of a clear acrylic plastic, elastic membrane 112 is comprised of polyvinyl chloride sheeting, which is about 0.014 in thick and which is hermetically sealed to the first side 720 of rigid component 714 of pumping cassette 503. Since the elasticity of membrane 112 disposed on the second side 722 of pumping cassette 503 does not substantially contribute to its performance, it is not necessarily preferred to use an elastic material for membrane 712. However, for convenience and ease of fabrication, membrane 712 can be comprised of the same material as membrane 112, and can be hermetically sealed the second side 722 of rigid component 714 of pumping cassette 503 in a similar fashion as membrane 112.

In the embodiment illustrated by FIG. 24, door 702 is hinged to the body of the reusable component and can be opened or closed by an operator of the system, either manually, or in some embodiments, under computer control of the processor controlling the system, so that pumping cassette 503 can be properly inserted and mated with mating block 704. Preferably, pumping cassette 503, mating block 704, and door 702 are shaped and configured so that pumping cassette 503 can only mate with the reusable component in the proper orientation for operative association. In preferred embodiments, door 702 latches to the reusable component when closed. In some embodiments, the pumping system may include detectors and circuitry for determining the position of the door and is configured to allow operation of the system only when pumping cassette 503 has been properly installed and door 702 has been properly closed. Also, in preferred embodiments, the pumping system is configured to prevent the door from being opened during operation of the system, so that the fluid-tight seal that is formed between pumping cassette 503 and the reusable system is not compromised while the system is in operation. Door 702 also, in preferred embodiments, includes an inflatable piston bladder 734 having an inlet line 736 which is in fluid communication with a fluid supply of the pumping system when the system is in operation. Also, in preferred embodiments, adjacent to piston bladder 734 and pumping cassette 503 is an essentially planar piston surface 738. After inserting pumping cassette 503 and closing door 702, but before operating pumping cassette 503, the system supplies pressurized fluid to piston bladder 734 to create a compressive force against pumping cassette 503 so as to create fluid-tight seals within the system.

Pumping cassette 503 and reusable component 502, as shown in FIG. 24 together provide a unique means of operating the valves within pumping cassette 503. Inlet valve 116 and outlet valve 120 include valving chambers 740 and 742 which are formed from the combination of depressions 724 and 726 within rigid component 714 and flexible membrane 112. Each valving chamber includes at least one occludable port 744, 746 and at least one other port 748, 750. In the embodiment shown, ports 748, 750 are not occludable by flexible membrane 112. In other embodiments, ports 748 and 750 may be occludable and similar in construction to occludable ports 744 and 746. As shown, ports 744 and 750 comprise holes within rigid component 714 of pumping cassette 503 allowing fluid communication between liquid flow paths 114 and 118 present on the second side 722 of pumping cassette 503 and valving chambers 740 and 742 located on the first side 720 of pumping cassette 503. Occludable ports 744 and 746 also provide fluid communication between the valving chambers and liquid flow paths within the pumping cassette. Occludable ports 744 and 746 are constructed so that holes through which a liquid flows are located on members 749 that protrude from the base of the depression forming the valving chambers. In preferred embodiments, protruding members 749 have a truncated conical shape, wherein ports 744 and 746 comprise holes in the truncated apex of the conical protruding members.

Mated to valving chambers 740 and 742, when the pumping cassette is in operative association with the reusable component, are valve actuating chambers 752 and 754 formed from depressions 708 and 710 within mating block 704. In order to close the valves to restrict or block flow therethrough, pumping system 500 includes valve actuators (provided in this embodiment by the valve actuating chambers as shown) configured to selectively and controllably apply a force to flexible membrane 112 tending to force the flexible membrane against an adjacent occludable port, thus occluding the port. Inlet valve 116 is shown in such a closed configuration. To open a valve, the pumping system can release the positive force applied to flexible membrane 112 and, in some embodiments, can apply a negative force to flexible membrane 112 tending to move the membrane into the valve actuating chamber. Outlet valve 120 is shown in FIG. 10 in such an open configuration. Pumping system 500 is configured as shown to open and close the valves within pumping cassette 503 by selectively applying a measurement gas to the valve actuating chambers at a pressure sufficient to occlude the occludable ports contained within the valving chambers. Such pressure will exceed the pressure of any liquid contained in the valving chamber.

Gas inlet lines 756 and 758 supplying valve actuating chambers 752 and 754 are connected so that they are able to be placed in fluid communication with a pressurized measurement gas supply source(s) contained in pumping system 500. It should be understood that in other embodiments not shown, pumping system 500 may include valve actuators using alternative means as a force applicator for applying a force to flexible membrane 112 in order to occlude occludable ports 744 and 746. In alternative embodiments, the system may include a valve actuator that includes a force applicator comprising, for example, a mechanically actuated piston, rod, surface, etc., or some other force applicator using an electrical or magnetic component, disposed adjacent to the flexible membrane. In preferred embodiments, as shown, the system comprises a valve actuator comprising a valve actuating chamber, where the force applicator for applying a force to the flexible membrane comprises a pressurized gas or other fluid. As with other particular features described herein, this valve and mechanism for operating the valve is not required in all embodiments of the present invention; and, in the context of a system design, any other type of valve and valve actuator may be used.

Also shown in FIG. 24 is a preferred mechanism for providing a pressure measuring component for determining the pressure in control chamber 110, which may be used in some (but not all) embodiments of the present invention. Pumping system 500 as shown in FIG. 24 is configured so that pressure transducers are resident on a circuit board contained within processor 506 (not shown in FIG. 24), which transducers are connected in fluid communication with various chambers and components in the system via tubing or channels. For example, pressure transducer 122 (not shown) for measuring the pressure in control chamber 110 is connected in fluid communication with control chamber 110 via line 760 and port 762 in fluid communication with control chamber 110.

Preferably, after mating pumping cassette 503 to the reusable component and before commencement of operation, pumping system 500 is configured to perform a variety of integrity tests on pumping cassette 503 to assure the proper operation of the pumping system. In such embodiments, pumping system 500 includes an inlet and outlet tube occluder (not shown) for blocking the flow of fluid to and from pumping cassette 503 and for isolating the chambers and flow paths of pumping cassette 503. After coupling pumping cassette 503 to the reusable component but before priming pumping cassette 503 with liquid, a dry pumping cassette integrity test can be performed. The test involves opening the inlet and outlet line occluding means so that pumping cassette 503 is not isolated from the surroundings and supplying all of the control chambers and valve actuating chambers in the system with a measurement gas at a predetermined positive or negative pressure. The system then continuously monitors the measurement gas pressure within the various chambers of the reusable component over a predetermined period of time. If the change in pressure exceeds a maximum allowable predetermined limit, the system will indicate a fault condition and terminate operation. This dry pumping cassette integrity test is useful for detecting holes or other leaks within flexible membrane 112. The dry pumping cassette integrity test integrity test briefly described above is discussed in more detail in commonly owned co-pending application Ser. No. 09/193,337 incorporated by reference herein in its entirety.

After performing the dry pumping cassette integrity test above, but before operation, a wet pumping cassette integrity test can also be performed. The test involves first priming all of the chambers and flow paths of pumping cassette 503 with liquid and then performing the following two tests. First, the integrity of the valves within the pumping cassette is tested by applying positive pressure to valve actuating chambers 752 and 754 to close valves 116 and 120 within the pumping cassette, and then applying the maximum system measurement gas pressure to the control chamber 110 coupled to the pump chamber 108. The system is configured to measure the volume of the pump chamber 108 within the pumping cassette, as described previously, before the application of pressure, and again after the pressure has been applied to the pump chamber for a predetermined period of time. The system then determines the difference between the measured volumes and creates an alarm condition if the difference exceeds an acceptable predetermined limit. The second test involves determining the fluid tightness of the various fluid flow paths in chambers within pumping cassette 503. This test is designed to prevent the system from operating when a cassette has been manufactured so that there may be leakage between flow paths and undesirable mixing of liquids within the pumping cassette. The test is performed in a similar fashion as that described immediately above except that the valves within pumping cassette 503 are maintained in an open configuration with the inlet and outlet line occlusion means being actuated by the system to isolate the pumping cassette from its surroundings. As before, a maximum measurement gas pressure is applied to the control chamber of the reusable component, and the volume contained in the pump chamber is determined before and after application of pressure. Again, the system is configured to create an alarm condition and discontinue operation if the differences in measured volume exceed an allowable predetermined limit. It should be understood that while the various integrity tests and preferred modes of operating a pumping cassette have been described in the context of system 500 and pumping cassette 503 illustrated in FIG. 24, the methods and tests can also be applied and employed for other configurations of the pumping cassette and reusable system.

Figure 25A:
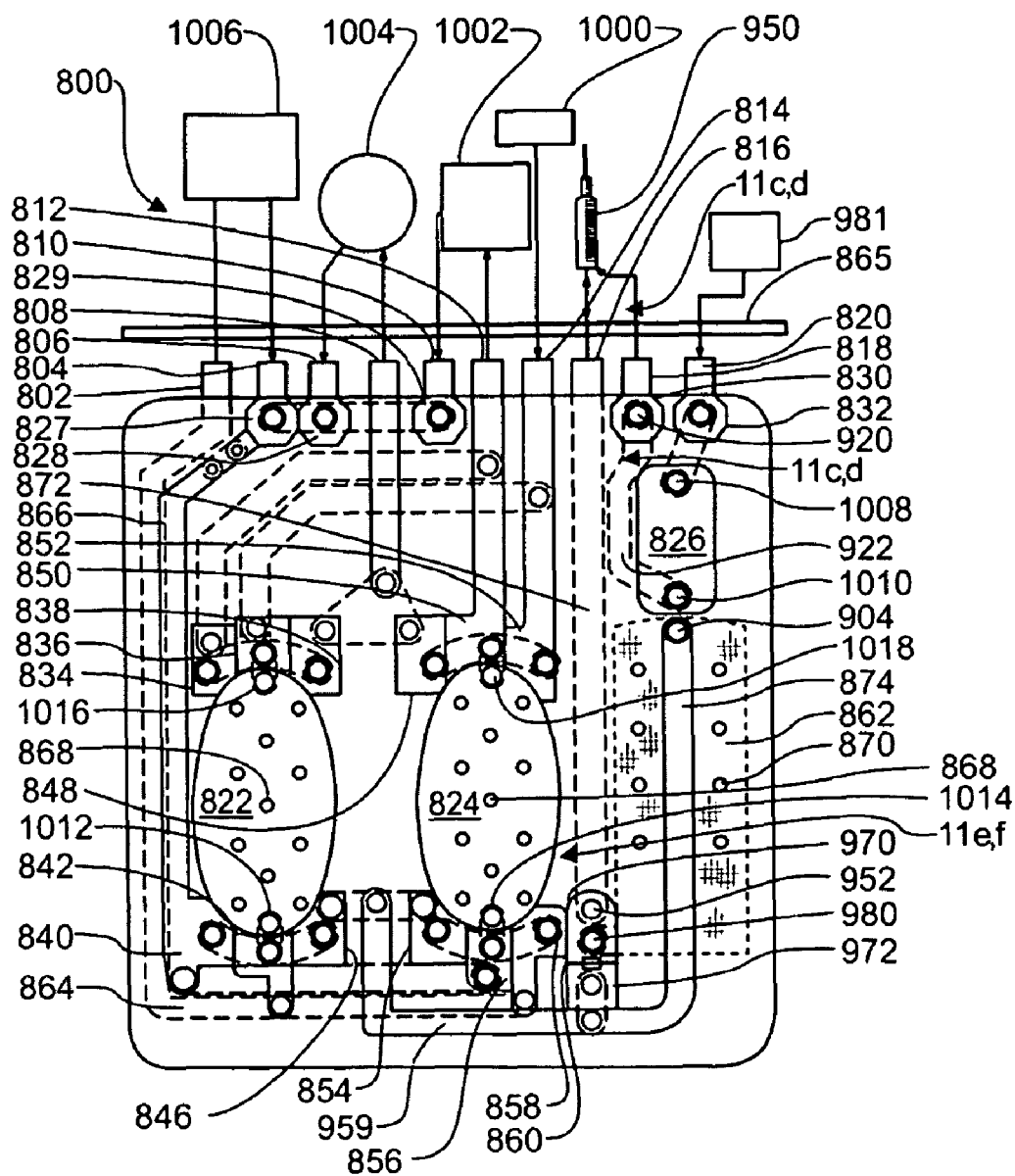
FIG. 25A is a schematic illustration of a pumping cassette according to one embodiment of the invention.

FIGS. 25A-25F show various views and features of one particular embodiment of a multi-functional pumping cassette according to the invention which includes a plurality of pump chambers, valving chambers, and fluid flow paths. The pumping cassette shown in FIGS. 25A-25F is similar in construction to pumping cassette 503 shown in FIG. 24, in that the pumping cassette includes a substantially rigid component with various depressions and channels/grooves covered on each side with a flexible membrane that is hermetically sealed thereto. FIG. 25A is an enface view of the first side of pumping cassette 800, which first side is coupled to and in contact with an interface of a mating block on a complementary reusable system when the pumping cassette is in operation. Except for the particular arrangement and number of components, pumping cassette 800 is similar in overall design to that described previously in the context pumping cassette 503 of FIG. 24.

Pumping cassette 800 includes a plurality of inlet and outlet lines 802, 804, 806, 808, 810, 812, 814, 816, 818, and 820 for connecting the various flow paths of the pumping cassette in fluid communication with lines external to the pumping cassette. In one preferred embodiment, pumping cassette 800 is utilized for pumping blood from the body of a patient, treating the blood, or components thereof, and returning treated blood and other fluids to the body of the patient. For such embodiments, pumping cassette 800 is preferably disposable and designed for a single use, and is also preferably biocompatible and sterilizable so that it may be provided to the user as part of a sterile, single-use package.

As shown in FIG. 25a, pumping cassette 800 includes two large pump chambers 822 and 824 and a third smaller pump chamber 826. Pumping cassette 800 also includes a plurality of valving chambers 827, 828, 829, 830, 832, 834, 836, 838, 840, 842, 846, 848, 850, 852, 854, 856, and 858 for controlling and directing the flow of liquid through the various liquid flow paths and pump chambers provided within pumping cassette 800. The construction of each of the pump chambers and valving chambers above is similar to that shown previously for pumping cassette 503 shown in FIG. 24. Pumping cassette 800 also includes a bypass valve provided by bypass valving chamber 860 and an integrated filter element 862.

In operation, pumping cassette 800 is coupled in operative association with a complimentary mating block of a reusable component having depressions and pneumatic (in appropriate embodiments) connections therein for actuating the various pump chambers and valving chambers of the pumping cassette in a similar fashion as that previously described. The reusable component also preferably includes an occluder 865 disposed adjacent to tubing in fluid communication with the various inlet/outlet ports of the pumping cassette, for occluding the various inlet and outlet lines in fluid communication with the pumping cassette when performing various integrity tests as described previously and/or for other purposes where it is desirable to fluidically isolate the pumping cassette. In preferred embodiments, the occluder 865 is constructed and configured to occlude the tubing unless a force is applied to the occluder 865, for example by supplying a pressurized fluid to a bladder tending to move the occluder 865 to unocclude the various tubing. In such embodiments, in a fail safe condition (e.g. during a power failure) the occluder 865 will be configured to occlude the tubing, thus preventing undesirable liquid flow to and/or from a source or destination (especially when such source or destination is the body of a patient.

The reusable system that is constructed and arranged for operative association with pumping cassette 800 will also include various processors (or a single processor configured to perform multiple functions, or other suitable hardware or software mechanisms) to selectively control and operate the various components of pumping cassette 800 for performing various user designated pumping applications. It will be understood by those of ordinary skill in the art that pumping cassette 800 can be used for an extremely wide variety of potential pumping and fluid metering applications depending on the manner in which the various components contained therein are operated and controlled. Each of such uses and applications are deemed to be within the scope of the present invention.

The flow paths within pumping cassette 800 which are comprised of channels formed on the first side of the pumping cassette (the side facing the viewer), for example flow path 866, are shown as solid lines. Flow paths that are formed from channels disposed on the second (opposite) side of pumping cassette 800, for example flow path 872, are shown in FIG. 25A by dashed lines. As can be seen in FIG. 25A, in the embodiment shown, filter element 862 is also disposed on the second side of pumping cassette 800. As will be described in more detail below, a preferred function of filter element 862 can be to filter fluids being pumped from pumping cassette 800 to the body of a patient in order to remove any blood clots or aggregated material.

Figure 25B:
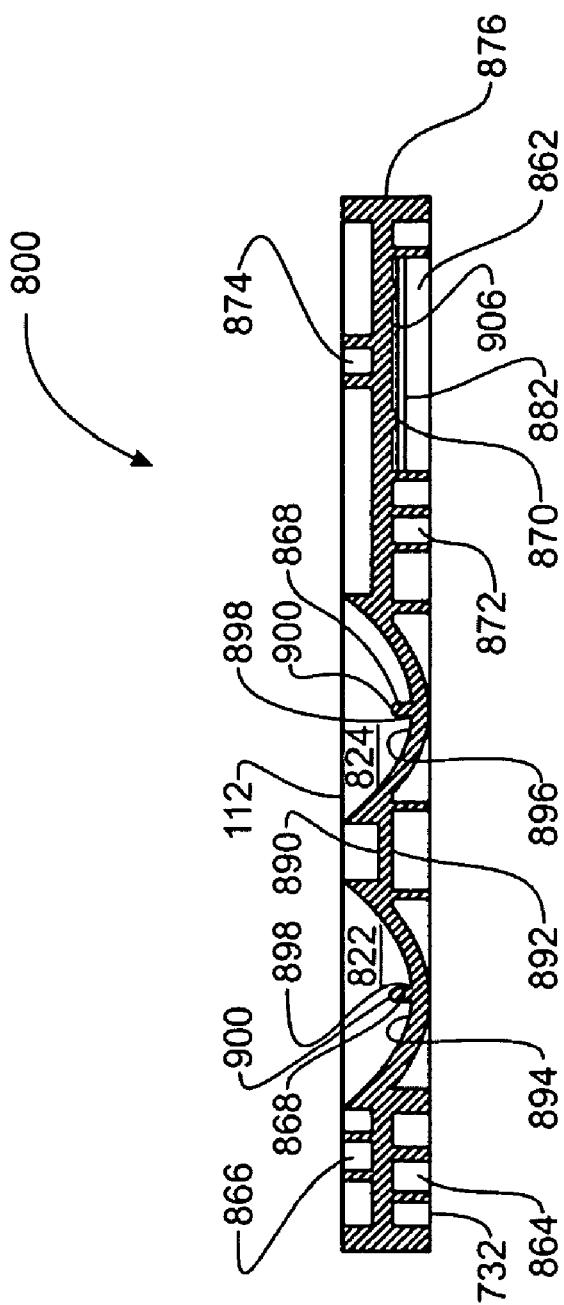
FIG. 25B is a cross-sectional illustration of the pumping cassette of FIG. 25A.

The structure of pumping cassette 800 can be seen more clearly from the cross-sectional view of FIG. 25B. Pumping cassette 800 includes a substantially rigid component 876 having a series of depressions and channels therein forming the various chambers and flow paths of the pumping cassette. Pumping cassette 800 has a first side 890, which is disposed against a mating block of the reusable component in operation, and a second side 892, which is disposed against the door of the pump housing component when in operation. First side 890 is covered by flexible membrane 112 hermetically sealed around the periphery of rigid component 876. Second side 892 is similarly covered by flexible membrane 732. Clearly visible are liquid flow paths 866 and 874, both of which are disposed on first side 890 of pumping cassette 800 and liquid flow paths 864 and 872 disposed on second side 892 of pumping cassette 800. Pump chambers 822 and 824 are formed from curved depressions 894 and 896 in first side 890 of rigid component 876. Clearly visible are spacers 868 which comprise elongated protuberances having bases 898 attached within the pump chambers to rigid component 876 and ends 900 extending into pump chambers 822 and 824 toward flexible membrane 112. As previously described, these spacers prevent contact of flexible membrane 112 with the base of depressions 894 and 896 in rigid component 876 during pumping and provide a dead space which inhibits pumping of gas from the pump chambers during operation. In this embodiment, the spacers are small, evenly spaced protuberances located on a wall of the pump chamber. The size, shape and positions of the spacers can be changed and still serve the purpose of reducing risk of passing gas through the pump chamber.

Referring to FIG. 25B, filter element 862 includes a filter 882 disposed on second side 892 of rigid component 876. Filter 882 is preferably substantially planar and is disposed adjacent to second side 892, spaced apart by spacers 870, so that the filter and the region of second side 892 to which it is attached are essentially coplanar. During operation of the pumping cassette for pumping liquid to a patient, fluid to be pumped to the patient is directed along flow path 874 to the inlet port 904 of filter element 862 (see FIG. 25A) into space 906 separating filter 882 from second side 892, through filter 882, and out of filter element 862 through occludable port 980 (see FIG. 25A). In order to prevent fluid from bypassing filter 882 within filter element 862, filter element 862 should be sealed to second side 892 of rigid component 876 along its periphery in a fluid-tight fashion. Also, for embodiments where filter element 862 is functioning as a blood clot filter, filter 882 preferably has pores therein which are larger in diameter than the diameter of a typical human blood cell, but which are small enough to remove a substantial fraction of clotted blood or aggregated blood cells that may be present in a liquid pumped therethrough. In preferred embodiments, filter 882 comprises a polyester screen, in one embodiment having pore sizes of about 200 microns with about a 43% open area.

Figure 25C:
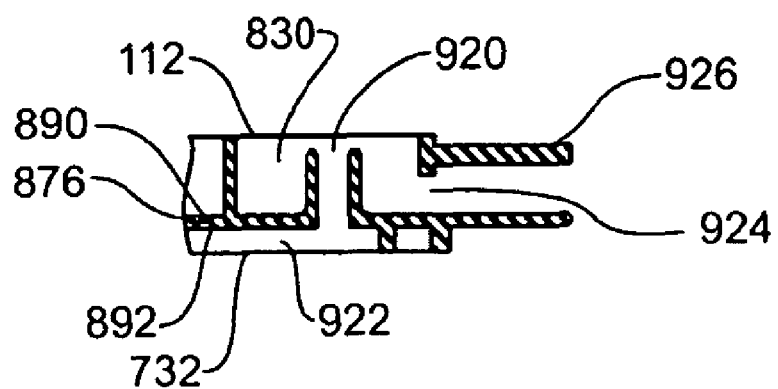
FIG. 25C is a partially-cutaway cross-sectional illustration of a valve provided by the pumping cassette of FIG. 25A.

FIG. 25C is a cross-sectional view of outlet valving chamber 830. Outlet valve 830 has a structure which is representative of the valving chambers provided in pumping cassette 800. The structure of valving chamber 830 is substantially similar to the structure of the valving chambers in pumping cassette 503 shown in FIG. 24 previously. Valving chamber 830 is formed in first side 890 of rigid component 876 of pumping cassette 800 and includes one occludable port 920 in fluid communication with liquid flow path 922 on second side 892 of the pumping cassette and a non-occludable port 924 in fluid communication with outlet line 926.

Figure 25D:
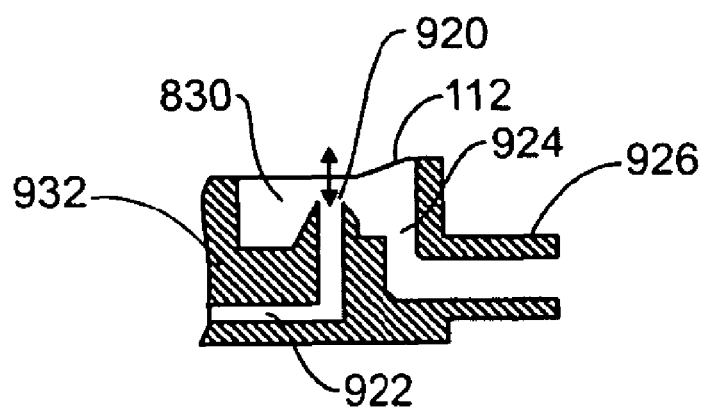
FIG. 25D is a partially-cutaway cross-sectional illustration of the valve of FIG. 25C, according to an alternative embodiment of the invention.

FIG. 25D shows an essentially equivalent valving chamber for an alternative embodiment of a pumping cassette having an essentially rigid component 932 covered on only a single side by a flexible membrane. Analogous components of the alternative valve embodiment of FIG. 25D are given the same figure labels as in FIG. 25C for comparison.

Referring again to FIG. 25A, the function of bypass valving chamber 860 and filter element 862, as well as the flexibility of operation of pumping cassette 800, will be explained in the context of a particular embodiment involving an application utilizing pumping cassette 800 that includes removing blood from the body of a patient, pumping the blood to various selectable destinations with pumping cassette 800, and returning treated blood or other fluids to the body of a patient. It may be desirable in such an embodiment to pump fluids which are being returned to the body of a patient through filter element 862 to remove any clots or aggregates, and to bypass filter element 862 when withdrawing blood from a patient with pumping cassette 800. When in operation, pumping cassette 800 is preferably coupled to a reusable component such that pumping cassette 800 is oriented essentially vertically with the various inlet and outlet lines pointing up. As illustrated, inlet/outlet port 816 is in fluid communication with a vascular access 950 of a patient. Blood withdrawn from the patient and fluid returned to the patient flows through inlet/outlet 816 and along liquid flow path 872 within pumping cassette 800. Liquid flow path 872 is in fluid communication with bypass valving chamber 860 via a first port 952. Also in the illustrated embodiment, inlet valve 832 of small pump chamber 826 is in fluid communication with a supply of anticoagulant 981, and outlet valve 830 of pump chamber 826 is in fluid communication with the vascular access 950 of a patient. In this configuration, small pump chamber 826 can be utilized as an anticoagulant delivery pump for pumping an anticoagulant to an injection site of a patient in order to keep the injection site from blocking and in order to provide anticoagulant to blood removed from the patient.

The function of bypass valving chamber 860 is to selectively permit liquid flow along a first liquid flow path bypassing filter element 862, or alternatively, to block flow along the first fluid flow path and direct flow along a second liquid flow path, which second liquid flow path directs the liquid so that it flows through filter element 862. Also, as discussed below, valving chamber 860 also permits liquid flow along both liquid flow paths above to be simultaneously blocked if desired. For the present embodiment where blood is being removed from a patient and, subsequently, liquids are being returned to a patient, the first liquid flow path described above will be selected by the system, by utilizing bypass valving chamber 860, when removing blood from the patient, and the second liquid flow path described above will be selected by the system, utilizing bypass valving chamber 860, when liquids are being pumped from the pumping cassette to the patient.

Bypass valving chamber 860 is comprised of two adjacent subchambers 970, 972 separated by a partition 974, which has an aperture permitting unrestricted fluid communications between the two subchambers. "Subchamber(s)" as used herein refers to regions of a chamber within a pumping cassette that are adjacent and are separated from one another by an internal partition, where the internal partition allows unrestricted fluid communication between the regions.

Figure 25E:
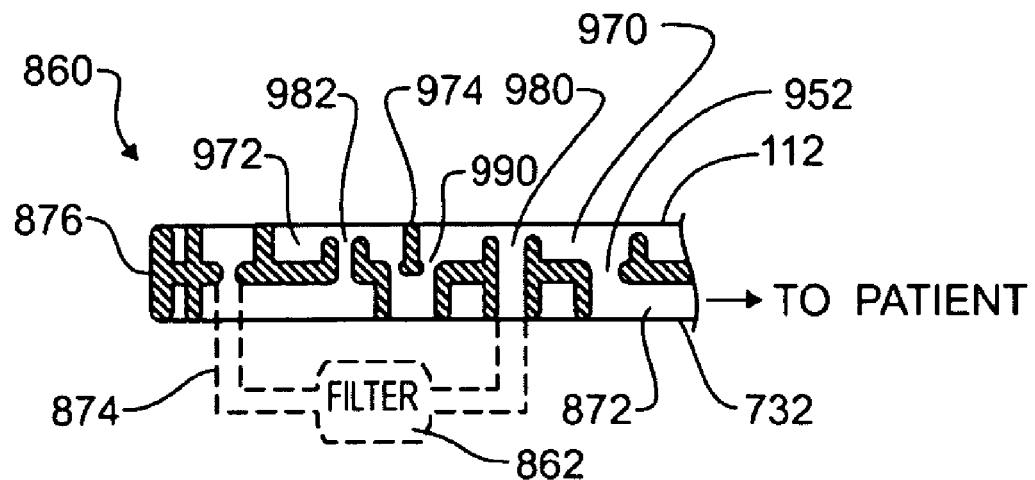
FIG. 25E is a partially-cutaway cross-sectional illustration of a bypass valving chamber of the pumping cassette of FIG. 25A.

The structure of bypass valving chamber 860 is shown in greater detail in the cross-sectional view of FIG. 25E. Referring to FIG. 25E, partition 974 separates the bypass valving chamber into subchambers 970 and 972 and is in fluid-tight contact with flexible membrane 112 when the pumping cassette is coupled to a reusable component. When coupled with a reusable component, subchamber 970 and subchamber 972 can each be coupled adjacent to and in operative association with a separate and independently controllable valve actuating chamber in the reusable component, which is each disposed adjacent to the subchamber. The valve actuating chambers can be independently operated to selectively occlude and open occludable port 980 in subchamber 970 and occludable port 982 in subchamber 972.

Also shown in FIG. 25E, for the purposes of illustrating the function of bypassing valving chamber 860, is a schematic representation of a second liquid flow path through the bypass valving chamber where the liquid is forced through filter element 862. Referring to both FIGS. 25A and 25E together, consider a first step in a pumping method using the pumping cassette during which blood is withdrawn from the patient by filling pump chamber 822 and/or 824. During this step, as discussed above, it is desirable to flow blood from the patient through bypass valving chamber 860 along a first liquid flow path which bypasses filter element 862. This can be accomplished by occluding occludable port 980 in subchamber 970 while leaving occludable port 982 in subchamber 972 non-occluded. In such a situation, blood will flow from the patient, along liquid flow path 872 into subchamber 970 through port 952, from subchamber 970 to subchamber 972 through opening 990 in partition 974, and will exit subchamber 972 through occludable port 982. For a situation where treated blood or another liquid such as plasma or saline is being pumped with pump chamber 822 and/or 824 through line 959 to bypass valving chamber 860 to be reinfused into a patient, as discussed above, it is desirable to operate the bypass valving chamber so that the liquid flows along the second liquid flow path, which passes the liquid through filter element 862 prior to returning it to the patient. In such a situation, the second liquid flow path can be selected by occluding occludable port 982 in subchamber 972 and leaving non-occluded occludable port 980 in subchamber 970. In which case fluid will flow along liquid flow path 959 and subsequently along liquid flow path 874 to the inlet port 904 of filter element 862. Liquid will not be able to enter subchamber 972 due to the occlusion of occludable port 982. The liquid, after entering filter element 862, will pass through filter 882 and exit filter element 862 by entering subchamber 970 through occludable port 980. The liquid will then exit subchamber 970 through port 952 and flow along liquid path 872 for return to the patient.

Figure 25F:
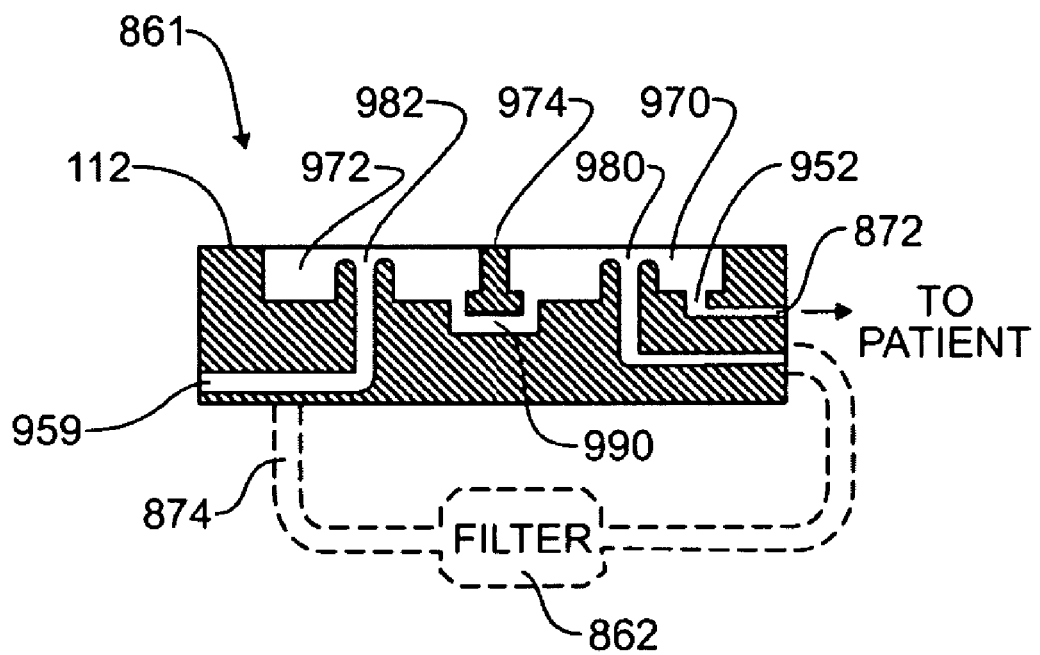
FIG. 25F is a partially-cutaway cross-sectional illustration of the bypass valving chamber of FIG. 25E, according to an alternative embodiment of the invention.

FIG. 25F shows an essentially equivalent bypass valving chamber 861 for an alternative embodiment of a pumping cassette having an essentially rigid component 932 covered on only a single side by a flexible membrane. Analogous components of the alternative bypass valve embodiment of FIG. 25F are given the same figure labels as in FIG. 25E for comparison.

During other operations utilizing pumping cassette 800, it may be desirable to operate bypass valving chamber in order to block liquid flow along both the first liquid flow path (bypassing the filter element) and along the second liquid flow path (wherein the liquid is passed through the filter element). Flow can be blocked along both the above-mentioned liquid flow paths utilizing bypass valving chamber 860 simply by occluding both occludable port 980 and 982 simultaneously.

While the operation of bypass valving chamber has been described in the context of pumping blood and liquids to and from a patient and for the purpose of selectively passing such liquids through a filter or bypassing the filter, the bypass valving chamber provided by the invention can be used for a wide variety of other purposes, wherein it is desirable to selectively choose liquid flow along a first and second liquid flow path. Also, while in the above-mentioned embodiment liquids flowing along a first and second liquid flow path through bypass valving chamber 860 flow through the chamber in a particular direction, in other embodiments, the direction of liquid flows along the first and second liquid flow path could be reversed or could be co-directional in either direction.

Referring again to FIG. 25A, a variety of exemplary sources and destinations in fluid communication with pumping cassette 800 are illustrated in the exemplary embodiment shown, in addition to anticoagulant source 981 and vascular access port 950, pumping cassette 800 is also connected to a source of saline 1000, a venous storage container 1002, an external filter 1004, and an oxygenator/heat exchanger 1006. By selectively operating the various pump chambers and valving chambers within the pumping cassette, liquids can be pumped to and from various sources and destinations for a variety of purposes and treatments as would be apparent to those of ordinary skill in the art.

In general, pump chambers 822, 824 and 826 of pumping cassette 800 can be operated utilizing a reusable component including a pump drive system constructed according to any of the embodiments previously described for such systems. Pump chambers 822, 824, and 826, when pumping a liquid to the body of a patient, preferably are operated utilizing pump stroke cycles including air detection and purging steps, as described previously. FIG. 25A illustrates that pumping cassette 800 includes several additional design safeguards for preventing air, or other gas, from being pumped to the body of a patient. For example, pump chamber 826, which is configured in this example to pump an anticoagulant to the injection port of a patient for certain embodiments where the pumping cassette is utilized for blood pumping, has an inlet port 1008 located at the top of the pump chamber and an outlet port 1010 located at the bottom of the pump chamber. This configuration results in any air in the pump chamber rising toward the top of the pump chamber so that it is less likely to be pumped through the outlet port before being detected by the system. Similarly, all liquid pumped to the patient by pump chambers 822 and 824 are pumped along liquid flow path 959, which is in fluid communication with valving chambers 846 and 854 which, in turn, are in fluid communication with ports 1012 and 1014 located at the bottom of pump chamber 822 and 824, respectively. Thus, as with pump chamber 826, any liquid pumped to the body of a patient using pump chambers 822 or 824 must exit the pump chambers through the bottom port. Similarly, filter element 862 is constructed so that its inlet 904 is located near the top of the filter element, and its outlet 980 is located near the bottom. This arrangement provides an additional layer of protection in that any liquids being pumped to the patient from pump chambers 822 or 824 are first diverted through filter element 862 by bypass valving chamber 860, and any gases contained in such liquids will tend to collect near the top of the filter element and will be inhibited from being pumped to the patient. In contrast, FIG. 25A shows that the majority of liquid flow paths in fluid communication with destinations other than the body of a patient, for example venous storage 1002 and external filter 1004, are, in turn, in fluid communication with ports 1016 and 1018 located at the top of pump chambers 822 and 824, respectively. When pumping to such destinations, it is typically not critical if air is present in the pumped liquid. During operation, these destinations, for example port 808 and 812, may be used by the system as locations to which to purge any air that is detected in pump chambers 822 and 824 during pump cycles in which a liquid is being pumped to the body of a patient. Any air detected in pump chamber 826 during operation may similarly by purged to port 820 in fluid communication with the anticoagulant supply.

FIG. 25A also shows that both pump chambers 822 and 824 contain similar fluidic connections to all of the sources and destinations provided by a pumping cassette 800 (except ports 818 and 820 utilized solely by pump chamber 826). Accordingly, pump chambers 822 and 824 may be operated individually and independently of each other, in some embodiments, so that liquids pumped with each chamber have a different source and destination or, in other embodiments, pump chambers 822 and 824 may be operated so that their inlet and outlet ports are in fluid communication with common sources and destinations. In the latter embodiments, the pumping system utilizing pumping cassette 800 can be operated so that the fill and pump strokes of pump chambers 822 and 824 are synchronized so that as one chamber is filling the other chamber is dispensing, and vice versa. Utilizing such an operating protocol, it is possible to operate pump chambers 822 and 824 to achieve a nearly continuous, uninterrupted flow between a desired source and destination.

For embodiments where pump chamber 826 is utilized as an anticoagulant pump, the desired average flow rate to be delivered by the pump chamber may be quite low. In such embodiments, it may be preferable to operate pump chamber 826 utilizing the pulsed delivery protocol described previously. As described previously, in such embodiments, pump chamber 826 is first filled with anticoagulant, inlet valve 832 is closed, a force is applied to flexible membrane 112 adjacent to the pump chamber, and outlet valve 830 is pulsed by selectively opening and closing the outlet valve for predetermined periods of time at predetermined intervals, which intervals and predetermined periods of time are controlled to yield a desired average liquid flow rate. Anticoagulant pump chamber 826 is typically operated to deliver anticoagulant only while either pump chamber 822 or 824 is being filled with blood withdrawn from the body of the patient. Additionally, anticoagulant pump chamber 826 may also be advantageously utilized to dispense anticoagulant when pump chambers 822 and 824 are not pumping liquids to or from the body of the patient but are being utilized for other purposes. In such cases, it may be desirable to continuously, or intermittently dispense a small quantity of anticoagulant with pump chamber 826 in order to assure that vascular access port 950 remains unoccluded. A pulsed delivery, as described above, may be utilized for operating the anticoagulant pump in such applications. For such applications, it is believed that the pulsed delivery of anticoagulant to the injection can have beneficial effects for keeping the site from clotting and dislodging small clots when compared to a continuous delivery of anti coagulant to the site. In addition, preferred embodiments of systems configured to provide pulsed delivery of anticoagulant are configured to continuously monitor the quantity/flow rate of anticoagulant to the patient and can adjust the flow rate by changing and controlling the positive pressure applied to the pump chamber during pulsed delivery as well as by changing the pulse duration and interval between pulses. Such capability allows for improved flow rate delivery volume control for applications where the anticoagulant is being delivered to a site at variable pressure, for example an artery of a patient.

When anticoagulant pump 826 is being utilized to dispense anticoagulant while pump chambers 822 and/or 824 are filling with blood from the patient, the pulse duration and interval between pulses of outlet valve 830 for delivering anticoagulant from pump chamber 826 can be selected, in preferred embodiments, so that the average liquid delivery rate of the anticoagulant is a desired predetermined fraction of the flow rate of blood to pump chambers 822 and/or 824 while they are being filled with blood from the patient. In other embodiments, it may be desirable to operate pump chamber 826 to provide an average liquid flow rate delivered from the pump chamber that is a predetermined fraction of the liquid flow rate of pump chamber 822 and/or 824 during a liquid delivery stroke. In yet other embodiments, pump chamber 826 may be operated so that the average liquid flow rate delivered from the chamber is a predetermined fraction of a liquid flow rate measured for a complete pump stroke (including fill and delivery) of pump chamber 822 and/or 824 or, in yet another embodiment, is a predetermined fraction of an average liquid flow rate (calculated over several pump stroke cycles) of pump chambers 822 and/or 824. It is also to be understood that instead of pump chamber 826 being operated to provide a liquid flow rate that is a predetermined fraction of a liquid flow rate provided by pump chambers 822 and/or 824, alternatively, pump chamber 822 could be operated to provide a liquid flow rate which is a predetermined fraction of a liquid flow rate of pump chamber 824, or vice versa.

Fluid Management Systems to Detect Volume of Liquid and Air in a Pump Chamber

Systems for circulating blood extracorporeally must have robust means of determining extracorporeal blood flow rates, as well as means to detect the presence of gases such as air in the pumping chambers of the blood flow circuit. Certain embodiments of the present invention include methods and systems for determining the volume of liquid present in a pumping chamber, and for detecting the presence of a gas in an isolatable pumping chamber. Such methods and systems may utilize pump chambers having at least one moveable surface, where, in some embodiments the moveable surface is a flexible membrane, which, in some embodiments is elastic. The term "membrane" as used herein refers to a movable surface which comprises at least a portion of a wall of a pump chamber. The term "flexible membrane" as used herein refers to a moveable surface having at least a portion that is movable by bending and/or stretching upon application of a force. A flexible membrane that is "elastic" or an "elastic membrane" as used herein refers to a flexible membrane that provides a resistance to bending and/or stretching by an applied force, in which the resistance is proportional to an amount of the displacement/stretching of the membrane from an equilibrium configuration in the absence of the force. A force applied to an elastic membrane that displaces the membrane from a relaxed equilibrium position will tend to create a stress in the membrane which resists further displacement and creates a restoring force tending to return the membrane to its relaxed equilibrium position. An "equilibrium condition" as used herein for elastic membranes or other movable surfaces refers to the configuration of the membrane/surface in a condition where there are no applied forces tending to move or displace the membrane/surface from a stationary position. A "relaxed equilibrium condition" as used herein refers to an equilibrium condition wherein a stress within a membrane/surface is at a minimum level allowed by the configuration of the pump chamber. For example, in a pump chamber that includes an elastic membrane, a relaxed equilibrium condition could be the configuration of the membrane at its minimum level of strain (stretching) when forces on both sides of the membrane are essentially balanced and equal.

In one embodiment, the method involves isolating a pumping chamber at least partially filled with a liquid by closing an inlet and an outlet valve in fluid communication with the pumping chamber. The method of this embodiment further involves determining a measured parameter related to the volume of the pumping chamber when a predetermined amount of force is applied to a moveable surface of the pumping chamber. The method further involves determining the measured parameter related to the volume of the pumping chamber when a different level of force is applied to the moveable surface of the pumping chamber. The measured parameters determined at each condition of the pumping chamber can then be compared to determine whether gas is also present within the pumping chamber.

The method of this embodiment is based at least in part on the fact that any gas present in a pumping chamber is relatively much more compressible that the liquid in the chamber. Gas within a pumping chamber allows the movable surface of the chamber to experience greater displacement in response to the application of a force on the movable member. In some embodiments, the method can involve the determination of a measured parameter related to the volume of the pumping chamber determined with at least two substantially differing levels of force applied to a moveable surface of the pumping chamber. For example, a first determination of the measured parameter related to the volume of the pumping chamber at a first condition can be made with a positive force applied to the moveable surface of the pumping chamber, such force tending to decrease the volume of the pumping chamber, and a second determination at a second condition can be made with a negative (or lesser) force to the moveable surface of the pumping chamber, the force tending to increase the volume of the pumping chamber. If the pumping chamber is essentially completely filled with a liquid, the relative incompressibility of the liquid will cause the measured parameter related to the volume of the pumping chamber at a first condition (e.g., with the positive force applied to the moveable surface of the pump chamber) to be nearly identical to the value of the measured parameter related to the volume of the pumping chamber measured with the pumping chamber at the second condition (e.g., with a negative force applied to the moveable surface of the pump chamber). In contrast, if the pump chamber also contains a quantity of a gas, such as air, the relative compressibility of the gas will cause the measured parameter related to the volume of the pumping chamber measured at the first condition to differ from the value of the measured parameter measured with the pumping chamber at the second condition by an amount proportional to the quantity of gas within the pumping chamber. In short, when a gas is present within the pumping chamber, the volume of the pumping chamber measured utilizing a positive force applied to a moveable surface thereof can be measurably different from the volume of the pump chamber determined utilizing a negative force applied to a moveable surface thereof. By comparing the measured parameters related to the volume of the pumping chamber determined at the first and second conditions above, it can be determined whether there is any gas present within the pumping chamber and in some embodiments, roughly, the relative amount of such gas.

A "measured parameter related to a volume" as used herein refers either to a measure of the volume itself or to a measured parameter determined by the system that can be converted to the volume by arithmetic or mathematical transformations utilizing one or more additional parameters that are either constant conversion factors or variables that are not functions of the volume (e.g., unit conversion factors, calibration constants, curve-fit parameters, etc.). In other words, rather than determining the volume of the pumping chamber directly, one need only determine parameters that are typically proportional to the volume and from which the volume could be calculated. In some embodiments, such measured parameters can include, for example, pressures and combinations of pressures, products of pressures and known fixed volumes of components of the pumping system, acoustical signals, temperatures, combinations of temperatures and pressures, values of linear displacement, and the like. A "condition" as used above in the context of the determination of a measured parameter related to the volume of a chamber, refers herein to a particular state of a pumping chamber, or other chamber in which a measured parameter is being determined. The state of the pumping chamber is associated with at least one measurable parameter related to the volume of the chamber upon application of a particular level of force or range of forces to an movable external surface of the chamber during the volume measurement procedure.

Force can be applied to the external movable surface of a pumping chamber in a number of ways, including, for example: moveable members in contact with the movable external surface of the pump chamber (e.g. pistons, push rods, plungers, etc.), pressurized fluids in contact with the movable external surface of the pump chamber, magnetic or electrostatic fields that are able to exert a force on the movable external surface of the pump chamber, and many others.

A pumping system that includes a movable member in contact with the external surface of the pump chamber can include a motor and linear actuator for moving the surface in contact with the pump chamber, so as to create a variable force on the surface of the pump chamber, and can further include a detector for measuring a linear displacement or position of the moveable member, the linear displacement or position acting as the measured parameter related to the volume of the pump chamber. Similarly, systems that utilize a magnetic or electrostatic field to exert a force on the movable external surface of the pump chamber can include detectors or measuring devices to determine either field strengths and/or displacements of the external movable surface of the pump chamber, the measurements constituting a measured parameter related to the volume of the pump chamber. Other systems and measurable parameters for determining the volume of the pump chamber for alternative systems may also be used.

One preferred embodiment for detecting the presence of a gas in a pump chamber utilizes pressurized fluids in contact with a moveable, or flexible, surface of the pumping chamber in order to apply a force to the surface. In a preferred system, fluid is brought into contact with a moveable or flexible external surface of a pump chamber at different and selectable pressures. In some embodiments using fluid sources to apply forces to movable surfaces of pump chambers, the movable surface is comprised, at least in part, by an elastic flexible membrane. The term "fluid source(s)" as used herein refers to one or more components of a pumping system that alone, or in combination, are able to supply or withdraw a quantity of fluid to another component, or components, of the pumping system with which they are, or are able to be placed, in fluid communication. A fluid source can include, but is not limited to, pumps, compressors, pressurized or evacuated tanks, and combinations thereof. The fluids used preferably include a gas, such as air, but may also include liquids. Such fluids, which are provided by the fluid supply components of certain embodiments of the pumping systems according to the invention are hereinafter collectively referred to as "measurement fluids." "Measurement fluids" (e.g., measurement gases or measurements liquids) as used herein refer to fluids that are used to determine a volume, or a measured parameter related to a volume of a container within the pumping system, such as, for example a pump chamber. Preferably, measurement fluids are not in fluid communication with a liquid being pumped or metered by a pumping chamber of the system. In an embodiment, the measurement fluid sources can comprise one or more components of a measurement fluid supply system constructed and arranged to pressurize one or more components of the pumping system. "Constructed and arranged to pressurize" a component, as used herein, refers to a system containing the necessary sources of fluid, together with the associated components (e.g., plumbing and pneumatic or other connections), that are necessary to enable the system to change the pressure of a fluid contained within the component.

Figure 26:
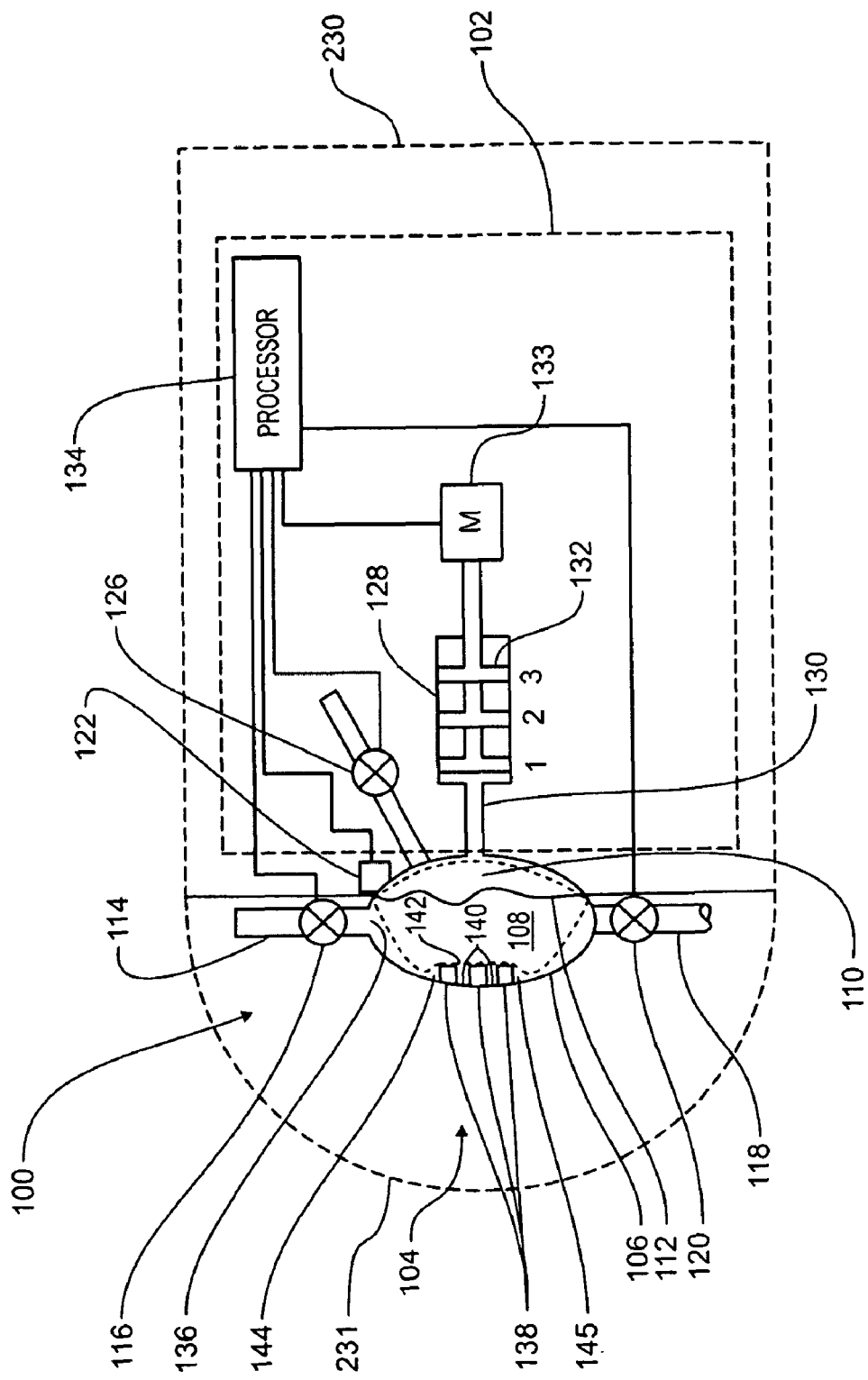
FIG. 26 is a schematic illustration of a pumping system according to one embodiment of the invention.

One embodiment of a pumping system that utilizes a measurement gas to actuate a pump chamber to pump a liquid and to detect the presence of a gas in the pumping chamber is shown schematically in FIG. 26. Pumping system 100 includes a fluid supply system 102 containing a fixed quantity of a measurement gas and a mechanism for changing the volume of the measurement gas within the system. Pumping system 100 also includes a pump 104 comprising a substantially rigid container 106 that includes a pump chamber 108 and a control chamber 110 disposed therein. Pump chamber 108 and control chamber 110 are fluidically isolated (i.e., not able to be placed in fluid communication) from each other by a flexible membrane 112, disposed between the two chambers, such that pump chamber 108 is coupled to control chamber 110 and in operative association therewith. Such a membrane may (as just one example) be constructed of medical grade polyvinyl chloride.

"Substantially rigid" as used herein refers to a material, or a component constructed therefrom, that does not flex or move substantially under the application of forces applied by the pumping system. A "control chamber" as used herein refers to a chamber of a pumping system that is coupled to, or contains, a volumetric chamber, for example a pump chamber, for the purpose of exerting a force on the volumetric chamber and, in preferred embodiments, for determining a measured parameter related to the volume of the volumetric container. The term "coupled to" as used in this context with respect to chambers or other components of the pumping system, refers to the chambers or components being attached to, or interconnected with, another component of the pumping system, such that the other component is able to exert a force on an external surface of the chamber or component to which it is coupled.

Liquid to be pumped by pump system 100 enters pump chamber 108 via inlet line 114 including an inlet valve 116. Liquid can be pumped from pump chamber 108 to a desired downstream destination through outlet line 118 including an outlet valve 120 therein. Control chamber 110 includes a pressure measuring component 122 for determining the pressure of the measurement gas within the control chamber. A "pressure measuring component" as used herein refers to a device that is able to convert a fluid pressure into a measurable signal or parameter. Pressure measuring components that may be useful in this embodiment include but are not limited to: transducers; pressure gauges; manometers; piezoresistive elements; and others as apparent to those of ordinary skill in the art.

Preferred embodiments of control chamber 110 of pumping system 100 also include a vent line 124 including a vent valve 126 therein. Control chamber 110 is connected in fluid communication with a variable volume cylinder 128 via a measurement gas inlet line 130. Variable volume cylinder 128 which includes a piston 132 therein which is moved and actuated by motor 133 for compressing, or expanding the volume of the measurement gas contained within the system.

Pumping system 100 also preferably contains a processor 134 which is in electrical communication with the various valves, pressure transducers, motors, etc. of the system and is preferably configured to control such components according to a desired operating sequence or protocol. Reference to a processor being "configured" to perform certain tasks herein refers to such processor containing appropriate circuitry, programming, computer memory, electrical connections, and the like to perform a specified task. The processor may be implemented as a standard microprocessor with appropriate software, custom designed hardware, or any combination thereof. As discussed in more detail below, processor 134, in addition to including control circuitry for operating various components of the system, also preferably includes a comparer that is configured to determine a measured parameter related to the volume of pump chamber 108 and to detect the presence of any gas contained within pump chamber 108 during operation of pump 104. A "comparer" as used herein refers to a processor (e.g., with appropriate programming) or circuit or component thereof that is able to compare the values of two or more measured parameters or other parameters derived therefrom.

In embodiments where allowing gas to migrate through die system is problematic, pump chamber 108 is oriented in an essentially vertical configuration during operation such that inlet line 114 is disposed above outlet line 118. The above-described orientation is advantageous for preventing any gas which may be present in pump chamber 108 during operation from being pumped from the pump chamber to a downstream destination through outlet line 118. Instead, any gas contained within pump chamber 108 will tend to rise towards the top of the pump chamber, for example the region adjacent to inlet port 136, and will be detected by the system, as described in more detail below, before being pumped from the pump chamber.

In some embodiments, pump chamber 108 includes the novel inclusion of a plurality of spacers 138 included therein. The spacers 138 function to prevent flexible membrane 112 from contacting an inner surface 140 of the pump chamber when the liquid contained within pump chamber 108 is being pumped through outlet line 118. During the pump stroke, the maximum displacement of flexible membrane 112 which is permitted by spacers 138 is shown in FIG. 26 by dashed line 142. It can be seen that even with flexible membrane 112 at its maximum displacement into pump chamber 108, as defined by dashed line 142, spacers 138 create a dead space 144 to contain any gas which may be present in pump chamber 108, thus inhibiting the gas from being pumped through the pump chamber. Spacers 138, in combination with the vertical orientation of pump chamber 108, also serve to assist any gas present in pump chamber 108 to rise to the top of the pump chamber so that it may more easily be purged from the pump chamber, as described in more detail below.

Pump chamber 108 of pumping system 100 is essentially defined by a substantially rigid wall 145 (e.g., made of a rigid plastic such as a polyacrylate) having a flexible membrane 112 disposed over the wall, thus forming a volumetric chamber. An alternative embodiment for providing a pump chamber and a control chamber is shown in FIG. 2. Pump 152 of pumping system 150 includes a pump chamber 154 which comprises an essentially flexible container 156 disposed within a substantially rigid enclosure 158 having an interior volume surrounding pump chamber 154 which comprises a control chamber 160. In other embodiments (not shown), the pump chamber may be differently configured or disposed within the control chamber and may include substantially rigid, but moveable surfaces, as opposed to the flexible surfaces of pumping systems 100 and 150 described above.

Figure 27A:
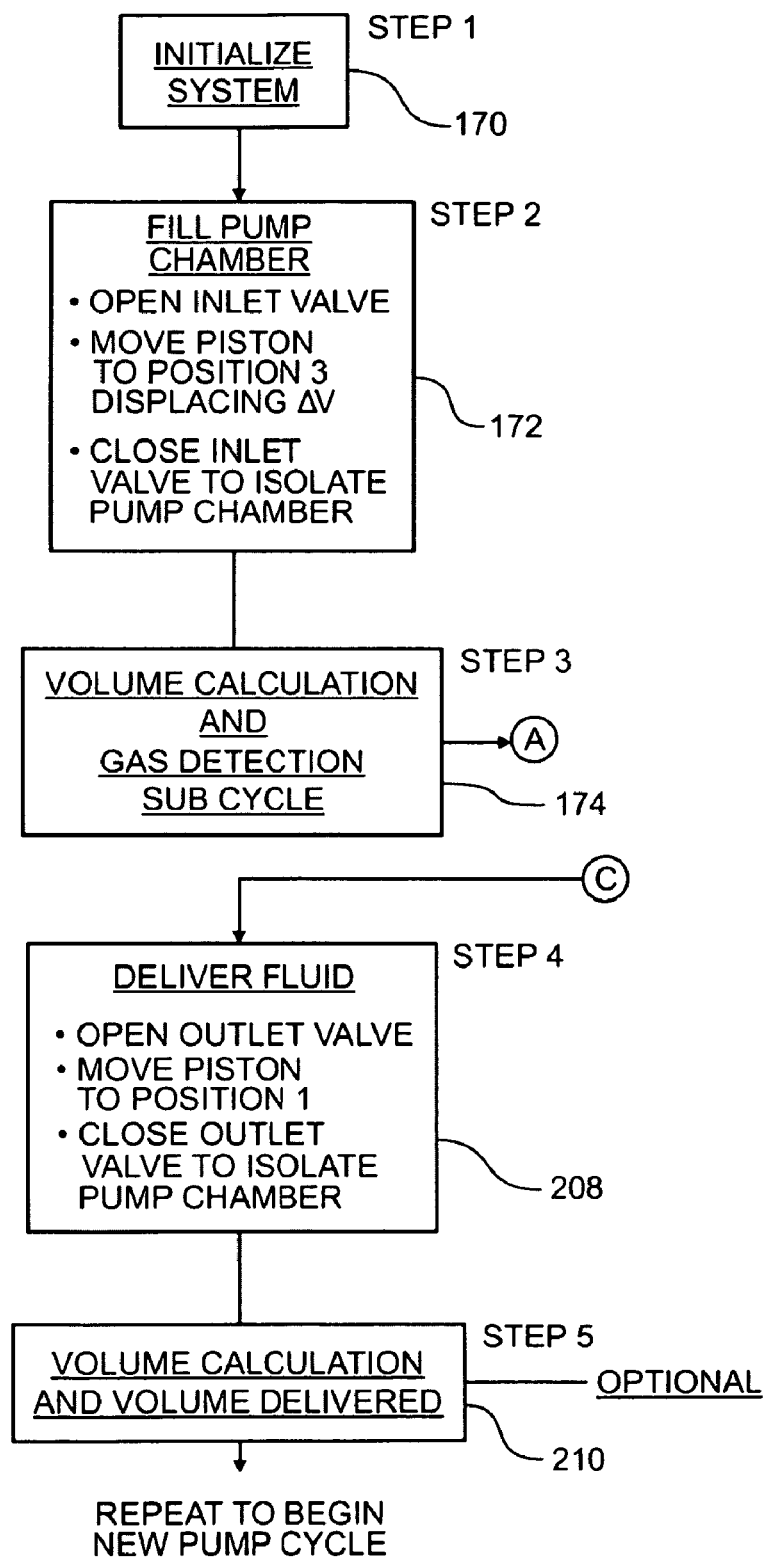
FIG. 27A is a flow chart illustrating a series of steps in a pumping cycle according to one embodiment of the invention.
Figure 27B:
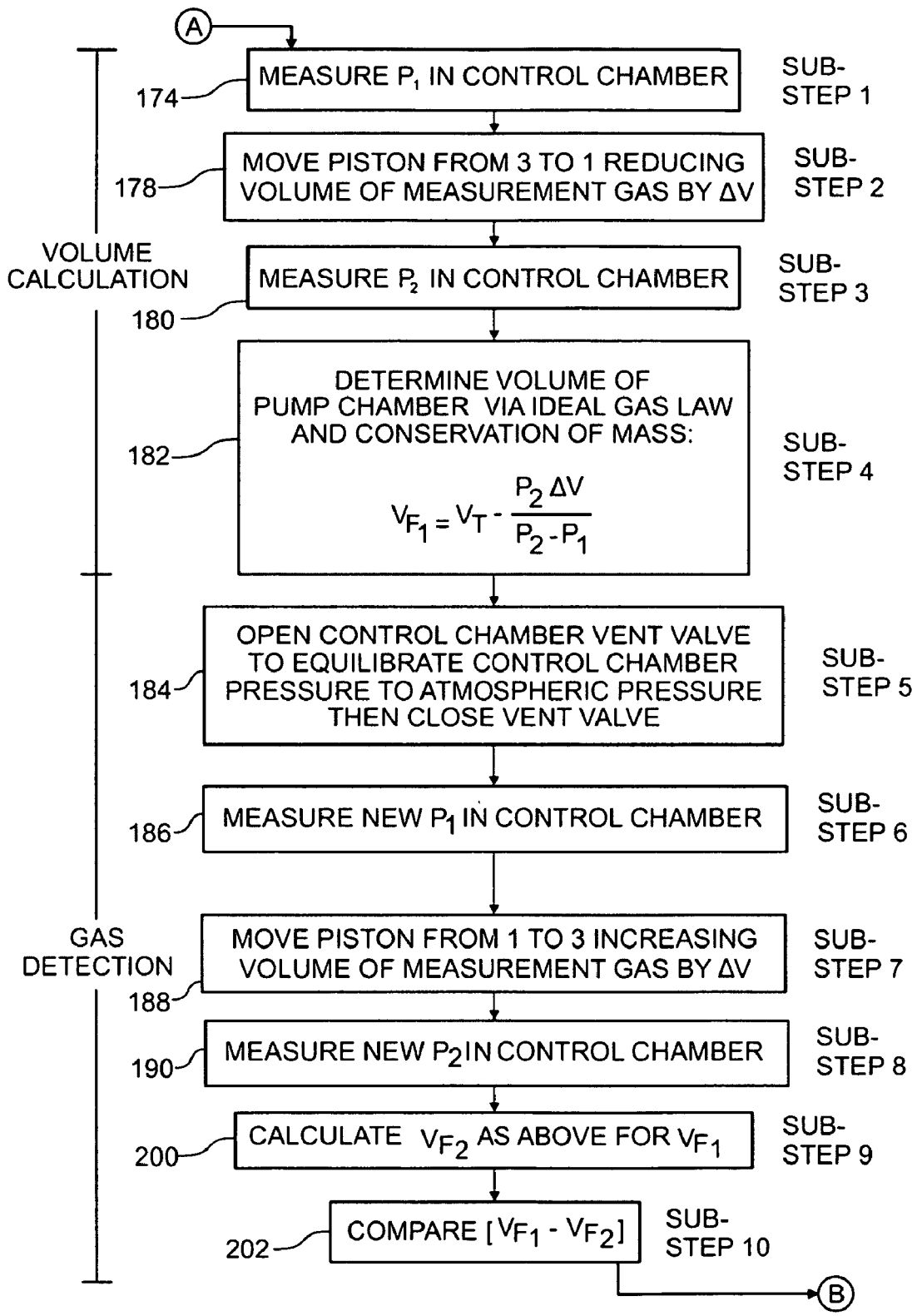
FIG. 27B is a flow chart illustrating a series of substeps of the pumping cycle of FIG. 27A for performing volume calculation and air detection.
Figure 27C:
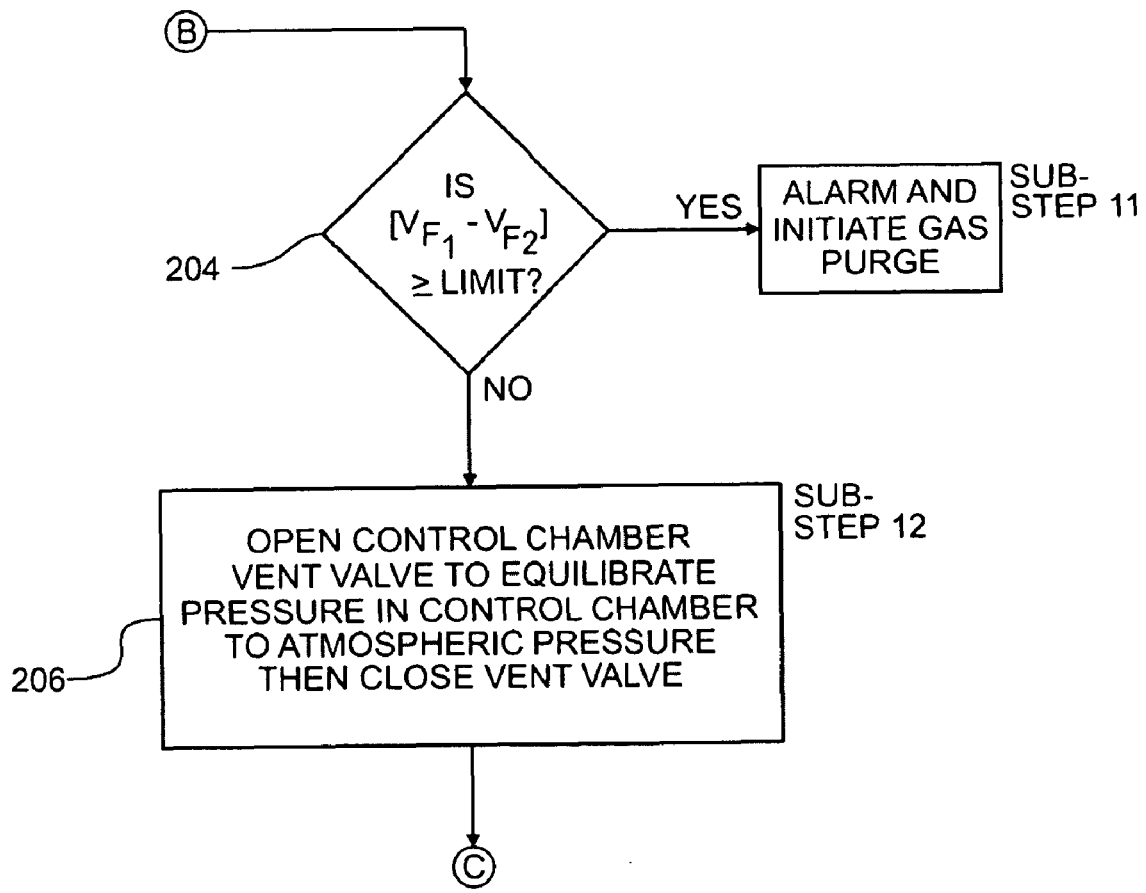
FIG. 27C is a flow chart illustrating a series of substeps of the pumping cycle of FIG. 27A for detecting the presence of a gas in a pump chamber.

One embodiment of a method for operating the pumping system 100 shown in FIG. 26 for pumping a liquid with pump chamber 108, and for detecting the presence of a gas in pump chamber 108, is shown in detail in the flow charts of FIGS. 27A-27C. Referring to FIG. 27A, an exemplary pump cycle utilizing pumping system 100 will be described. The pump cycle illustrated utilizes changes in displacement of the piston to change the pressure of a measurement fluid within the system in order to apply selected forces to membrane 112 for pumping and air detection. The embodiment illustrated also utilizes an equation of state (e.g. the ideal gas law) in determining pump chamber volumes from measured or known values of pressure and volume.

For embodiments employing a protocol for detecting air/gas where pump and/or control chamber volumes are determined, at least in part, from measured pressures by utilizing an equation of state describing the pressure-volume behavior of a measurement gas, the pump chamber preferably includes a movable surface which comprises an elastic membrane. The restoring force of the elastic membrane, when stretched or displaced from a relaxed equilibrium condition, enables the pressure on each side of the membrane (i.e. in the pump chamber and control chamber) to be different, where the degree of difference in the pressures, and the resistance to further displacement/stretching (stress/elastic energy stored in the membrane), is a function of the degree of stretch or displacement from the relaxed equilibrium condition of the membrane. In such embodiments, it is also preferred that the measurement gas pressures applied to the elastic membrane during the determination of pump/control chamber volumes at the first and second conditions of applied force for detecting air/gas in the pump chamber discussed above, tend to stretch the elastic membrane (if air/gas is present in the pump chamber), from its equilibrium configuration before the pressure is applied, by a different extent for each condition, so that the stress in the membrane and its resistance to further displacement in response to a given level of applied pressure will be different for the first and second condition (or in other words, the force/displacement response of the elastic membrane for the first and second conditions will be asymmetrical). In such embodiments, the difference in the pressure in the control chamber versus the pressure in the pump chamber, at an equilibrium condition, will be different for the first condition of applied pressure versus the second condition of applied pressure. In such embodiments, without being tied to any particular physical mechanism, it is believed that the different level of stress and strain of the elastic membrane during measurements of pump/control volume determined at the first and second conditions above create, at least in part, deviations in the pressure-volume behavior of the measurement gas from that predicted for each condition by the equation of state, which deviations can create and/or enhance a difference in the volume of the pump/control chamber determined for each condition by using the equation of state.

In some embodiments, one way to achieve or enhance such asymmetry in the response of the elastic membrane to the applied measurement gas pressures utilized during volume determinations for gas detection is to perform the volume determination steps when the pump chamber flexible elastic membrane has already been stretched, from the configuration it has at a relaxed equilibrium condition, with essentially equal fluid pressures on each side of the membrane, before the application of pressurized measurement gas to the membrane for the purpose of volume measurement. This can be accomplished, for example, by performing the volume determinations related to air/gas detection after filling the pump chamber with sufficient liquid so that the elastic membrane is at least somewhat stretched, and preferably substantially stretched, by displacement of the membrane in the direction of the control chamber, and by using a positive measurement gas pressure during volume measurement at the first condition and a negative measurement gas pressure during volume measurement at the second condition (or vice-versa. In alternative embodiments the desired asymmetry in the response of the elastic membrane during volume determinations involved in air/gas detection could also be achieved by utilizing levels of measurement gas pressures applied to the elastic membrane for volumetric determinations performed at the first and second conditions of measurement that are selected to impart a different, and preferably substantially different degree of elastic stretch to the membrane. While preferred embodiments of pump chambers for use when utilizing an equation of state based procedure for calculating pump/control chamber volumes include a moveable surface at least partially comprised of an elastic membrane, in alternative embodiments, non-elastic movable surfaces could potentially be used, as long as the measurement fluid pressures applied to the surface during volume measurement at the first condition and second condition create different levels of stress in the surface and differences in the equilibrium pressures within the control and pump chamber. Such embodiments could, for example, utilize a non-elastic movable surface or flaccid membrane, where measurement fluid pressures applied during the first condition of volume determination tend to move the surface/membrane (if a gas is present in the pump chamber) to its maximum allowed displacement so that the surface is no longer free to move in response to the applied force, a stress is created in the surface/membrane, and a pressure difference exists between the pump and control chambers. Measurement of volume at a second condition for such embodiments could apply a different measurement fluid pressure to the surface, the pressure tending to move the surface/membrane (if a gas is present in the pump chamber) to reduce or substantially eliminate the stress within the surface/membrane so that at equilibrium, the difference in pressure in the pump and control chambers is reduced or essentially eliminated.

Referring again to the protocol of FIG. 27, it will be assumed initially that pump chamber 108 has been emptied, and that elastic membrane 112 is extending into pump chamber 108 at its maximum allowable displacement defined by line 142. Piston 132 is assumed to be at its far left position of travel (shown as position 1 in FIG. 26). Referring to FIG. 27A, step 1 (170) involves initializing the system so that all valves are closed and piston 132 and flexible membrane 112 are in the positions described above. Step 2 (172) involves filling the pump chamber 108 with a liquid to be pumped. The step involves first opening inlet valve 116, then actuating motor 133 so as to move piston 132 to position 3 shown in FIG. 26, thereby increasing the volume of pump chamber 108 by an amount defined as .DELTA.V. Then, inlet valve 116 is closed in order to isolate pump chamber 108. Step 3 (174) of the exemplary pumping cycle involves a series of sub, and for detecting the presence of any gas contained within pump chamber 108. Step 3 (174) is described in greater detail in FIG. 27B. Referring again to FIG. 27A, step 4 (208) of the pumping cycle involves delivering the liquid contained in pump chamber 108. First, outlet valve 120 is opened. Motor 134 is then actuated to move piston 132 from position 3 to position 1, thereby delivering a volume of fluid .DELTA.V. Outlet valve 120 is then closed in order to isolate pump chamber 108. In some embodiments in which die accuracy of determining the volume delivered by pump chamber 108 is critical, the volume of pump chamber 108 after step 4 (208) may be determined, for example, by repeating substeps 1-4 (176, 178, 180, 182) of the volume calculation and air detection subcycle of FIG. 27B. In that case, the volume delivered for the above described pump stroke can be determined by taking a difference in the volume of pump chamber 108 determined in step 3 (174) and in step 5 (210). Finally, if multiple pump strokes are desired, the entire pump cycle of FIG. 27A may be repeated.

FIGS. 27B-27C show one embodiment of a volume calculation and gas detection method shown at step 3 (174) of FIG. 27A. Substep 1 (176) of subcycle 174 involves measuring the pressure P.sub.1 of the measurement gas in control chamber 110 with pressure transducer 122 and recording or storing the pressure with processor 134. In substep 2 (178) piston 132 is moved from position 3 to position 1 thereby reducing the volume of the measurement gas contained within the system by .DELTA.V. In substep 3 (180) the pressure of the measurement gas in control chamber 110 is measured again and recorded as P.sub.2. It will be appreciated that P.sub.2 will be greater than P.sub.1 due to the compression of measurement gas within the system. The volume of fluid contained in pump chamber 108 is then determined in substep 4 (182), with the pump chamber at this first condition, using an appropriate equation of state for the measurement fluid being utilized. In the case of a measurement gas, such as air, for systems utilizing pumping pressures which are relatively low (typical pumping pressures utilized by pumping systems according to the invention range from abut −14 psig to about 15 psig) the ideal gas law can be employed. Recognizing that no measurement gas was added to or removed from the system, and utilizing the ideal gas law combined with conservation of mass, the volume of fluid contained in pump chamber 108 is determined by Equation 1 (see FIG. 27B, Substep 4):

$$V_{F1} = V_T - (P_2 \Delta V)/(P_2 - P_1)$$

Equation 1 assumes that any temperatures changes or differences caused by changing the volume of measurement gas are minimal and that the system is essentially isothermal. It will be appreciated that for systems where temperature changes may be significant, the temperature dependence of the measurement fluid, as defined by the equation of state being used, may be incorporated into the volume calculation of substep 4 (182) in a straightforward fashion, as apparent to those of ordinary skill in the art. V.sub.F in equation 1 refers to the internal volume of pump chamber 108 and V.sub.T refers to the known total volume of the system including pump chamber 108, control chamber 110, and the volumes contained within measurement fluid inlet line 130 and cylinder 128.

The remaining substeps of the volume calculation subcycle 174 involve re-determining the volume of the pump chamber 108 at a different condition and comparing the volumes determined at the first and second conditions. In substep 5 (184) of FIG. 27B, control chamber vent valve 126 is opened to equilibrate the pressure in control chamber 110 with the surrounding atmosphere. Vent valve 126 is then closed. A new pressure P.sub.1 is measured with transducer 122 in control chamber 110 in substep 6 (186). In substep 7 (188) piston 132 is moved from position 1 to position 3 thereby increasing the volume of measurement gas within the system by .DELTA.V. In substep 8 (190) the new pressure P.sub.2 in control chamber 110, which will be below atmospheric pressure, is measured and recorded. In substep 9 (200) the volume of pump chamber 108 V.sub.F is calculated as described above in substep 4 (182). Substep 10 (202) involves determining the difference between V.sub.F determined in substep 4 (182) and V.sub.F determined in substep 9 (200) and taking an absolute value of the difference. In substep 11 (204), shown in FIG. 27C, the above difference is compared to a predetermined limit that is proportional to a maximum allowable quantity of air or other gas which can be present in pump chamber 108 during operation. The predetermined limit is typically determined empirically, and chosen such that air volume exceeding dead space 144 volume will also exceed the predetermined limit. If the difference exceeds the predetermined limit the processor 134 will create an alarm condition and initiate an air purge.

If the difference in measured volumes is less than the allowable limit (204), the system will proceed to pump the liquid contained in pump chamber 108. In substep 12 (206) the system opens control chamber vent valve 126 in order to equilibrate the pressure in control chamber 110 and the surrounding atmosphere, and then closes vent valve 126. Pumping system 100 is now in condition to deliver the liquid contained in pump chamber 108.

As described above, the measured volumes at the two different conditions can be compared to detect the presence of gas in the pump chamber. If the presence of a gas is detected in the pump chamber and is of sufficient quantity to cause the system to set off an alarm, as described above in substep 11 (204) FIG. 27C, instead of proceeding to deliver the fluid to a desired downstream destination as described above, the pumping system 100 will instead initiate an air purge. During the air purge, instead of outlet valve 120 being opened while fluid is being pumped from pump chamber 108, inlet valve 116 is opened, and the fluid, including any gas in the pump chamber, is pumped from the pump chamber through inlet line 114 to a safe purge destination.

While the above described example of a pump stroke cycle for pumping system 100 was described as being fully controlled, and regulated by a processor, the method could equivalently be performed under manual operator control without utilizing such a processor or by using any other mechanism to control the operation. In addition, while the above described methods involve an essentially ideal gas as a measuring fluid, other embodiments of the invention may utilize non-ideal measurement gases, or liquids as measurement fluids. When such alternative measurement fluids are used, the ideal gas law may no longer be an appropriate equation of state to utilize for determining volumetric measurements but instead an equation of state appropriate for the measurement fluid being used may be utilized. In addition, as discussed earlier, a variety of other techniques for measuring the volume contained in a volumetric container can be used to determine a measured parameter related to the volume of a pump chamber having a movable surface or flexible membrane at a first and second condition of applied force, such alternative means of volumetric measurement being apparent based on the disclosure herein and are within the scope of the present invention. In addition, the skilled practitioner will envision many alternative mechanisms for applying a variable level of force to a moveable wall, for example flexible elastic membrane 112, or other movable wall configuration, of a pump chamber, which can be substituted for the pressurized gas pump drive system 230 described in FIG. 26. It should also be emphasized that the particular steps described as part of the exemplary pump cycle methods described herein may be performed in a different sequence, and certain steps may be substituted or eliminated, without affecting the overall performance of the methods. For example, when detecting the presence of a gas in the pump chamber, instead of applying a positive pressure to the flexible membrane of the pump chamber to calculate a first volume followed by applying a negative pressure to the flexible membrane of the pump chamber to calculate a second volume, these steps could easily be interchanged or both pressures may be positive or negative, as long as they differ by a sufficient amount to enable the detection of gas in the pump chamber.

It should be appreciated that the particular ways in which the various tanks, valves, pumps, and chambers of the various pumping systems described herein are arranged, configured, and interconnected can be varied considerably without changing the overall performance or operation of the pump drive system. A variety of alternative configurations for the pumping systems described herein have been previously described in U.S. Pat. Nos. 4,778,451, 4,808,161, 4,826,482, 4,976,162, 5,088,515, and 5,178,182, each of which is commonly owned and incorporated herein by reference in its entirety.

Fluid Management Systems Using Variable Flow Valves

One embodiment of the present invention involves the novel incorporation of a variable size orifice valve in a fluid supply system for measuring the volume of a volumetric chamber and, in some embodiments, for providing a pressurized fluid in contact with the moveable surface of a pump chamber. Referring to FIGS. 23 and 28, a preferred pump drive system according to the invention includes a variable size orifice valve which can be controlled by the processor of the system in order to more precisely control the pressure of measurement gas applied to the control chamber during filling and dispensing of liquid from the pump chamber.

A preferred arrangement of components for providing a pump drive system according to the invention is shown in FIG. 23. Pumping system 500 includes a pump 104 including a pump chamber 108 separated from a control chamber 110 by a flexible membrane 112, similar to that described previously. Pumping system 500 includes a pump drive system 502 including a fluid supply system 504 connected in fluid communication with control chamber 110. Pump drive system 502 includes a processor 506 configured for controlling the various components of the system for pumping a liquid with pump chamber 108, and including a comparer for determining the presence of a gas in pump chamber 108 from measured parameters related to the volume of pump chamber 108, as described previously. Fluid supply system 504 includes a positive pressure source comprising a positive pressure tank 508 containing a measurement gas under positive pressure. Positive pressure tank 508 includes a pressure transducer 510 configured to measure the pressure of the measurement gas and send a signal to processor 506. Fluid supply system 504 also includes a negative pressure source comprising a negative pressure tank 512 containing a measurement gas under negative pressure. Negative pressure tank 512 includes a pressure transducer 514 for measuring the pressure of a measurement gas within the tank.

Fluid supply system 504 also contains a pump 516 positioned and configured to pump measurement gas from negative tank 512 through line 518, valve 520, valve 522 and line 524 to positive pressure tank 508, so as to establish a pressure difference between the measurement gas contained in positive pressure tank 508 and negative pressure tank 512. Positive pressure tank 508 has an outlet line 526 and negative pressure tank 512 has an outlet line 528, each line being in fluid communication with a switch valve 530. The outlet of switch valve 530 can be placed in fluid communication with both control chamber 110 and reference chamber 532 of the system. Switch valve 530 is preferably a solenoid-operated three-way type valve which is controlled by processor 506, so that in a first position, positive pressure tank 508 is placed in fluid communication with control chamber 110 and/or reference chamber 532; and in a second position negative pressure tank 512 is placed in fluid communication with control chamber 110 and/or reference chamber 532.

Outlet line 534 from switch valve 530 can include a variable-sized orifice valve 536. Preferably, valve 536 has an orifice the size of which is selectively adjustable over an essentially continuous range of values in order to control the flow rate of a fluid. The size of the orifice in variable size orifice valve 536 is controlled, in preferred embodiments, by processor 506 in order to selectively vary the pressure of the measurement gas downstream of variable size orifice valve 536. Variable size orifice valves for use in the invention are known in the art and have been utilized for other purposes. Such valves are available, for example, from Parker Hannilin Corp., Pneutronics Division.

Referring to FIG. 23, the outlet of variable size orifice valve 536 is in fluid communication with measurement fluid inlet line 538, which provides measurement gas to control chamber 110. The outlet of variable size orifice valve 536 is also in fluid communication with valve 540 on inlet line 542 of reference chamber 532. Reference chamber 532, in preferred embodiments, also includes a vent line 544 through which measurement gas can be vented to the atmosphere by opening valve 546. Reference chamber 532 also includes a pressure transducer 548 that measures the pressure of a measurement gas in the reference chamber.

Figure 28A:
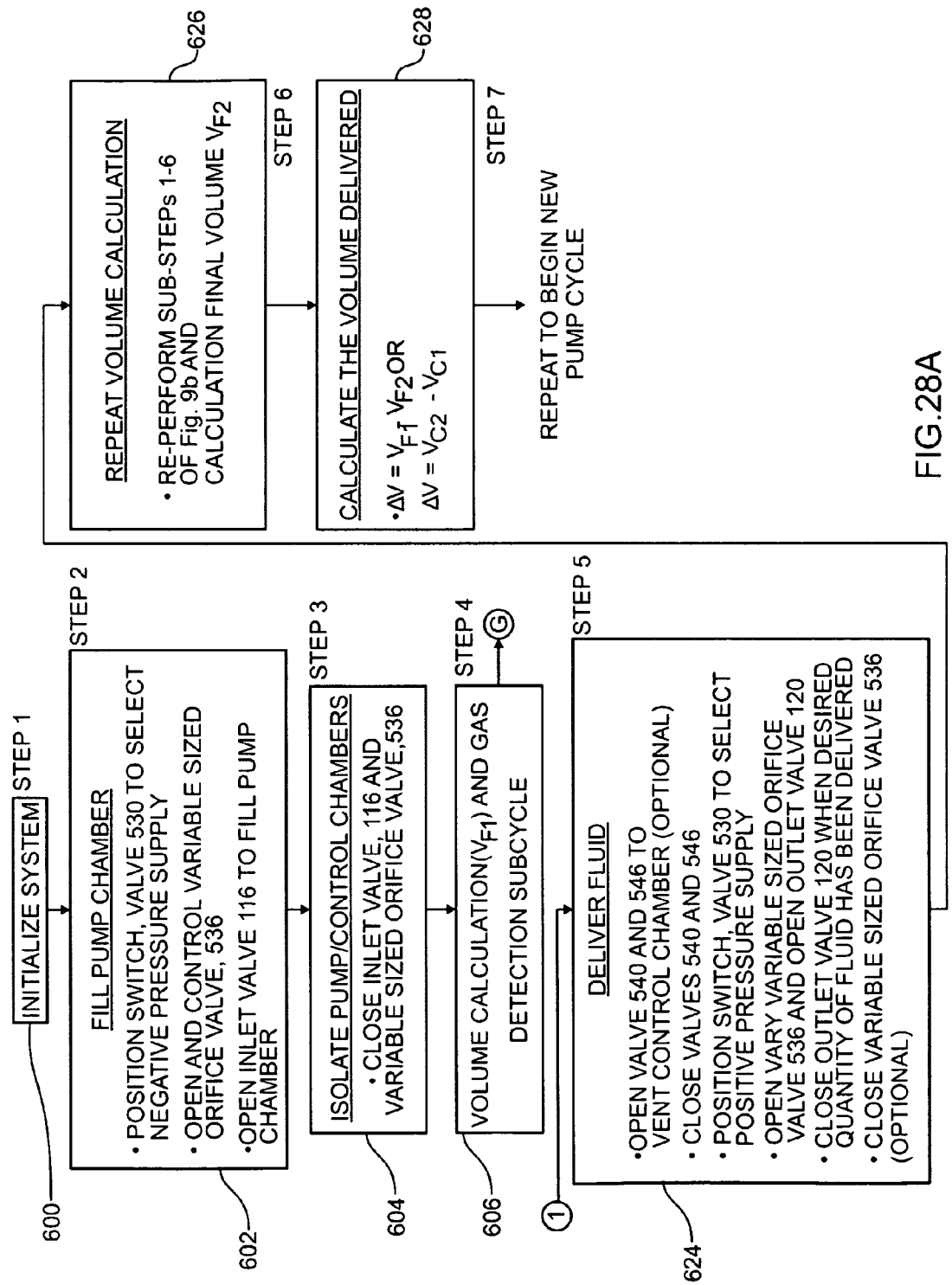
FIG. 28A is a flow chart illustrating a series of steps in a pumping cycle according to one embodiment of the invention.
Figure 28B:
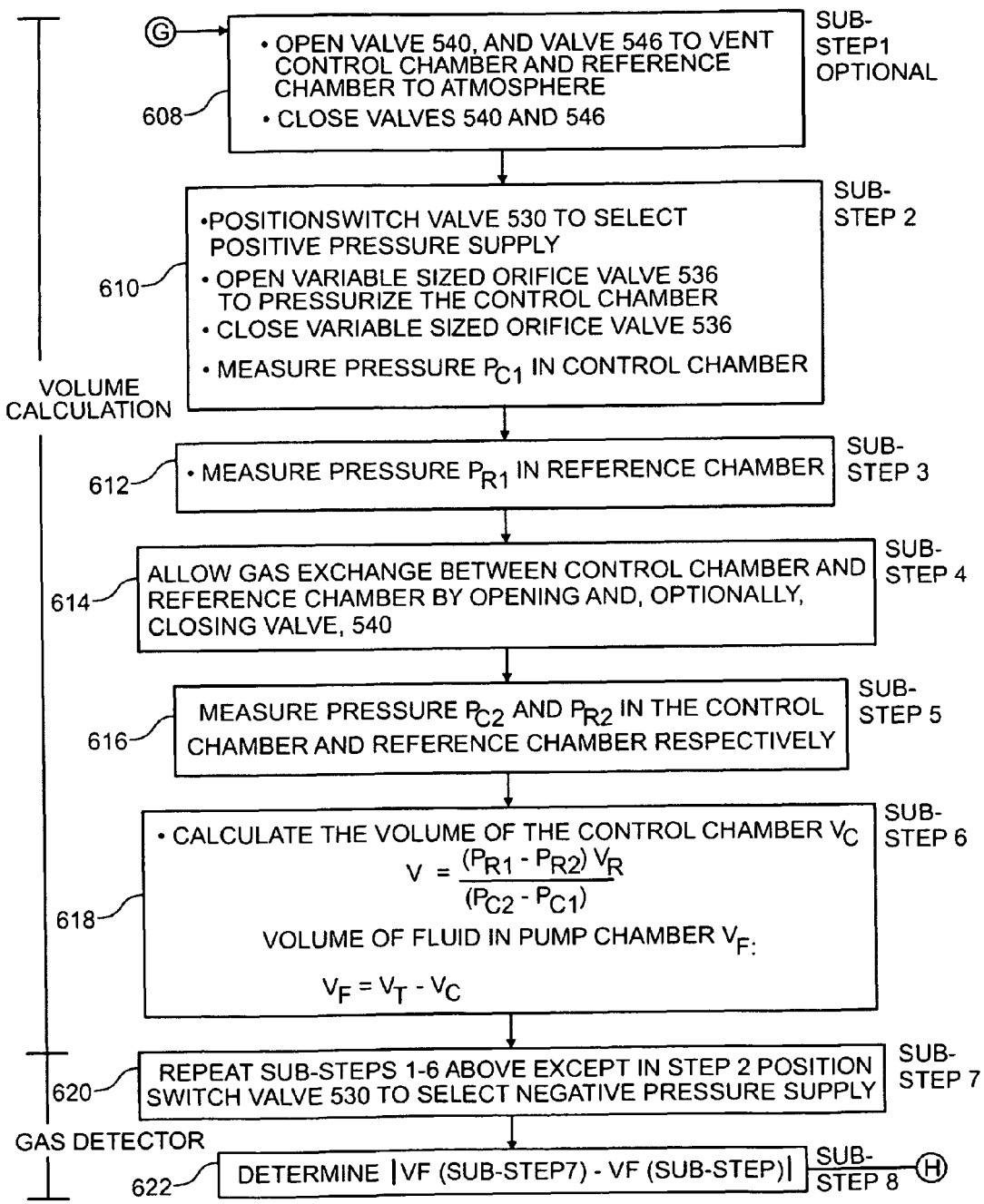
FIG. 28B is a flow chart illustrating a series of substeps of the pumping cycle of FIG. 28A for performing volume calculation and air detection.
Figure 28C:
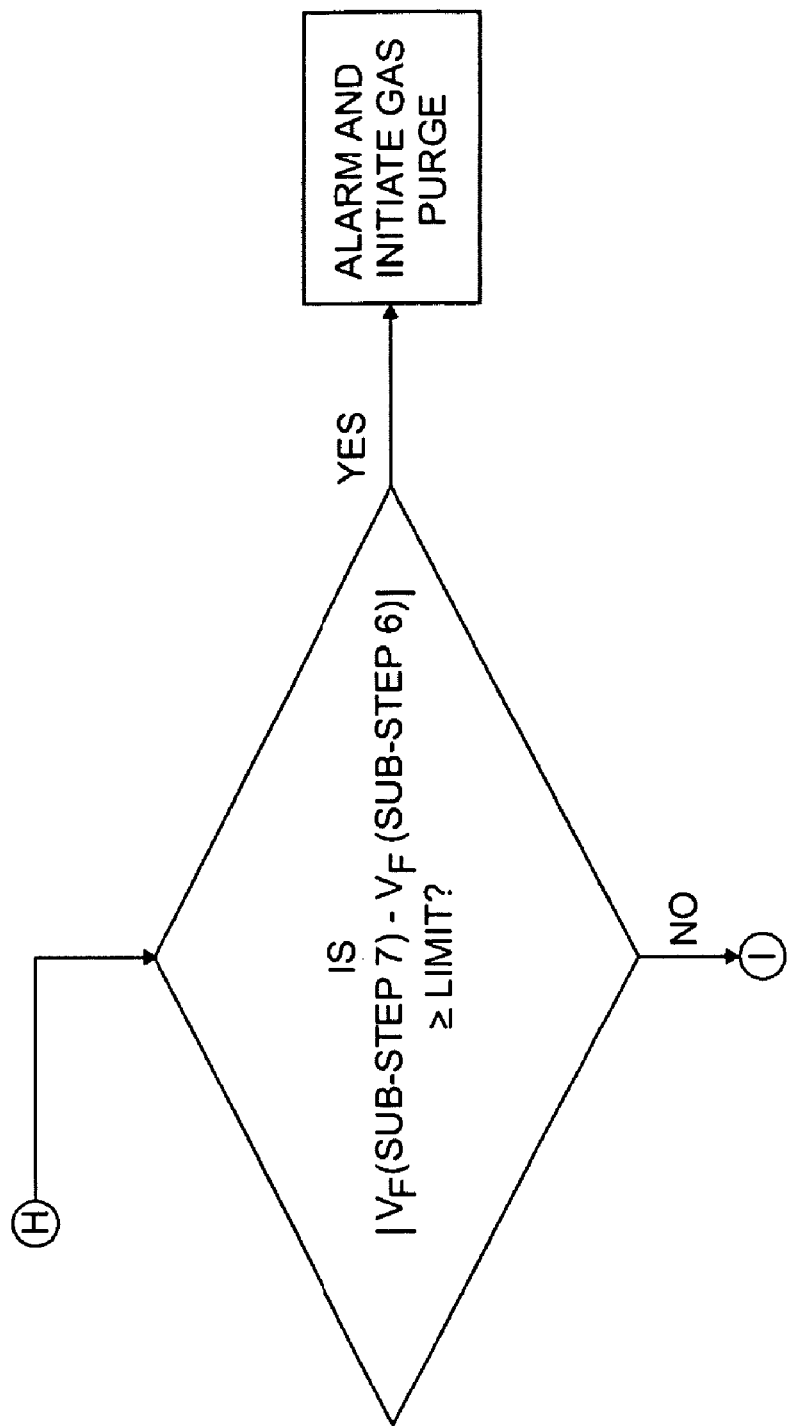
FIG. 28C is a flow chart illustrating a series of substeps of the pumping cycle of FIG. 28A for detecting the presence of a gas in a pump chamber.

One embodiment of a method for operating pumping system 500 is shown in FIGS. 28A-28C. The preferred pump stroke cycle includes steps for filling and dispensing a liquid from pump chamber 108, as well as steps for determining the volume of a volumetric container using the ideal gas law equation of state and conservation of mass, so as to determine a volume of liquid pumped and to detect the presence of any gas in pump chamber 108. As above, it is assumed initially that pump chamber 108 has been emptied of liquid and that flexible membrane 112 is extending to the maximum permissible extent allowed by spacers 138 into pump chamber 108. Preferably, membrane 112 is an elastic membrane when, as here, pump chamber volumes are determined using the ideal gas law or other equation of state (as previously discussed), Step 1 (600) involves initializing the system. The initialization of the system involves opening valves 520 and 522 and operating pump 516 to create a desired pressure of measurement gas in positive pressure tank 508 and negative pressure tank 512, followed by discontinuing the operation of pump 516 and closing valves 520 and 522. It is also assumed as an initial condition that all valves of the system are closed and that switch valve 530 is positioned so that its outlet is in fluid communication with positive pressure tank 508.

Step 2 (602) involves filling pump chamber 108 with liquid through inlet line 114 and inlet valve 116. First, switch valve 530 is positioned to select negative pressure tank 512. Next, inlet valve 116 is opened and variable size orifice valve 536 is opened until pump chamber 108 has filled with liquid. In preferred embodiments, variable size orifice valve 536 is also selectively controlled during filling so as to provide an essentially constant negative pressure in control chamber 110, as described in more detail below. As will also be described in more detail below, the ability to vary the pressure in control chamber 110 via control of variable size orifice valve 536 enables system 500 to detect when flexible membrane 112 is distended into control chamber 110 to its maximum permissible extent indicating that pump chamber 108 is completely full of liquid. Thus, in preferred embodiments, system 500 can detect when pump 104 has reached the end of a stroke, either in the filling or emptying of pump chamber 108.

In step 3 (604) pump chamber 108 and control chamber 110 are isolated by closing inlet valve 116 and variable size orifice valve 536 respectively. Step 4 (606) comprises a subcycle which determines the volume of the volumetric container comprising pump chamber 108 and/or the volumetric container comprising control chamber 110, and determines the presence of any gas in pump chamber 108 utilizing the determined volumes. The various substeps of step 4 (606) are outlined in detail in FIGS. 28B and 28C.

Referring to FIG. 28B, substep 1 (608), which is optional, involves equilibrating the pressure in control chamber 110 and reference chamber 532 with the atmosphere by opening valve 540 and valve 546 in order to vent the control chamber and the reference chamber through vent line 544. Substep 2 (610) involves positioning switch valve 530 to select positive pressure supply tank 508, and opening variable size orifice valve 536 in order to pressurize control chamber 110. In some embodiments, variable size orifice valve 536 can be opened for a sufficient period of time so that the pressure of measurement gas in positive pressure supply tank 508 in control chamber 110 is allowed to equilibrate. In such embodiments, the pressure measured by transducer 122 on control chamber 110 should be essentially the same as that measured with pressure transducer 510 on the positive pressure tank. If these pressures do not agree, processor 506 can be configured to indicate that there is a system fault and can shut down operation of the system. After pressurizing control chamber 110, variable size orifice valve 536 is closed and the measured pressure $P_{C1}$ in control chamber 110 is recorded. In substep 3 (612) the pressure $P_{R1}$ in reference chamber 532, as measured with pressure transducer 548 (which will be different from that in control chamber 110) is stored by processor 506.

Substep 4 (614) involves allowing for measurement gas exchange between control chamber 110 and reference chamber 532. The gas exchange is enabled by opening and, optionally, closing valve 540. In some embodiments, valve 540 may be opened for a sufficient period of time to equilibrate the pressures in reference chamber 532 and control chamber 110 to essentially the same value. For such embodiments, it should be appreciated that pressure transducer 122 in fluid communication with control chamber 110 is optional since the measurement gas pressures in control chamber 110 can be determined, for various steps of the method, with pressure transducers 548, 510, or 514. In substep 5 (616), after allowing gas exchange, pressure $P_{C2}$ and $P_{R2}$ in control chamber 110 and reference chamber 532 respectively are measured and stored by processor 506. The volume $V_C$ of the control chamber and, optionally, the volume $V_F$ of pump chamber 108 at this first condition can be calculated from the known volume $V_R$ of reference chamber 532 and the above-measured pressures utilizing the ideal gas equation of state and conservation of mass.

In order to detect the presence of any gas in pump chamber 108, in substep 7 (620), substeps 1-6 (608, 610, 612, 614, 616, 618) are repeated as described above except that in substep 2 (610) switch valve 530 is positioned to select negative pressure supply tank 512. In substep 8 (622) processor 506 determines an absolute value of the difference between volume measurements determined in substep 7 (620) (i.e. at the second condition) and substep 6 (618) above and, as shown in FIG. 28C, compares this difference to a predetermined permissible limit and creates an alarm condition and initiates an air purge from pump chamber 108, in a manner substantially similar to that previously described, if the value exceeds the limit. If the value does not exceed the predetermined limit, the system proceeds to deliver the liquid in pump chamber 108, as described in FIG. 28A, steps 5-7.

Referring again to FIG. 28A, in step 5 (624), liquid is delivered from pump chamber 108 by, optionally, opening valves 546 and 540 to vent control chamber 110, followed by closing valves 540 and 546, positioning switch valve 530 to select positive pressure tank 508, and opening outlet valve 120 on outlet line 118 of pump chamber 108 while opening and controlling the orifice size of variable size orifice valve 536 to yield a desired pressure in control chamber 110 for pumping the liquid from the pump chamber. In preferred embodiments, variable size orifice valve 536 is controlled by processor 506 to maintain the pumping pressure in control chamber 110 at a desired value during the pump chamber emptying stroke. In such embodiments, processor 506 preferably includes a controller, for example a PID closed loop control system, which allows the processor to selectively change the size of the orifice within the variable size orifice valve 536 based, at least in part, on a difference between a pressure measured within control chamber 110 by transducer 122, and a desired predetermined pumping pressure. As discussed above in the context of filling pump chamber 108, pumping system 500 also preferably includes a method for controlling variable size orifice valve 536 so that the system is able to determine when flexible membrane 112 has stopped moving into pump chamber 108 indicating that liquid flowing from pump chamber 108 has stopped. This end of stroke detection method is described in more detail below. After a desired quantity of fluid has been delivered from pump chamber 108 or after an end of stroke condition has been determined as discussed above, outlet valve 120 downstream of pump chamber 108 is closed and, optionally, variable size orifice valve 536 is closed in order to isolate the pump chamber and control chamber.

Step 6 (626) of the pump cycle involves repeating the volume calculation routine by re-performing substeps 1-6 (608, 610, 612, 614, 616, 618) shown in FIG. 28B to calculate a final volume $V_{F2}$ of pump chamber 108 after delivery of the liquid. Finally, in step 7 (628) the volume delivered by pump 104 during the pump cycle $\Delta V$ can be determined by taking a difference in the pump chamber or control chamber volume determined after filling pump chamber 108 (determined in step 4) and the volume determined after pumping the liquid from pump chamber 108 (determined in step 6). If desired, a new pump cycle can be initiated by repeating the steps outlined in FIG. 28A.

The flow rate of the liquid delivered from the pump chamber for each pump stroke will be a function of the force applied to the flexible membrane of the pump chamber during the filling steps and delivery steps discussed above, and a function of the upstream and downstream liquid pressures in fluid communication with the pump chamber inlet line and outlet line respectively during filling and delivery. Typically, the forces applied to the flexible membrane, for example due to the pressure of the measurement gas in the control chamber, during the filling and delivery steps are chosen to yield a desired liquid flow rate for a given pump stroke cycle. For applications where the pumping system is being utilized to pump a liquid to the body of a patient, the fill and delivery pressures are preferably chosen to be compatible with acceptable pressures for infusion of liquid to a patient. Typically, for delivery of liquids to the vasculature of a patient, the maximum measurement gas pressure in the pumping system will not exceed about 8 psig and the minimum measurement gas pressure in the pumping system will not exceed about −8 psig.

When liquid delivery involves performing a multiple number of pump stroke cycles, as described above, over a period of time, in addition to determining a liquid flow rate for a given stroke, preferred pumping systems will include a processor that also is configured to determine an average pump flow rate over the entire period of operation. An average pump flow rate or average liquid flow rate is defined as the volume of liquid dispensed by the pump during multiple pump stroke cycles divided by the total time elapsed during the cycles. For applications involving multiple pump stroke cycles, in addition to controlling liquid flow rate via selection and control of the force applied to the pump chamber membrane, the system can also control the average liquid flow rate by selectively varying the length of a dwell period that can be inserted between individual pump stroke cycles prior to filling and/or delivering liquids from the pump chamber. The pumping systems according to the invention can also be configured to deliver a desired total liquid volume during operation, as well as to deliver a desired liquid flow rate as described above.

The predetermined limit to which the differences in measured volumes (or measured parameters related to volumes) of the pump chamber are compared for determining when the amount of gas in the pump chamber has exceeded an acceptable value can be determined in a variety of ways. The predetermined value may be chosen, for example, to reflect the difference in volumes determined for an amount of gas present in the pump chamber that is equal to or somewhat less than the volume of the dead space in the pump chamber created by spacers. For applications in which preventing air from being pumped from the pump chamber is critical (for example, when pumping liquid to the body of a patient), the predetermined threshold limit may be chosen to be very small. In some embodiments, a predetermined limit can be determined by injecting a maximum permissible quantity of gas into the pump chamber, the remainder of which is filled with a liquid, and determining with the pumping system the difference in measured volume of the pump chamber at a first condition of applied force/pressures to the flexible membrane and a second condition of applied force/pressures to the flexible membrane. Fluid management systems methods are described in U.S. Pat. Nos. 4,808,161; 4,826,482; 4,976,162; 5,088,515; and 5,350,357, which are hereby incorporated herein by reference in their entireties.

Heat Exchanger Systems

An embodiment of the present invention relates generally to heat-exchanger systems that can be used to heat or cool a fluid such as blood. A blood cooling and heating system may be particularly useful for surgical procedures requiring cardiopulmonary bypass, which in some cases use deep hypothermic cardiac arrest, or which may be prolonged and require maintenance of a certain body temperature. Of course, it should be noted that such a heat-exchanger system may be used in other applications for heating and/or cooling fluids in general and body fluids in particular. Furthermore, while the exemplary heat-exchanger systems described below incorporate pod pumps of the types described above, it should be noted that embodiments are not limited to the use of pod pumps.

Figure 29:
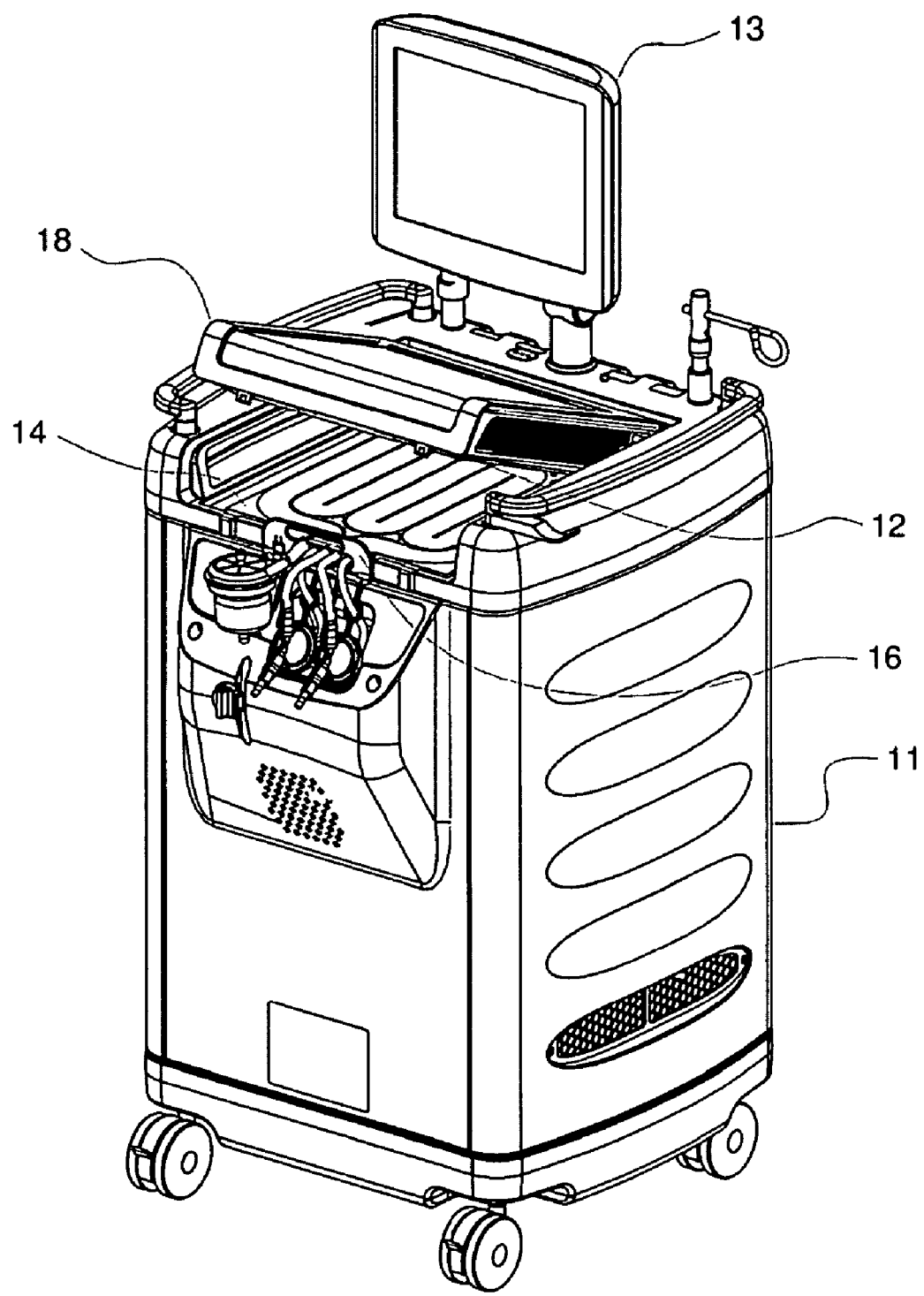
FIG. 29 is a perspective view of an extracorporeal-blood-heat exchange system having a base unit with a disposable unit according to one embodiment of the invention.

FIG. 29 shows a base unit 11 on which is situated a heat-exchanger 12 in accordance with an exemplary embodiment of the present invention. The heat-exchanger 12 accepts a disposable unit 16. As described further below, the disposable unit 16 is installed into the heat exchanger 12 such that a heat-exchanger bag (e.g., a heat-exchanger bag 21 as shown in FIG. 14) of the disposable unit 16 rests within a receptacle within the heat exchanger portion of the base unit 11. As blood from a patient circulates through the disposable unit 16, and specifically through the heat-exchanger bag 21, the blood can be cooled or heated by the heat exchanger and returned to the patient. During such circulation, the blood remains within the disposable unit 16 and generally does not come into contact with components of the base unit 11. The disposable unit 16 is considered to be "disposable" in that it is generally discarded after a patient treatment, whereas the base unit 11 can be re-used repeatedly by simply installing a new disposable unit 16. In fact, the base unit 11 may include mechanisms to prevent re-use of a disposable unit (e.g., using a bar code, RFID tag, or other identifier associated with the disposable unit).

Base Unit for Heat Exchanger

Figure 30:
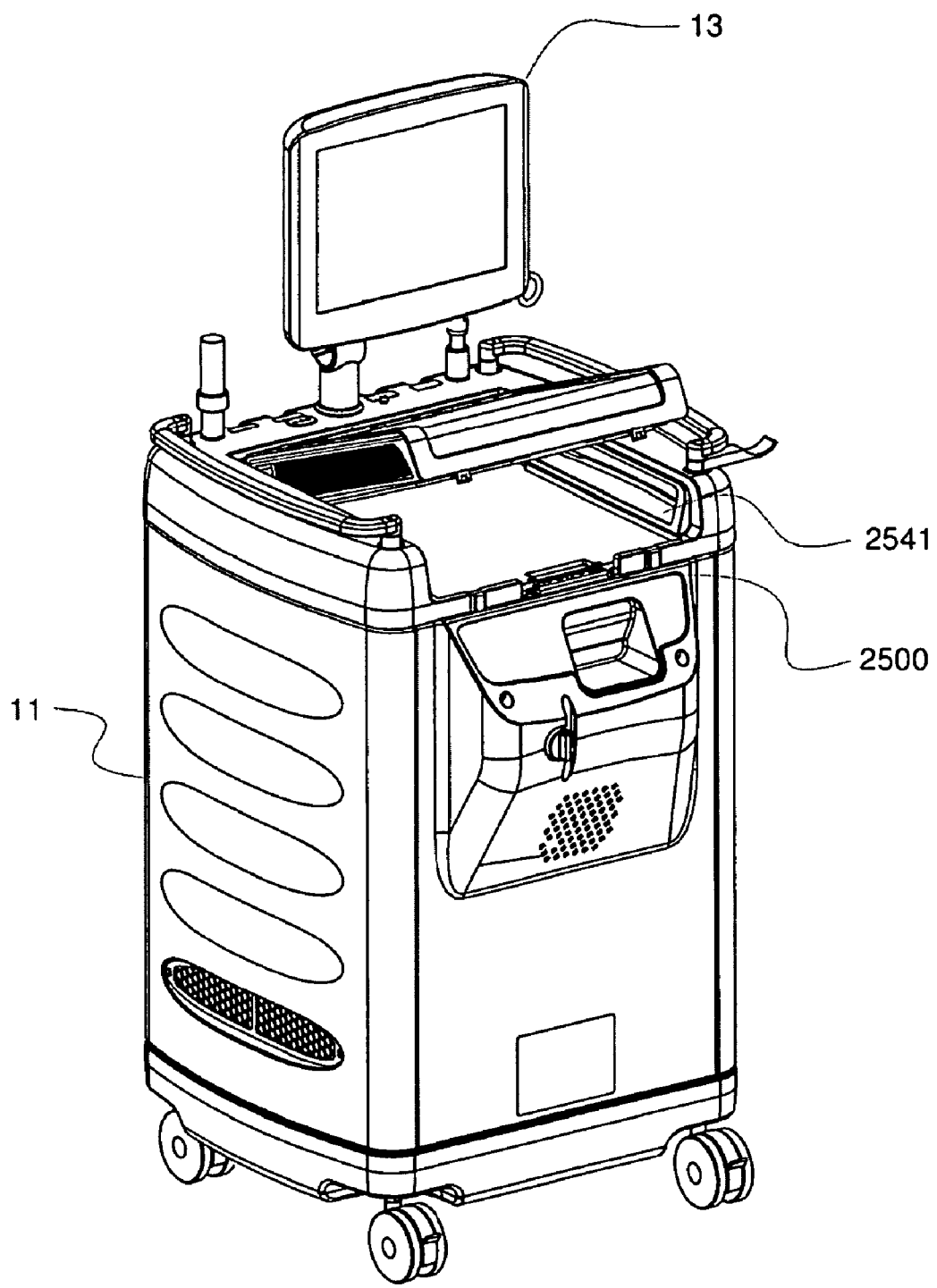
FIG. 30 shows the base unit of FIG. 29, in accordance with an exemplary embodiment of the present invention.

FIG. 30 shows the base unit 11 in accordance with an exemplary embodiment of the present invention. The base unit 11 includes, among other things, a heat exchanger 2541, a pneumatic actuation system, a disposables interface 2500 (also referred to as a manifold interface), a patient interface, a controller, a user interface console 13, and a ventilation system. The pneumatic actuation system may be generally of the type schematically shown in FIG. 18, but with separate pneumatic interfaces, valves, and sensors for each of two pod pumps. The disposables interface may include two sensors that provide both thermal and electrical connectivity to a disposable unit to allow for monitoring blood temperature both upstream and downstream of the heat exchanger and also to allow for monitoring other parameters. The patient interface may include one or more temperature inputs for receiving temperature information (specifically patient temperature information) from one or more temperature probes. The user interface console 13 allows the user to control and monitor operation of the system. In an exemplary embodiment, the controller controls operation of the heat exchanger and the pod pumps based on, among other things, blood temperature information received from the disposables interface, pressure information received from the pneumatic actuation system, patient temperature information received from the patient interface, and user inputs received from the user interface console.

Disposable Heat Exchanger Unit Configurations

As mentioned above, a disposable unit for a heat-exchanger system typically includes a heat-exchanger bag through which blood flows while passing through the heat exchanger. The heat-exchanger bag may include one or more fluid paths. In one exemplary embodiment described below, a heat-exchanger bag includes a single fluid path connecting two fluid inlets to a common fluid outlet. In another exemplary embodiment described below, a heat-exchanger bag includes a single fluid path having a single inlet and a single outlet. Heat-exchanger bags are typically made of a flexible plastic material, although the heat-exchanger bag may be made from other materials and may include a metallic material or other material to improve thermal conductivity.

FIG. 14 shows relevant components of a disposable unit 16, in accordance with an exemplary embodiment of the present invention. The disposable unit 16 includes, among other things, a heat-exchanger bag 21 (also referred to as a "flow-path bag") with a manifold 130 and a panel 2017 holding (or configured to hold) two pod pumps 25a and 25b and a filter/air eliminator 29. The disposable unit 16 preferably also includes a handle that is used to mechanically interconnect the above-referenced components into a cohesive unit that can be readily installed into the base unit 11, which preferably includes a manifold interface (described below) for receiving the manifold 130 and providing pneumatic connections for operating the pumps 25a, 25b. The bag 21 includes a fluid path 150 through which fluid can be pumped. In this embodiment, the manifold 130 is integrated with the heat-exchanger bag 21 and is configured with appropriate tubing connections and supports that are used to interconnect the heat-exchanger bag 21 with the two pod pumps 25a and 25b.

In the embodiment shown in FIG. 14 the manifold 130 includes two flow-path inlets 23a and 23b (also referred to as "heat-exchanger bag inlets") in fluid communication with one end of the fluid path 150 and a flow-path outlet 2027 (also referred to as a "heat-exchanger bag outlet") in fluid communication with the other end of the fluid path 150. The blood is preferably pumped from the patient and through the heat-exchanger bag 21, in this embodiment by a pair of self-contained pod pumps 25a, 25b (referred to individually as a pod pump 25), which are preferably reciprocating positive-displacement pumps of the types described herein. In this embodiment, the manifold 130 includes pneumatic passageways 2028a, 2028b to facilitate establishment of pneumatic connections respectively to the pod pumps 25a, 25b (typically using tubing). It should be noted that embodiments are not limited to the use of two pod pumps or, for that matter, to the use of pod pumps.

In this embodiment, each pod pump 25 includes an inlet 34 and an outlet 37 (i.e., pod pump 25a has an inlet 34a and an outlet 37a, while pod pump 25b has an inlet 34b and an outlet 37b). In an exemplary configuration, the pod pumps 25a, 25b may be coupled upstream of the heat-exchanger bag 21 such that the pump inlets 34a, 34b are coupled to receive blood directly from the patient (e.g., through a "Y" connector), the pump outlets 37a, 37b are connected respectively to the heat-exchanger-bag inlets 23a, 23b by tubes 2026a, 2026b, and the filter/air eliminator 29 is connected to the heat-exchanger-bag outlet 27 by tube 2027. In this way, the pod pumps 25a, 25b are operable to urge blood through the heat-exchanger bag 21, from which the blood exits through the flow-path outlet 27 and then passes through the filter/air eliminator 29 before returning to the patient. In a second configuration (not shown), the pod pumps 25a, 25b may be coupled downstream of the heat-exchanger bag 21 such that blood from the patient enters the heat-exchanger-bag inlets 23a, 23b (e.g., through a "Y" connector), the pump inlets 34a, 34b are coupled to the flow-path outlet 27 (e.g., through a "Y" connector), and the pump outlets 37a, 37b are coupled (e.g., through a "Y" connector) to return blood to the patient via the filter/air eliminator 29. In this way, the pod pumps 25a, 25b draw blood through the heat-exchanger bag 21 and pump the blood through the filter/air eliminator 29 to the patient. It should be noted, in an alternate embodiment, the heat-exchanger bag 21 could include separate outlets, which could facilitate its coupling with the pod pumps in some situations. In the embodiments shown in FIG. 14, the filter/air eliminator 29 is preferably provided with a purge port to allow air to escape from the filter.

It should be noted that alternative embodiments may employ other pod pump configurations as part of the disposable unit 16. For example, various alternative embodiments could employ the pod pump assembly 2004 shown in FIGS. 15A and 15B, the pump cassette 2015 shown in FIGS. 16A and 16B, or the dual-housing arrangement 2016 shown in FIG. 17. With regard to pod pump assembly 2004, the common inlet 54 may be coupled to receive blood from the patient and the common outlet 57 may be coupled to provide blood to the heat-exchanger bag 21, or the common inlet 54 may be coupled to receive heated blood from the heat-exchanger bag 21 and the common outlet 57 may be coupled to provide blood to the filter/air eliminator 29. Similarly, with regard to pump cassette 2015, the common inlet 2005 may be coupled to receive blood from the patient and the common outlet 2006 may be coupled to provide blood to the heat-exchanger bag 21, or the common inlet 2005 may be coupled to receive heated blood from the heat-exchanger bag 21 and the common outlet 2006 may be coupled to provide blood to the filter/air eliminator 29.

Various components of the disposable unit 16 may be provided separately and/or in various assemblies and sub-assemblies, and therefore the word "unit" is not intended to require that the disposables be provided as a complete system or kit. Thus, for example, the pod pumps (or pod pump assemblies/cassettes) could be provided separately from the rest of the disposable unit 16. Among other things, providing the pod pumps separately could allow pod pumps of different volumes to be easily integrated, without requiring separate versions of the main disposable unit for different pump volumes.

Furthermore, the disposable unit 16 could be provided with some tubing connections already in place, e.g., with the pump outlets 37a, 37b already coupled to the heat-exchanger-bag inlets 23a, 23b and/or with the pump inlets 34a, 34b already coupled to a "Y" connector and/or with the flow-path outlet 27 already coupled to the filter/air eliminator 29.

In one embodiment, the pneumatically actuated pumps and/or valves can be provided in disposable cassettes. As discussed above, if the number of pneumatically actuated pumps and/or valves in a cassette is large enough, the cassette containing these pumps and valves can become so large—and the pressures involved can become so great—that it may become difficult to properly seal and position all of the pumps and valves. This difficulty may be alleviated by placing the valves and pumps in a main cassette, from which connecting tubes lead from pneumatic ports, so that pneumatic communication is provided between valves and pumps in the main cassette and a smaller, secondary tube-support cassette, which is provided with a pneumatic interface for each of the tubes, as shown in FIG. 17. In this way, the proper positioning and sealing of all the pneumatic interfaces can be accomplished more easily with the smaller tube-support cassette than it would be if the pneumatic actuation needed to be applied to the larger main cassette directly. Additionally, or alternatively, valves in the main cassette may be ganged together in some embodiments, so that several valves may be actuated simultaneously through a single pneumatic interface on the tube-support cassette and through a single connecting tube between the pneumatic interface and the valves.

It should be noted that one or more pumps (e.g., pod pumps) may be integral with a manifold such as the manifold 130 and placed in a base unit as a single cassette. The assembly could include pneumatic connections from the pneumatic ports (which are connected to the base unit) directly to the pump control chambers so that no external tubing would be needed to make the pneumatic connections to the pod pumps. The assembly could additionally or alternatively include fluidic connections (e.g., from the pump outlets to the interface with the heat-exchanger bag) so that no external tubing would be needed between the pump outlets and the manifold or bag.

Heat Exchanger Control System

In typical embodiments, the same controller preferably controls both pod pumps (items 25a and 25b of FIGS. 102 and 148) of the disposable unit 16, and preferably (although not necessarily) causes the two pod pumps to pump out of phase (i.e., one pumping chamber is emptying while the other is filling) during normal blood-pumping operation in order to provide for more continuous flow to/from the patient and through the heat exchanger. In some embodiments, it may be preferable to have the controller cause the two pod pumps to pump in phase in order to produce pulsatile blood flow.

The controller preferably uses a closed-loop control scheme based on, among other things, patient temperature information (e.g., received through a patient temperature interface), blood temperature information (e.g., received via thermal wells in the manifold 130 and the corresponding sensors in the manifold interface 2500), and pump status information (e.g., reservoir pressure, control chamber pressure, end-of-stroke detection, volumetric measurements, air detection, occlusion detection, leak detection) to attain/maintain patient body temperature and ensure that blood is not overheated or overcooled locally (e.g., even if the patient body temperature is at a safe level, it may be possible for the blood to overheat or overcool in the heat-exchanger component, for example, if the heat exchanger malfunctions or blood is not pumped at a sufficient rate). Furthermore, the controller typically receives multiple patient temperature inputs. The controller may adjust the heat exchanger and/or pump operation dynamically based on patient temperature information and blood temperature information.

The bag-inlet temperature sensor and the bag-outlet temperature sensor may be mounted permanently in the base unit 11 adjacent where the inlet and outlet of the bags are located. In order to improve thermal conductivity between the blood flowing within the bag and the temperature sensors located outside of the bag—and thereby improve the accuracy of the temperature readings—the bag may be provided with metal thermowells which extend into the flowpath of the blood at the bag's inlet and outlet. When the bag is placed between the heating plates, the thermowells can accommodate and receive the temperature sensors extending from the base unit 11. The metal thermowells can also be used as electrical conductors and thus be used to detect leaks or air in the bag 21.

In various alternative embodiments, the controller may detect abnormal conditions in the system based on several factors including: (i) the difference in the bag-inlet and bag-outlet temperatures measured respectively by the bag-inlet and bag-outlet sensors (ii) the volumetric flow rate of blood through the disposable unit 16, and (iii) the power being provided to the base unit's heating/cooling plates. If each of the pod pump 25a, 25b expels the same, known volume of blood during each expel stroke, the volumetric flow rate can be measured by simply measuring the rate of expel strokes, and multiplying that rate by volume expelled per stroke. (The flow rate can be determined in this way as long as full pump strokes are being performed. As discussed above, the controller in a preferred embodiment monitors whether full strokes are being performed by dithering the valving mechanism and analyzing the pressure information from the control-chamber-pressure transducers.) The product of three factors—the measured flow rate, the measured increase in blood temperature, and the specific heat of the blood—should be proportional to the power going into the heating plates. If this proportion varies significantly during a procedure, the controller preferably generates an alarm signal, which may be used to cause an indication to a medical technician monitoring the procedure or which may be used directly to stop the procedure.

Preferably, the controller generates two estimates based on a given set of temperature and flow-rate measurements, with one estimate based on all the uncertainties biased one way and the other estimate based on all the uncertainties biased the other way. The electrical power being consumed by the heating/cooling plates should always be below one estimate and above the other estimate; if the power measurement falls outside of this range, the controller will preferably generate the alarm signal.

As discussed above, the controller of the heat-exchanger system may monitor patient body temperature using at least two temperature probes. In actuality, the controller really only needs temperature readings from a single temperature probe; the second temperature probe essentially provides a control against which readings from the first temperature probe can be compared. In certain embodiments, then, a single temperature probe may be used to provide patient temperature readings to the controller. In such embodiments, an operator could independently monitor a second temperature probe and manually abort the procedure if the two temperature readings do not match sufficiently.

Heat Exchanger Components

Figure 31:
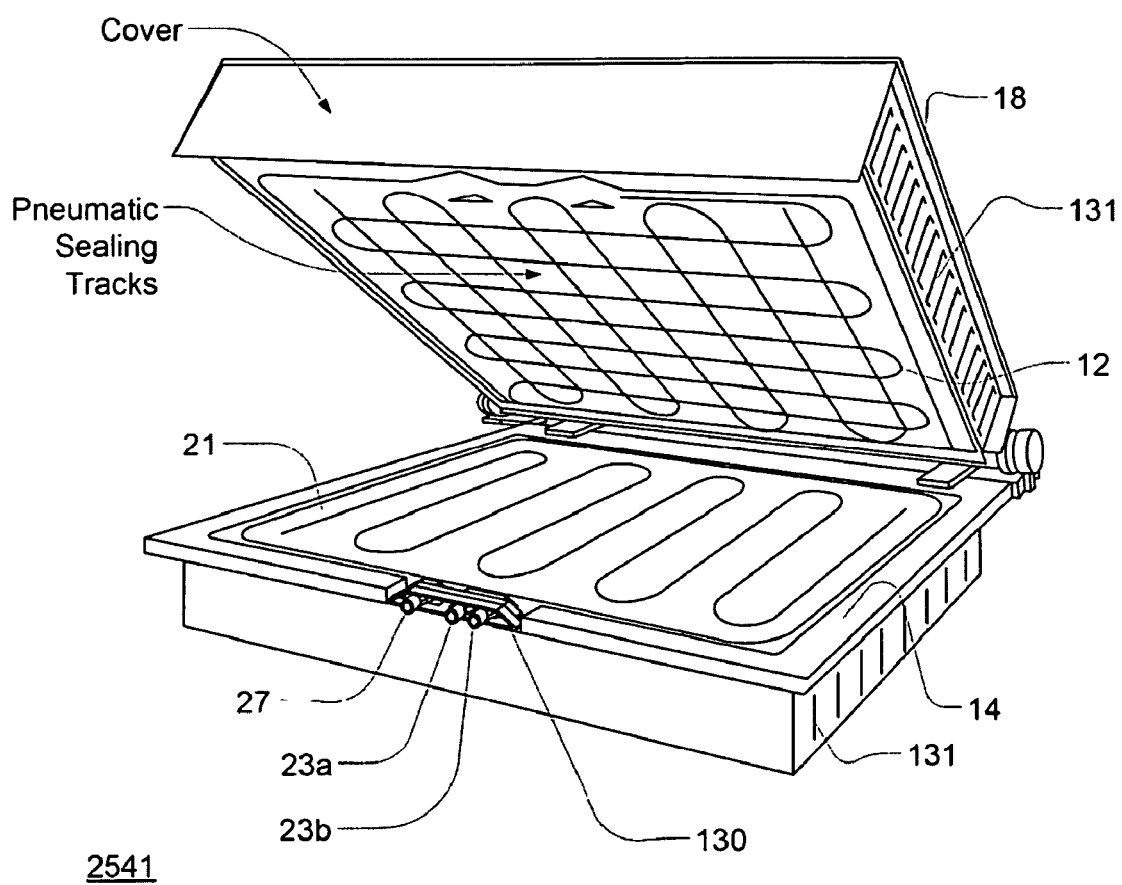
FIG. 31 is a perspective view of the components from the system of FIG. 29 used for transferring heat to or from the blood.

FIG. 31 shows greater detail of the heat exchanger 2541 shown in FIG. 30. In this embodiment, an upper heating/cooling plate 12 is mounted in a door 18 located at the top of the base unit 11. A lower heating/cooling plate 14 is located in the base unit 11 under the door 18. The heat-exchanger bag 21, which is part of the disposable unit 16, is placed on top of the lower heating plate 14, such that when the door 18 is closed, the bag 21 rests between the two heating/cooling plates 12, 14. This arrangement generally permits more heat to be transferred to and from the blood more quickly than a single-plate arrangement would, although alternative embodiments may use a single plate either above or below the heat-exchanger bag 21 and/or may use other types of heating/cooling elements. The door 18 and/or the upper plate 12 may include pneumatic sealing tracks to evacuate air from the heat exchanger or produce a better coupling between the upper plate 12 and the bag 21 (e.g., by producing a vacuum that pulls the upper surface of the bag 21 into contact with the upper plate 12.

Each of the heating/cooling plates 12, 14 may include a single heating/cooling element or multiple heating/cooling elements. The heating/cooling elements can be tubing through which a heated or cooled liquid is made to flow. In practice, platens may be interposed between heat exchanger bag 21 and the heated or cooled tubings to provide a more uniform distribution of heat transfer.

In order to improve thermal coupling between the heating plates 12, 14 and the heat-exchanger bag, the door 18 may produce a substantially air-tight seal when closed. Furthermore, air may be evacuated from around the heat-exchanger bag to achieve better thermal coupling between the bag and the plates. In this regard, a compressor (not shown) that may be used to produce the positive and/or negative pressures for the pod pump controls may be used to evacuate air from around the heat-exchanger bag. Cooling fins 131 or other elements may be provided to draw away excess heat.

The temperature inside the heat exchanger may be monitored and controlled to ensure a desired range of blood temperature. In an embodiment, each heating plate is provided with two temperature sensors located near the outlet 27 at points near where the blood should have achieved maximum heat transfer. The controller preferably receives temperature information from the temperature sensors and may generate an alarm, discontinue operation, thermostatically adjust the heating/cooling elements, and/or take other action if either (or both) of the temperature sensors indicates an unsafe temperature or if the difference in temperature readings measured by the two sensors exceeds a predetermined limit. The maximum and minimum temperature of the plates should not be allowed to exceed the maximum and minimum allowable blood temperature, because otherwise, if the flow of blood were to stop or slow, the blood within the heat exchanger could dangerously exceed the temperature limits.

In certain embodiments, one or both of the heating/cooling plates 12, 14 may be translatable in a vertical direction when the door is closed, e.g., to facilitate evacuation of air from the heat-exchanger bag 21 during priming or to squeeze residual blood out of the heat-exchanger bag 21 and back into the patient at the end of the heat transfer procedure. The plates may additionally or alternatively be tiltable so that the bag may be tilted, e.g., in order to assist in removing air bubbles from the bag during priming or to assist with returning blood to the patient. Such vertical translation and/or tilting could be performed manually or could be performed automatically, for example, under control of the controller 49.

Thus, at the end of the blood heat transfer procedure, the membranes in the pod pumps 25a, 25b may be urged against the pumping-chamber wall so as to minimize the volume of the pumping chambers and expel as much blood as possible back toward the patient. Furthermore, in embodiments that include vertically translatable and/or tiltable plates, the heat-exchanger bag 21 may be squeezed and/or tilted to direct as much blood as possible back toward the patient.

User Interface for Heat Exchanger

Figure 32:
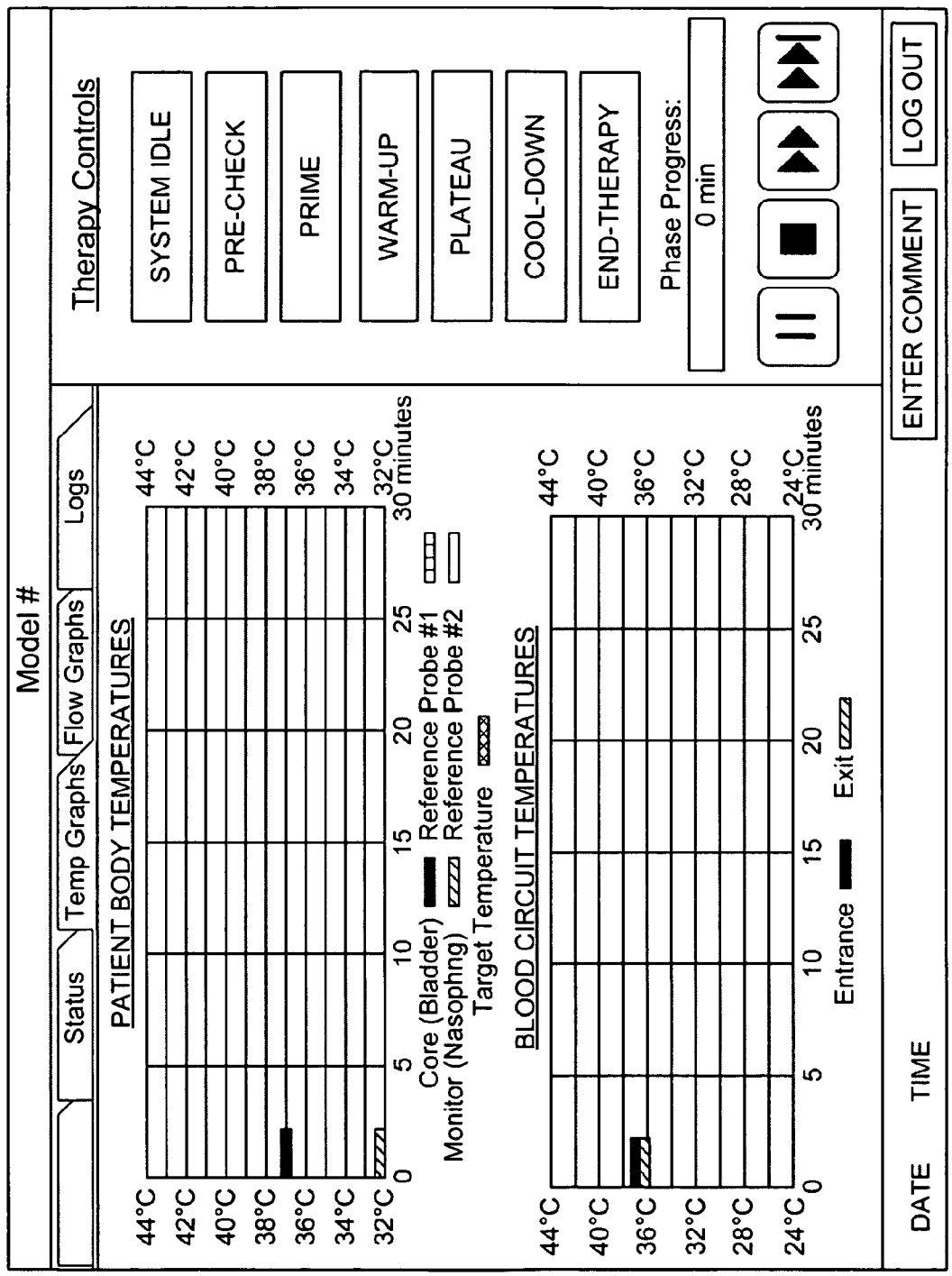
FIG. 32 shows an exemplary user interface screen in accordance with an exemplary embodiment of the present invention.

FIG. 32 shows an exemplary user interface screen for the heat exchanger system. The right-hand side of the screen includes various therapy controls including (from top to bottom) indicators for the various therapy phases (i.e., system idle, pre-check, prime, warm-up, plateau, cool-down, and end-therapy) for displaying the current phase of treatment (in this example, "warm-up" is highlighted, indicating that the therapy is currently in the warm-up phase), a phase progress indicator for showing, e.g., the time remaining or time elapsed in the current phase, and four control buttons through which the operator can control the therapy (e.g., pause treatment, stop treatment, start or re-start treatment, and step to the next phase). It should be noted that these four control buttons prevent an operator from stepping backward to a previous stage. The left-hand side of the screen allows the operator to tab through screens providing patient information, status information, temperature graphs, flow graphs, and logs.

Alternative Heat-Exchanger Embodiments

In the embodiments described above, fluid is heated or cooled by running the fluid through a heat-exchanger bag that is placed between two plates of a heat exchanger. Of course, the present invention is in no way limited to the use of a heat-exchanger bag or plates. In alternative embodiments, heat-exchanger bags may be used with other types of heat exchangers (e.g., a heat-exchanger bag could be rolled up and placed in a tubular chamber or could be placed in other types of heat exchangers, such as a water bath or radiator. These embodiments are exemplary and are not intended to represent all of the types of heat-exchanger components that can be used in heat-exchanger systems of the types described herein. Additional embodiments of a heat-exchanger system are described in commonly owned co-pending U.S. patent application Ser. No. 11/787,213, which is hereby incorporated by reference in its entirety.

Thermal and Conductivity Sensors

In one embodiment of the invention, a thermal well is used to accommodate a temperature sensing probe. The thermal well comes into direct contact with a subject media (e.g., a liquid such as blood) and the sensing probe does not. Based on heat transfer dictated in large part by the thermodynamic properties of the thermal well and sensing probe construction, the sensing probe can determine the properties of the subject media without coming into direct contact with die subject media. The accuracy and efficiency of the sensor apparatus arrangement depends on many factors including, but not limited to: construction material and geometry of both the probe and the thermal well.

Figure 33A:
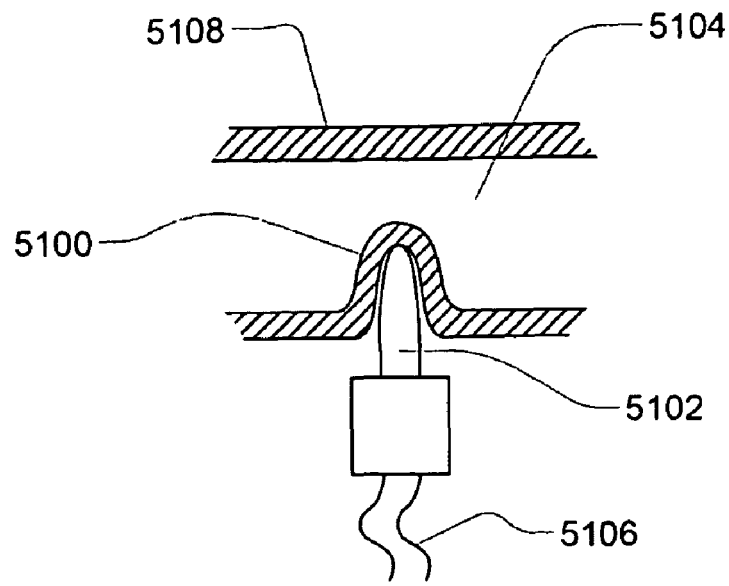
FIGS. 33A-33B are embodiments of the sensing apparatus where the thermal well is a continuous part of the fluid line.
Figure 33B:
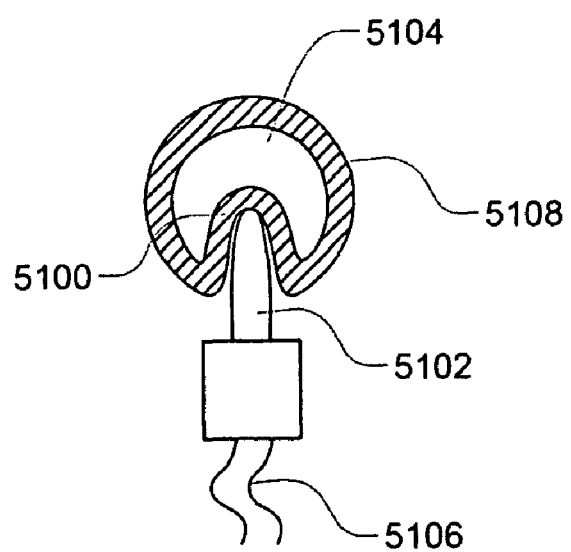

Referring now to FIGS. 33A and 33B, an embodiment of the sensor apparatus having the thermal well 5100 and the sensing probe 5102, is shown in relation to a fluid line 5108. In these embodiments, the thermal well 5100 is integrated into the fluid line 5108. Data from the sensing probe is transmitted using at least one lead 5106. An end view of FIG. 150A is shown in FIG. 150B.

In other embodiments, the thermal well 5100 is not completely integrated into the fluid line 5108, i.e., the thermal well 5100 can be made from different materials from the fluid line 5108. In some embodiments, the thermal well 5100 can be integrated into a container, chamber, machine, protective sleeve, fluid pump, pump cassette, disposable unit, manifold, or other assembly, sub-assembly, or component.

In this embodiment, the thermal well 5100 is one piece with the fluid line 5108. The total area of the thermal well 5100 can vary. By varying the geometry of the thermal well 5100, the variables, including, but not limited to, the thermal conductivity characteristic of the thermal well 5100 and thus, the heat transfer between the thermal well 5100 and the sensing probe 5102 will vary. In some embodiments, the fluid line 5108 is made from a material having a desired thermal conductivity. This material may vary depending on the purpose. The material can include, but is not limited to, any plastic, ceramic, metals or alloys of metals or combinations thereof.

Figure 34:
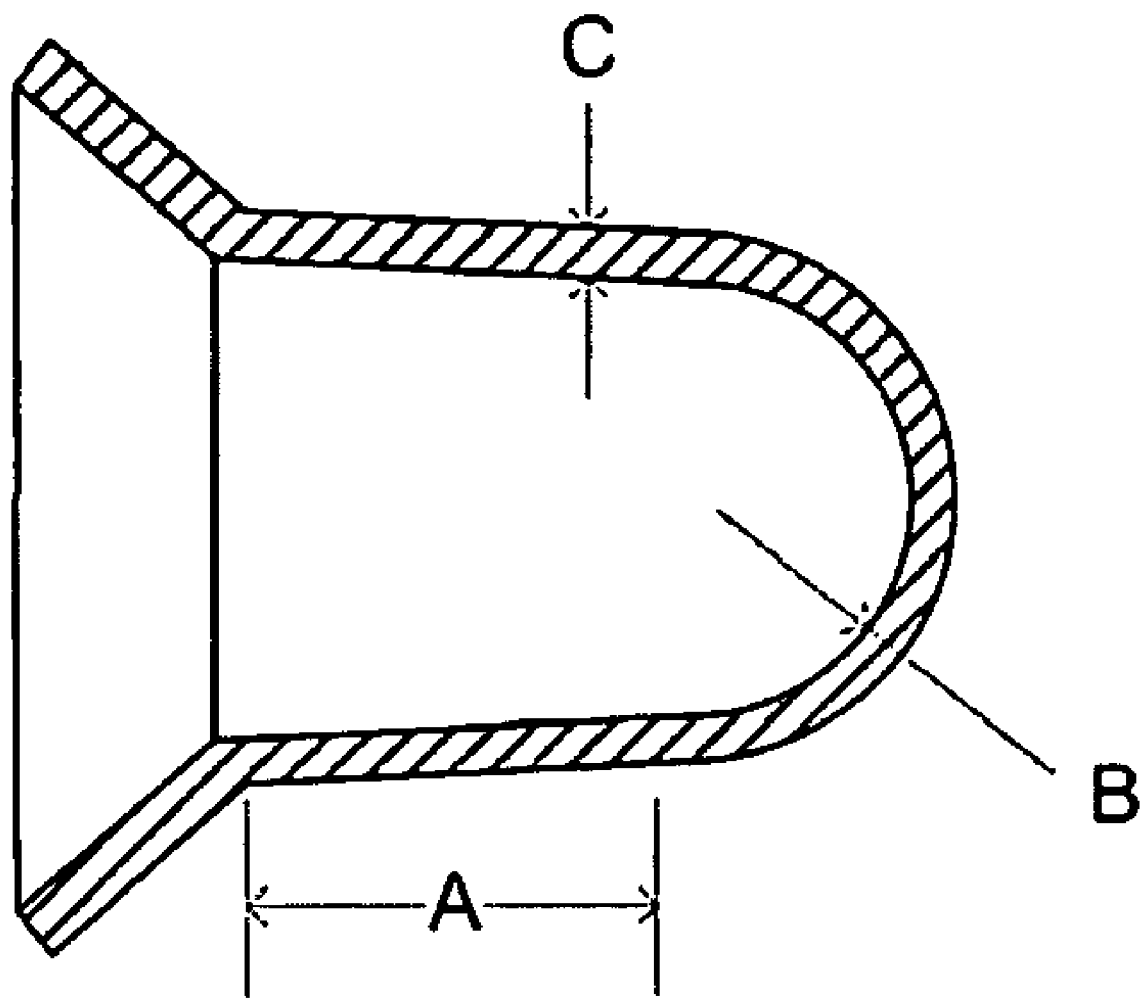
FIG. 34 is a cross sectional view of an exemplary embodiment of the thermal well.

As shown in FIG. 34, thermal well 5100 can have, for example a length A of approximately 0.113 inches (with a range from 0-0.379 inches), a radius B of approximately 0.066 inches and a wall thickness C ranging from approximately 0.003-0.009 inches. Depending on the circumstances and intended use of the sensing apparatus, the thermal well 5100 dimensions may vary. It should also be noted that the illustrations provided herein may not be proportional.

Figure 35A:
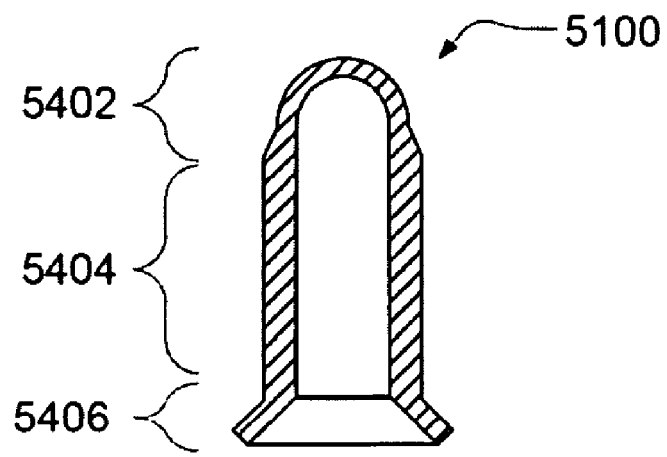
FIG. 35A-35B show section views of embodiments of thermal wells having variable wall thickness.
Figure 35B:
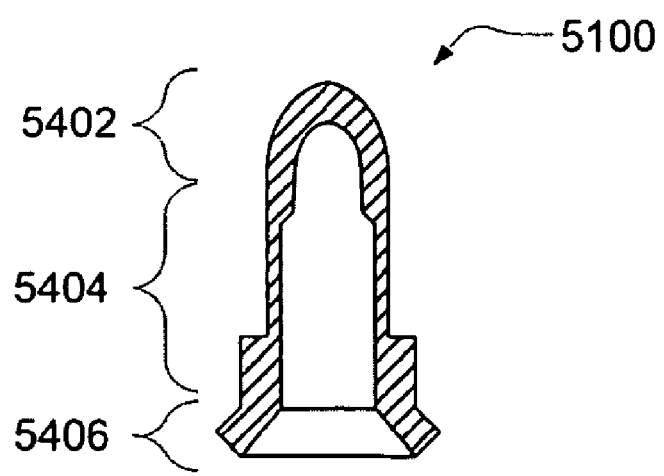

Referring now to FIGS. 35A and 35B, zone 5402 can be thicker or thinner as desired. An advantage of the thinner zone 5402 is that it may provide for a faster sensing time while a thicker zone may be useful for harsh environments or where sensor damping is desired. In addition, zone 5404 can be made thicker, for example, for greater strength, or thinner for greater isolation from ambient conditions. Zone 5406 can be thinner or thicker depending on the fastening method desired. For these embodiments, the thermal well 5100 can be made from any materials, including but not limited to, plastic, metal, ceramic or a combination thereof.

Figure 36:
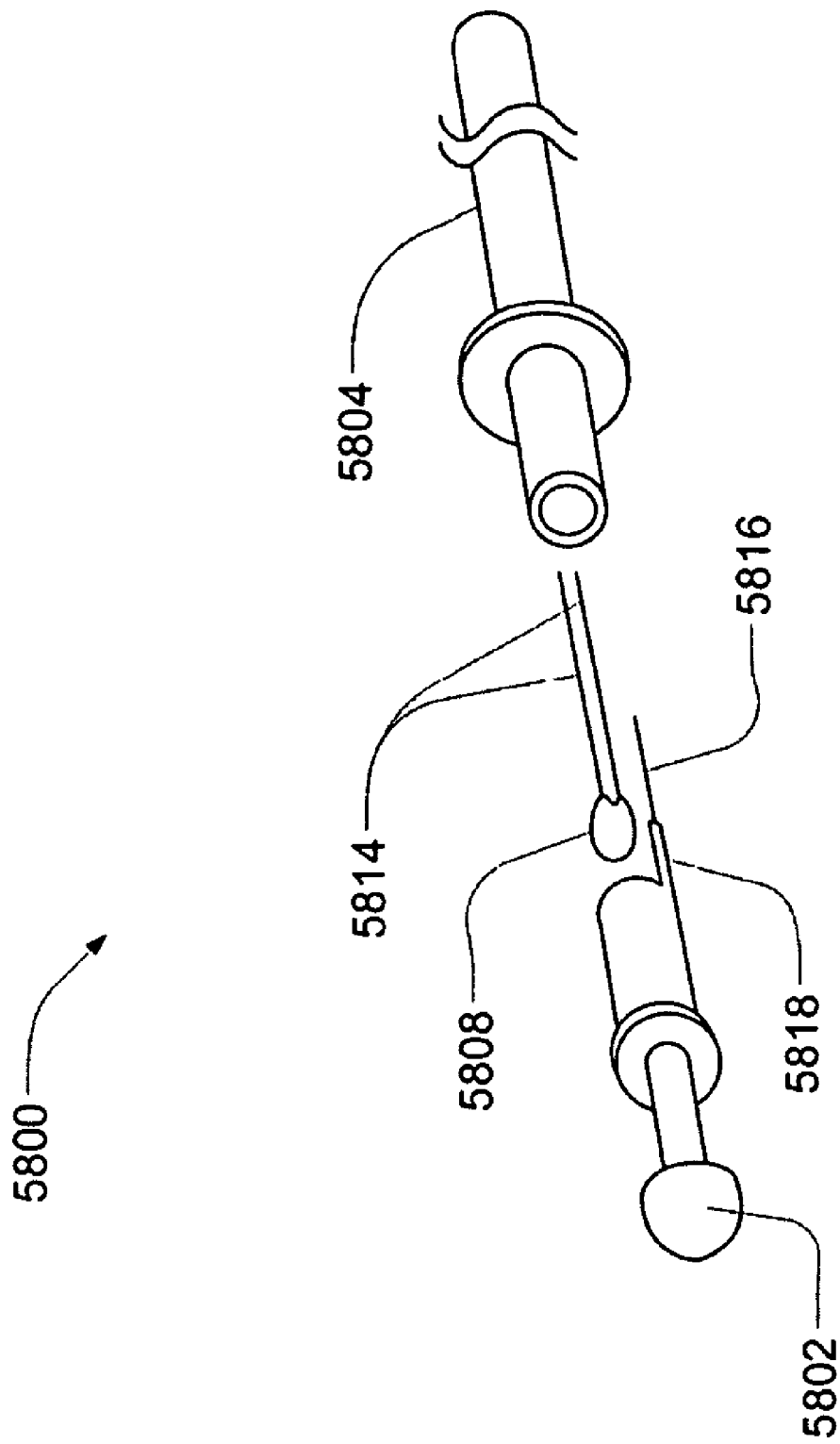
FIG. 36 is an exploded view of one embodiment of a sensing probe.

An exemplary embodiment of a sensing probe 5800 is shown in FIG. 36. The housing 5804 is a hollow structure that attaches to the tip 5802. The tip is made of a highly thermally conductive material. The housing 5804, in the exemplary embodiment, is made from a thermally insulative material. In some embodiments, the housing is made of a thermally and electrically insulative material. In an embodiment, the housing 5804 is made of plastic which is a thermally insulative and electrically insulative material. The tip 5802 either contacts the subject media directly, or else is mated with a thermal well.

The tip 5802 can be attached to the housing 5804 using a urethane resin or another thermal insulator between the tip 5802 and the housing 5804. Urethane resin additionally adds structural support. Other fabrication and joining methods can be used to join the tip 5802 to the housing 5804. The tip 5802 of the sensing probe 5800 can be made of a thermally conductive material, such as, for example, copper, silver or steel. In one exemplary embodiment, the tip 5802 is made from copper. In other embodiments, the material can be an alloy of copper or silver, or either solid or an alloy of any thermally conductive material or element, including but not limited to metals and ceramics. The tip 5802 can be shaped to couple thermally with a thermal well as described above. The tip 5802 may be shaped to insulate the thermal sensor 5808 from ambient conditions. In the exemplary embodiment, the tip 5802 is made from metal. Alternatively, a non-electrically conductive material such as ceramic can used for the tip, which may be preferred when it is necessary to electrically insulate the thermal well from the probe.

The thermal sensor 5808 can be a thermistor, thermocouple, or any other temperature sensing device. The choice of thermal sensor 5808 may depend on the intended use of the sensing apparatus. Leads 5814 from the thermal sensor 5808 exit the back of the housing 5804. The thermal sensor 5808 communicates via leads 5814 with equipment that can determine and optionally control the temperature of the subject media based on input from the thermal sensor 6014. A third lead 5816 from the tip 5802 can also be included. This third lead 5816 is attached to the tip on tab 5818. This can be useful, for example, when the tip 5802 is metal and the housing is plastic. In alternate embodiments, the housing 5804 is metal, thus the third lead 5816 may be attached to the housing 5804.

Figure 37:
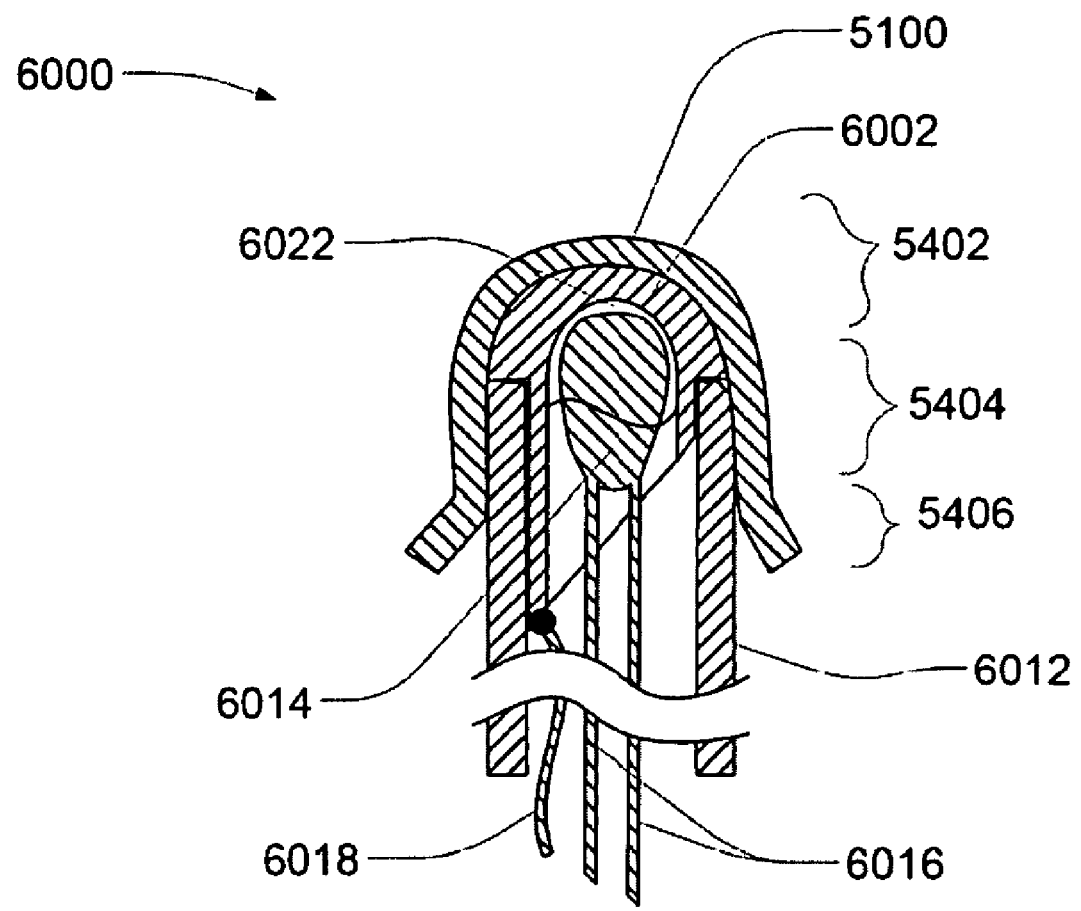
FIG. 37 is a sectional view of one exemplary embodiment of the sensor apparatus.

As shown in FIG. 37, a representative sensing probe 6012 is positioned within thermal well 5100. As described above, the thermal well 5100 can be in a fluid line, a protective sleeve, any disposable, machine, chamber, cassette or container, depending on where it may be desirable to determine thermal and/or conductive properties of a subject media.

Sensors to detect the conductivity of a subject medium can have several applications in CPB and other systems using extracorporeal circulation. For example, the conductivity of a flow path containing cardioplegia solution or blood can be monitored and used to control the rate of infusion of a potassium solution. Sudden changes in conductivity of a flow path can be used to infer the presence of an air bubble or a contaminant in the line. Appropriately located, a conductivity sensor can be used to detect leaks of blood or other liquids on an otherwise dry surface.

Figure 38:
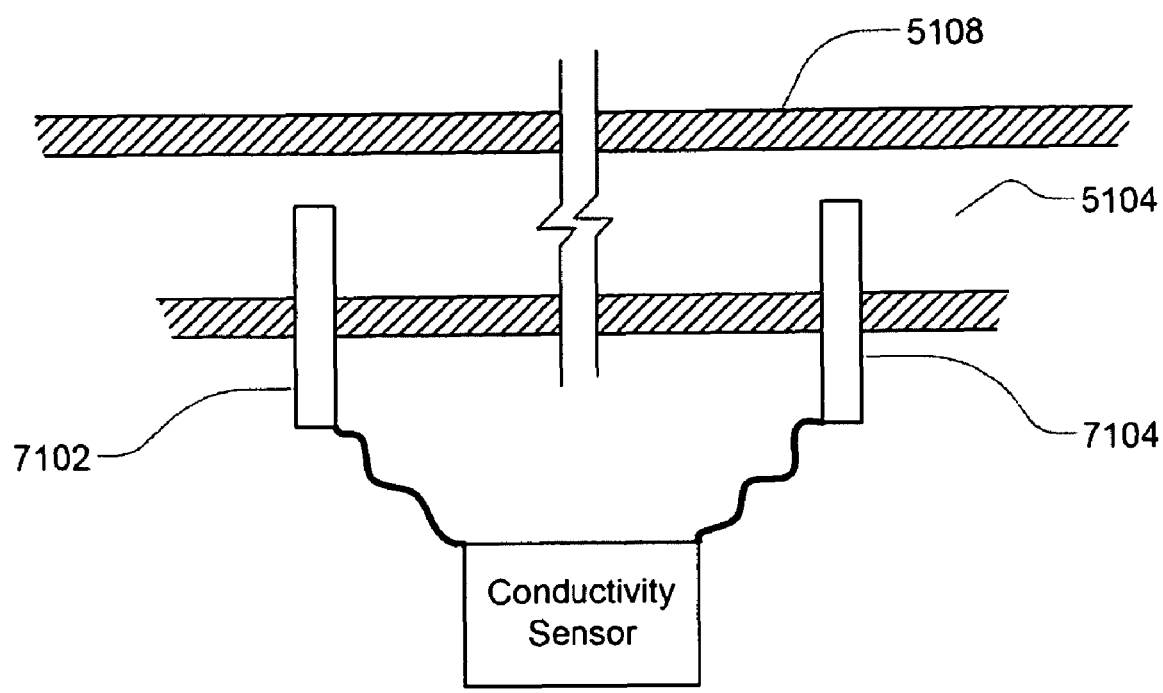
FIG. 38 is a side view of a fluid line including two sensors suitable for use as conductivity sensors.

Referring now to FIG. 38, for conductivity sensing, a pair of sensors 7102, 7104 is located in an area containing the subject media. In the embodiment shown, the area containing the subject media is a fluid path 5104 inside a fluid line 5108. The conductivity sensors 7102, 7104 can be a sensing probe as described above, with or without a thermal well. In those embodiments where both temperature and conductivity sensing is desired, a sensing probe typically includes at least three leads, where two of these leads may be used for temperature sensing and the third used for conductivity sensing. However, the second conductivity sensor of a pair can be any electrical sensor known in the art. Thus, in the systems described herein, conductivity and temperature can be sensed through using either one of the sensor apparatus or one of the sensor probes as described herein and a second capacitance sensor, or one of the sensor apparatus or one of the sensor probes as described herein and an electrical sensor.

The conductivity sensor elements and temperature sensor elements can be any conductivity or temperature sensor elements known in the art. In one embodiment, the conductivity sensor elements are graphite posts. In other embodiments, the conductivity sensor elements are posts made from stainless steel, titanium, platinum or any other metal coated to be corrosion resistant and still be electrically conductive. The conductivity sensor elements can include an electrical lead that transmits the probe information to a controller or other device. In some embodiments, the sensor elements are located outside of a pump module or cassette, in a separate housing, or may be connected to a pump module or cassette via a fluid line.

In some embodiments, at least a portion of a sensing probe assembly can be reusable. The thermal well may be the only part of a sensing probe assembly that contacts blood or other body fluids. In that case, the thermal well can be built into the disposable portion of a device (such as, for example, a pump module, cassette, or blood tubing). The sensing probe that mates with the thermal well, on the other hand, can be part of a receptacle, control bracket or other part of a base unit to which the disposable device attaches. Other configurations of sensing probes, assemblies, and thermal wells are possible, and are described in detail in commonly owned co-pending U.S. patent application Ser. No. 11/787,112, which is hereby incorporated by reference in its entirety.

Combination Filter for CPB

Figure 39:
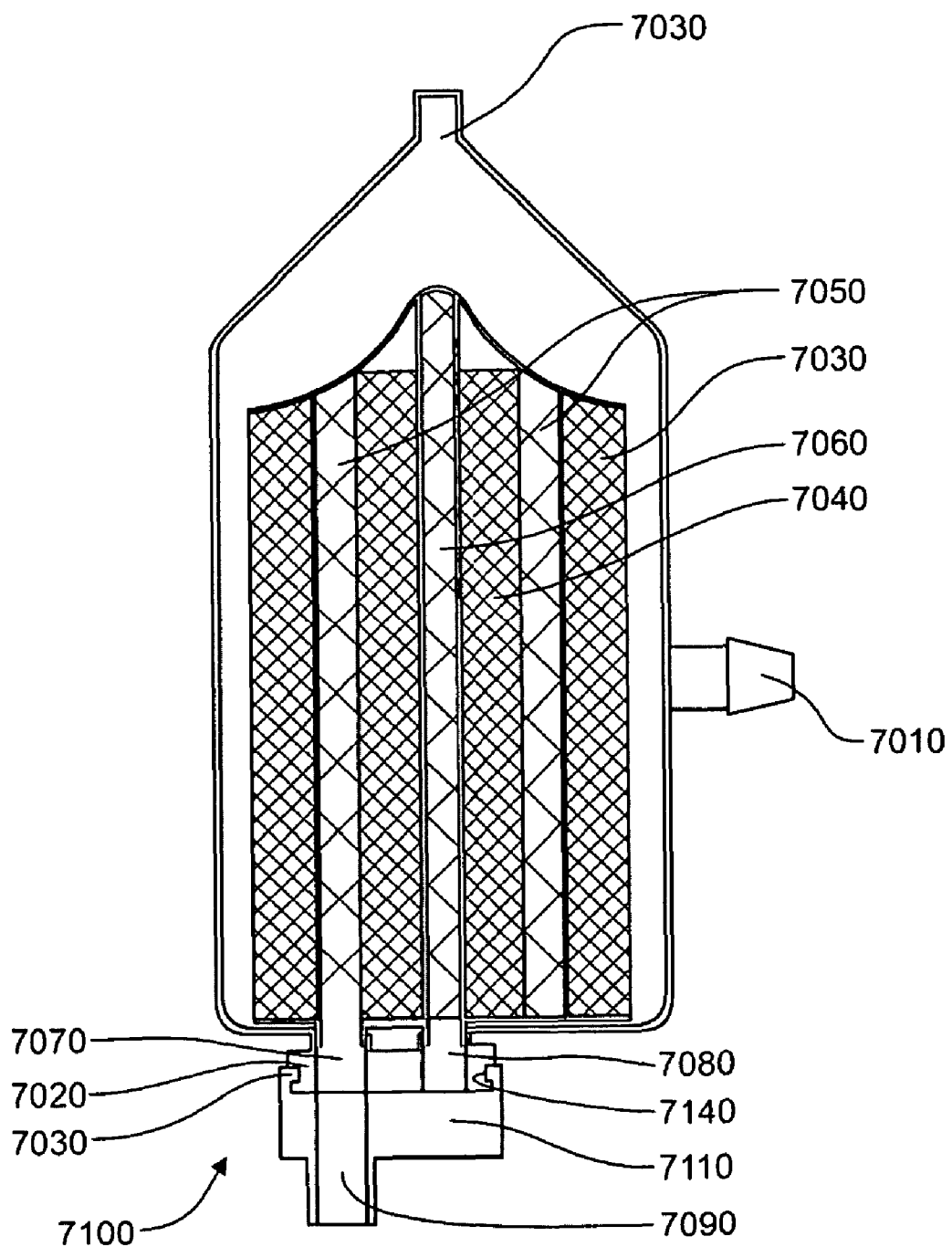
FIG. 39 is a cross-sectional view of a combination filter in accordance with an exemplary embodiment of the invention.

FIG. 39 is a cut-away view of an embodiment of a combination filter, which in this example is a combination air eliminator/arterial filter/leukocyte reduction filter. This type of filter can be used in an extracorporeal blood circuit, and more particularly in a CPB circuit. By combining several functions in one device, the priming volume of a CPB circuit can be reduced, and the amount of plastic surfaces to which the blood is exposed can be minimized.

The combination filter incorporates a tiered structure for removal of gas bubbles, particles over a first specified size, and particles over a size that is less than the first specified size. Liquid is made to flow first through an air elimination chamber, then through an intermediate pore-size filter, and finally through a small pore-size filter. The liquid flow path preferably includes the air eliminator followed by the larger pore-size filter. The fluid path is then directed by a selector valve at the outlet of the combination Filter, allowing a user to direct the liquid either to exit the combination filter, or pass through the smaller pore-size filter before exiting the combination filter. Although the two filters can be tiered within the combination filter in a number of ways (for example in an outward flow direction vs. an inward flow direction), one preferred method is to cause the liquid to flow progressively from the outer portion of the combination filter to the inner portion of the combination filter.

In a preferred embodiment, combination filter 7000 in FIG. 39 has a blood inlet 7010 located in an upper portion of filter housing 7020. In an embodiment, filter housing 7020 defines an inner volume of filter 7000 that is circular or oval in horizontal cross-section. Thus the inner volume of filter 7000 can be cylindrical or cylindroid in shape. Inlet 7010 is positioned in an approximately tangential relationship with the curvature of housing 7020. As a liquid enters filter 7000, it is directed along the inner wall of housing 7020, helping to minimize turbulence of the liquid as it circulates down the wall of housing 7020 toward the bottom of housing 7020. The centrifugal forces associated with circular flow of liquid along the inner wall of housing 7020 also help to separate gas bubbles from the liquid. Gas bubbles within the liquid will tend to separate from the circulating liquid and gather or coalesce toward the central region of housing 7020. A gas purge vent 7030 at the top of filter 7000 allows the gas to be vented out of housing 7020. In an embodiment, suction can be applied to gas purge vent 7030 to facilitate removal of accumulated gas within filter 7000.

Two separate filter media can be located within housing 7020. The more porous filter element 7030 (which in CPB may be a 40-micron filter) is positioned in contact with the liquid circulating along the inner wall of housing 7020. In an embodiment, filter element 7030 is generally cylindrical in shape, and can be constructed with different wall thicknesses. Determining the wall thickness of filter element 7030 may require weighing, for example, the filtering efficiency desired against the liquid flow rate that filter 7000 must accommodate.

A second filter element 7040 can be embedded within the volume defined by the inner wall of filter element 7030. In an embodiment, the second filter element 7040 is also generally cylindrical in shape. Filter element 7040 can be less porous than filter element 7030 in order to filter smaller matter from the liquid. For example, in blood flow circuits, filter element 7040 can be a leukocyte reduction filter (leukocytes having a diameter of approximately 9-16 microns). The outer wall of filter element 7040 can be spaced apart from the inner wall of filter element 7030 in order to permit the collection of liquid that has been filtered by filter element 7030 into primary space 7050. Primary outlet 7070 is constructed to be in fluid communication with primary space 7050 in order to provide an outlet for liquid filtered only by filter element 7030.

A secondary space 7060 near the center of combination filter 7000 serves to accumulate liquid that has been filtered by filter element 7040. Secondary outlet 7080 is constructed to be in fluid communication with secondary space 7060.

Selector valve 7100 can direct the flow of liquid through two different paths. In a first position of the valve, liquid flow is directed from filter element 7030 through primary space 7050 and then exits combination filter 7000 via primary outlet 7070 and selector valve outlet 7090. In a second position of the valve, liquid flow is directed from primary space 7050 through filter element 7040 and secondary space 7060, and ultimately exits combination filter 7000 via secondary outlet 7080 and selector valve outlet 7090. It is apparent to one of ordinary skill that selector valve 7100 can be constructed in a number of ways.

In an embodiment, selector valve 7100 has two disc-like components: stationary component 7120 that mates in a face-to-face manner with rotatory component 7110 rotatory component 7110 is capable of rotating in a horizontal plane with respect to stationary component 7120. The two components are connected to one another by an interlocking feature 7130 capable of allowing rotatory component 7110 to slide rotationally in groove 7140 of stationary component 7120. Rotatory component 7110 is capable of rotating about a vertical axis centered between outlets 7070 and 7080, the axis of rotation positioned to align selector valve outlet 7090 alternately with both primary outlet 7070 and secondary outlet 7080. In an embodiment, an elastomeric seal can be positioned between stationary component 7120 and rotatory component 7110 to prevent leaking of liquids from the interlocking joint formed by feature 7130. Non-limiting examples of a seal include a flat gasket positioned between components 7110 and 7120, or an O-ring positioned in a recess adjacent to the interlocking joint formed by feature 7130.

In another embodiment, the system additionally includes a combination blood filter having an upper inlet and first and second lower outlets comprising: a housing defining a first cylindroid volume for directing blood in a circular downward path; a particulate filter for removing air and particulate matter from blood, the particulate filter defining a second volume and being located within the first volume, the second volume fluidly connected to the first outlet; a leukocyte filter for removing leukocytes from blood, the leukocyte filter defining a third volume and being located within the second volume, the third volume fluidly connected to the second outlet; and a selector valve for selectably directing blood flow through the first outlet with the selector valve in a first mode, and for selectably directing blood flow through the second outlet with the selector valve in a second mode.

The present invention is directed to each individual feature, system, or method described herein. In addition, any combination of two or more such features, systems, or methods—provided that such features, systems, or methods are not mutually inconsistent—is included within the scope of the present invention. The features, configurations and systems described herein are meant to be exemplary, and the preferred embodiments will depend upon the specific application for which the systems and methods of the present invention are used. The foregoing embodiments are presented by way of example only and, within the scope of the appended claims and equivalents thereof, the invention may be practiced in a manner other than as specifically described. Those skilled in the art will recognize, or be able to ascertain using no more than routine experimentation, that various modifications or equivalents to the specific embodiments described herein may be contemplated without departing from the true scope of the invention.

We claim:

1. An extracorporeal blood flow system comprising:
   an air removal container having an upper blood inlet, a lower blood outlet and an air vent near the top of the air removal container, the air vent sealingly connected to, a negative pressure source;
   a blood pump having a pump inlet and a pump outlet;
   a fluid path from the outlet of the air removal container to the inlet of the blood pump;
   a reservoir containing a liquid with a blood inlet and a blood outlet;
   a reservoir inlet fluid path branching from the pump outlet and fluidly connected to the inlet of the reservoir;
   a reservoir outlet fluid path branching from the pump inlet and fluidly connected to the outlet of the reservoir;
   a first valve means to control flow of blood from the reservoir to the pump inlet and a second valve means to control flow of blood from the pump outlet to the reservoir;
   a pressure sensor in fluid communication with the air vent, and configured to measure air pressure within the air removal container; and
   a controller configured to receive the pressure information from the pressure sensor, and configured to control the valve means, wherein
   the controller configured to monitor the air pressure within the air removal container, and control the first and second valve means to cause the liquid from the reservoir to flow into the blood pump upon detection of a change in the air pressure within the air removal container.

2. The system of claim 1, wherein the controller is configured to signal the first valve means to open upon detection of a decrease in pressure measured by the pressure sensor.

3. The system of claim 1, wherein the controller is configured to signal the second valve means to open upon detection of an increase in pressure measured by the pressure sensor.

4. The system of claim 1, further comprising a secondary pump, the secondary pump having an inlet in fluid communication through a third valve means with the reservoir outlet fluid path, and having an outlet in fluid communication through a fourth valve means with the reservoir inlet fluid path.

5. The system of claim 4, wherein the controller is configured to control the first, second, third and fourth valve means and the secondary pump in order to control the flow of blood into or out of the reservoir.

6. The system of claim 4, wherein the blood pump and secondary pump each comprises a reciprocating positive displacement pump, and both pumps are fluidly connected to a common blood outflow path.

7. The system of claim 6, wherein the controller is configured to control the blood pump, the secondary pump and the first, second, third and fourth valve means in order to alternate pump strokes to the common blood outflow path.

8. The system of claim 6, wherein the blood pump, secondary pump, and, the first, second, third and fourth valve means are pneumatically actuated.

9. The system of claim 1, further comprising a liquid volume sensor associated with the reservoir, and capable of transmitting information to the controller relating to the liquid volume in the reservoir, wherein
   the controller is configured to control the volume of liquid in the reservoir to within a pre-determined range.

10. The system of claim 1, wherein the reservoir comprises a flexible or collapsible bag.

11. An extracorporeal blood flow system comprising:
- an air trap having an upper inlet, a lower outlet and an air vent above the upper inlet, the air vent fluidly connected to a negative pressure source;
- a first pump having a pump inlet and a pump outlet, the pump inlet fluidly connected to the lower outlet of the air trap;
- a reservoir configured to hold a variable volume of liquid and having a reservoir inlet and a reservoir outlet, the reservoir inlet fluidly connected to the outlet of the pump, and the reservoir outlet fluidly connected to the inlet of the pump;
- a first valve configured to control flow of liquid from the reservoir to the pump inlet and a second valve configured to control flow of liquid from the pump outlet to the reservoir, the first and second valves controllable by a controller; and
- a pressure sensor in fluid communication with the air vent, and configured to measure air pressure within the air trap, the pressure sensor configured to transmit pressure information to the controller; wherein
- the controller is configured to monitor the air pressure within the air trap, and upon detection of a change in the air pressure within the air trap, the controller configured to control the first and second valves to allow liquid from the reservoir to flow to the inlet of the blood pump or to allow liquid to flow from the outlet of the blood pump to the reservoir.

12. The system of claim 11, wherein the controller is configured to signal the first valve to open upon detection of a decrease in pressure measured by the pressure sensor.

13. The system of claim 11, wherein the controller is configure to signal the second valve to open upon detection of an increase in pressure measured by the pressure sensor.

14. The system of claim 11, further comprising a second pump, the second pump having an inlet in fluid communication through a third valve with the reservoir outlet, and having an outlet in fluid communication through a fourth valve with the reservoir inlet, wherein the third and fourth valves are controllable by the controller.

15. The system of claim 14, wherein the controller is configured to control the first, second, third and fourth valves and the second pump in order to control the liquid flowing into or out of the reservoir.

16. The system of claim 11, further comprising a liquid volume sensor associated with the reservoir, and capable of transmitting information to the controller relating to the liquid volume in the reservoir, wherein
- the controller is configured to control the volume of liquid in the reservoir to within a pre-determined range.

17. The system of claim 11, wherein the reservoir comprises a flexible or collapsible bag.

18. The system of claim 11, wherein the first pump and second pump each comprises a reciprocating positive displacement pump, and both pumps are fluidly connected to a common liquid outflow path.

19. The system of claim 18, wherein the controller is configured to control the first and second pumps, and the first, second, third and fourth valves in order to alternate pump strokes to the common liquid outflow path.

20. The system of claim 18, wherein the first and second pumps, and the first, second, third and fourth valves are pneumatically actuated.

21. An extracorporeal blood flow system comprising:
- an air trap having an upper inlet, a lower outlet and an air vent above the upper inlet, the air vent fluidly connected to a negative pressure source;
- a first pump having a pump inlet and a pump outlet, the pump inlet fluidly connected to the lower outlet of the air trap;
- a reservoir configured to hold a variable volume of liquid and having a reservoir inlet and a reservoir outlet, the reservoir inlet fluidly connected to the outlet of the first pump, and the reservoir outlet fluidly connected to the inlet of the first pump;
- a first valve configured to control flow of liquid from the reservoir to the first pump inlet and a second valve to control flow of liquid from the first pump outlet to the reservoir, the first and second valves controllable by a controller;
- a second pump having an inlet in fluid communication through a third valve with the reservoir outlet and an outlet in fluid communication through a fourth valve with the reservoir inlet, the third and fourth valves controllable by the controller; and
- a liquid volume sensor associated with the reservoir and configured to transmit information to the controller relating to the liquid volume in the reservoir; wherein
the controller is configured to control the volume of liquid in the reservoir to within a pre-determined range.

22. The system of claim 21 further comprising a pressure sensor in fluid communication with the air vent, and capable of measuring air pressure within the air trap, the pressure sensor configured to transmit pressure information to the controller; wherein
- the controller is configured to monitor the air pressure within the air trap, and upon detection of a change in the air pressure within the air trap, the controller can control the first or the second pump, and the first, second, third or fourth valves to allow liquid from the reservoir to flow to the inlet of the first pump or to allow liquid to flow from the outlet of the first pump to the reservoir.

* * * * *